United States Patent [19]
Rose et al.

[11] Patent Number: 5,925,733
[45] Date of Patent: Jul. 20, 1999

[54] DNA POLYMERASE OF GAMMA HERPES VIRUSES ASSOCIATED WITH KAPOSI'S SARCOMA AND RETROPERITONEAL FIBROMATOSIS

[75] Inventors: Timothy M. Rose, Seattle; Marnix L. Bosch, Bellevue; Kurt Strand, Issaquah; George J. Todaro, Seattle, all of Wash.

[73] Assignee: University of Washington, Seattle, Wash.

[21] Appl. No.: 08/680,326

[22] Filed: Jul. 11, 1996

Related U.S. Application Data

[60] Provisional application No. 60/001,148, Jul. 14, 1995.

[51] Int. Cl.$^6$ .......................... A61K 39/02; C07H 21/04; C07K 1/00; C12N 9/00
[52] U.S. Cl. .................. 530/350; 424/186.1; 424/229.1; 435/6; 435/69.1; 435/320.1; 435/235.1; 514/44; 530/300; 536/23.2; 536/23.72; 536/24.3
[58] Field of Search .............................. 536/23.2, 23.72, 536/24.3; 435/320.1, 235.1, 6, 69.1; 514/44; 530/350, 300; 424/229.1, 186.1

[56] References Cited

U.S. PATENT DOCUMENTS

| | | |
|---|---|---|
| 5,120,639 | 6/1992 | Haffey et al. . |
| 5,171,568 | 12/1992 | Burke et al. . |
| 5,223,391 | 6/1993 | Coen et al. . |
| 5,244,792 | 9/1993 | Burke et al. . |
| 5,350,671 | 9/1994 | Houghton et al. . |
| 5,354,653 | 10/1994 | Matsumoto et al. . |

FOREIGN PATENT DOCUMENTS 0337441  10/1989  European Pat. Off. .

OTHER PUBLICATIONS

Martin, III et al., "Kaposi sarcoma" *Medicine* (1993) 72:245–261.

Finesmith et al., "Kaposi's sarcoma" *Int. J. Derm.* (1994) 33:755–762.

Berel et al., "Kaposi's sarcoma among persons with AIDS: a sexually transmitted infection?" *Lancet* (1990) 335:123–128.

Chang et al., "Identification of herpesvirus–like DNA sequences in AIDS–associated Kaposi's sarcoma" *Science* (1994) 266:1865–1869.

Ambroziak et al., "Herpes–like sequences in HIV–infected and uninfected Kaposi's sarcoma patients" *Science* (1995) 268:582–583.

Lisitsyn et al., "Cloning the differences between two complex genomes" *Science* (1993) 259:946–951.

Moore et al., "Detection of herpesvirus–like DNA sequences in Kaposi's sarcoma in patients with and those without HIV infection" *New Engl. J. Med.* (1995) 332:1181–1185.

Cesarman et al., "Kaposi's sarcoma–associates herpesvirus–like DNA sequences in AIDS–related body–cavity–based lymphomas" *New Engl. J. Med.* (1995) 332:1186–1191.

Emery et al., "Herpesviruses" *Molecular and Cell Biology of Opportunistic Infections in AIDS* (1992) Myint and Cann, eds., Chapman and Hall, London, pp. 257–277.

Karlin et al., "Molecular evolution of herpesviruses: Genomic and protein sequence comparisons" *J. Virol.* (1994) 68:1866–1902.

Giddens, Jr. et al., "Enzootic retroperitoneal fibromatosis in macaca spp." *Viral and Immunological Diseases in Nonhuman Primates* (1983) pp. 249–253.

Tsai et al., "Retroperitoneal fibromatosis and acquired immunodeficiency syndrome in macaques: Clinical and immunologic studies" *Lab. Animal Sci.* (1986) 36:119–124.

Derbyshire et al., "The 3'–5' exonuclease of DNA polymerase I of *Escherichia coli*: contribution of each amino acid at the active site to the reaction" *EMBO J.* (1991) 10:17–24.

Bernad et al., "A conserved 3'→5' exonuclease active site in prokaryotic and eukaryotic DNA polymerases" *Cell* (1989) 59:219–228.

Simon et al., "The 3' to 5' exonuclease activity located in the DNA polymerase δ subunit of *Saccharomyces cerevisiae* is required for accurate replication" *EMBO J.* (1991) 10:2165–2171.

Soengas et al., "Site–directed mutagenesis at the Exo III motif of φ29 DNA polymerase; overlapping structural domains for the 3'–5' exonuclease and strand–displacement activities" *EMBO J.* (1992) 11:4227–4237.

(List continued on next page.)

*Primary Examiner*—Jeffrey Stucker
*Assistant Examiner*—Phuong T. Bui
*Attorney, Agent, or Firm*—Fish & Richardson P.C.

[57] ABSTRACT

This invention provides isolated polynucleotides encoding DNA polymerases of three members of a subfamily of gamma herpes viruses. Two were obtained from macaque monkeys affected with retroperitoneal fibromatosis, the other from human AIDS patients affected with Kaposi's sarcoma. A 454-base pair fragment encoding a region near the active site of the DNA polymerase is 69–83% identical amongst the three viruses, but only 54–68% identical with other known gamma herpes sequences and <55% identical with alpha and beta herpes sequences. Also provided are polynucleotides encoding DNA polymerase from related viruses in the RFHV/KSHV subfamily. Polynucleotides prepared according to the sequence data can be used as reagents to detect and characterize related sequences. Such reagents may be used to detect members of the RFHV/KSHV subfamily, including but not limited to RFHV, RFHV2, and KSHV. Corresponding polypeptides and peptide fragments may be obtained by expressing the polynucleotide or by chemical synthesis. They may be used for detecting specific antibody potentially present in the serum of infected subjects. They may also be used for designing or screening pharmaceutical compounds that limit viral replication by inhibiting DNA polymerase activity.

7 Claims, 35 Drawing Sheets

OTHER PUBLICATIONS

Dorsky et al., "Expression of herpes simplex virus type 1 DNA polymerase gene by in vitro translation and effects of gene deletions on activity" *J. Virol.* (1988) 62:3224–3232.

Dorsky et al., "Site–specific mutageneiss of a highly conserved region of the herpes simplex virus type 1 DNA polymerase gene" *J. Virol.* (1990) 64:1394–1397.

Bernad et al., The highly conserved amino acid sequence motif Tyr–Gly–Thr–Asp–Ser in α–like DNA polymerases is required by phage φ29 DNA polymerase for protein–primed initiation and polymerization *Proc. Natl. Acad. Sci. USA* (1990) 87:4610–4614.

Gibbs et al., "Identification of amino acids in herpes simplex virus DNA polymerase involved in substrate and drug recognition" *Proc. Natl. Acad. Sci. USA* (1988) 85:6672–6676.

Blasco et al., "Structural and functional studies on ø29 DNA polymerase" *Chromosoma* (1992) 102:S32–S38.

Blasco et al., "φ29 DNA polymerase active site" *J. Biol. Chem.* (1992) 267:19427–19434.

Digard et al., "Specific inhibition of herpes simplex virus DNA polymerase by helical peptides corresponding to the subunit interface" *Proc. Natl. Acad. Sci. USA* (1995) 92:1456–1460.

Stow, "Sequences at the C–terminus of the herpes simplex virus type 1 UL30 protein are dispensable for DNA polymerase activity but not for viral original–dependent DNA replication" *Nucl. Acids Res.* (1993) 21:87–92.

Meier et al., Varicella–zoster virus DNA polymerase and major DNA–binding protein genes have overlapping divergent promoters *J. Virol.* (1993) 67:7573–7581.

Yeung et al., "Differences in the capacity of two herpes simplex virus isolates to spread from eye to brain map to 1610 base pairs of DNA found in the gene for DNA polymerase" *Curr. Eye Res.* (1991) 10 (Suppl):31–37.

*Gen Bank Search*, sequence i.d.1, Database: Non–redundant GenBank+EMBL+DDBJ+PDB sequences 245,156 sequences; 342,555,758 total letters, 10 pages total.

*Gen Bank Search*, sequence i.d.2, Database: Non–redundant Genbank CDS translations+PDB+SwissProt+SPudate+PRI 203,899 sequences; 57,984351 total letters, 12 pages total.

*Gen Bank Search*, sequence i.d.3, Database: Non–redundant GenBank+EMBL+DDBJ+PDB sequences 245,156 sequences; 342,555,758 total letters, 10 pages total.

*Gen Bank Search*, sequence i.d.4, Database: Non–redundant GenBank+EMBL+DDBJ+PDB sequences 245,156 sequences; 342,555,758 total letters, 12 pages total.

VanDevanter et al., "Detection and analysis of diverse herpesviral species by consensus primer PCR" *J. Clin. Microbiol.* (1996) 34:1666–1671.

Gibbs et al., "Polymerization activity of an α–like DNA polymerase requires a conserved 3'–5' exonuclease active site" *Mol. Cell Biol.* (1991) 11:4786–4795.*Mol. Cell. Biol.* (1991) 11:4786–4795.*Mol. Cell. Biol.* (1991) 11:4786–4785.

Albrecht et al., "Structural organization of the conserved gene block of *Herpesvirus saimiri* coding for DNA polymerase, glycoprotein B, and major DNA binding protein" *Virology* (1990) 174:533–542. The related EMBL Sequence Data Library, Heidelberg, BRD, XP002021595, Accession No. P24907 is also enclosed.

Dang et al., "Structural and functional analyses of a yeast mitochondrial ribosomal protein homologous to ribosomal protein S15 of *Escherichia coli*" *Nucleic Acids Research* (1990) 18:6895–6901. The related EMBL Sequence Data Library, Heidelberg, BRD, XP002021631, Accession No. S12797 is also enclosed.

Hillier et al., "ya03b03.r2 *Homo sapiens* cDNA clone 60365 5"EMBL Sequence Data Library, Heidelberg, BRD, XP002021632, Accession No. T39269. 1 page total.

Telford et al., "The DNA sequence of equine herpesvirus 2" *J. Mol. Biol.* (1995) 249:520–528. The related EMBL Sequence Data Library, Heidelberg, BRD, XP002021596, Accession No. U20824 is also enclosed.

Roizman et al., "New viral footprints in Kaposi's sarcoma" *New Engl. J. Med.* (1995) 332:1227–1228.

Schalling et al., "A role for a new herpes virus (KSHV) in different forms of Kaposi's sarcoma" *Nature Medicine* (1995) 1:707–702.

Chang et al. Science vol. 266, Dec. 16, 1994, pp. 1865–1869.

Albrecht et al. J Virol, vol. 66, No. 8, Aug. 1992, pp. 5047–5058.

```
KSHV       GTGTTCGACTTTGCTAGCCTCTACCCCAGTATCATCCAAGCGCACAACTTGTGCTACTCC   60
           V  F  D  F  A  S  L  Y  P  S  I  I  Q  A  H  N  L  C  Y  S
(DFASA>)   gtgttcgacttygcnagyytntaycc KSHV       ACACTGATACCCGGCGATTCGCTCCACCTGCACCCACACCTCTCCCCGGACGACTACGAA  120
           T  L  I  P  G  D  S  L  H  L  H  P  H  L  S  P  D  D  Y  E KSHV       ACCTTTGTCCTCAGCGGAGGTCCGGTCCACTTTGTAAAAAAACACAAAAGGGAGTCCCTT  180
           T  F  V  L  S  G  G  P  V  H  F  V  K  K  H  K  R  E  S  L KSHV       CTTACCAAGCTTCTGACGGTATGGCTCGCGAAGAGAAAAGAAATAAGAAAGACCCTGGCA  240
           L  T  K  L  L  T  V  W  L  A  K  R  K  E  I  R  K  T  L  A KSHV       TCATGCACGGACCCCGCACTGAAAACTATTCTAGACAAACAACAACTGGCCATCAAGGTT  300
           S  C  T  D  P  A  L  K  T  I  L  D  K  Q  Q  L  A  I  K  V (PCLNA>) gtcgcctctggcatcctnccntgyctnaa
                              (ILPCA>) ggcatcctaccgtgcctgaac
                          (VASGA>) cgtcgcttccggcatcctacc
              T  C  N  A  V  Y  G  F  T  G  V  A  S  G  I  L  P  C  L  N
RFHV       ACGTGCAACGCGGTGTACGGGTTTACGGGCGTCGCTTCCGGCATCCTACCGTGCCTGAAC  360
           **  ***********  *****  **  ********  **  **  ****  **  **  ****  ***
KSHV       ACCTGCAACGCGGTTTACGGCTTCACGGGCGTTGCCTCTGGCATACTGCCTTGCCTAAAC  360
           T  C  N  A  V  Y  G  F  T  G  V  A  S  G  I  L  P  C  L  N
 (VYGA>) acgtgcaacgcggtgtayggnktnacngg         (CLNIA>) ctgccttgcctaaac·
              (SGILA>) gcgttgcctctggcatactg (GISPA>) tctcaggcgttcgta·
              (KMLEA>) cagggccggaagatgctggaracrtcncargc
              I  A  E  T  V  T  L  Q  G  R  K  M  L  E  I  S  Q  A  F  V
RFHV       ATCGCAGAGACGGTGACCCTCCAGGGCAGGAAAATGCTGGAAACGTCTCAGGCGTTCGTA  420
           **  **  *****  *****  **  **  **  *  **  ********  *  ********  **  ***
KSHV       ATAGCGGAGACCGTGACACTACAAGGGCGAAAGATGCTGGAGAGATCTCAGGCCTTTGTA  420
           I  A  E  T  V  T  L  Q  G  R  K  M  L  E  R  S  Q  A  F  V
           -atagcg (CLNIA>)
```

FIG. 1A

```
                                                      (<PEARB) ccgcagaggc-
           -garggnathtcncc (GISPA>)        (<PIEAB) ctggctagctccgcagaggc-
            E  G  I  S  P  I  A  L  A  D  L  L  Q  R  P  I  E  A  S  P
RFHV        GAGGGAATCTCGCCAACGGCACTGGCAGACCTACTGCAGCGACCGATCGAGGCGTCTCCG    480
            ****  ********    ** **  *   ** **** * ** ** ** *  ** **
KSHV        GAGGCCATCTCGCCGGAACGCCTAGCGGGTCTCCTGCGGAGGCCAATAGACGTCTCACCC    480
            E  A  I  S  P  E  R  L  A  G  L  L  R  R  P  I  D  V  S  P
                                          (<IEASB) tccggttatctgcagagtgg
                                          (<EARFB) gcagagtggg- -cttcggtccaa (<PEARB)
-c (<PIEAB)
            E  A  R  F  K  V  I  Y  G  D  T  D  S  V  F  V  A  C
RFHV        GAAGCCAGGTTTAAAGTGATATACGGCGACACCGACTCCGTGTTTGTCGCATGCCG      536
            ** ***  * **  ** ** ********************************
KSHV        GACGCCCGATTCAAGGTCATATACGGCGACACCGACTCCGTGTTTGTCGCATGCCG      536
            D  A  R  F  K  V  I  Y  G  D  T  D  S  V  F  V  A  C
                    (<GDTD1B) atrccnctrtgnctgaggcacaaacagcgtacggc
            -ctgcgggctaa (<EARFB)
```

FIG. 1B

```
hHV6    V---------------MDSV-SFFNPYLEA--------------------NRLKK
hHSV1   MFSGG---GGPLSPGGKSAARAASGFFAPAGPRGAGR-GPPPCLRQNFYNPYLAPVGTQQ
hHSV2   MFCAA---GGPASPGGKSAARAASGFFAPHNPRGATQTAPPPCRRQNFYNPHLAQTGTQP
hVZV    M--------AIR---------TGFCNPFLTQASGI----------KYNPRTGRGSN--
eHV1    M--------AAREQANSVRR--SGFFNPFIGKRP-----------FFRPGSGQTAETE
hEBV    M-----------------SGGL--FYNPFL---------------RPNKGLLKKPD--
sHV1    M-----------------D-----FYNPYL---------------SKKPTDTKTPKLH
mCMV    M-----------------DTCVETFFNPYL-----RRK----PRRDWRR---CED----
gpCMV   M---------------SAPV--FFNPYLCGGAARRRNG-CSTVDSRR---VNGPTKK
hCMV    M---------------------FFNPYLSGGVTGGAVA-GGRRQRSQPGSAQGSGKR
iHV1    MDRNAVLYGVLEHRLPKWVELSDDTDLEPFFFSSVRYITAGS----------EDAIMIQA hHV6    KSRS-----------SYIRILPRGIMHDGAA----GLIKDVCDSEPRMFYRDRQYLLSK
hHSV1   KPTGPTQRHTYYSECDEFRFIAPRVLDEDAPPEKRAGVHDGHLKRAPKVYCGGDERDV-L
hHSV2   KAPGPAQRHTYYSECDEFRFIAPRSLDEDAPAEQRTGVHDGRLRRAPKVYCGGDERDV-L
hVZV    --REF--LHSYKTTMSSFQFLAPKCLDEDVPMEERKGVHVGTLSRPPKVYCNGKEVPI-L
eHV1    RPRPP--QHSYCTEVGSFKFIAPRCLDEEAPADQRRGVHVGTLERPPKVYCDGSEYDV-L
hEBV    --KE------------YL-RLIPKCFQTPGAA----GVVDVRGPQPPLCFYQDSLTVVGG
sHV1    TTRQ-----------SICRLVPKCFRNPTEK----GVVSVSSFALPTYFFKGNENKVYL
mCMV    N-NK-----------NFLQVVPRGVLYDGAT----GLIKVQSGMEPRMFYAEKEYVLNP
gpCMV   G-KK-----------SFLQVVRRGVIYDGEK----GLIKKVTQHPPRMFYNNVQYLLEP
hCMV    PPQK-----------QFLQIVPRGVMFDGQT----GLIKHKTGRLPLMFYREIKHLLSH
iHV1    LNLNTDEIVVFLVTNLNFMALIPTVYIENPGIRQLIASTPISYRSPITVFNGD------- hHV6    EMTWPSL--DIARSKDY------DHM-RMK-FHIYDAVETL--MFTDSIENLPFQYRHFV
hHSV1   RVGSGGFWPRRSRLWGGVDHAPAGFNPTVTVFHVYDILENVEHAYGMRAAQFHARFMDAI
hHSV2   RVGPEGFWPRRLRLWGGADHAPEGFDPTVTVFHVYDILEHVEHAYSMRAAQLHERFMDAI
hVZV    DFRCSSPWPRRVNIWGEIDFRGDKFDPRFNTFHVYDIVETTEAA----SNGDVSRFATAT
eHV1    NFASGGCWPRRIRVWNGQDFRGDGFNPRFERFHVYDIVETSESA----SHDDPSRFAELS
hEBV    DEDGKGMWWRQRAQEGTARPEADTHGSPLD-FHVYDILETV--YTHEKCAVIPSDQGYV
sHV1    -ENGKSMWHLRRPCKNALLEEQ-----SIT-FHIYDIVETT--YSEDRCNDIPFKFQTDI
mCMV    DKPWP-----TLRTRGWCRGPYSDD---VR-FHTYDQVVNL--VLADSDEQISPRWNSHV
gpCMV   QMSWP-----TLPCRETCRVGCGREQ-PLR-FHTFDQIDST--VYADSVEQIFLGYRRHV
hCMV    DMVWPCPWRETLVGRV--------VG-PIR-FHTYDQTDAV--LFFDSPENVSPRYRQHL
iHV1    ----------LKKWMDCDLFVFGTMAAQKAF------IKAGNSVLGSLGGNVYTGDHV hHV6    IPSGTVIRMFGR-TEDGE----KICVNVFGQEQYFY---------CECVDGRSLKATINN
hHSV1   TPTGTVITLLGL-TPEGH----RVAVHVGTRQYFYMNKEEVDRHLQCRAPRDLCERMAA
hHSV2   TPAGTVITLLGL-TPEGH----RVAVHVGTRQYFYMNKAEVDRHLQCRAPRDLCERLAA
hVZV    RPLGTVITLLGM-SRCGK----RVAVHVGICQYFYINKAEVDTACGIRSGSELSVLLAE
eHV1    RPSGSVVTLLGM-SECGK----RVAVHVYGVRHYFYMAKAEVDSACGITTEAELVRAMVD
hEBV    VPCGIVIKLLGRRKADGA----SVCVNVFGQQAYFY---------ASAPQGLDVEFAVLS
sHV1    IPNGTVLKLLGR-TLEGA----SVCVNVFGQRNYFY---------VKVPEGGNITYLIKQ
mCMV    VPAGNVIRMFGA-TDEGV----SVCVNVFGQKAYFY---------CERMQSEDLKNTVYD
gpCMV   VPCGNVIRMFGR-TCDGS----SVCVNVFGQPSYFY---------CEYDGSEGYLDNYLS
hCMV    VPSGNVLRFFGA-TEHGY----SICVNVFGQRSYFY---------CEYSDTDRLREVIAS
iHV1    SNFDGNTPVLQNNLMCSHVYYTRYKTDVYAPWEFYYDQKRDQGYL------MSLPAIIPR
```

FIG. 2A

```
hHV6    LMLTGE----VK----------------------MSCSFVIEPADKLSLYGYNANTVVN
hHSV1   ALRESP---------------GASF-----RGISADHFEAEVVERTDVYYYETRPAL-
hHSV2   ALRESP---------------GASF-----RGISADHFEAEVVERADVYYYETRPTL-
hVZV    CLRSSM-ITQNDATLNGDKNAFHGTSF-----KSASPESFRVEVIERTDVYYYDTQPCA-
eHV1    CAHSSA-LSAALGNGNGGKQSGGSGGGWWGG-KHVSADCFKVETVCHTTLYYFGSKPAL-
hEBV    -ALKAS-TFDRR----------------------TPCRVSVEKVTRRSIMGYGNHA-GD
sHV1    -ALNEK--FS------------------------PSCAYQTEAVKKKILSRYDPEE-HD
mCMV    IADKVP-EPCSP----------------------FSVSISPVTKSSFYGYGLGHIPN
gpCMV   TVLKET-EDVTK----------------------IVFTLDAQRVHKYSLFGYNTKYIEN
hCMV    VGELVP-EPRTP----------------------YAVSVTPATKTSIYGYGTRPVPD
iHV1    CKREGAFDIETIVHENAMDQDLNCQKFFKSEFRSMEESQVLIQRFREAGVTGLPPSPFVG hHV6    LFKVSFGNFYVSQRIGKILQN-EGFVVYEIDVDVLTRFFVDN-GFLSFGWYNVKKYIPQD
hHSV1   FYRVYVRSGRVLSYLCDNFCP--AIKKYEGGVDATTRFILDNPGFVTFGWYRLKPGRNNT
hHSV2   YYRVFVRSGRALAYLCDNFCP--AIRKYEGGVDATTRFILDNPGFVTFGWYRLKPGRGNA
hVZV    FYRVYSPSSKFTNYLCDNFHP--ELKKYEGRVDATTRFLMDNPGFVSFGWYQLKPGVDGE
eHV1    YYRVSASSSRLGGFICDNFHP--EITKFEGSVDVTTRLLLDNENFTSFGWYRLRPGTHGE
hEBV    YHKITLSHPNSVCHVATWLQDKHGCRIFEANVDATRRFVLDN-DFVTFGWYSCRRAIPRL
sHV1    VFKVTVSSSLSVYKISDSLVS-NGCEVFETNVDAIRRFVIDN-DFSTFGWYTCKSACPRI
mCMV    LYRLSFNNWNMCRKIGKRMLE-EGRKVYELGVDPLARFLIDR-KIPSFGWCLARRYSVRA
gpCMV   LYRVTLNNWPVCKRLAQNLQS-RGLRVYEAGVDPVARFCVDR-KIPSFGWCVIKRFYARS
hCMV    LQCVSISNWTMARKIGEYLLE-QGFPVYEVRVDPLTRLVIDR-RITTFGWCSVNRYDWRQ
iHV1    ITQKLHEIVSISLVVCNYHKTGPKKKEY------------------YVYYNTKK-----

EXO 1
hHV6    MGK-------GSNLEVEINCHVSDLVSL-EDVNWPLYGCWSFDIECLGQNGN---FPDAE
hHSV1   LAQPRAPMAFGTSSDVEFNCTADNLAIEGGMSDLPAYKLMCFDIECKAGGEDELAFPVAG
hHSV2   PAQPRPPTAFGTSSDVEFNCTADNLAVEGAMCDLPAYKLMCFDIECKAGGEDELAFPVAE
hVZV    RVRVRPASRQLTLSDVEIDCMSDNLQAIPNDDSWPDYKLLCFDIECKSGGSNELAFPDAT
eHV1    RVQLRPVERHVTSSDVEINCTPDNLEPIPDEAAWPDYKLMCFDIECKAGTGNEMAFPVAT
hEBV    QHR-------DSYAELEYDCEVGDLSVRREDSSWPSYQALAFDIECLGEEG----FPTAT
sHV1    TNR-------DSHTDIEFDCGYYDLEFHADRTEWPPYNIMSFDIECIGEKG----FPCAK
mCMV    AGY-------VSRAQLEIDCDVADILPIEEQSNWPFYRCLSFDIECMSGTGA---FPAAE
gpCMV   SGL-------ASFCDIEIDCEIGDVEADDSDMSWPEYRCASFDIECMSGGDR---FPDSS
hCMV    QGR-------ASTCDIEVDCDVSDLVAVPDDSSWPRYRCLSFDIECMSGEGG---FPCAE
iHV1    ---MENPMEMIPVEHLHLDASRIKFEACKNE----FYMLLAF-INRLRKSVNVL-YVYNA hHV6    NLGDIVIQISVISFDTEG---------------------DRDERHLFTLGTCEKID-
hHSV1   HPEDLVIQISCLLYDLST-TALEHVLLFSLG-SCDLPESHLNELAARGL--------P
hHSV2   RPEDLVIQISCLLYDLST-TALEHILLFSLG-SCDLPESHLSDLASRGL--------P
hVZV    HLEDLVIQISCLLYSIPR-QSLEHILLFSLG-SCDLPQRYVQEMKDAGL--------P
eHV1    NQEDLVIQISCLLYSLAT-QNHEHTLLFSLG-SCDISEEYSFACVQRGE--------P
hEBV    NEADLILQISCVLWSTGEEAGRYRRI---------------LLTLGTCEDIE-
sHV1    NEGDLIIQISCVFWHAGALDTT-RNM---------------LLSLGTCSAVE-
mCMV    NVDDIIIQISCVCF------GVGEMVHHAYDVHADLSTPAVPEN---HLFTIGPCAPI-P
gpCMV   MVDDIVIQISVICY------AVGRSGAESDGVSG--AEAAVREHQ--HLFTLGPCAPI-P
hCMV    KSDDIVIQISCVCYETGGNTAVDQGIPNGNDGRGCTSEGVIFGHSGLHLFTIGTCGQVGP
iHV1    QFDIQVIQQRLRYYAFKQRAPR---------CCKGHDDIPHEWGKALMEKWEAFLSVKP
```

FIG. 2B

```
                                             EXO 2
hHV6    GVHIYEFASEFELLLGFFIFLRIESPEFITGYNINNFDLKYLCIRMDKIYHYDIGCFSKL
hHSV1   TPVVLEFDSEFEMLLAFMTLVKQYGPEFVTGYNIINFDWPFLLAKLTDIYKVPLDGYGRM
hHSV2   APVVLEFDSEFEMLLAFMTFVKQYGPEFVTGYNIINFDWPFVLTKLTEIYKVPLDGYGRM
hVZV    EPTVLEFDSEFELLIAFMTLVKQYAPEFATGYNIVNFDWAFIMEKLNSIYSLKLDGYGSI
eHV1    RPTVLEFDSEYELLVAFLTFLKQYSPEFATGYNIVNFDWAYIVNKVTSVYNIKLDGYGKF
hEBV    GVEVYEFPSELDMLYAFFQLIRDLSVEIVTGYNVANFDWPYILDRARHIYSINPASLGKI
sHV1    NTEVYEFPSEIDMLHGFFSLIRDFNVEIITGYNISNFDLPYLIDRATQIYNIKLSDYSRV
mCMV    DVKIYTFPSEYEMLRGFFIFLSWYSPEFITGYNINGFDIKYILTRAEKLYKMDVGQFTKL
gpCMV   GTHVYEFPSEYELLLGFFIFFKAYPPDILTGYNINLFDIKYLLQRMEKIYHANVSEFTKL
hCMV    DVDVYEFPSEYELLLGFMLFFQRYAPAFVTGYNINSFDLKYILTRLEYLYKVDSQRFCKL
iHV1    QL----FKA--QILMG-QDILKANYLKLLEGIGSVLAQAKSTMAKMCTI-KERIDSYRKM hHV6    K---NGKIGIS-VPHEQYRKGFLQA--------------QTKVFTSGVLYLDMYPVYSSKI
hHSV1   N--GRGVFRVWDIGQSHFQK------------------RSKIKVNGMVNIDMYGIITDKI
hHSV2   N--GRGVFRVWDIGQSHFQK------------------RSKIKVNGMVNIDMYGIITDKV
hVZV    N--RGGLFKIWDVGKSGFQR------------------RSKVKINGLISLDMYAIATEKL
eHV1    N--KGGLFKVWDIATNHFQK------------------KSKVKINGLISLDMYSVATEKL
hEBV    RA--GGVCEVR-RPHDA-GKGFLRA-------------NTKVRITGLIPIDMYAVCRDKL
sHV1    KT--GSIFQVH-TPKDT-GNGFMRS-------------VSKIKISGIIAIDMYIVCKDKL
mCMV    RR--GGRMFVF-SPEKG-------------KAGFGTSNTVKVFWSGTVVLDMYPVCTAKA
gpCMV   RF--GGRFSIY-VPVGT------------KPRNASSASIKVHCTGTVVLDMYPVCVAKT
hCMV    PTAQGGRFFLH-SPAVGFKRQYAAAFPSASHNNPASTAATKVYIAGSVVIDMYPVCMAKT
iHV1    KDTVQN-FKSHGFGCDIIDMMYV------CKRKEFEAKDGSLNTVAQLIIKKFKPHKATP

EXO 3
hHV6    TAQNYKLDTIAKICLQQEKEQLSYKEIPKKFISGPSGRAVVGKYCLQDSVLVVRLFKQIN
hHSV1   KLSSYKLNAVAEAVLKDKKKDLSYRDIPAYYATGPAQRGVIGEYCIQDSLLVGQLFFKFL
hHSV2   KLSSYKLNAVAEAVLKDKKKDLSYRDIPAYYASGPAQRGVIGEYCVQDSLLVGQLFFKFL
hVZV    KLSSYKLDSVAREALNESKRDLPYKDIPGYYASGPNTRGIIGEYCIQDSALVGKLFFKYL
eHV1    KLPSYKLDAVVGDVLGEHKIDLPYKEIPSYYAGGPDRRGVIGEYCIQDSRLVGKLFFKYL
hEBV    SLSDYKLDTVARHLLGAKKEDVHYKEIPRLFAAGPEGRRRLGMYCVQDSALVMDLLNHFV
sHV1    SLSNYKLDTVANHCIGAKKEDVSYKDIMPLFMSGPEGRAKIGLYCVIDSVLVMKLLKFFM
mCMV    SSPNYKLDTMAEIYLKKKKDDLSYKEIPVQFSAGDEGRAPGGKYCLQDAVLVRELFEMLA
gpCMV   SAPNYKLETMAEMYLNEHKDDLSYKEIPPTFLANDNGRAVVGRYCIKDALLVKRLFEKLN
hCMV    NSPNYKLNTMAELYLRQRKDDLSYKDIPRCFVANAEGRAQVGRYCLQDAVLVRDLFNTIN
iHV1    KI-------------HKMDDITYDKLDGYYRAGGTKIAECLIYNLIDSLLVIRIAKNLK hHV6    YHFEVAEVARLAHVTARCVVFEGQQKKIFPCILTEAKRRNMILPSMVS------------
hHSV1   PHLELSAVARLAGINITRTIYDGQQIRVFTCLLRLADQKGFILPDTQGRFRGAGGE----
hHSV2   PHLELSAVARLAGINITRTIYDGQQIRVFTCLLRLAGQKGFILPDTQGRFRGLDKE----
hVZV    PHLELSAVARLARITLTKAIYDGQQVRIYTCLLGLASSRGFILPD---------------
eHV1    PHLELSAVAKLARITLTRVIFDGQQIRVYTCLLKLARERNFILPDNRRRFDSQADA----
hEBV    IHVEVAEIAKIAHIPCRRVLDDGQQIRVFSCLLAAAQKENFILPM---------------
sHV1    IHVEISEIAKLAKIPTRRVLTDGQQIRVFSCLLAAARAENYILPV---------------
mCMV    FHFEAAAIARLARIPLRKVIFDGQQIRIYTCLLEECSGRDMILPNMPSLG----------
gpCMV   YHYEAASVARLARIPLRSVIFEGQQIRIYSCILEEAGERNMILPSFLTAK----------
hCMV    FHYEAGAIARLAKIPLRRVIFDGQQIRIYTSLLDECACRDFILPNHYSKGTTVPETNSVA
iHV1    -------------PMEEYIY-----RQLACYNIDTAAHT---RGVMNFCGFIQSTKVVE
```

FIG. 2C

```
hHV6    ----------------------------------------------------------
hHSV1   -------------------------APKRPAAAREDEERP-----EEEG-EDEDEREE
hHSV2   -------------------------APKRPAVPRGEGERPGDGNGDEDK-DDDEDGDE
hVZV    ----------------------------GGYPATFEYKDVIPDVGDVEEEMD
eHV1    -------------------------ASETSELAMDSQSHAFDSTDEPDGVDGTPDAAG
hEBV    ----------------------------------------------------------
sHV1    ----------------------------------------------------------
mCMV    -------------------------------------HGAAAAIEEAAAGG---EGD
gpCMV   -------------------------------------RPGELATESSPVASFEEDSE
hCMV    VSPNAAIISTAAVPGDAGSVAAMFQMSPPLQSAPSSQDGVSPGSGSNSSSSVGVFSVGSG
iHV1    VSRNKARLDAGIVMATDYIRNSLF----------------------------------
```

```
                                          REGION 2
                                          (DFASA>)
hHV6    -------------SHNRQGIG YKGATVLEPKTG-YYAVPTVVF----DFQSLYPSIMMAH
hHSV1   GGGEREPEGARETAGRH--VG YQGAKVLDPTSG-FHVNPVVVF----DFASLYPSIIQAH
hHSV2   DGDERE-EVARETGGRH--VG YQGARVLDPTSG-FHVDPVVVF----DFASLYPSIIQAH
hVZV    EDESVSPTGTSSG--RN--VG YKGARVFDPDTG-FYIDPVVVL----DFASLYPSIIQAH
eHV1    SGATSENGGGKPGVGRA--VG YQGAKVLDPVSG-FHVDPVVVF----DFASLYPSIIQAH
hEBV    -------------PSASDRDG YQGATVIQPLSG-FYNSPVLVV----DFASLYPSIIQAH
sHV1    -------------SNDVNADG FQGATVINPIPG-FYNNAVLVV----DFASLYPSIIQAH
mCMV    ETSE---GENSNNSRT---VG YQGATVLEPECG-FHHVPVCVF----DFASLYPSIIMSN
gpCMV   QTSDSSLGEVSSQGSSDGGVG YQGATVLEPDVG-FYDTPVAVF----DFASLYPSIIMRH
hCMV    SSGGVGVSNDNHGAGGTAAVS YQGATVFEPEVG-YYNDPVAVF----DFASLYPSIIMAH
iHV1    ----------------TPETIR RRGGFVMAPLTGLFFARPTQCFELCLDFTSMYPSMMCDL
```

```
        2 cont.                                                 REGION 4
hHV6    NLCYS TLVLDE--RQIAG--------LSES-DILTVKLGDETH-RFVKPCIRE SVLGSL-
hHSV1   NLCFS TLSLRAD--AVAH--------LEAG-KDYLEIEVGGRRLFFVKAHVRE SLLSIL-
hHSV2   NLCFS TLSLRPE--AVAH--------LEAD-RDYLEIEVGGRRLFFVKAHVRE SLLSIL-
hVZV    NLCFT TLTLNFE--TVKR--------LNPS--DYATFTVGGKRLFFVRSNVRE SLLGVL-
eHV1    NLCFT TLALDEV--DLAG--------LQPS-VDYSTFEVGDQKLFFVHAHIRE SLLGIL-
hEBV    NLCYS TMITPGEEHRLAG--------LRPG-EDYESFRLTGGVYHFVKKHVHE SFLASL-
sHV1    NLCYS TLIPHHALHNYPH-------LKSS--DYETFMLSSGPIHFVKKHIQA SLLSRL-
mCMV    NLCYS TLLVEG--SPE----------VPEK-DVLRVEIGDQCH-RFVRENVHR SLLAEL-
gpCMV   NLCYS TYLPLG--RDD-G--------LSDD-DVFLLEFDDGTRYGFVREHVRK SILGEL-
hCMV    NLCYS TLLVPG--GEY-P--------VDPA-DVYSVTLENGVTHRFVRASVRV SVLSEL-
iHV1    NISPE TIVDSDKTNRVGDYMGYDWSKIDQGFEKFTLVLRVDRTDPENPKLVRH TSDTSLS
```

```
                                          REGION 3
        4 cont.                           (VYGA>)
hHV6    LKDWLAKRREVK AEMQNCSDPMMKLLI DKKQIALKTTCNSVYGVTGAAHGLLPCVAIAAS
hHSV1   LRDWLAMRKQIR SRIPQ-SSPEEAVLL DKQQAAIKVVCNSVYGFTGVQHGLLPCLHVAAT
hHSV2   LRDWLAMRKQIR SRIPQ-SPPEEAVLL DKQQAAIKVVCNSVYGFTGVQHGLLPCLHVAAT
hVZV    LKDWLAMRKAIR ARIPG-SSSDEAVLL DKQQAAIKVVCNSVYGFTGVAQGFLPCLYVAAT
eHV1    LRDWLAMRKAVR ARIPT-STPEEAVLL DKQQSAIKVICNSVYGFTGVANGLLPCLRIAAT
hEBV    LTSWLAKRKAIK KLLAACEDPRQRTIL DKQQLAIKCTCNAVYGFTGVANGLFPCLSIAET
sHV1    LTVWLSKRKAIR QKLAECEDLDTKTIL DKQQLAIKVTCNAVYGFTGVASGLLPCISIAET
mCMV    LVRWLTQRKLVR EAMKQCTNEMQRMIM DKQQLALKVTCNAFYGFTGVAAGMLPCLPIAAS
gpCMV   LARWLAKRKSVR KVLAECQDEVEKLIL DKYQLALKVTCNAFYGFTGVSSGMMPCLPIAAA
hCMV    LNKWVSQRRAVR ECMRECQDPVRRMLI DKEQMALKVTCNAFYGFTGVVNGMMPCLPIAAS
iHV1    LKRYLRLRTEHK RALKQSSGSVAEYH- NRLQNEMKICTNTHYGVSEHTCSLM--------
```

FIG. 2D

```
         REGION 3 cont.
hHV6    |VTCLGREML|CSTVDYVNSKMQSEQFFCEEF---------------------GLTSSDFT
hHSV1   |VTTIGREML|LATREYVHARWAAFEQLLADF-----------------PE-AADMRAPG--
hHSV2   |VTTIGREML|LATRAYVHARWAEFDQLLADF-----------------PE-AAGMRAPG--
hVZV    |VTTIGRQML|LSTRDYIHNNWAAFERFITAF-----------------PDIESSVLSQK--
eHV1    |VTTIGRDML|LKTRDYVHSRWATRELLEDNF-----------------PG-AIGFRNHK--
hEBV    |VTLQGRTML|ERAKAFVEA-LSPANLQALAPSPDAWAPLNPEG-----------------
sHV1    |VTLQGRTML|EKSKIFIEA-MTPDTLQEIVPHI---VKHEPDA-----------------
mCMV    |ITKIGRDML|ATAGHIEDRCNRPDFLRTVL---------------------GLPPEAID
gpCMV   |ITRIGRDML|MSVVDYVNTYMGHAEFWLRYL---------------------G--EEDLT
hCMV    |ITRIGRDML|ERTARFIKDNFSEPCFLHNFFNQEDYVVGTREGDSEESSALPEGLETSSGG
iHV1    |ITTQGQHKI|KLVNEFIKTLNRTGHSLFPN-----------------------------
                     REGION 1
                     (<GDTD1B)
hHV6    GD---LE|VEIYGDTDSIFMSVRN|MVNQSLRRIAPMIAKHITDRLFKSPIKLEFEKILCP
hHSV1   ----PYSM|RIIYGDTDSIFVLCRG|LTAAGLTAMGDKMASHISRALFLPPIKLECEKTFTK
hHSV2   ----PYSM|RIIYGDTDSIFVLCRG|LTGEALVAMGDKMASHISRALFLPPIKLECEKTFTK
hVZV    ----AYEV|KVIYGDTDSVFIRFKG|VSVEGIAKIGEKMAHIISTALFCPPIKLECEKTFIK
eHV1    ----PYSV|RVIYGDTDSVFIKFVG|LTYEGVSELGDAMSRQISADLFRAPIKLECEKTFQR
hEBV    ------QL|RVIYGDTDSLFIECRG|FSESETLRFADALAAHTTRSLFVAPISLEAEKTFSC
sHV1    ------KF|RVIYGDTDSLFVECVG|YSVDTVVKFGDFLAAFTSEKLFNAPIKLESEKTFQC
mCMV    PEALRV--|KIIYGDTDSVFAAFYG|IDKEALLKAVGALAANVTNALFKEPVRLEFEKMFVS
gpCMV   GDALNV--|KVIYGDTDSVFVICGG|VKCGSVLEHGEAIAGHITRALFREPIKLEFEKVFVN
hCMV    SNERRVEA|RVIYGDTDSVFVRFRG|LTPQALVARGPSLAHYVTACLFVEPVKLEFEKVFVS
iHV1    --------|---YGDTDSTMLYHPS|DESETQLEDMVTLEDEMRAEL---------------
                REGION 7         REGION 5
hHV6    LILIQ|KKRYIGR-QD|D|SLLIFKGVDLVRKTSQ|DFVKGVVKDIVDLLFFDEEVQTAAVEFS
hHSV1   LLLIA|KKKYIGVIYG|G|KML-IKGVDLVRKNNQ|AFINRTSRALVDLLFYDDTVSGAAAALA
hHSV2   LLLIA|KKKYIGVICG|G|KML-IKGVDLVRKNNQ|AFINRTSRALVDLLFYDDTVSGAAAALA
hVZV    LLLIT|KKKYIGVIYG|G|KVL-MKGVDLVRKNNQ|QFINDYARKLVELLLYDDTVSRAAAEAS
eHV1    LLLIT|KKKYIGVING|G|KML-MKGVDLVRKNNQ|SFINLYARHLVDLLLYDEDVATAAAEVT
hEBV    LMLIT|KKRYVGVLTD|G|KTL-MKGVELVRKTAQ|KFVQTRCRRVLDLVLADARVKEAASLLS
sHV1    LLLLA|KKRYIGILSN|D|KLL-MKGVDLVRKTAQ|KFVQNTSSKILNLILKDPEVKAAAQLLS
mCMV    LMMIQ|KKRYIGKVHG|S|QNLSMKGVDLVRRTAQ|GFVKAVVSDVLHMVFNDETVSEGTMKLS
gpCMV   LMMIQ|KKRYVGRIYG|Q|TKLSMKGIELVRKTAQ|EYVKSTVRNVLNMIFFEDDVSAGAVELS
hCMV    LMMIQ|KKRYIGKVEG|A|SGLSMKGVDLVRKTAQ|EFVKGVTRDVLSLLFEDREVSEAAVRLS
iHV1    ----|-REYMLKKLSA|E|-LVNRVKEKTKRTD-|TFVQSFLSDV-ETVLFDDMVEK----LR hHV6    HMTQTQLREQGVPVGIHKILRRLCEAREELFQNRADVRHLMLSSVLSKEMAAYKQPNLAH
hHSV1   ERPAEEWLARPLPEGLQAFGAVLVDAHRRITDPERDIQDFVLTAELSRHPRAYTNKRLAH
hHSV2   ERPAEEWLARPLPEGLQAFGAVLVDAHRRITDPERDIQDFVLTAELSRHPRAYTNKRLAH
hVZV    CVSIAEWNRRAMPSGMAGFGRIIADAHRQITSPKLDINKFVMTAELSRPPSAYINRRLAH
eHV1    DVPPAEWVGRPLPSGFDKFGRVLVEAYNRITAPNLDVREFVMTAELSRSPESYTNKRLPH
hEBV    HRPFQESFTQGLPVGFLPVIDILNQAYTDLREGRVPMGELCFSTELSRKLSAYKSTQMPH
sHV1    TKDPDYAFREGLPDGFLKVIDILNESHKNLRTGQVPVEELTFSTELSRPISSYKTENLPH
mCMV    RMTFDDLKKNGIPCEFGPVVSRLCRARDDLHLKKVPVPELTLSSVLSQELSCYKQKNLPH
gpCMV   RMTMDDVKRHGVPSGFYRIVEALSNARDELYLNRVDVKKLVLSASLSQEVSAYKQQNLPH
hCMV    RLSLDEVKKYGVPRGFWRILRRLVQARDDLYLHRVRVEDLVLSSVLSKDISLYRQSNLPH
iHV1    LFSQGEVIEPFKDGGTWWVVDPLTGIWMD-----------------CSTPFSSELICK
```

FIG. 2E

```
hHV6     LSVIRRLAQRKEEIPNVGDRIMYVLIAPSI-------------------------------
hHSV1    LTVYYKLMARRAQVPSIKDRIPYVIVAQTREVEETVARLAALRELDAAAPGDEPAPPAAL
hHSV1    LTVYYKLMARRAQVPSIKDRIPYVIVAQTREVEETVARLAALRELDAAAPGDEPAPPAAL
hVZV     LTVYYKLVMRQGQIPNVRERIPYVIVAPTDEVEADAKSVALLRG-----------DPLQ
eHV1     LTVYFKLAMRNEELPSVKERIPYVIVAQTEAAEREAGVVNSMRG-----------TAQN
hEBV     LAVYQKFVERNEELPQIHDRIQYVFVEP--------------------------------
sHV1     LTVYKKIITRHEEPPQVHDRIPYVFV----------------------------------
mCMV     LAVIRRLAARKEELPAVGDRVEYVLTLP-----D-GCKKN--------------------
gpCMV    LRVIQRLAARRPELPSVGDRVPYVLIAP-----PPGSSKN--------------------
hCMV     IAVIKRLAARSEELPSVGDRVFYVLTAPGVRTAPQGSSDNGDSVTAGVVSRSDAIDGTDD
iHV1     L----------------------------------------------------------- hHV6     -----------------GNKQTH-------NYELAEDPNYVIEHKIPIHAEKYFDQIIKA
hHSV1    PSPAKRPRETPSHADPPGG--ASKPRKLLVS-ELAEDPAYAIAHGVALNTDYYFSHLLGA
hHSV2    PSPAKRPRETPSHADPPGG--ASKPRKLLVS-ELAEDPGYAIARGVPLNTDYYFSHLLGA
hVZV     NTAGKRC-GEAK-------------RKLIIS-DLAEDPIHVTSHGLSLNIDYYFSHLIGT
eHV1     PVVTKTARPQPK-------------RKLLVS-DLAEDPTYVSENDVPLNTDYYFSHLLGT
hEBV     ------------KGGVKGARKT---------EMAEDPAYAERHGVPVAVDHYFDKLLQG
sHV1     --------------GKTTSCIS---------NMAEDPTYTVQNNIPIAVDLYFDKLIHG
mCMV     ------------------------------VPNYEIAEDPRHVVEAKLSINAEKYYEQVVKA
gpCMV    ------------------------------VPNYEISEDPGYVIEHKLPVNGEKYFEHVVKT
hCMV     DADGGGVEESNRRGGEPAKKRARKPPSAVCNYEVAEDPSYVREHGVPIHADKYFEQVLKA
iHV1     ------------------------------EYENASSIGCHVAKKMVSIGSTYL------ hHV6     VTNAISPIFPKTDI-KKEKLLLYLLPMKVYLDET----------F---------------
hHSV1    ACVTFKALFGN-NAKITESLLKRFIPEV-WHPPDDVAARLRAAGF------------GAV
hHSV2    ACVTFKALFGN-NAKITESLLKRFIPET-WHPPDDVAARLRAAGF------------GPA
hVZV     ASVTFKALFGN-DTKLTERLLKRFIPET-RVVNVKMLNRLQAAGFVCIHAPCWDNKMNTE
eHV1     ISVTFKALFGN-DVRTTENLLKRFIPETPHKTPTKTQALLERAGF---------EKLTP-
hEBV     AANILQCLFDN-NSGAALSVLQNFTARPPF------------------------------
sHV1     VANIIQCLF-K-DSSKTVSVLYNFVSTPVLFSYE----------LL--------------
mCMV     VTNTLMPVFPR-DMPKREKFFSLVVPQRIYIPDQ----------FL--HLCGNVNELARG
gpCMV    VTNVLGPIIPK-DCARKEKFLSYVLPQRVYVSRP----------FM--PYACAANELVVG
hCMV     VTNVLSPVFPGGETARKDKFLHMVLPRRLHLEPA----------FL--PYSVKAHE----
iHV1     -------FFKKIS----------LYHVRVWR------------MCADTDGSPSHLYFP hHV6     -----------------SAIAEVM--
hHSV1    GAGATAEETRRMLHRAFDTL------A
hHSV2    GAGATAEETRRMLHRAFDTL------A
hVZV     AEITEEEQSHQIMRRVFCIPKAILHQS
eHV1     --FTPEEESRRILHTVFCTLEAAPHQS
hEBV     ---------------------------
sHV1     ------------------TDHSVKA
mCMV     GDDSDGGDSEKENMDTERSSSHEAMET
gpCMV    -------------------------V
hCMV     ------------------------CC
iHV1     VSLSRTRAKQRGDH-------------
```

FIG. 2F

```
hHV6   GTGGTGTTTGATTTTCAAAGTTTGTATCCGAGCATTATGATGGCGCATAATCTGTGTTATAGTACTTTAGTTTTGGAT
hCMV   GCCGTGTTCGACTTTGCCAGCCTCTACCCTTCCATCATCATGGCCCACAACCTCTGCTACTCCACCCTGCTGGTGCCG
gpCMV  GCCGTCTTCGATTTCGCCAGTCTGTATCCGTCTATCATTATGCGACACAACCTGTGTTACTCGACGTATCTTCCGCTC
mCMV   TGCGTGTTCGATTTCGCCAGTCTGTATCCGTCCATCATCATGTCCAACAATCTGTGCTACTCCACCCTCTTGGTGGAG hHSV1  GTGGTGTTCGACTTTGCCAGCCTGTACCCCAGCATCATCCAGGCCCACAACCTGTGCTTCAGCACGCTCTCCCTGAGG
hHSV2  GTGGTGTTTGACTTTGCCAGCCTGTACCCCAGCATCATCCAGGCCCACAACCTGTGCTTCAGTACGCTCTCCCTGCGG
hVZV   GTCGTATTGGATTTTGCAAGTTTATATCCAAGTATAATTCAGGCCCATAACTTATGTTTTACCACGCTAACGTTAAAT
eHV1   GTGGTGTTTGACTTCGCTAGCTTATACCCAAGCATTATCCAGGCCCATAACCTCTGTTTCACCACCCTGGCGCTCGAT hEBV   CTGGTGGTGGACTTTGCCAGCCTCTACCCGAGCATCATTCAGGCTCATAATCTCTGTTATTCTACCATGATAACGCCG
sHV1   TTAGTAGTAGACTTTGCTAGCCTGTATCCTAGTATTATACAAGCTCATAATCTATGCTACTCCACTCTTATACCCCAC iHV1   CTGTGTCTGGACTTTACCAGCATGTACCCCAGTATGATGTGCGATCTCAACATCTCTCCTGAAACCATCGTGGACAGC

5'-gtgttcgacttygcnagyytntaycc-3'
          DFASA 256-fold 26mer>

5'-gtgttcgacttycaragyytntaycc-3'
          DFQSA 128-fold 26mer>
```

FIG. 3

| | |
|---|---|
| hHV6 | GCTCTGAAAACAACATGTAACTCGGTGTACGGTGTCACGGGAGCGGCGCACGGG |
| hCMV | GCGCTCAAAGTAACGTGCAACGCTTTCTACGGTTTTACCGGCGTGGTCAACGGT |
| gpCMV | GCCCTCAAAGTGACGTGCAACGCGTTTTACGGTTTTCACCGGGGTCAGCAGCGGC |
| mCMV | GCCCTCAAAGTAACGTGCAACGCTTTCTACGGTTTTCACGGGGGTAGCGGCCGGG |
| | |
| hHSV1 | GCCATCAAGGTCGTGTGTAACTCGGTGTACGGGTTCACGGGAGTGCAGCACGGA |
| hVZV | GCGATAAAAGTAGTTTGTAATTCCGTGTACGGTTTTACTGGAGTTGCGCAGGGA |
| eHV1 | GCGATTAAGGTGATATGCAACTCGGTTTACGGATTCACGGGGGTGGCAAACGGC |
| | |
| hEBV | GCCATCAAGTGCACGTGCAACGCCGTCTACGGCTTCACCGGGGTGGCCAACGGC |
| sHV1 | GCTATTAAAGTAACTTGTAATGCTGTGTATGGGTTTACAGGAGTTGCGTCAGGC |
| | |
| iHV1 | GAAATGAAGATCTGTACAAACACCCACTACGGGGTCTCTGAGCACACGTGTTCG |

```
5'-acgtgcaacgcggtgtayggnktnacngg-3'
   VYGA 256-fold 30mer>

5'-acgtgcaacgcggtgtacggsgtsacsgg-3'
   VYGCA 8-fold GC-rich 30mer>

5'-acgtgcaacgcggtgta>-3'
   VYGSQA 17mer>
```

FIG. 4

| | |
|---|---|
| hHV6 | GTAATTTATGGTGATACGGATAGCATCTTTATGTCTGTCAGAAAT |
| hCMV | ATCATCTACGGGGACACGGACTCCATATTTGTGCTGTGCCGCGGC |
| gpCMV | GTGATATACGGGGACACGGACAGCGTCTTTGTCATATGCGGCGGT |
| mCMV | ATCATCTACGGCGACACCGACAGTGTGTTTGCGGCTTTCTACGGC |
| | |
| hHSV1 | ATCATCTACGGGGACACGGACTCCATATTTGTGCTGTGCCGCGGC |
| hVZV | GTTATATATGGAGATACGGATTCTGTGTTTATCCGATTCAAGGGT |
| eHV1 | GTTATCTACGGAGACACCGACTCCGTGTTTATCAAGTTTGTGGGC |
| | |
| sHV1 | GTCATATATGGAGACACAGACTCTCTATTTGTAGAATGTGTTGGG |
| hEBV | GTCATCTACGGGGACACGGACTCGCTGTTTATCGAGTGCCGGGGG |
| | |
| iHV1 | CCCAATTATGGGGATACGGATAGTACGATGCTGTACCACCCATCG |

5'-tayggngayacngactccgtgtttgtcgcatgccg-3'

3'-atrccnctrtgnctgaggcacaaacagcgtacggc-5'
<GDTD1B 64-fold 35mer

3'-aggcacaaacagcgtacggc-5'
<GDTDSQB 20mer

FIG. 5

```
RFHV  CGTCGCTTCCGGCATCCTACCGTGCCTGAACATCGCAGAGACGGTGACCCTCCAGGGCAGGAAAAT
KSHV  ...T..C..T.....A..G..T.....A.....A..G.....C.....A..A..A..GC.A..G..
eHV2  ...G..C..G........G..C..T..C..G..A..C........C...T...........CGC..
sHV1  A..T..G..A...T.G..G..A...A.A.G...T........T..T..T.....A...C...CG..
EBV   G..G..CAA....C..T.T..C.....CTC......C...........G..G......C.C.CG..

RFHV  GCTGGAAACGTCTCAGGCGTTCGTAGAGGGAATCTCGCCAACGGCACTGGCAGACCTACTGCAGCG
KSHV  ......G.GA.........C..T.......CC........GGAACGC..A..G.GT..C....G.A.
eHV2  ......G.AC..CA..CGC.A.A.......GG.GA.C..CGA..GG.........A..T..GGCA.
sHV1  ...A....AA..AA.AATA...A....A.C...GA.A..TGATA....TCA...AA.TG.T.CT.A
EBV   .T....GCG.G.CA....C.....G....CCC.GAGC..CG.CAAC...CAG.C...GGCC.CCTC

RFHV  ACCGATCGAGGCGTCTCCG--------GAAGCCAGGTTTAAAGTGATA
KSHV  G..A..A..C.TC..A..C---------.C...C.A..C..G..C...
eHV2  G.G.G.G...TGCG.C..C---------.T.....T.....G..C..C
sHV1  TATAG.GA..CATGAA..T---------.T..G.A...C.G...C...
EBV   C...GA..CCTG.G.G..CCTCAACCCC..G.G.CA.C..CG...C..C

"." = identical residues
"-" = deletions
```

FIG. 6

```
RFHV    VASGILPCLNIAETVTLQGRKMLETSQAFVEGISPTALADLLQRPIEASP···EARFKVI
KSHV    ........................R......A...ER..G..R...DV..···D......
eHV2    ........K......F...R...N.KRYI..VT.EG...I.G.RV.CA.···D.S....
sHV1    ....L...IS..........T...K.KI.I.AMT.DT.QEIVPHIVKHE.···D.K.R..
EBV     ..N.LF...S..........T...RAK....AL..AN.QA.APS.DAWA.LNP.GQLR..
```

"." = identical residues
"-" = deletions

Class I:

IAETVTL

Class II:

```
            CLNIAET         SQAFVE
    VASGILP         QGRKMLE                             ARFKVI
            GILPCLN
```

Class III:

```
                    LETSQAF     ADLLQRP
                    LERSQAF     AGLLRRP
                        EGISPTA     QRPIEAS
                        EAISPER     RRPIDVS
                                        IEASP···EA
                                        IDVSP···DA
```

FIG. 7

| | | |
|---|---|---|
| RFHV | VASGILPCLNIAETVTLQGRKMLETSQAFVEGISPTALADLLQRP------------------------------------ | -IEASPEARFKVI |
| KSHV | VASGILPCLNIAETVTLQGRKMLERSQAFVEAISPERLAGLLRRP------------------------------------ | -VDVSPDARFRVI |
| eHV2 | VASGILPCLKIAETVTFQGRRMLENSKRYIEGVTPEGLADILGRR------------------------------------ | -VECAPDASFKVI |
| sHV1 | VASGLLPCISIAETVTLQGRTMLEKSKIFIEAMTPDTLQEIVPHI------------------------------------ | -VKHEPDAKFRVI |
| hEBV | VANGLFPCLSIAETVTLQGRTMLERAKAFVEALSPANLQALAPSP------------------------------------ | DAWAPLNPEGQLRVI |
| hCMV | VVNGMPCLPIAASITRIGRDMLERTARFIKDNFSEPCFLHNFFNQEDYVVGTREGDSEESSALPEGLETSSGGSNERRVEARVI | |
| mCMV | VAAGMLPCLPIAASITKIGRDMLATAGHIEDRCNRPDFLRTVLG------------------------------------- | LPPEAIDPEALRVKII |
| gpCMV | VSSGMPCLPIAAAITRIGRDMLMSVVDYVNTYMGHAEFWLRYLG------------------------------------- | -EEDLTGDALNVKVI |
| hHV6-A | AAHGLLPCVAIAASVTCLGREMLCSTVDYVNSKMQSEQFFCEEFG------------------------------------ | -LTSSDFTGDLEVEVI |
| hVZV | VAQGFLPCLPCLYVAATVTIGRQMLLSTRDYIHNNWAAFERFITAFP----------------------------------- | -DIESSVLSQKAYYEVKVI |
| hHSV1 | VQHGLLPCLHVAATVTTIGREMLLATREYVHARWAAFEQLLADFP------------------------------------ | -EAADMRAPGPYSMRII |
| hHSV2 | VQHGLLPCLHVAATVTTIGREMLLATRAYVHARWAEFDQLLADFP------------------------------------ | -EAAGMRAPGPYSMRII |
| eHV1 | VANGLLPCLRIAATVTTIGRDMLLKTRDYVHSRWATRELLEDNFP------------------------------------ | -GAIGFRNHKPYSVRVI |
| hPOLd | AQVGKLPCLEISQSVTGFGFGRQMIEKTKQLVESKYTV-------------------------------------------- | -ENGYSTSAKVV |
| bPOLd | AQVGRLPCLEISQSVTGFGFGRQMIEKTKQLVETKYTV-------------------------------------------- | -ENGYSTSAKVV |

FIG. 8

```
              G  V  A  S  G  I  L  P  C  L  N  I  A  E  T  V  T  L  Q  G  R  K  M
RFHV   GGCGTCGCTTCCGGCATCCTACCGTGCCTGAACATCGCAGAGACGGTGACCCTCCAGGGCAGGAAAATG
KSHV   GGCGTTGCCTCTGGCATACTGCCTTGCCTAAACATAGCGGAGACCGTGACACTACAAGGGCGAAAGATG
eHV2   GGCGTGGCCTCGGGCATCCTGCCCTGTCTCAAGATAGCCGAGACGGTCACCTTCCAGGGCAGGCGCATG
sHV1   GGAGTTGCGTCAGGCTTGCTGCCATGCATAAGCATTGCAGAGACTGTTACTCTCCAAGGCCGGACGATG
EBV    GGGGTGGCCAACGGCCTCTTTCCCTGCCTCTCCATCGCCGAGACGGTGACGCTGCAGGGCCGCACGATG
```

5'-gtcgcctctggcatcctnccntgyctnaa>-3'       5'-cagggccggaagatg
   PCLNA 128-fold 29mer>                       KMLEA 32-fold
                                                32mer>

```
              L  E  T  S  Q  A  F  V  E  G  I  S  P  T  A  L  A  D  L  L  Q  R  P
RFHV   CTGGAAACGTCTCAGGCGTTCGTAGAGGGAATCTCGCCAACGGCACTGGCAGACCTACTGCAGCGACCG
KSHV   CTGGAGAGATCTCAGGCCTTTGTAGAGGCCATCTCGCCGGAACGCCTAGCGGGTCTCCTGCGGAGGCCA
eHV2   CTGGAGAACTCCAAGCGCTACATAGAGGGGGTGACCCCCGAGGGGCTGGCAGACATATTGGGCAGGCGG
sHV1   CTAGAAAAATCAAAAATATTCATAGAAGCAATGACACCTGATACACTTCAAGAAATTGTTCCTCATATA
EBV    TTGGAGCGGGCCAAGGCCTTCGTGGAGGCCCTGAGCCCCGCCAACCTGCAGGCCCTGGCCCCCTCCCCG
``` ctggaracrtcncargc>-3'
(KMLEA cont'd>)

5'-tctcaggcgttcgtagarggnathtcncc-3'
   GISPA 96-fold 29mer>

```
              I  E  A  S  P  -  -  -  E  A  R  F  K  V  I
RFHV   ATCGAGGCGTCTCCG---------GAAGCCAGGTTTAAAGTGATA
KSHV   GTAGACGTCTCACCC---------GACGCCCGATTCAGGGTCATA
eHV2   GTGGAGTGCGCCCCC---------GATGCCAGTTTTAAGGTCATC
sHV1   GTGAAGCATGAACCT---------GATGCGAAGTTCAGAGTCATA
EBV    GACGCCTGGGCGCCCCTCAACCCCGAGGGCCAGCTTCGAGTCATC
```

FIG. 10

```
                    CVNVA>
           gacgaccgcagcgtgtgcgtgaaygtnttyggnca
           D D R S V C V N V F G Q R C Y F Y T L A
           GACGACCGCAGCGTGTGCGTGAAYGTNTTYGGNCAGCGCTGCTACTTCTACACACTAGCA      60

P Q G V N L T H V L Q Q A L Q A G F G R
           CCCCAGGGGGTAAACCTGACCCACGTCCTCCAGCAGGCCCTCCAGGCTGGCTTCGGTCGC     120

A S C G F S T E P V R K K I L R A Y D T
           GCATCCTGCGGCTTCTCCACCGAGCCGGTCAGAAAAAAAATCTTGCGCGCGTACGACACA     180

Q Q Y A V Q K I T L S S S P M M R T L S
           CAACAATATGCTGTGCAAAAAAATAACCCTGTCATCCAGTCCGATGATGCGAACGCTTAGC    240

D R L T T C G C E V F E S N V D A I R R
           GACCGCCTAACAACCTGTGGGTGCGAGGTGTTTGAGTCCAATGTGGACGCCATTAGGCGC     300

F V L D H G F S T F G W Y E C S N P A P
           TTCGTGCTGGACCACGGGTTCTCGACATTCGGGTGGTACGAGTGCAGCAACCCGGCCCCC     360

R T Q A R D S W T E L E F D C S W E D L
           CGCACCCAGGCCAGAGACTCTTGGACGGAACTGGAGTTTGACTGCAGCTGGGAGGACCTA     420

K F I P E R T E W P P Y T I L S F D I E
           AAGTTTATCCCGGAGAGGACGGAGTGGCCCCCATACACAATCCTATCCTTTGATATAGAA    480

C M G E K G F P N A T Q D E D M I I Q I
           TGTATGGGCGAGAAGGGTTTTCCCAACGCGACTCAAGACGAGGACATGATTATACAAATC    540

S C V L H T V G N D K P Y T R M L L G L
           TCGTGTGTTTTACACACAGTCGGCAACGATAAACCGTACACCCGCATGCTACTGGGCCTG    600

G T C D P L P G V E V F E F P S E Y D M
           GGGACATGCGACCCCCTTCCTGGGGTGGAGGTCTTTGAGTTTCCTTCGGAGTACGACATG   660

L A A F L S M L R D Y N V E F I T G Y N
           CTGGCCGCCTTCCTCAGCATGCTCCGCGATTACAATGTGGAGTTTATAACGGGGTACAAC    720

I A N F D L P Y I I A R A T Q V Y D F K
           ATAGCAAACTTTGACCTTCCATACATCATAGCCCGGGCAACTCAGGTGTACGACTTCAAG    780

L Q D F T K I K T G S V F E V H Q P R G
           CTGCAGGACTTCACCAAAATAAAAACTGGGTCCGTGTTTGAGGTCCACCAACCCAGAGGC    840

G S D G G N F M R S Q S K V K I S G I V
           GGTTCCGATGGGGGCAACTTCATGAGGTCCCAGTCAAAGGTCAAAATATCGGGGATCGTC    900

P I D M Y Q V C R E K L S L S D Y K L D
           CCCATAGACATGTACCAGGTTTGCAGGGAAAAGCTGAGTCTGTCAGACTACAAGCTGGAC   960
```

FIG. 13A

```
T  V  A  K  Q  C  L  G  R  Q  K  D  D  I  S  Y  K  D  I  P
ACAGTGGCTAAGCAATGCCTCGGTCGACAAAAAGATGACATCTCATACAAGGACATACCC    1020

P  L  F  K  S  G  P  D  G  R  A  K  V  G  N  Y  C  V  I  D
CCGCTTTTTAAATCTGGGCCTGATGGTCGCGCAAAGGTGGGAAACTACTGTGTTATTGAC    1080

S  V  L  V  M  D  L  L  R  F  Q  T  H  V  E  I  S  E  I
TCGGTCCTGGTTATGGATCTTCTGCTACGGTTTCAGACCCATGTTGAGATCTCGGAAATA    1140

A  K  L  A  K  I  P  T  R  R  V  L  T  D  G  Q  Q  I  R  V
GCCAAGCTGGCCAAGATCCCCACCCGTAGGGTACTGACGGACGGCCAACAGATCAGGGTA    1200

F  S  C  L  L  E  A  A  A  T  E  G  Y  I  L  P  V  P  K  G
TTTTCCTGCCTCTTGGAGGCTGCTGCCACGGAAGGTTACATTCTCCCCGTCCCAAAAGGA    1260

D  A  V  S  G  Y  Q  G  A  T  V  I  S  P  S  P  G  F  Y  D
GACGCGGTTAGCGGGTATCAGGGGGCCACTGTAATAAGCCCCTCTCCGGGATTCTATGAC    1320

D  P  V  L  V  V  D  F  A  S  L  Y  P  S  I  I  Q  A  H  N
GACCCCGTACTCGTGGTGGATTTTGCCAGCTTGTACCCCAGTATCATCCAAGCGCACAAC    1380

L  C  Y  S  T  L  I  P  G  D  S  L  H  L  H  P  H  L  S  P
TTGTGCTACTCCACACTGATACCCGGCGATTCGCTCCACCTGCACCCACACCTCTCCCCG    1440

D  D  Y  E  T  F  V  L  S  G  G  P  V  H  F  V  K  K  H  K
GACGACTACGAAACCTTTGTCCTCAGCGGAGGTCCGGTCCACTTTGTAAAAAAACACAAA    1500

R  E  S  L  L  A  K  L  L  T  V  W  L  A  K  R  K  E  I  R
AGGGAGTCCCTTCTTGCCAAGCTTCTGACGGTATGGCTCGCGAAGAGAAAAGAAATAAGA    1560

K  T  L  A  S  C  T  D  P  A  L  K  T  I  L  D  K  Q  Q  L
AAGACCCTGGCATCATGCACGGACCCCGCACTGAAAACTATTCTAGACAAACAACAACTG    1620

A  I  K  V  T  C  N  A  V  Y  G  F  T  G  V  A  S  G  I  L
GCCATCAAGGTTACCTGCAACGCCGTTTACGGCTTCACGGGCGTTGCCTCTGGCATACTG    1680

P  C  L  N  I  A  E  T  V  T  L  Q  G  R  K  M  L  E  R  S
CCTTGCCTAAACATAGCGGAGACCGTGACACTACAAGGGCGAAAGATGCTGGAGAGATCT    1740

Q  A  F  V  E  A  I  S  P  E  R  L  A  G  L  L  R  R  P  V
CAGGCCTTTGTAGAGGCCATCTCGCCGGAACGCCTAGCGGGTCTCCTGCGGAGGCCAGTA    1800

D  V  S  P  D  A  R  F  K  V  I  Y  G  D  T  D  S  L  F  I
GACGTCTCACCCGACGCCCGATTCAAGGTCATATACGGCGACACTGACTCTCTTTTCATA    1860

C  C  M  G  F  N  M  D  S  V  S  D  F  A  E  E  L  A  S  I
TGCTGCATGGGTTTCAACATGGACAGCGTGTCAGACTTCGCGGAGGAGCTAGCGTCAATC    1920

T  T  N  T  L  F  R  S  P  I  K  L  E  A  E  K  I  F  K  C
ACCACCAACACGCTGTTTCGTAGCCCCATCAAGCTGGAGGCTGAAAAGATCTTCAAGTGC    1980
```

FIG. 13B

```
L  L  L  L  T  K  K  R  Y  V  G  V  L  S  D  D  K  V  L  M
CTTCTGCTCCTGACTAAAAAGAGATACGTGGGGGTACTCAGTGACGACAAGGTTCTGATG         2040

K  G  V  D  L  I  R  K  T  A  C  R  F  V  Q  E  K  S  S  Q
AAGGGCGTAGACCTCATTAGGAAAACAGCCTGTCGTTTTGTCCAGGAAAAGAGCAGTCAG         2100

V  L  D  L  I  L  R  E  P  S  V  K  A  A  A  K  L  I  S  G
GTCCTGGACCTCATACTGCGGGAGCCGAGCGTCAAGGCCGCGGCCAAGCTTATTTCGGGG         2160

Q  A  T  D  W  V  Y  R  E  G  L  P  E  G  F  V  K  I  I  Q
CAGGCGACAGACTGGGTGTACAGGGAAGGGCTCCCAGAGGGGTTCGTCAAGATAATTCAA         2220

V  L  N  A  S  H  R  E  L  C  E  R  S  V  P  V  D  K  L  T
GTGCTCAACGCGAGCCACCGGGAACTGTGCGAACGCAGCGTACCAGTAGACAAACTGACG         2280

F  T  T  E  L  S  R  P  L  A  D  Y  K  T  Q  N  L  P  H  L
TTTACCACCGAGCTAAGCCGCCCGCTGGCGGACTACAAGACGCAAAACCTCCCGCACCTG         2340

T  V  Y  Q  K  L  Q  A  R  Q  E  E  L  P  Q  I  H  D  R  I
ACCGTGTACCAAAAGCTACAAGCTAGACAGGAGGAGCTTCCACAGATACACGACAGAATC        2400

P  Y  V  F  V  D  A  P  G  S  L  R  S  E  L  A  E  H  P  E
CCCTACGTGTTCGTCGACGCCCCAGGTAGCCTGCGCTCCGAGCTGGCAGAGCACCCCGAG         2460

Y  V  K  Q  H  G  L  R  V  A  V  D  L  Y  F  D  K
TACGTTAAGCAGCACGGACTGCGCGTGGCGGTGGACCTGTATTTCGACAAG                  2511
                              atraarctrttygacgaggtgcctcatcgatt
                                            (<YFDKB)
```

FIG. 13C

```
TR1910_KSH    ..................................................
TR2108_EBV    ...............-MSGGLFYNPFLRPN.....KGLLKKPDKE.............
TR2109_eHV    ...................-MSFYNPYLVKR-TFLKKAAPSRPTKE.............
TR2110_hHS    MFSGGGGPLSPGGKSAARAASGFFAPAGPRGAGRGPPPCLRQNFYNPYLAPVGTQQKPTG
TR2111_hVZ    ................-MAIRTGFCNPFLTQASG......IKYNPRTG..R..GSNRE...
TR2112_hHV    ................-MDSVSFFNPYLEANRLK......KKSRSS.............
TR2113_hCM    ......................-MFFNPYLSGGVTGGAVAGGRRQRSQP...........G
TR2114_EBV    ...............-MSGGLFYNPFLRPN.....KGLLKKPDKE.............
TR2115_sHV    ................-MDFYNPYLSKKPTDTKTPKLHTTRQS.............

TR1910_KSH    ..................................................
TR2108_EBV    .............YLRLIPKCFQTPG....AAGVVDVRGPQPPLCFYQDSLTVVGGDEDG
TR2109_eHV    .............YTRIIPKCFKTPG....AAGVVPHTSTLDPVCFVGDKETPILYGDGS
TR2110_hHS    PTQRHTYYSECDEFRFIAPRVLDEDAPPEKRAGVHDGHLKRAPKVYCGGDERDVLRVGS-
TR2111_hVZ    --FLHSYKTTMSSFQFLAPKCLDEDVPMEERKGVHVGTLSRPPKVYCNGKEVPILDFRC-
TR2112_hHV    .............YIRILPRGIMHDG....AAGLIKDVCDSEPRMFYRDRQYLLSKEMTW
TR2113_hCM    SAQGSGKRPPQKQFLQIVPRGVMFDG....QTGLIKHKTGRLPLMFYREIKHLLSHDMVW
TR2114_EBV    .............YLRLIPKCFQTPG....AAGVVDVRGPQPPLCFYQDSLTVVGGDEDG
TR2115_sHV    .............ICRLVPKCFRNPT....EKGVVSVSSFALPTYFFKGNENKVYLENG-

TR1910_KSH    ..................................................
TR2108_EBV    KGMWWRQRAQEGTARP-EADTHGSPLDFHVYDILETVYTHE--KCAVIPSDKQGYVVPCG
TR2109_eHV    RSLWSAGGRGGPGTGA-GQGHTPVALTFHVYDIIETVYGQD--RCDHVPFQFQTDIIPSG
TR2110_hHS    GGFWPRRSRLWGGVDHAPAGFNPTVTVFHVYDILENVEHAYGMRAAQFHARFMDAITPTG
TR2111_hVZ    SSPWPRRVNIWGEIDFRGDKFDPRFNTFHVYDIVETTEAAS----NGDVSRFATATRPLG
TR2112_hHV    PSLDIARSKD........YDHMR..MKFHIYDAVETLMFTD..SIENLPFQYRHFVIPSG
TR2113_hCM    PCPWRETLVG........RVVGP..IRFHTYDQTDAVLFFD..SPENVSPRYQHLVPSG
TR2114_EBV    KGMWWRQRAQEGTARP-EADTHGSPLDFHVYDILETVYTHE--KCAVIPSDKQGYVVPCG
TR2115_sHV    KSMWHLRRPCKNALLE-EQ.....SITFHIYDIVETTYSED--RCNDIPFKFQTDIIPNG

TR1910_KSH    ................-RCYFYTLAP.........QGVNLTHVLQQALQAGF..
TR2108_EBV    IVIKLLGRRKADGASVCVNVFGQQAYFYASAP.........QGLDVEFAVLSALKAST..
TR2109_eHV    TVLKLLG-RTSDDRSVCVNVFRQELYFYVRVP.........EGLKLDFLIQQCSRENF..
TR2110_hHS    TVITLLG-LTPEGHRVAVHVYGTRQYFYMNKEEVDRHLQCRAPRDLCERMAAALRE....
TR2111_hVZ    TVITLLG-MSRCGKRVAVHVYGICQYFYINKAEVDTACGIRSGSELSVLLAECLRSSMIT
TR2112_hHV    TVIRMFG-RTEDGEKICVNVFGQEQYFYCECV.........DGRSLKATINNLMLTG...
TR2113_hCM    NVLRFFG-ATEHGYSICVNVFGQRSYFYCEYS.........DTDRLREVIASVGELVP..
TR2114_EBV    IVIKLLGRRKADGASVCVNVFGQQAYFYASAP.........QGLDVEFAVLSALKAST..
TR2115_sHV    TVLKLLG-RTLEGASVCVNVFGQRNYFYVKVP.........EGGNITYLIKQALNEKF..
                                 ***                              .  .
```

FIG. 14A

```
TR1910_KSH    ---------------GR--ASCGFSTEPVRKKILRAYDTQQYAVQKITLSSS-PMMRT
TR2108_EBV    ----------------FDRRTPCRVSVEKVTRRSIMGYGNHAGDYHKITLSHPNSVCHV
TR2109_eHV    ----------------NF--SQGRYRYEKTSKRVLREYCVEAREVYRVFASSQ-GFVDL
TR2110_hHS    -----------SPGASFRGISADHFEAEVVERTDVYYYETRPALFYRVYVRSG-RVLSY
TR2111_hVZ    QNDATLNGDKNAFHGTSFKSASPESFRVEVIERTDVYYYDTQPCAFYRVYSPSS-KFTNY
TR2112_hHV    ----------------EVK-MSCSFVIEPADKLSLYGYNANTVVNLFKVSFGNFYVSQR
TR2113_hCM    ----------------EPR-TPYAVSVTPATKTSIYGYGTRPVPDLQCVSISNWTMARK
TR2114_EBV    ----------------FDRRTPCRVSVEKVTRRSIMGYGNHAGDYHKITLSHPNSVCHV
TR2115_sHV    ----------------S---PSCAYQTEAVKKKILSRYDPEEHDVFKVTVSSS-LSVYK
                                                     .  .  *

TR1910_KSH    LSDRLTTCGCEVFESNVDAIRRFVLDH-GFSTFGWYECSNPAPR--------TQARDSWTE
TR2108_EBV    ATWLQDKHGCRIFEANVDATRRFVLDN-DFVTFGWYSCRRAIPR--------LQHRDSYAE
TR2109_eHV    LAGGLTAAGCEVFETNVDAARRFIIDN-GFSTFGWYSCAAAVPRQ-----GGAARDSWTE
TR2110_hHS    LCDNFCP-AIKKYEGGVDATTRFILDNPGFVTFGWYRLKPGRNNTLAQPRAPMAFGTSSD
TR2111_hVZ    LCDNFHP-ELKKYEGRVDATTRFLMDNPGFVSFGWYQLKPGVDGERVRVRPASRQLTLSD
TR2112_hHV    IGKILQNEGFVVYEIDVDVLTRFFVDN-GFLSFGWYNVKKYIPQ--------DMGKGSNLE
TR2113_hCM    IGEYLLEQGFPVYEVRVDPLTRLVIDR-RITTFGWCSVNRYDWR--------QQGRASTCD
TR2114_EBV    ATWLQDKHGCRIFEANVDATRRFVLDN-DFVTFGWYSCRRAIPR--------LQHRDSYAE
TR2115_sHV    ISDSLVSNGCEVFETNVDAIRRFVIDN-DFSTFGWYTCKSACPR--------ITNRDSHTD
                .*   **   *   .*      .***                           . .

TR1910_KSH    LEFDCSWEDLKFIPERTEWPPYTILSFDIECMGEKG----FPNATQDEDMIIQISCVLHT
TR2108_EBV    LEYDCEVGDLSVRREDSSWPSYQALAFDIECLGEEG----FPTATNEADLILQISCVLWS
TR2109_eHV    LEYDCAAGDLEFHAGRADWPGYNVLSFDIECLGENG----FPNASRDEDMILQISCVIWK
TR2110_hHS    VEFNCTADNLAIEGGMSDLPAYKLMCFDIECKAGGEDELAFPVAGHPEDLVIQISCLLYD
TR2111_hVZ    VEIDCMSDNLQAIPNDDSWPDYKLLCFDIECKSGGSNELAFPDATHLEDLVIQISCLLYS
TR2112_hHV    VEINCHVSDLVSLEDVN-WPLYGCWSFDIECLGQNGN---FPDAENLGDIVIQISVISFD
TR2113_hCM    IEVDCDVSDLVAVPDDSSWPRYRCLSFDIECMSGEGG---FPCAEKSDDIVIQISCVCYE
TR2114_EBV    LEYDCEVGDLSVRREDSSWPSYQALAFDIECLGEEG----FPTATNEADLILQISCVLWS
TR2115_sHV    IEFDCGYYDLEFHADRTEWPPYNIMSFDIECIGEKG----FPCAKNEGDLIIQISCVFWH
               .*  *    *       * *  .*****        **  *   *...***  .

TR1910_KSH    VGNDK--------------PYTRMLLGLGTCDPLPG------------VEV
TR2108_EBV    TGEEAG-------------RYRRILLTLGTCEDIEG------------VEV
TR2109_eHV    AGSGE--------------APRSVLLNLGTCEEIEG------------VEV
TR2110_hHS    LSTTA--------------LEHVLLFSLGSCDLPESHLNELAARGLPTPVV
TR2111_hVZ    IPRQS--------------LEHILLFSLGSCDLPQRYVQEMKDAGLPEPTV
TR2112_hHV    TEG---------DRDER-----------HLFTLGTCEKIDG----------VHI
TR2113_hCM    TGGNTAVDQGIPNGNDGRGCTSEGVIFGHSGLHLFTIGTCGQVGPD-----------VDV
TR2114_EBV    TGEEAG-------------RYRRILLTLGTCEDIEG------------VEV
TR2115_sHV    AGALD--------------TTRNMLLSLGTCSAVEN------------TEV
                                    *  .*.*                .
```

FIG. 14B

```
TR1910_KSH    FEFPSEYDMLAAFLSMLRDYNVEFITGYNIANFDLPYIIARATQVYDFKLQDFTKIKTGS
TR2108_EBV    YEFPSELDMLYAFFQLIRDLSVEIVTGYNVANFDWPYILDRARHIYSINPASLGKIRAGG
TR2109_eHV    YQCPSELDLLYLFFTMIRDADVEFVTGYNISNFDFPYVIDRATQVYNLNLKEFTRVRSSS
TR2110_hHS    LEFDSEFEMLLAFMTLVKQYGPEFVTGYNIINFDWPFLLAKLTDIYKVPLDGYGRMNGRG
TR2111_hVZ    LEFDSEFELLIAFMTLVKQYAPEFATGYNIVNFDWAFIMEKLNSIYSLKLDGYGSINRGG
TR2112_hHV    YEFASEFELLLGFFIFLRIESPEFITGYNINNFDLKYLCIRMDKIYHYDIGCFSKLKNGK
TR2113_hCM    YEFPSEYELLLGFMLFFQRYAPAFVTGYNINSFDLKYILTRLEYLYKVDSQRFCKLPTAQ
TR2114_EBV    YEFPSELDMLYAFFQLIRDLSVEIVTGYNVANFDWPYILDRARHIYSINPASLGKIRAGG
TR2115_sHV    YEFPSEIDMLHGFFSLIRDFNVEIITGYNISNFDLPYLIDRATQIYNIKLSDYSRVKTGS
               •  ** ••*  *    •      ****• **  ••  •   •*      •

TR1910_KSH    ---------------VFEVHQPRGGSDGGNFMRSQSKVKISGIVPIDMYQVCREKLSLSD
TR2108_EBV    ---------------VCEVRRPHDAGKG--FLRANTKVRITGLIPIDMYAVCRDKLSLSD
TR2109_eHV    ---------------IFEVHKPKNSSAG--FMRAVSKVKVAGVVPIDMYQVCRDKLSLSN
TR2110_hHS    ------------------VFRVWDIGQS--HFQKRSKIKVNGMVSIDMYGIITDKIKLSS
TR2111_hVZ    ------------------LFKIWDVGKS--GFQRRSKVKINGLISLDMYAIATEKLKLSS
TR2112_hHV    -------------------IGISVPHEQYRKG-FLQAQTKVFTSGVLYLDMYPVYSSKITAQN
TR2113_hCM    GGRFFLHSPAVGFKRQYAAAFPSASHNNP-ASTAATKVYIAGSVVIDMYPVCMAKTNSPN
TR2114_EBV    ---------------VCEVRRPHDAGKG--FLRANTKVRITGLIPIDMYAVCRDKLSLSD
TR2115_sHV    ---------------IFQVHTPKDTGNG--FMRSVSKIKISGIIAIDMYIVCKDKLSLSN
                                •*•      *  •***  •       *

TR1910_KSH    YKLDTVAKQCLGRQKDDISYKDIPPLFKSGPDGRAKVGNYCVIDSVLVMDLLLRFQTHVE
TR2108_EBV    YKLDTVARHLLGAKKEDVHYKEIPRLFAAGPEGRRRLGMYCVQDSALVMDLLNHFVIHVE
TR2109_eHV    YKLDTVAGECVGAKKEDVSYKEIPHLFRQGPGGRARLGLYCVKDSALVLDLLRYFMTHVE
TR2110_hHS    YKLNAVAEAVLKDKKKDLSYRDIPAYYAAGPAQRGVIGEYCIQDSLLVGQLFFKFLPHLE
TR2111_hVZ    YKLDSVAREALNESKRDLPYKDIPGYYASGPNTRGIIGEYCIQDSALVGKLFFKYLPHLE
TR2112_hHV    YKLDTIAKICLQQEKEQLSYKEIPKKFISGPSGRAVVGKYCLQDSVLVVRLFKQINYHFE
TR2113_hCM    YKLNTMAELYLRQRKDDLSYKDIPRCFVANAEGRAQVGRYCLQDAVLVRDLFNTINFHYE
TR2114_EBV    YKLDTVARHLLGAKKEDVHYKEIPRLFAAGPEGRRRLGMYCVQDSALVMDLLNHFVIHVE
TR2115_sHV    YKLDTVANHCIGAKKEDVSYKDIMPLFMSGPEGRAKIGLYCVIDSVLVMKLLKFFMIHVE
               ***  ••*  •    *   •*••*  •    •   •*  **• *• **   *     **

TR1910_KSH    ISEIAKLAKIPTRRVLTDGQQIRVFSCLLEAAATEGYILPVPKG----------------
TR2108_EBV    VAEIAKIAHIPCRRVLDDGQQIRVFSCLLAAAQKENFILPMPSA----------------
TR2109_eHV    ISEIAKIAKIPTRRVLTDGQQIRVFSCLLDVAGREGYILPVDRH----------------
TR2110_hHS    LSAVARLAGINITRTIYDGQQIRVFTCLLRLADQKGFILPDTQGRFRGAGGEAPKRPAAA
TR2111_hVZ    LSAVARLARITLTKAIYDGQQVRIYTCLLGLASSRGFILPDGG-------------YPAT
TR2112_hHV    VAEVARLAHVTARCVVFEGQQKKIFPCILTEAKRRNMILPSMVS----------------
TR2113_hCM    AGAIARLAKIPLRRVIFDGQQIRIYTSLLDECACRDFILPNHYSKGTTVPETNSVAVSPN
TR2114_EBV    VAEIAKIAHIPCRRVLDDGQQIRVFSCLLAAAQKENFILPMPSA----------------
TR2115_sHV    ISEIAKLAKIPTRRVLTDGQQIRVFSCLLAAARAENYILPVSND----------------
               •*••*  •    •  •***  ••• ••*   •         ***
```

FIG. 14C

```
TR1910_KSH    ................................................
TR2108_EBV    ................................................
TR2109_eHV    ................................................
TR2110_hHS    REDEERPEEEGEDEDEREEG---------------------------GGE
TR2111_hVZ    FEYKDVIPDVGDVEEEMDE-----------------------------D
TR2112_hHV    ................................................
TR2113_hCM    AAIISTAAVPGDAGSVAAMFQMSPPLQSAPSSQDGVSPGSGSNSSSSVGVFSVGSGSSGG
TR2114_EBV    ................................................
TR2115_sHV    ................................................

TR1910_KSH    ------DAVSG------YQGATVISPSPGFYDDPVLVVDFASLYPSIIQAHNLCYSTLIP
TR2108_EBV    ------SDRDG------YQGATVIQPLSGFYNSPVLVVDFASLYPSIIQAHNLCYSTMIT
TR2109_eHV    ------ADAEG------YQGATVIDPSPGFYNTPVLVVDFASLYPTIIQAHNLCYSTMIP
TR2110_hHS    REPDGARETAGRH--VGYQGARVLDPTSGFHVNPVVVFDFASLYPSIIQAHNLCFSTLSL
TR2111_hVZ    ESVSPTGTSSGRN--VGYKGARVFDPDTGFYIDPVVVLDFASLYPSIIQAHNLCFTTLTL
TR2112_hHV    ---SHNRQGIG------YKGATVLEPKTGYYAVPTVVFDFQSLYPSIMMAHNLCYSTLVL
TR2113_hCM    VGVSNDNHGAGGTAAVSYQGATVFEPEVGYYNDPVAVFDFASLYPSIIMAHNLCYSTLLV
TR2114_EBV    ------SDRDG------YQGATVIQPLSGFYNSPVLVVDFASLYPSIIQAHNLCYSTMIT
TR2115_sHV    ------VNADG------FQGATVINPIPGFYNNAVLVVDFASLYPSIIQAHNLCYSTLIP
                    *     •• ••   * * *•    * ** ****•*•  *****••*•

TR1910_KSH    GDS-LHLHPHLSPD-DYETFVLS-GGPVHFVKKHKRESLLAKLLTVWLAKRKEIRKTLAS
TR2108_EBV    PGE-EHRLAGLRPGEDYESFRLT-GGVYHFVKKHVHESFLASLLTSWLAKRKAIKKLLAA
TR2109_eHV    GDR-LCLHPHLGPG-DYETFELA-SGPVHFVKKHKAVSLLATLLNVWLAKRKAIRRELAT
TR2110_hHS    RAD---AVAHLEAGKDYLEIEVG-GRRLFFVKAHVRESLLSILLRDWLAMRKQIRSRIPQ
TR2111_hVZ    NFE---TVKRLNP-SDYATFTVG-GKRLFFVRSNVRESLLGVLLKDWLAMRKAIRARIPG
TR2112_hHV    DERQ---IAGLSES-DILTVKLG-DETHRFVKPCIRESVLGSLLKDWLAKRREVKAEMQN
TR2113_hCM    PGG----EYPVDPA-DVYSVTLENGVTHRFVRASVRVSVLSELLNKWVSQRRAVRECMRE
TR2114_EBV    PGE-EHRLAGLRPGEDYESFRLT-GGVYHFVKKHVHESFLASLLTSWLAKRKAIKKLLAA
TR2115_sHV    HHA-LHNYPHLKSS-DYETFMLS-SGPIHFVKKHIQASLLSRLLTVWLSKRKAIRQKLAE
                •    *    •      **•    * *  **  *•• *•  ••   •

TR1910_KSH    CTDPALKTILDKQQLAIKVTCNAVYGFTGVASGILPCLNIAETVTLQGRKMLERSQAFVE
TR2108_EBV    CEDPRQRTILDKQQLAIKCTCNAVYGFTGVANGLFPCLSIAETVTLQGRTMLERAKAFVE
TR2109_eHV    VSDEAVRTILDKQQLAIKVTCNAVYGFTGVASGILPCLKIAETVTFQGRRMLENSKRYIE
TR2110_hHS    SS-PEEAVLLDKQQAAIKVVCNSVYGFTGVQHGLLPCLHVAATVTTIGREMLLATREYVH
TR2111_hVZ    SS-SDEAVLLDKQQAAIKVVCNSVYGFTGVAQGFLPCLYVAATVTTIGRQMLLSTRDYIH
TR2112_hHV    CSDPMMKLLLDKKQLALKTTCNSVYGVTGAAHGLLPCVAIAASVTCLGREMLCSTVDYVN
TR2113_hCM    CQDPVRRMLLDKEQMALKVTCNAFYGFTGVVNGMMPCLPIAASITRIGRDMLERTARFIK
TR2114_EBV    CEDPRQRTILDKQQLAIKCTCNAVYGFTGVANGLFPCLSIAETVTLQGRTMLERAKAFVE
TR2115_sHV    CEDLDTKTILDKQQLAIKVTCNAVYGFTGVASGLLPCISIAETVTLQGRTMLEKSKIFIE
              •*** * *•* **• ** **   * **• •* ••*  ** **  •  ••
```

FIG. 14D

```
TR1910_KSH   AIS--PERLAGLLRRP-----------------------VDVSPDARFKVIYGDTDS
TR2108_EBV   ALS--PANLQALAPSPD----------------------AWAPLNPEGQLRVIYGDTDS
TR2109_eHV   GVT--PEGLADILGRR-----------------------VECAPDASFKVIYGDTDS
TR2110_hHS   ARWAAFEQLLADFPEAAD---------------------MRAPGPYSMRIIYGDTDS
TR2111_hVZ   NNWAAFERFITAFPDIESS--------------------VLSQKAYEVKVIYGDTDS
TR2112_hHV   SKMQSEQFFCEEFG-------------------LTSSDFTG--DLEVEVIYGDTDS
TR2113_hCM   DNFSEPCFLHNFFNQEDYVVGTREGDSEESSALPEGLETSSGGSNERRVEARVIYGDTDS
TR2114_EBV   ALS--PANLQALAPSPD----------------------AWAPLNPEGQLRVIYGDTDS
TR2115_sHV   AMT--PDTLQEIVPHI-----------------------VKHEPDAKFRVIYGDTDS
                                                            .*******

TR1910_KSH   LFICCMGFNMDSVSDFAEELASITTNTLFRSPIKLEAEKIFKCLLLLTKKRYVGVLS-DD
TR2108_EBV   LFIECRGFSESETLRFADALAAHTTRSLFVAPISLEAEKTFSCLMLITKKRYVGVLT-DG
TR2109_eHV   LFIHCRGYRPEQVTGFCDELAAHMTRTLFVDPIKLEAEKTFKCLILLTKKRYIGMMT-TD
TR2110_hHS   IFVLCRGLTAAGLTAMGDKMASHISRALFLPPIKLECEKTFTKLLLIAKKKYIGVIY-GG
TR2111_hVZ   VFIRFKGVSVEGIAKIGEKMAHIISTALFCPPIKLECEKTFIKLLLITKKKYIGVIY-GG
TR2112_hHV   IFMSVRNMVNQSLRRIAPMIAKHITDRLFKSPIKLEFEKILCPLILICKKRYIGRQD-DS
TR2113_hCM   VFVRFRGLTPQALVARGPSLAHYVTACLFVEPVKLEFEKVFVSLMMICKKRYIGKVEGAS
TR2114_EBV   LFIECRGFSESETLRFADALAAHTTRSLFVAPISLEAEKTFSCLMLITKKRYVGVLT-DG
TR2115_sHV   LFVECVGYSVDTVVKFGDFLAAFTSEKLFNAPIKLESEKTFQCLLLLAKKRYIGILS-ND
              .*.  .       .*   .  ** *. ** **  *....**.*.*

TR1910_KSH   KVLMKGVDLIRKTACRFVQEKSSQVLDLILREPSVKAAAKLISGQATDWVYREGLPEGFV
TR2108_EBV   KTLMKGVELVRKTACKFVQTRCRRVLDVVLADARVKEAASLLSHRPFQESFTQGLPVGFL
TR2109_eHV   RLLMKGVDLVRKTACRFVQETTKAILDLVMGDEAVRAAAERLCAMRVEEVCARGPPVGFL
TR2110_hHS   KMLIKGVDLVRKNNCAFINRTSRALVDLLFYDDTVSGAAAALAERPAEEWLARPLPEGLQ
TR2111_hVZ   KVLMKGVDLVRKNNCQFINDYARKLVELLLYDDTVSRAAAEASCVSIAEWNRRAMPSGMA
TR2112_hHV   LLIFKGVDLVRKTSCDFVKGVVKDIVDLLFFDEEVQTAAVEFSHMTQTQLREQGVPVGIH
TR2113_hCM   GLSMKGVDLVRKTACEFVKGVTRDVLSLLFEDREVSEAAVRLSRLSLDEVKKYGVPRGFW
TR2114_EBV   KTLMKGVELVRKTACKFVQTRCRRVLDVVLADARVKEAASLLSHRPFQESFTQGLPVGFL
TR2115_sHV   KLLMKGVDLVRKTACKFVQNTSSKILNLILKDPEVKAAAQLLSTKDPDYAFREGLPDGFL
              ***.*†**. * *.    .. *. ↑  *  **   .           * *

TR1910_KSH   KIIQVLNASHRELCERSVPVDKLTFTTELSRPLADYKTQNLPHLTVYQKLQARQEELPQI
TR2108_EBV   PVIDILNQAYTDLREGRVPMGELCFSTELSRKLSAYKSTQMPHLAVYQKFVERNEELPQI
TR2109_eHV   KVVDILNDSYRKLRLNRVPVGQLSFSTELSRPISYYKTLTLPHLVVYHKIMQRNEELPQI
TR2110_hHS   AFGAVLVDAHRRITDPERDIQDFVLTAELSRHPRAYTNKRLAHLTVYYKLMARRAQVPSI
TR2111_hVZ   GFGRIIADAHRQITSPKLDINKFVMTAELSRPPSAYINRRLAHLTVYYKLVMRQGQIPNV
TR2112_hHV   KILRRLCEAREELFQNRADVRHLMLSSVLSKEMAAYKQPNLAHLSVIRRLAQRKEEIPNV
TR2113_hCM   RILRRLVQARDDLYLHRVVEDLVLSSVLSKDISLYRQSNLPHIAVIKRLAARSEELPSV
TR2114_EBV   PVIDILNQAYTDLREGRVPMGELCFSTELSRKLSAYKSTQMPHLAVYQKFVERNEELPQI
TR2115_sHV   KVIDILNESHKNLRTGQVPVEELTFSTELSRPISSYKTENLPHLTVYKKIITRHEEPPQV
              . .  .     .    .. **.   *   . *.*  .  . * .*.
```

FIG. 14E

```
TR1910_KSH    HDRIPYVFVDAP
TR2108_EBV    HDRIQYVFVEPKGG
TR2109_eHV    HDRIAYVFVQSPK
TR2110_hHS    KDRIPYVIVAQTREVEETVARLAALRELDAAAPGDEPAPPAALPSPAKRPRETPSPADPP
TR2111_hVZ    RERIPYVIVAPTDEVEADAKSVALLRGDPLQN············TAGKR···········
TR2112_hHV    GDRIMYVLIAPSIGNKQ
TR2113_hCM    GDRVFYVLTAPGVRTAPQGSSDNGDSVTAGVVSRSDAIDGTDDDADGGGVEESNRRGGEP
TR2114_EBV    HDRIQYVFVEPKGG
TR2115_sHV    HDRIPYVFVGKT
              .*. **

TR1910_KSH    ···········GSLRSELAEHPEYVKQHGLRVAVDLYFDK···················
TR2108_EBV    ········VKGARKTEMAEDPAYAERHGVPVAVDHYFDKLLQGAANILQCLFDNNSGAAL
TR2109_eHV    ··········GKLRSEMAEDPAYAAQHNIPPAVDLYFDKVIHGAANILQCLFENDSDKAA
TR2110_hHS    G···GASKPRKLLVSELAEDPAYAIAHGVALNTDYYFSHLLGAACVTFKALFGNNAKITE
TR2111_hVZ    ····CGEAKRKLIISDLAEDPIHVTSHGLSLNIDYYFSHLIGTASVTFKALFGNDTKLTE
TR2112_hHV    ···········THNYELAEDPNYVIEHKIPIHAEKYFDQIIKAVTNAISPIFPKTDIK-K
TR2113_hCM    AKKRARKPPSAVCNYEVAEDPSYVREHGVPIHADKYFEQVLKAVTNVLSPVFPGGETARK
TR2114_EBV    ········VKGARKTEMAEDPAYAERHGVPVAVDHYFDKLLQGAANILQCLFDNNSGAAL
TR2115_sHV    ··········TSCISNMAEDPTYTVQNNIPIAVDLYFDKLIHGVANIIQCLFK-DSSKTV
                       .**↑*        ..   .** .

TR1910_KSH    ·····················
TR2108_EBV    SVLQNFTARPPF
TR2109_eHV    RVLYNFADLP···PDDL
TR2110_hHS    SLLKRFIPEVWHPPDDVTARLRAAGFGAVGAG···········ATAEETRRMLHRAFDT
TR2111_hVZ    RLLKRFIPETRVVNVKMLNRLQAAGFVCIHAPCWDNKMNTEAEITEEEQSHQIMRRVFCI
TR2112_hHV    EKLLLYLLPMKVYLDETFSAIAEVM
TR2113_hCM    DKFLHMVLPRRLHLEPAFLPYSVKAHECC
TR2114_EBV    SVLQNFTARPPF
TR2115_sHV    SVLYNFVSTPVLFSYELLTDHSVKA

TR1910_KSH    ········
TR2108_EBV    ········
TR2109_eHV    ········
TR2110_hHS    LA······
TR2111_hVZ    PKAILHQS
TR2112_hHV    ········
TR2113_hCM    ········
TR2114_EBV    ········
TR2115_sHV    ········
```

FIG. 14F

```
             VASGILPCLNIAETVTLQGRKMLETSQAFVEGISPTALADLLQRPIEASP---EARFKVI
RFHVMn       ............................................................
RFHVMm       ...........................KD.S...I....D......D......
KSHV-KS7     ....................R......ER..G..R..VDV....D...R..
KSHV-KSF2    ....................R......A...ER..G..R....DV....D...R..
KSHVpath1    ....................R......ER..G..R..VDV....D......
KSHVpath2    ....................R......A...ER..G..R..VDV....D...R..
eHV2         .....K......F...R...N.KRYI..VT.EG...I.G.RV.CA....D.S...
sHV1         ...L..IS............T...K.KI.I.AMT.DT.QEIVPHIVKHE.---D.K.R..
EBV          ..N.LF...S..........T...RAK....AL..AN.QA.APS.DAWA.LNP.GQLR..
```

FIG. 15

```
        (DFASA>)gtgttcgacttygcnagyytntaycc                                      1
RFMn                     (QAHNA>)ccaagtatcathcargcncavaaCCTCTGTTATTCTAC
RFMm                                              ...A.....C.....
KS                                                .T.G..C..C..C..

20              40              60              80
RFMn    CCTGATTACAGGAAGCGCCCTACACGGGCACCCCGAACTGACCCCCGACGACTACGAAACCTTCCACCTG
RFMm    .......CAG..G.A....A.T.T.TC.........GT.......GA.............A........A
KS      A.....AC.C..CGATT.G..C...CT......AC.C..CT....G................TGT...C 100             120             140
RFMn    AGCGGGGGAACGGTACACTTTGTAAAAAAGCACGTCCGCGAGTCACTACTGTCCAAACTGCTCACAACAT
RFMm    .....A...C....G.....C........A.....A....A.A......T.......A.....T..G..G..T.
KS      .....A..TC....C.............A...AAAA.G.....C..T..TA....G..T..G..GGT..

160             180             200             220
RFMn    GGCTGGCCAAGAGGAAAGAGATCCGCAAAAATTTAGCCTCGTGCACAGACCCCACCATGCGCACCATACT
RFMm    ....AA.A..A..A.................C.C.....GG.....A........A.....C..
KS      ....C..G.....A.....A..AA.A..G.CCC.G..A..A.....G......G.AC..AAA..T..T..

260             280
                    240        (VYGA>)acgtgcaacgcggtgtayggnktnacngg
RFMn    GGATAAACAACAGCTGGCCATCAAGGTCACATGTAACGCGGTGTACGGGTTCACGGGCGTCGCTTCCGGC
RFMm    T.....G..G...................T.................T..C........C.....T
KS      A..C........A........T..C..C........T.....C............T..C..T...

300             320             340             360
RFMn    ATCCTACCGTGCCTGAACATCGCAGAGACGGTGACCCTCCAGGGCAGGAAAATGCTGGAAACGTCTCAGG
RFMm    ..T............T..T.....A..A..C.............A........A........C....
KS      ..A..G..T....A.....A..G.....C.....A..A..A..GC.A..G........G.GA.......

380             400             420
RFMn    CGTTCGTAGAGGGAATCTCGCCAACGGCACTGGCAGACCTACTGCAGCGACCGATCGAGGCGTCTCCGGA
RFMm    ....T........C...A.......AA.AC...T.......GA.A..A..T........C..T..C... .
KS      .C..T.......CC........GGAACGC..A..G.GT..C....G.A.G..A..A..C.TC..A..C..

440        454
RFMn    AGCCAGGTTTAAAGTGATAtayggngayacngactccgtgtttgtcgcatgccg(<GDTDB complement)
RFMm    C...................
KS      C...C.A..C..G..C...
```

FIG. 16

```
                    20                        40
RFHVMn  SIMQAHNLCYSTLITGSALHGHPELTPD-DYETFHLSGGTV
RFHVMm  ...........................·..............
KSHV    ..I..........P.DS..L..H.S..-.....V....L.
eHV2    T.I.........M.P.DR.CL..H.G.G-.....E.AS.P.
sHV1    ..I..........PHH...NY.H.KSS-.....M..S.PI
EBV     ..I.........M..PGEE.RLAG.R.GE...S.R.T..VY 60                        80
RFHVMn  HFVKKHVRESLLSKLLTTWLAKRKEIRKNLASCTDPTMRTI
RFHVMm  ........................................
KSHV    ......K.....T....V..........T.......ALK..
eHV2    ......KAV...AT..NV......A..RE..TVS.EAV...
sHV1    ......IQA....R...V..S...A..QK..E.E.LDTK..
EBV     .......H..F.AS...S......A.K.L..A.E..RQ...

100                       120
RFHVMn  LDKQQLAIKVTCNAVYGFTGVASGILPCLNIAETVTLQGRK
RFHVMm  ........................................
KSHV    ........................................
eHV2    ............................K......F...R
sHV1    .............................L...IS........T
EBV     .........C..................N.LF...S........T

140
RFHVMn  MLETSQAFVEGISPTALADLLQRPIEASP---EARFKVI
RFHVMm  ..............KD.S..I....D...---D......
KSHV    ..........A...ER..G..R...DV..---D......
eHV2    ...N.KRYI..VT.EG...I.G.RV.CA.---D.S....
sHV1    ...K.KI.I.AMT.DT.QEIVPHIVKHE.---D.K.R..
EBV     ...RAK....AL..AN.QA.APS.DAWA.LNP.GQLR..
```

FIG. 17

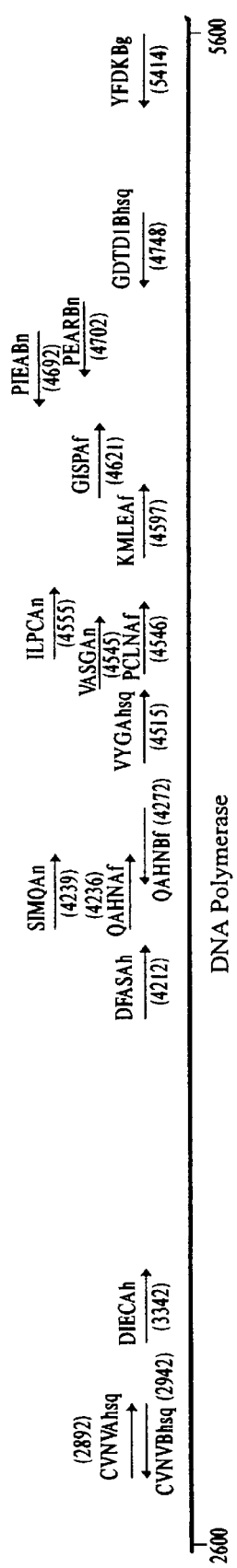
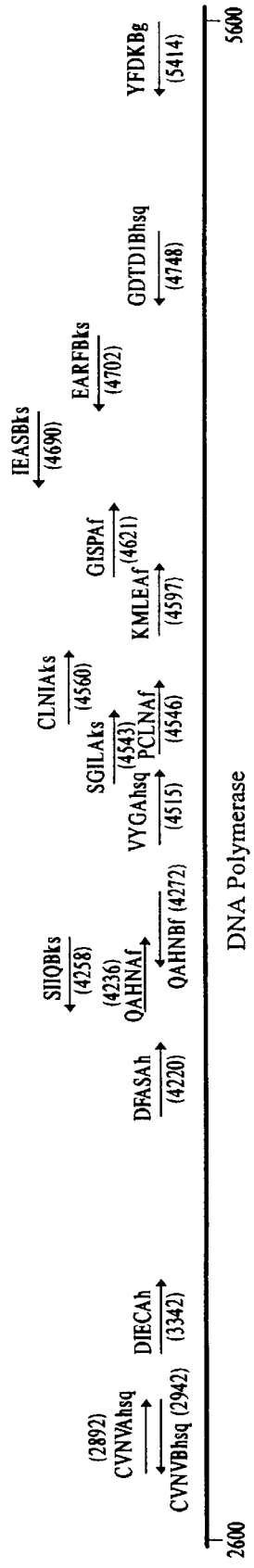
FIG. 19B

SEQUENCE LISTING (1) GENERAL INFORMATION:

(iii) NUMBER OF SEQUENCES: 152

(2) INFORMATION FOR SEQ ID NO:1:

(i) SEQUENCE CHARACTERISTICS:
(A) LENGTH: 536 base pairs
(B) TYPE: nucleic acid
(C) STRANDEDNESS: double
(D) TOPOLOGY: linear (xi) SEQUENCE DESCRIPTION: SEQ ID NO:1:

```
GTGTTCGACT TTGCTAGTCT TTACCCCAGC ATCATGCAGG CACACAACCT CTGTTATTCT     60

ACCCTGATTA CAGGAAGCGC CCTACACGGG CACCCCGAAC TGACCCCCGA CGACTACGAA    120

ACCTTCCACC TGAGCGGGGG AACGGTACAC TTTGTAAAAA AGCACGTCCG CGAGTCACTA    180

CTGTCCAAAC TGCTCACAAC ATGGCTGGCC AAGAGGAAAG AGATCCGCAA AAATTTAGCC    240

TCGTGCACAG ACCCCACCAT GCGCACCATA CTGGATAAAC AACAGCTGGC CATCAAGGTC    300

ACATGTAACG CGGTGTACGG GTTCACCGGC GTCGCTTCCG GCATCCTACC GTGCCTGAAC    360

ATCGCAGAGA CGGTGACCCT CCAGGGCAGG AAAATGCTGG AAACGTCTCA GGCGTTCGTA    420
```

```
GAGGGAATCT CGCCAACGGC ACTGGCAGAC CTACTGCAGC GACCGATCGA GGCGTCTCCG      480

GAAGCCAGGT TTAAAGTGAT ATACGGCGAC ACCGACTCCG TGTTTGTCGC ATGCCG         536
```

(2) INFORMATION FOR SEQ ID NO:2:

(i) SEQUENCE CHARACTERISTICS:
        (A) LENGTH: 178 amino acids
        (B) TYPE: amino acid
        (C) STRANDEDNESS: single
        (D) TOPOLOGY: linear (xi) SEQUENCE DESCRIPTION: SEQ ID NO:2:

```
Val Phe Asp Phe Ala Ser Leu Tyr Pro Ser Ile Met Gln Ala His Asn
1               5                   10                  15

Leu Cys Tyr Ser Thr Leu Ile Thr Gly Ser Ala Leu His Gly His Pro
                20                  25                  30

Glu Leu Thr Pro Asp Asp Tyr Glu Thr Phe His Leu Ser Gly Gly Thr
            35                  40                  45

Val His Phe Val Lys Lys His Val Arg Glu Ser Leu Leu Ser Lys Leu
        50                  55                  60

Leu Thr Thr Trp Leu Ala Lys Arg Lys Glu Ile Arg Lys Asn Leu Ala
65                  70                  75                  80

Ser Cys Thr Asp Pro Thr Met Arg Thr Ile Leu Asp Lys Gln Gln Leu
                85                  90                  95

Ala Ile Lys Val Thr Cys Asn Ala Val Tyr Gly Phe Thr Gly Val Ala
                100                 105                 110

Ser Gly Ile Leu Pro Cys Leu Asn Ile Ala Glu Thr Val Thr Leu Gln
                115                 120                 125

Gly Arg Lys Met Leu Glu Thr Ser Gln Ala Phe Val Glu Gly Ile Ser
            130                 135                 140

Pro Thr Ala Leu Ala Asp Leu Leu Gln Arg Pro Ile Glu Ala Ser Pro
145                 150                 155                 160

Glu Ala Arg Phe Lys Val Ile Tyr Gly Asp Thr Asp Ser Val Phe Val
                165                 170                 175

Ala Cys
```

(2) INFORMATION FOR SEQ ID NO:3:

(i) SEQUENCE CHARACTERISTICS:
        (A) LENGTH: 536 base pairs
        (B) TYPE: nucleic acid
        (C) STRANDEDNESS: double
        (D) TOPOLOGY: linear (xi) SEQUENCE DESCRIPTION: SEQ ID NO:3:

```
GTGTTCGACT TGCTAGCCT CTACCCCAGT ATCATCCAAG CGCACAACTT GTGCTACTCC      60

ACACTGATAC CCGGCGATTC GCTCCACCTG CACCCACACC TCTCCCCGGA CGACTACGAA     120

ACCTTTGTCC TCAGCGGAGG TCCGGTCCAC TTTGTAAAAA AACACAAAAG GGAGTCCCTT     180

CTTACCAAGC TTCTGACGGT ATGGCTCGCG AAGAGAAAAG AAATAAGAAA GACCCTGGCA     240

TCATGCACGG ACCCCGCACT GAAAACTATT CTAGACAAAC AACAACTGGC CATCAAGGTT     300

ACCTGCAACG CGGTTTACGG CTTCACGGGC GTTGCCTCTG GCATACTGCC TTGCCTAAAC     360

ATAGCGGAGA CCGTGACACT ACAAGGGCGA AAGATGCTGG AGAGATCTCA GGCCTTTGTA     420

GAGGCCATCT CGCCGGAACG CCTAGCGGGT CTCCTGCGGA GGCCAATAGA CGTCTCACCC     480

GACGCCCGAT TCAAGGTCAT ATACGGCGAC ACCGACTCCG TGTTTGTCGC ATGCCG         536
```

(2) INFORMATION FOR SEQ ID NO:4:

(i) SEQUENCE CHARACTERISTICS:
        (A) LENGTH: 178 amino acids
        (B) TYPE: amino acid
        (C) STRANDEDNESS: single
        (D) TOPOLOGY: linear (xi) SEQUENCE DESCRIPTION: SEQ ID NO:4:

```
Val Phe Asp Phe Ala Ser Leu Tyr Pro Ser Ile Ile Gln Ala His Asn
 1               5                  10                  15

Leu Cys Tyr Ser Thr Leu Ile Pro Gly Asp Ser Leu His Leu His Pro
            20                  25                  30

His Leu Ser Pro Asp Asp Tyr Glu Thr Phe Val Leu Ser Gly Gly Pro
        35                  40                  45

Val His Phe Val Lys Lys His Lys Arg Glu Ser Leu Leu Thr Lys Leu
    50                  55                  60

Leu Thr Val Trp Leu Ala Lys Arg Lys Glu Ile Arg Lys Thr Leu Ala
65                  70                  75                  80

Ser Cys Thr Asp Pro Ala Leu Lys Thr Ile Leu Asp Lys Gln Gln Leu
                85                  90                  95

Ala Ile Lys Val Thr Cys Asn Ala Val Tyr Gly Phe Thr Gly Val Ala
            100                 105                 110

Ser Gly Ile Leu Pro Cys Leu Asn Ile Ala Glu Thr Val Thr Leu Gln
        115                 120                 125

Gly Arg Lys Met Leu Glu Arg Ser Gln Ala Phe Val Glu Ala Ile Ser
    130                 135                 140

Pro Glu Arg Leu Ala Gly Leu Leu Arg Arg Pro Ile Asp Val Ser Pro
145                 150                 155                 160

Asp Ala Arg Phe Lys Val Ile Tyr Gly Asp Thr Asp Ser Val Phe Val
                165                 170                 175

Ala Cys
```

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

GTGTTCGACT TYGCNAGYYT NTAYCC                                     26

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

GTGTTCGACT TYCARAGYYT NTAYCC                                     26

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:7:

ACGTGCAACG CGGTGTAYGG NKTNACNGG                                29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:8:

ACGTGCAACG CGGTGTACGG SGTSACSGG                                29

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:9:

ACGTGCAACG CGGTGTA                                             17

(2) INFORMATION FOR SEQ ID NO:10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:10:

TAYGGNGAYA CNGACTCCGT GTTTGTCGCA TGCCG                         35

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:11:

CGGCATGCGA CAAACACGGA GTCNGTRTCN CCRTA                         35

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:12:

CGGCATGCGA CAAACACGGA                                          20

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

```
CGTCGCTTCC GGCATCCTAC C                                               21

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:14:

GGCATCCTAC CGTGCCTGAA C                                               21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:15:

CCGGAGACGC CTCGATCGGT C                                               21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:16:

AACCTGGCTT CCGGAGACGC C                                               21

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:17:

GCGTTGCCTC TGGCATACTG                                                 20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:18:

CTGCCTTGCC TAAACATAGC G                                               21

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

GGTGAGACGT CTATTGGCCT                                                 20
```

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

```
AATCGGGCGT CGGGTGAGAC G                                                    21
```

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:21:

```
GTCGCCTCTG GCATCCTNCC NTGYCTNAA                                            29
```

(2) INFORMATION FOR SEQ ID NO:22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:22:

```
CAGGGCCGGA AGATGCTGGA RACRTCNCAR GC                                        32
```

(2) INFORMATION FOR SEQ ID NO:23:

(i) SEQUENCE CHARACTERISTICS:
        (A) LENGTH: 3027 base pairs
        (B) TYPE: nucleic acid
        (C) STRANDEDNESS: double
        (D) TOPOLOGY: linear (xi) SEQUENCE DESCRIPTION: SEQ ID NO:23:

```
ATGAGTTTCT ACAACCCCTA CTTGGTCAAG AGGACCTTTC TTAAAAAGGC CGCCCCCTCG    60

CGGCCGACCA AGGAATATAC CAGGATAATT CCAAAATGCT TCAAGACCCC AGGCGCCGCG   120

GGGGTGGTGC CCCACACCAG CACCCTGGAC CCGGTGTGCT TCGTGGGGGA CAAGGAGACC   180

CCCATCCTGT ACGGGACGG GAGCAGGAGC CTGTGGAGCG CGGGTGGGCG GGCGGGCCG     240

GGGACGGGCG CGGGCCAGGG CCACACGCCT GTGGCCCTGA CCTTCCACGT CTATGACATA   300

ATAGAGACGG TGTACGGCCA GGACAGGTGC GACCACGTGC CCTTTCAGTT TCAGACGGAC   360

ATCATCCCCA GCGGGACGGT CCTCAAGCTG CTGGGTCGCA CCTCGGACGA CCGCAGCGTG   420

TGCGTGAACG TGTTCAGGCA GGAGCTGTAC TTTTACGTGC GCGTGCCCGA GGGGCTCAAG   480

CTGGACTTTC TCATCCAGCA GTGCTCGCGG GAGAACTTTA ACTTTAGCCA GGGCCGGTAC   540

CGATATGAGA AAACAAGCAA GCGCGTGTTG CGCGAGTACT GCGTCGAGGC GCGGGAGGTG   600

TACCGGGTGT TCGCGTCGAG CCAGGGGTTC GTGGACCTCC TGGCCGGGGG GCTCACGGCC   660

GCGGGGTGCG AGGTCTTCGA GACAAACGTG GACGCGGCCA GGCGGTTCAT CATAGACAAC   720

GGGTTCTCCA CCTTCGGGTG GTACTCGTGC GCGGCGGCCG TCCCGCGCCA GGGGGGCGCG   780

GCCAGGGACT CCTGGACGGA GTTGGAGTAC GACTGCGCCG CGGGGGACCT GGAGTTTCAC   840

GCGGGGCGGG CGGACTGGCC GGGCTACAAC GTCCTCTCCT TCGATATAGA GTGCCTGGGG   900
```

```
GAGAACGGGT TCCCCAACGC GAGCAGGGAC GAGGACATGA TCCTGCAGAT CTCCTGCGTG    960

ATCTGGAAGG CGGGGTCGGG GGAGGCGCCC AGGAGCGTGC TCCTGAACCT GGGCACGTGC   1020

GAGGAGATAG AGGGGGTGGA GGTGTACCAG TGCCCCTCGG AGCTGGACCT GCTCTACCTC   1080

TTTTTCACCA TGATCAGGGA CGCGGACGTG GAGTTTGTGA CGGGCTACAA CATCTCCAAC   1140

TTTGACTTCC CCTACGTGAT AGACAGGGCC ACGCAGGTGT ACAACCTGAA CCTGAAAGAG   1200

TTCACCCGGG TGCGCTCCTC GTCCATCTTC GAGGTGCACA AGCCCAAGAA CAGCTCAGCG   1260

GGCTTCATGC GCGCGGTGTC CAAGGTCAAG GTGGCCGGGG TGGTGCCCAT AGACATGTAC   1320

CAGGTGTGCA GGGACAAGCT GAGCCTGTCC AACTACAAGC TGGACACGGT GGCCGGGGAG   1380

TGCGTGGGCG CCAAGAAGGA GGACGTCTCC TACAAGGAGA TCCCCCACCT GTTCAGGCAG   1440

GGACCGGGGG GCAGGGCCAG GCTGGGGCTG TACTGCGTCA AGGATTCCGC CCTGGTGCTG   1500

GACCTGCTGA GGTACTTTAT GACGCACGTG GAGATCTCTG AGATAGCCAA GATAGCCAAG   1560

ATCCCCACGC GGCGGGTGCT CACGGACGGG CAGCAGATCA GGGTCTTCTC CTGCCTGCTG   1620

GACGTGGCCG GCGGGAGGG CTACATCCTG CCAGTGGACA GGCACGCGGA CGCGGAGGGC   1680

TACCAGGGGG CCACGGTCAT AGACCCCTCG CCCGGGTTCT ACAACACCCC GGTGCTGGTG   1740

GTGGACTTTG CCAGCCTGTA CCCCACCATC ATCCAGGCCC ACAACCTCTG CTACTCCACC   1800

ATGATCCCCG GAGACAGGCT GTGCCTGCAC CCGCACCTCG GGCCGGGCGA CTACGAGACC   1860

TTTGAGCTCG CGAGCGGGCC GGTGCACTTT GTCAAGAAGC ACAAGGCGGT CTCGCTGCTG   1920

GCCACGCTGC TGAACGTGTG GCTGGCCAAG AGGAAGGCCA TCAGGCGCGA GCTGGCCACG   1980

GTCTCGGACG AGGCCGTCAG GACCATCCTG GACAAGCAGC AGCTGGCCAT CAAGGTCACC   2040

TGCAACGCGG TGTACGGGTT CACGGGCGTG GCCTCGGGCA TCCTGCCCTG TCTCAAGATA   2100

GCCGAGACGG TCACCTTCCA GGGCAGGCGC ATGCTGGAGA ACTCCAAGCG CTACATAGAG   2160

GGGGTGACCC CCGAGGGGCT GGCAGACATA TTGGGCAGGC GGGTGGAGTG CGCCCCCGAT   2220

GCCAGTTTTA AGGTCATCTA CGGGGACACG GACTCCCTGT TTATCCACTG CCGGGGCTAC   2280

CGCCCAGAGC AGGTCACGGG GTTCTGCGAC GAGCTGGCCC TCACATGAC CCGAACCCTG   2340

TTCGTGGACC CCATCAAGCT GGAGGCCGAA AAGACCTTCA AGTGCCTGAT CTTACTGACC   2400

AAAAAGAGGT ACATAGGCAT GATGACCACC GACAGGCTGC TCATGAAGGG GGTGGACCTG   2460

GTGCGCAAGA CGGCGTGCAG GTTCGTGCAG GAGACCACCA AGGCCATCCT GGACCTGGTG   2520

ATGGGGGACG AGGCGGTGCG GCGGCGGCC GAGCGCCTGT GCGCCATGAG GGTGGAGGAG   2580

GTGTGCGCGC GGGGGCCCCC CGTCGGGTTC CTCAAGGTGG TGGACATCCT CAACGACAGC   2640

TACAGGAAAC TAAGGCTCAA CCGGGTGCCC GTGGGCCAGC TGTCCTTCTC CACCGAGCTG   2700

AGCAGGCCCA TCTCCTATTA CAAGACCCTG ACCCTGCCCC ACCTGGTGGT GTACCACAAG   2760

ATCATGCAGA GGAACGAGGA GCTCCCCCAG ATCCACGATA GGATAGCCTA CGTGTTTGTG   2820

CAGTCCCCCA AGGGGAAGCT GAGGTCCGAG ATGGCCGAGG ACCCCGCCTA CGCGGCCCAG   2880

CACAACATCC CCCGGCCGT GGACCTGTAC TTTGACAAGG TCATACACGG GCGGCCAAC   2940

ATCCTGCAGT GCCTGTTTGA GAACGACAGC GATAAGGCCG CGAGGGTGCT GTACAACTTT   3000

GCGGACCTGC CCCCGACGA CCTGTGA                                        3027
```

(2) INFORMATION FOR SEQ ID NO:24:

(i) SEQUENCE CHARACTERISTICS:
        (A) LENGTH: 3030 base pairs
        (B) TYPE: nucleic acid
        (C) STRANDEDNESS: double (D) TOPOLOGY: linear (xi) SEQUENCE DESCRIPTION: SEQ ID NO:24:

```
ATGGATTTTT ACAACCCATA TCTAAGTAAA AAGCCAACAG ATACAAAGAC ACCTAAGCTT      60
CATACAACTA GACAATCTAT ATGTAGGTTA GTCCCTAAAT GTTTTAGAAA TCCTACTGAA     120
AAAGGCGTAG TGTCTGTGTC TTCTTTTGCT CTTCCAACTT ACTTTTTCAA AGGTAATGAG     180
AATAAAGTAT ATCTTGAAAA TGGTAAGTCT ATGTGGCACT TAAGAAGACC GTGTAAGAAC     240
GCGTTGCTAG AAGAACAATC TATTACGTTC CATATTTATG ACATAGTAGA AACTACTTAT     300
TCAGAAGACA GATGTAACGA TATTCCTTTT AAGTTTCAAA CAGACATAAT ACCTAATGGA     360
ACAGTGTTGA AACTACTTGG AAGAACACTA GAGGGTGCGA GCGTATGTGT TAACGTGTTT     420
GGACAAAGAA ATTATTTTTA TGTTAAAGTT CCGGAAGGTG GCAACATAAC CTATCTTATA     480
AAACAAGCTT TGAATGAAAA ATTTAGCCCA TCTTGTGCAT ACCAAACTGA AGCAGTAAAG     540
AAGAAGATAC TATCTAGATA TGATCCAGAA GAACATGATG TGTTTAAGGT GACAGTGTCT     600
TCTTCCCTTT CTGTTTATAA GATATCAGAT TCTTTAGTGT CTAATGGTTG TGAAGTTTTT     660
GAAACAAATG TAGATGCTAT AAGAAGATTT GTAATTGATA ATGACTTTTC TACATTTGGT     720
TGGTACACAT GTAAGTCTGC ATGTCCTCGA ATCACAAATA GAGACTCTCA TACTGACATT     780
GAGTTTGACT GCGGGTACTA TGACTTAGAA TTTCATGCTG ATAGAACAGA ATGGCCACCT     840
TACAACATAA TGTCTTTTGA TATAGAATGT ATAGGAGAAA AAGGATTTCC TTGTGCAAAA     900
AATGAAGGAG ATTTAATAAT TCAGATTTCA TGTGTGTTTT GGCACGCTGG GGCGCTTGAT     960
ACAACTAGAA ATATGCTATT ATCTTTAGGA ACGTGCTCAG CTGTTGAAAA TACTGAAGTT    1020
TATGAGTTCC CTAGTGAAAT AGACATGCTG CATGGGTTTT TTTCATTAAT TAGAGACTTT    1080
AATGTTGAAA TAATTACTGG TTATAATATT TCTAACTTTG ACTTACCTTA TCTAATTGAT    1140
AGAGCTACTC AAATTTATAA TATAAAGCTA TCTGATTATT CAAGAGTTAA AACAGGGTCT    1200
ATTTTTCAAG TTCATACACC AAAAGATACA GGAAATGGGT TTATGAGATC TGTCTCTAAA    1260
ATAAAAATTT CAGGAATTAT AGCAATTGAC ATGTACATTG TGTGCAAAGA CAAACTCAGT    1320
CTGTCTAATT ACAAGCTTGA TACAGTTGCT AATCACTGTA TTGGTGCAAA AAAGGAAGAT    1380
GTGTCTTACA AAGATATTAT GCCTCTTTTT ATGTCCGGAC CAGAAGGCAG AGCTAAGATA    1440
GGACTATACT GTGTAATAGA TTCTGTTCTT GTGATGAAAC TTTTGAAATT TTTTATGATT    1500
CATGTTGAAA TTTCTGAGAT AGCAAAACTC GCTAAAATCC CCACAAGAAG AGTTCTTACA    1560
GATGGGCAAC AAATAAGAGT TTTTTCTTGT CTGCTTGCAG CAGCTCGTGC AGAAAACTAT    1620
ATACTGCCTG TGTCAAATGA TGTCAATGCG GATGGGTTTC AAGGAGCTAC CGTTATAAAT    1680
CCAATTCCTG GATTTTATAA CAATGCTGTA TTAGTAGTAG ACTTTGCTAG CCTGTATCCT    1740
AGTATTATAC AAGCTCATAA TCTATGCTAC TCCACTCTTA TACCCACCA TGCTTTACAC    1800
AACTACCCTC ACTTAAAATC TAGTGACTAT GAGACTTTCA TGCTCAGTTC TGGACCTATA    1860
CACTTTGTGA AAAACACAT TCAGGCATCT CTTCTATCTA GGCTCTTAAC TGTGTGGCTT    1920
TCTAAGAGAA AAGCTATTAG GCAAAAGCTT GCTGAATGTG AAGACCTAGA CACTAAAACT    1980
ATTCTAGATA AACAGCAACT CGCTATTAAA GTAACTTGTA ATGCTGTGTA TGGGTTTACA    2040
GGAGTTGCGT CAGGCTTGCT GCCATGCATA AGCATTGCAG AGACTGTTAC TCTCCAAGGC    2100
CGGACGATGC TAGAAAAATC AAAAATATTC ATAGAAGCAA TGACACCTGA TACACTTCAA    2160
GAAATTGTTC TCATATAGT GAAGCATGAA CCTGATGCGA AGTTCAGAGT CATATATGGA    2220
GACACAGACT CTCTATTTGT AGAATGTGTT GGGTATTCTG TAGACACAGT TGTTAAATTT    2280
```

-continued

| | |
|---|---|
| GGAGATTTCT TAGCTGCTTT TACTTCTGAA AAGCTCTTTA ATGCTCCTAT AAAGTTAGAG | 2340 |
| TCAGAAAAAA CATTTCAGTG TTTGCTATTG CTTGCTAAAA AAAGATACAT TGGAATACTG | 2400 |
| TCAAATGACA AATTGCTTAT GAAAGGTGTT GACTTAGTGA GAAAAACTGC TTGTAAATTT | 2460 |
| GTTCAAAATA CTAGCTCAAA AATTCTTAAT CTTATACTTA AAGACCCTGA GGTAAAAGCA | 2520 |
| GCTGCTCAGC TTTTGTCAAC AAAAGATCCA GACTATGCTT TTAGAGAAGG GCTTCCTGAT | 2580 |
| GGGTTTTTGA AAGTGATAGA CATTTTAAAT GAAAGCCACA AAAACCTCAG AACTGGGCAA | 2640 |
| GTGCCGGTAG AGGAATTAAC ATTTTCTACA GAATTGAGTA GACCTATTTC TTCTTACAAA | 2700 |
| ACTGAAAACT TGCCTCATTT AACTGTTTAT AAAAAAATTA TTACAAGGCA TGAAGAACCT | 2760 |
| CCACAAGTTC ATGACAGAAT CCCATACGTT TTTGTAGGCA AGACTACATC ATGCATATCA | 2820 |
| AACATGGCTG AAGACCCAAC ATACACGGTT CAAAATAATA TTCCAATTGC AGTGGATCTA | 2880 |
| TATTTTGATA AACTTATTCA CGGGGTAGCT AACATAATAC AGTGTCTCTT TAAAGACAGC | 2940 |
| AGTAAAACTG TGTCTGTTTT GTATAATTTT GTATCAACTC CTGTTTTATT TTCTTACGAG | 3000 |
| CTTCTAACTG ATCATTCTGT AAAAGCATAA | 3030 |

(2) INFORMATION FOR SEQ ID NO:25:

(i) SEQUENCE CHARACTERISTICS:
        (A) LENGTH: 3048 base pairs
        (B) TYPE: nucleic acid
        (C) STRANDEDNESS: double
        (D) TOPOLOGY: linear (xi) SEQUENCE DESCRIPTION: SEQ ID NO:25:

| | |
|---|---|
| ATGTCTGGGG GACTCTTCTA TAACCCTTTC CTAAGACCTA ATAAAGGCCT TCTGAAAAAG | 60 |
| CCTGACAAGG AGTACCTGCG TCTCATTCCC AAGTGTTTCC AGACACCAGG CGCCGCAGGG | 120 |
| GTGGTGGATG TGCGGGGGCC TCAGCCCCCC CTGTGCTTCT ACCAAGACTC CCTGACGGTG | 180 |
| GTGGGGGGTG ACGAGGATGG AAAGGGCATG TGGTGGCGCC AGCGTGCCCA AGAGGGCACG | 240 |
| GCAAGGCCGG AGGCAGACAC CCACGGAAGC CCTCTGGACT TCCATGTCTA CGACATACTC | 300 |
| GAGACGGTGT ACACGCACGA GAAATGCGCC GTCATTCCAT CGGATAAACA GGGGTATGTG | 360 |
| GTGCCATGTG GCATCGTCAT CAAGCTACTG GGCCGGCGCA AGGCCGATGG GGCCAGCGTG | 420 |
| TGTGTGAACG TGTTTGGGCA GCAGGCCTAC TTCTACGCCA GCGCGCCTCA GGGTCTGGAC | 480 |
| GTGGAGTTTG CAGTCCTCAG CGCCCTCAAG GCCAGCACCT TCGACCGCAG GACCCCCTGC | 540 |
| CGGGTCTCGG TGGAGAAGGT CACGCGCCGT TCCATTATGG GCTACGGCAA CCATGCCGGC | 600 |
| GACTACCACA AGATCACCCT CTCCCATCCC AACAGTGTGT GTCACGTGGC CACGTGGCTG | 660 |
| CAAGACAAGC ACGGGTGTCG GATCTTTGAG GCCAACGTGG ATGCCACGCG CCGCTTTGTC | 720 |
| CTGGACAATG ACTTTGTCAC CTTTGGCTGG TACAGCTGCC GCCGCGCCAT CCCCCGCCTC | 780 |
| CAGCACCGGG ACTCGTACGC CGAGCTCGAG TACGACTGTG AGGTGGGCGA CCTCTCGGTC | 840 |
| CGGCGTGAAG ACAGCTCCTG GCCCTCCTAC CAGGCCCTGG CCTTCGATAT CGAGTGTCTG | 900 |
| GGGGAGGAGG GCTTCCCCAC GGCCACCAAC GAGGCTGACC TGATCCTGCA GATATCCTGC | 960 |
| GTCCTCTGGT CGACAGGGGA GGAGGCCGGG CGCTATAGGC GCATCCTGCT GACGCTGGGC | 1020 |
| ACCTGCGAAG ACATAGAGGG GGTTGAGGTC TACGAGTTCC CATCGGAGCT GGACATGCTC | 1080 |
| TACGCCTTCT TCCAGCTCAT CAGAGACCTC AGCGTGGAGA TTGTGACCGG CTACAACGTG | 1140 |
| GCCAACTTTG ACTGGCCCTA CATTCTGGAC AGAGCCAGGC ACATCTACAG CATCAACCCA | 1200 |
| GCCTCTCTGG GCAAAATTAG GGCTGGGGGC GTCTGCGAGG TCAGGCGACC CCATGATGCG | 1260 |
| GGCAAGGGCT TCTTGCGGGC CAACACCAAG GTCCGCATCA CCGGCCTCAT CCCCATCGAC | 1320 |

```
ATGTACGCCG TGTGCCGGGA CAAGCTCAGC CTCTCAGACT ACAAGCTGGA CACAGTAGCC      1380
AGGCACCTAC TGGGGGCCAA GAAGGAGGAT GTGCATTACA AGGAGATTCC TCGCCTCTTT      1440
GCAGCGGGCC CCGAGGGGCG CAGGCGGCTC GGCATGTACT GCGTGCAGGA CTCGGCCCTG      1500
GTCATGGATC TGCTAAACCA TTTCGTGATC CACGTGGAGG TGGCAGAGAT TGCCAAGATC      1560
GCTCACATCC CCTGCAGGCG GGTGCTGGAC GATGGGCAGC AGATCCGCGT GTTCTCCTGC      1620
CTCCTGGCGG CCGCCCAAAA GGAAAACTTT ATCCTGCCCA TGCCCTCGGC CTCTGACCGG      1680
GACGGCTACC AGGGGCCAC CGTCATCCAG CCCCTGTCCG GATTCTACAA CTCCCCGGTT       1740
CTGGTGGTGG ACTTTGCCAG CCTCTACCCG AGCATCATTC AGGCTCATAA TCTCTGTTAT      1800
TCTACCATGA TAACGCCGGG AGAAGAGCAC AGGCTAGCCG GCCTGCGCCC GGGAGAAGAC      1860
TATGAGTCCT TCAGGCTCAC GGGGGGCGTC TACCACTTTG TAAAGAAGCA CGTGCACGAG      1920
TCCTTCTTGG CTAGTCTGTT GACCTCCTGG CTGGCCAAGC GCAAGGCCAT CAAGAAGCTG      1980
CTGGCGGCCT GCGAGGATCC GCGCCAAAGG ACCATCCTCG ACAAGCAGCA GCTGGCCATC      2040
AAGTGCACGT GCAACGCCGT CTACGGCTTC ACCGGGGTGG CCAACGGCCT CTTTCCCTGC      2100
CTCTCCATCG CCGAGACGGT GACGCTGCAG GGCCGCACGA TGTTGGAGCG GGCCAAGGCC      2160
TTCGTGGAGG CCCTGAGCCC CGCCAACCTG CAGGCCCTGG CCCCCTCCCC GGACGCCTGG      2220
GCGCCCCTCA ACCCCGAGGG CCAGCTTCGA GTCATCTACG GGACACGGA CTCGCTGTTT       2280
ATCGAGTGCC GGGGGTTTTC AGAGAGCGAG ACCCTGCGCT TGCCGATGC CCTGGCCGCC       2340
CACACCACCC GGAGCCTGTT TGTGGCCCCC ATCTCCCTGG AGGCCGAGAA GACCTTCTCC      2400
TGCCTGATGC TGATTACAAA GAAGAGATAT GTGGGGGTGC TGACGGACGG CAAGACCCTG      2460
ATGAAGGGGG TGGAGCTCGT CCGGAAGACG GCCTGCAAGT TTGTGCAGAC ACGCTGCCGG      2520
CGCGTGCTCG ACCTGGTGCT GGCGGATGCC CGGGTAAAGG AGGCGGCCAG CCTCCTCTCC      2580
CACCGGCCCT TCCAAGAGTC ATTTACACAA GGGCTACCTG TGGGCTTTTT GCCCGTCATT      2640
GACATCCTAA ACCAGGCCTA CACAGACCTC CGTGAAGGCA GGGTCCCCAT GGGGGAGCTC      2700
TGCTTTTCAA CGGAGCTCAG CCGCAAGCTC TCAGCCTACA AGAGCACCCA GATGCCTCAC      2760
CTGGCCGTCT ACCAGAAGTT CGTCGAGCGC AACGAGGAAC TGCCCCAGAT CCACGACCGC      2820
ATCCAGTACG TCTTTGTGGA GCCCAAGGGG GGAGTGAAGG GGGCGAGAAA GACGGAGATG      2880
GCCGAGGACC CGGCCTACGC CGAGCGGCAC GGCGTTCCCG TGGCCGTGGA TCATTATTTC      2940
GACAAGCTGC TCCAAGGAGC GGCCAACATC CTCCAGTGCC TCTTTGATAA CAACTCCGGG      3000
GCCGCCCTCT CCGTCCTCCA GAATTTTACA GCCCGGCCAC CATTCTAA                  3048

(2) INFORMATION FOR SEQ ID NO:26:

(i) SEQUENCE CHARACTERISTICS:
        (A) LENGTH: 3729 base pairs
        (B) TYPE: nucleic acid
        (C) STRANDEDNESS: double
        (D) TOPOLOGY: linear (xi) SEQUENCE DESCRIPTION: SEQ ID NO:26:

ATGTTTTTCA ACCCGTATCT GAGCGGCGGC GTGACCGGCG GTGCGGTCGC GGGTGGCCGG       60
CGTCAGCGTT CGCAGCCCGG CTCCGCGCAG GGCTCGGGCA AGCGGCCGCC ACAGAAACAG      120
TTTTTGCAGA TCGTGCCGCG AGGTGTCATG TTCGACGGTC AGACGGGGTT GATCAAGCAT      180
AAGACGGGAC GGCTGCCTCT CATGTTCTAT CGAGAGATTA AACATTTGTT GAGTCATGAC      240
ATGGTTTGGC CGTGTCCTTG GCGCGAGACC CTGGTGGGTC GCGTGGTGGG ACCTATTCGT      300
```

-continued

```
TTTCACACCT ACGATCAGAC GGACGCCGTG CTCTTCTTCG ACTCGCCCGA AAACGTGTCG      360

CCGCGCTATC GTCAGCATCT GGTGCCTTCG GGGAACGTGT TGCGTTTCTT CGGGGCCACA      420

GAACACGGCT ACAGTATCTG CGTCAACGTT TTCGGGCAGC GCAGCTACTT TTACTGTGAG      480

TACAGCGACA CCGATAGGCT GCGTGAGGTC ATTGCCAGCG TGGGCGAACT AGTGCCCGAA      540

CCGCGGACGC CATACGCCGT GTCTGTCACG CCGGCCACCA AGACCTCCAT CTATGGGTAC      600

GGGACGCGAC CCGTGCCCGA TTTGCAGTGT GTGTCTATCA GCAACTGGAC CATGGCCAGA      660

AAAATCGGCG AGTATCTGCT GGAGCAGGGT TTTCCCGTGT ACGAGGTCCG TGTGGATCCG      720

CTGACGCGTT TGGTCATCGA TCGGCGGATC ACCACGTTCG GCTGGTGCTC CGTGAATCGT      780

TACGACTGGC GGCAGCAGGG TCGCGCGTCG ACTTGTGATA TCGAGGTAGA CTGCGATGTC      840

TCTGACCTGG TGGCTGTGCC CGACGACAGC TCGTGGCCGC GCTATCGATG CCTGTCCTTC      900

GATATCGAGT GCATGAGCGG CGAGGGTGGT TTTCCCTGCG CCGAGAAGTC CGATGACATT      960

GTCATTCAGA TCTCGTGCGT GTGCTACGAG ACGGGGGGAA ACACCGCCGT GGATCAGGGG     1020

ATCCCAAACG GGAACGATGG TCGGGGCTGC ACTTCGGAGG GTGTGATCTT TGGGCACTCG     1080

GGTCTTCATC TCTTTACGAT CGGCACCTGC GGGCAGGTGG GCCCAGACGT GGACGTCTAC     1140

GAGTTCCCTT CCGAATACGA GCTGCTGCTG GGCTTTATGC TTTTCTTTCA ACGGTACGCG     1200

CCGGCCTTTG TGACCGGTTA CAACATCAAC TCTTTTGACT TGAAGTACAT CCTCACGCGT     1260

CTCGAGTACC TGTATAAGGT GGACTCGCAG CGCTTCTGCA AGTTGCCTAC GGCGCAGGGC     1320

GGCCGTTTCT TTTTACACAG CCCCGCCGTG GGTTTTAAGC GGCAGTACGC CGCCGCTTTT     1380

CCCTCGGCTT CTCACAACAA TCCGGCCAGC ACGGCCGCCA CCAAGGTGTA TATTGCGGGT     1440

TCGGTGGTTA TCGACATGTA CCCTGTATGC ATGGCCAAGA CTAACTCGCC CAACTATAAG     1500

CTCAACACTA TGGCCGAGCT TTACCTGCGG CAACGCAAGG ATGACCTGTC TTACAAGGAC     1560

ATCCCGCGTT GTTTCGTGGC TAATGCCGAG GCCGCGCCC AGGTAGGCCG TTACTGTCTG     1620

CAGGACGCCG TATTGGTGCG CGATCTGTTC AACACCATTA ATTTTCACTA CGAGGCCGGG     1680

GCCATCGCGC GGCTGGCTAA AATTCCGTTG CGGCGTGTCA TCTTTGACGG ACAGCAGATC     1740

CGTATCTACA CCTCGCTGCT GGACGAGTGC GCCTGCCGCG ATTTTATCCT GCCCAACCAC     1800

TACAGCAAAG GTACGACGGT GCCCGAAACG AATAGCGTTG CTGTGTCACC TAACGCTGCT     1860

ATCATCTCTA CCGCCGCTGT GCCCGGCGAC GCGGGTTCTG TGGCGGCTAT GTTTCAGATG     1920

TCGCCGCCCT TGCAATCTGC GCCGTCCAGT CAGGACGGCG TTTCACCCGG CTCCGGCAGT     1980

AACAGTAGTA GCAGCGTCGG CGTTTTCAGC GTCGGCTCCG GCAGTAGTGG CGGCGTCGGC     2040

GTTTCCAACG ACAATCACGG CGCCGGCGGT ACTGCGGCGG TTTCGTACCA GGGCGCCACG     2100

GTGTTTGAGC CCGAGGTGGG TTACTACAAC GACCCCGTGG CCGTGTTCGA CTTTGCCAGC     2160

CTCTACCCTT CCATCATCAT GGCCCACAAC CTCTGCTACT CCACCCTGCT GGTGCCGGGT     2220

GGCGAGTACC CTGTGGACCC CGCCGACGTA TACAGCGTCA CGCTAGAGAA CGGCGTGACC     2280

CACCGCTTTG TGCGTGCTTC GGTGCGCGTC TCGGTGCTCT CGGAACTGCT CAACAAGTGG     2340

GTTTCGCAGC GGCGTGCCGT GCGCGAATGC ATGCGCGAGT GTCAAGACCC TGTGCGCCGT     2400

ATGCTGCTCG ACAAGGAACA GATGGCGCTC AAAGTAACGT GCAACGCTTT CTACGGTTTT     2460

ACCGGCGTGG TCAACGGTAT GATGCCGTGT CTGCCCATCG CCGCCAGCAT CACGCGCATC     2520

GGTCGCGACA TGCTAGAGCG CACGGCGCGG TTCATCAAAG ACAACTTTTC AGAGCCGTGT     2580

TTTTTGCACA ATTTTTTTAA TCAGGAAGAC TATGTAGTGG GAACGCGGGA GGGGGATTCG     2640

GAGGAGAGCA GCGCGTTACC GGAGGGGCTC GAAACATCGT CAGGGGCTC GAACGAACGG     2700
```

```
CGGGTGGAGG CGCGGGTCAT CTACGGGAC ACGGACAGCG TGTTTGTCCG CTTTCGTGGC    2760

CTGACGCCGC AGGCTCTGGT GGCGCGTGGG CCCAGCCTGG CGCACTACGT GACGGCCTGT    2820

CTTTTTGTGG AGCCCGTCAA GCTGGAGTTT GAAAAGGTCT TCGTCTCTCT TATGATGATC    2880

TGCAAGAAAC GTTACATCGG CAAAGTGGAG GGCGCCTCGG GTCTGAGCAT GAAGGGCGTG    2940

GATCTGGTGC GCAAGACGGC CTGCGAGTTC GTCAAGGGCG TCACGCGTGA CGTCCTCTCG    3000

CTGCTCTTTG AGGATCGCGA GGTCTCGGAA GCAGCCGTGC GCCTGTCGCG CCTCTCACTC    3060

GATGAAGTCA AGAAGTACGG CGTGCCACGC GGTTTCTGGC GTATCTTACG CCGCTTGGTG    3120

CAGGCCCGCG ACGATCTGTA CCTGCACCGT GTGCGTGTCG AGGACCTGGT GCTTTCGTCG    3180

GTGCTCTCTA AGGACATCTC GCTGTACCGT CAATCTAACC TGCCGCACAT TGCCGTCATT    3240

AAGCGATTGG CGGCCCGTTC TGAGGAGCTA CCCTCGGTCG GGATCGGGT CTTTTACGTT    3300

CTGACGGCGC CCGGTGTCCG GACGGCGCCG CAGGGTTCCT CCGACAACGG TGATTCTGTA    3360

ACCGCCGGCG TGGTTTCCCG GTCGGACGCG ATTGATGGCA CGGACGACGA CGCTGACGGC    3420

GGCGGGGTAG AGGAGAGCAA CAGGAGAGGA GGAGAGCCGG CAAAGAAGAG GGCGCGGAAA    3480

CCACCGTCGG CCGTGTGCAA CTACGAGGTA GCCGAAGATC CGAGCTACGT GCGCGAGCAC    3540

GGCGTGCCCA TTCACGCCGA CAAGTACTTT GAGCAGGTTC TCAAGGCTGT AACTAACGTG    3600

CTGTCGCCCG TCTTTCCCGG CGGCGAAACC GCGCGCAAGG ACAAGTTTTT GCACATGGTG    3660

CTGCCGCGGC GCTTGCACTT GGAGCCGGCT TTTCTGCCGT ACAGTGTCAA GGCGCACGAA    3720

TGCTGTTGA                                                          3729

(2) INFORMATION FOR SEQ ID NO:27:

(i) SEQUENCE CHARACTERISTICS:
        (A) LENGTH: 3039 base pairs
        (B) TYPE: nucleic acid
        (C) STRANDEDNESS: double
        (D) TOPOLOGY: linear (xi) SEQUENCE DESCRIPTION: SEQ ID NO:27:

ATGGATTCGG TGTCGTTTTT TAATCCATAT TTGGAAGCGA ATCGCTTAAA GAAAAAAAGC      60

AGATCGAGTT ACATTCGTAT ACTTCCTCGC GGTATAATGC ATGATGGTGC GGCGGGATTA     120

ATAAAGGATG TTTGTGACTC TGAACCGCGT ATGTTTTATC GAGACCGACA GTATTTACTG     180

AGCAAAGAAA TGACCTGGCC GAGTTTGGAC ATAGCTCGGT CCAAGGATTA TGATCATATG     240

AGGATGAAGT TTCACATATA TGATGCTGTA GAAACGTTAA TGTTTACGGA TTCGATCGAG     300

AATCTTCCTT TTCAGTATAG ACATTTTGTG ATTCCTTCGG GGACAGTGAT TAGAATGTTT     360

GGGAGAACTG AGGACGGTGA GAAGATCTGC GTGAACGTGT TTGGACAGGA GCAATATTTC     420

TACTGCGAAT GCGTCGACGG AAGAAGCCTG AAGGCTACTA TAAACAATTT GATGTTAACC     480

GGCGAGGTTA AAATGTCGTG TTCTTTTGTC ATTGAGCCGG CTGATAAGTT GTCGTTGTAT     540

GGGTACAATG CCAACACTGT CGTTAATCTG TTTAAAGTGA GTTTTGGAAA TTTTTATGTA     600

TCTCAACGTA TTGAAAGAT TCTGCAGAAT GAGGGATTCG TAGTTTATGA AATCGACGTA     660

GATGTTTTGA CTCGTTTCTT CGTCGATAAT GGTTTTTTGA GTTTCGGATG GTATAATGTA     720

AAAAAATATA TTCCTCAAGA TATGGGAAAA GGGAGTAATC TTGAGGTGGA AATTAATTGT     780

CATGTCTCTG ATTTAGTTTC TCTGGAAGAC GTTAATTGGC CTTTATATGG ATGCTGGTCT     840

TTCGACATAG AGTGTTTGGG TCAAAATGGG AATTTCCCGG ATGCCGAAAA TTTAGGTGAT     900

ATAGTTATTC AGATTTCTGT AATTAGTTTC GATACGGAAG GTGACCGTGA TGAGCGACAT     960

CTGTTTACTC TGGGAACATG TGAAAAAATT GACGGCGTGC ATATATATGA ATTTGCGTCA    1020
```

```
GAGTTTGAAT TACTTTTGGG TTTTTTCATA TTTTTAAGGA TTGAGTCTCC GGAGTTTATT      1080

ACCGGTTATA ATATTAATAA TTTTGATTTA AAATATTTGT GTATAAGGAT GGATAAGATT      1140

TACCATTATG ATATTGGTTG TTTTTCGAAA CTGAAGAATG GAAAGATTGG AATCTCTGTC      1200

CCTCACGAAC AGTACAGGAA GGGGTTCCTT CAGGCGCAAA CCAAGGTGTT TACTTCCGGA      1260

GTGTTGTATC TGGATATGTA TCCCGTCTAT TCTAGTAAGA TAACGGCGCA GAATTACAAA      1320

CTGGATACTA TTGCTAAGAT CTGTCTCCAG CAAGAAAGG AGCAGTTATC GTACAAGGAA       1380

ATACCAAAGA AATTTATTAG TGGACCCAGT GGCAGGGCTG TTGTCGGTAA GTATTGTCTA      1440

CAGGACTCTG TCTTAGTTGT GCGTCTCTTT AAACAGATTA ATTATCATTT TGAGGTTGCC      1500

GAGGTCGCCA GATTGGCACA CGTCACGGCT AGATGTGTGG TGTTCGAGGG TCAGCAGAAG     1560

AAGATATTTC CCTGCATTCT TACGGAAGCA AAACGCCGTA ATATGATTCT TCCGAGTATG      1620

GTGTCTTCGC ACAATAGACA AGGGATAGGT TACAAAGGGG CTACCGTTTT GGAGCCTAAG     1680

ACGGGTTATT ATGCTGTGCC TACCGTGGTG TTTGATTTTC AAAGTTTGTA TCCGAGCATT     1740

ATGATGGCGC ATAATCTGTG TTATAGTACT TTAGTTTTGG ATGAACGACA GATAGCTGGA     1800

TTGTCAGAGA GTGACATCTT AACCGTGAAG TTGGGGGATG AGACTCATCG GTTTGTGAAG    1860

CCTTGTATCC GTGAGTCTGT GCTTGGGAGT CTACTAAAGG ACTGGCTGGC CAAGAGACGA    1920

GAAGTGAAGG CGGAGATGCA GAACTGTTCG GATCCGATGA TGAAACTTCT TCTGGATAAA    1980

AAGCAGCTCG CTCTGAAAAC AACATGTAAC TCGGTGTACG GTGTCACGGG AGCGGCGCAC    2040

GGGTTATTGC CGTGTGTTGC GATTGCTGCT TCTGTAACGT GTCTTGGAAG AGAGATGCTT    2100

TGTTCCACGG TGGATTATGT TAATTCCAAG ATGCAGTCCG AGCAATTTTT TTGCGAGGAA    2160

TTTGGTTTAA CGTCATCAGA TTTTACTGGT GATTTGGAAG TGGAGGTAAT TTATGGTGAT    2220

ACGGATAGCA TCTTTATGTC TGTCAGAAAT ATGGTTAATC AGTCTCTGCG AAGGATTGCG    2280

CCGATGATCG CCAAACATAT CACAGATCGT CTGTTCAAGT CGCCTATCAA GCTCGAGTTT    2340

GAAAAGATTT TATGTCCGCT AATTTTGATT TGTAAAAAAA GATACATTGG TAGACAGGAT    2400

GATTCGCTTT TAATTTTTAA GGGGGTAGAT CTGGTGAGAA AGACTTCTTG CGATTTTGTG    2460

AAGGGTGTGG TGAAAGATAT CGTGGACTTG TTGTTCTTTG ATGAAGAGGT TCAGACTGCT    2520

GCTGTGGAGT TTTCTCACAT GACACAGACA CAGTTGCGTG AACAAGGAGT GCCTGTGGGT    2580

ATTCATAAAA TTTTGCGTCG TCTGTGCGAA GCGCGGGAGG AGCTTTTTCA GAATCGGGCA    2640

GACGTGAGAC ATTTAATGTT GTCCTCTGTG CTTTCCAAAG AAATGGCTGC ATATAAGCAA    2700

CCGAATCTGG CTCACCTTAG CGTCATTAGA AGGTTGGCGC AGAGAAAGGA AGAAATTCCG    2760

AATGTAGGTG ACCGAATTAT GTACGTGTTA ATAGCACCAT CTATTGGCAA TAAACAGACG    2820

CATAACTATG AATTAGCAGA AGATCCCAAC TATGTGATAG AACACAAGAT TCCTATACAT    2880

GCGGAGAAGT ATTTCGATCA GATTATCAAG GCTGTGACTA ATGCGATCTC ACCCATTTTT    2940

CCGAAAACCG ATATAAAAAA AGAGAAGTTA CTATTGTATT TACTTCCTAT GAAAGTGTAT    3000

TTGGATGAAA CATTTTCTGC TATTGCAGAG GTAATGTGA                           3039

(2) INFORMATION FOR SEQ ID NO:28:

(i) SEQUENCE CHARACTERISTICS:
        (A) LENGTH: 3585 base pairs
        (B) TYPE: nucleic acid
        (C) STRANDEDNESS: double
        (D) TOPOLOGY: linear (xi) SEQUENCE DESCRIPTION: SEQ ID NO:28:
```

-continued

| | | | | | |
|---|---|---|---|---|---|
| ATGGCGATCA | GAACGGGGTT | TTGTAATCCC | TTTTTAACCC | AAGCATCAGG | GATTAAATAT | 60 |
| AACCCAAGAA | CCGGGCGCGG | TAGTAACAGA | GAATTTCTTC | ATAGTTACAA | AACTACCATG | 120 |
| TCATCGTTTC | AATTTTTGGC | CCCTAAATGT | TTAGATGAAG | ATGTGCCCAT | GGAAGAACGA | 180 |
| AAGGGGGTTC | ACGTCGGTAC | ACTTAGTCGA | CCGCCTAAAG | TTTACTGTAA | TGGAAAAGAA | 240 |
| GTTCCGATTC | TGGATTTTCG | TTGTTCCAGC | CCCTGGCCTA | GACGCGTGAA | TATTTGGGGG | 300 |
| GAAATCGACT | TTCGTGGGGA | TAAGTTTGAC | CCCCGCTTTA | ACACATTCCA | TGTATATGAT | 360 |
| ATTGTCGAAA | CAACAGAAGC | CGCGTCTAAT | GGAGATGTAT | CCCGGTTTGC | AACTGCAACA | 420 |
| CGACCGCTTG | GTACCGTTAT | TACTTTACTT | GGCATGTCCC | GATGTGGAAA | AAGGGTGGCA | 480 |
| GTTCATGTAT | ACGGCATCTG | TCAATATTTT | TATATAAACA | AAGCCGAGGT | GGATACCGCT | 540 |
| TGTGGCATAC | GTTCCGGTAG | CGAGTTATCT | GTATTACTTG | CCGAGTGTTT | ACGCAGTTCT | 600 |
| ATGATAACAC | AAAATGATGC | AACGTTAAAT | GGAGACAAGA | ACGCTTTTCA | TGGTACCTCG | 660 |
| TTTAAAAGCG | CATCTCCAGA | AAGCTTTCGC | GTTGAGGTTA | TTGAGCGCAC | AGATGTTTAT | 720 |
| TACTACGATA | CACAGCCATG | TGCGTTTTAC | AGGGTGTATT | CTCCCTCATC | TAAATTTACA | 780 |
| AATTATCTTT | GTGATAACTT | TCACCCGGAG | TTGAAAAAGT | ATGAAGGTCG | GGTAGACGCT | 840 |
| ACCACTCGTT | TTCTAATGGA | TAATCCCGGC | TTTGTTAGTT | TTGGTTGGTA | TCAACTAAAA | 900 |
| CCTGGAGTTG | ATGGGAACG | TGTTCGAGTT | CGACCGGCAA | GTCGCCAATT | AACGTTAAGC | 960 |
| GACGTTGAAA | TTGACTGCAT | GTCGGATAAT | CTGCAGGCTA | TACCAAACGA | TGACTCATGG | 1020 |
| CCTGACTACA | AGTTGTTATG | TTTCGATATT | GAATGTAAAT | CAGGAGGATC | TAATGAGCTG | 1080 |
| GCGTTTCCCG | ATGCAACACA | TCTGGAGGAT | CTTGTAATCC | AAATTTCTTG | TCTATTATAT | 1140 |
| TCAATCCCTC | GACAGTCTTT | AGAACACATT | TTACTGTTTT | CCCTTGGCTC | TTGTGACTTA | 1200 |
| CCACAAAGGT | ATGTACAAGA | AATGAAGGAC | GCGGGGTTAC | CGGAGCCGAC | TGTGCTGGAG | 1260 |
| TTTGATAGTG | AATTCGAGCT | ATTAATTGCA | TTTATGACCC | TCGTAAAACA | GTACGCTCCC | 1320 |
| GAGTTTGCCA | CAGGTTATAA | CATTGTTAAT | TTTGATTGGG | CGTTTATTAT | GGAGAAACTT | 1380 |
| AATTCTATAT | ACAGTCTCAA | GCTTGATGGT | TATGGCAGTA | TAAACCGTGG | GGGTCTGTTT | 1440 |
| AAGATATGGG | ATGTTGGCAA | ATCCGGATTT | CAGCGACGAA | GCAAGGTAAA | GATCAACGGT | 1500 |
| CTCATATCTC | TGGATATGTA | TGCAATTGCA | ACTGAAAAAT | TAAAACTCTC | GAGTTATAAA | 1560 |
| TTAGATTCGG | TTGCACGTGA | AGCTCTAAAT | GAGTCCAAGA | GAGATTTGCC | CTACAAAGAC | 1620 |
| ATTCCGGGAT | ATTACGCTAG | TGGACCGAAT | ACACGAGGAA | TTATTGGTGA | ATATTGTATA | 1680 |
| CAAGACTCGG | CTCTTGTGGG | GAAACTGTTT | TTTAAATATT | TACCACACCT | TGAGTTATCC | 1740 |
| GCGGTTGCAA | GGCTAGCTAG | AATTACTTTA | ACCAAGGCTA | TTTACGACGG | ACAGCAGGTT | 1800 |
| AGGATTTACA | CCTGTTTATT | AGGACTGGCT | TCGTCTCGAG | GATTTATTTT | ACCCGATGGG | 1860 |
| GGATACCCAG | CTACTTTTGA | ATATAAGGAT | GTTATTCCCG | ATGTCGGGGA | TGTTGAGGAA | 1920 |
| GAGATGGATG | AAGACGAGAG | CGTTTCTCCC | ACTGGTACGT | CAAGTGGGCG | AAATGTAGGA | 1980 |
| TATAAAGGAG | CCAGGGTTTT | TGACCCTGAT | ACGGGATTTT | TATCGATCC | GGTGGTCGTA | 2040 |
| TTGGATTTTG | CAAGTTTATA | TCCAAGTATA | ATTCAGGCCC | ATAACTTATG | TTTTACCACG | 2100 |
| CTAACGTTAA | ATTTTGAGAC | GGTTAAACGT | TTGAATCCAT | CCGATTATGC | CACCTTTACA | 2160 |
| GTTGGAGGAA | AACGTCTTTT | TTTTGTGCGC | TCTAACGTTC | GAGAAAGTCT | GCTGGGTGTT | 2220 |
| CTTTTAAAAG | ACTGGTTGGC | TATGCGCAAG | GCTATTAGAG | CGCGCATACC | CGGAAGTTCT | 2280 |
| TCAGATGAAG | CAGTGTTATT | AGACAAACAA | CAAGCCGCGA | TAAAGTAGT | TTGTAATTCC | 2340 |
| GTGTACGGTT | TTACTGGAGT | TGCGCAGGGA | TTTCTGCCAT | GTTTATACGT | AGCGGCCACT | 2400 |

```
GTCACTACAA TTGGCCGTCA AATGTTATTA AGTACCAGAG ATTATATTCA TAATAACTGG    2460

GCCGCATTTG AACGTTTTAT TACAGCGTTT CCAGACATTG AAAGTAGCGT TCTCTCCCAA    2520

AAAGCGTACG AGGTAAAGGT TATATATGGA GATACGGATT CTGTGTTTAT CCGATTCAAG    2580

GGTGTTAGTG TTGAGGGGAT AGCTAAAATC GGCGAGAAAA TGGCACATAT AATTTCAACG    2640

GCTCTGTTTT GTCCTCCTAT AAAGTTGGAG TGTGAAAAAA CTTTTATAAA ACTTTTGCTT    2700

ATAACAAAGA AAAAGTACAT TGGGGTAATT TACGGCGGAA AGGTTTTAAT GAAGGGAGTC    2760

GACTTGGTTA GAAAAAACAA CTGTCAATTT ATTAACGATT ATGCCCGCAA ACTTGTAGAA    2820

CTGTTGTTAT ATGACGACAC CGTCTCGCGT GCTGCGGCGG AGGCGTCGTG TGTTTCCATT    2880

GCTGAATGGA ATAGACGGGC CATGCCGTCT GGGATGGCCG GGTTTGGACG CATAATTGCA    2940

GATGCACATC GCCAGATTAC ATCACCCAAA TTGGATATTA ATAAGTTTGT TATGACGGCC    3000

GAGCTTAGTC GTCCACCATC CGCCTACATA AACCGTCGCT TGGCTCACTT AACAGTATAT    3060

TATAAATTAG TAATGAGACA GGGTCAAATC CCAAACGTTC GAGAACGCAT CCCTTATGTT    3120

ATTGTGGCCC CCACAGACGA AGTGGAGGCT GATGCAAAAA GTGTAGCTTT GCTACGTGGA    3180

GATCCTTTAC AGAATACCGC AGGTAAACGG TGTGGGAAG CAAAGCGTAA GTTAATAATA    3240

TCTGACTTAG CGGAAGATCC CATTCACGTA ACATCACACG GGCTGTCTTT AAACATTGAC    3300

TATTATTTTT CTCATCTCAT TGGGACGGCG AGTGTAACTT TTAAGGCGTT ATTTGGAAAC    3360

GACACTAAAC TCACAGAACG GCTTTTAAAA CGTTTTATTC CAGAGACACG AGTTGTTAAC    3420

GTTAAAATGC TAAACCGCTT GCAGGCGGCA GGCTTTGTTT GTATACACGC CCCGTGCTGG    3480

GATAATAAAA TGAACACTGA AGCTGAAATC ACCGAGGAGG AACAAAGTCA TCAAATAATG    3540

CGTAGAGTCT TTTGTATTCC AAAAGCAATT CTCCATCAAA GTTAA                    3585

(2) INFORMATION FOR SEQ ID NO:29:

(i) SEQUENCE CHARACTERISTICS:
        (A) LENGTH: 3708 base pairs
        (B) TYPE: nucleic acid
        (C) STRANDEDNESS: double
        (D) TOPOLOGY: linear (xi) SEQUENCE DESCRIPTION: SEQ ID NO:29:

ATGTTTTCCG GTGGCGGCGG CCCGCTGTCC CCCGGAGGAA AGTCGGCGGC CAGGGCGGCG      60

TCCGGGTTTT TTGCGCCCGC CGGCCCTCGC GGAGCCGGCC GGGGACCCCC GCCTTGCTTG     120

AGGCAAAACT TTTACAACCC CTACCTCGCC CCAGTCGGGA CGCAACAGAA GCCGACCGGG     180

CCAACCCAGC GCCATACGTA CTATAGCGAA TGCGATGAAT TTCGATTCAT CGCCCCGCGG     240

GTGCTGGACG AGGATGCCCC CCCGGAGAAG CGCGCCGGGG TGCACGACGG TCACCTCAAG     300

CGCGCCCCCA AGGTGTACTG CGGGGGGGAC GAGCGCGACG TCCTCCGCGT CGGGTCGGGC     360

GGCTTCTGGC CGCGGCGCTC GCGCCTGTGG GCGGCGTGG ACCACGCCCC GGCGGGGTTC     420

AACCCCACCG TCACCGTCTT TCACGTGTAC GACATCCTGG AGAACGTGGA GCACGCGTAC     480

GGCATGCGCG CGGCCCAGTT CCACGCGCGG TTTATGGACG CCATCACACC GACGGGGACC     540

GTCATCACGC TCCTGGGCCT GACTCCGGAA GGCCACCGGG TGGCCGTTCA CGTTTACGGC     600

ACGCGGCAGT ACTTTTACAT GAACAAGGAG GAGGTCGACA GGCACCTACA ATGCCGCGCC     660

CCACGAGATC TCTGCGAGCG CATGGCCGCG GCCCTGCGCG AGTCCCCGGG CGCGTCGTTC     720

CGCGGCATTT CCGCGGACCA CTTCGAGGCG GAGGTGGTGG AGCGCACCGA CGTGTACTAC     780

TACGAGACGC GCCCCGCTCT GTTTTACCGC GTCTACGTCC GAAGCGGGCG CGTGCTGTCG     840

TACCTGTGCG ACAACTTCTG CCCCGGCCATC AAGAAGTACG AGGGTGGGGT CGACGCCACC     900
```

-continued

| | |
|---|---|
| ACCCGGTTCA TCCTGGACAA CCCCGGGTTC GTCACCTTCG GCTGGTACCG TCTCAAACCG | 960 |
| GGCCGGAACA ACACGCTAGC CCAGCCGCGG GCCCCGATGG CCTTCGGGAC ATCCAGCGAC | 1020 |
| GTCGAGTTTA ACTGTACGGC GGACAACCTG GCCATCGAGG GGGGCATGAG CGACCTACCG | 1080 |
| GCATACAAGC TCATGTGCTT CGATATCGAA TGCAAGGCGG GGGGGGAGGA CGAGCTGGCC | 1140 |
| TTTCCGGTGG CCGGGCACCC GGAGGACCTG GTCATCCAGA TATCCTGTCT GCTCTACGAC | 1200 |
| CTGTCCACCA CCGCCCTGGA GCACGTCCTC CTGTTTTCGC TCGGTTCCTG CGACCTCCCC | 1260 |
| GAATCCCACC TGAACGAGCT GGCGGCCAGG GGCCTGCCCA CGCCCGTGGT TCTGGAATTC | 1320 |
| GACAGCGAAT TCGAGATGCT GTTGGCCTTC ATGACCCTTG TGAAACAGTA CGGCCCCGAG | 1380 |
| TTCGTGACCG GGTACAACAT CATCAACTTC GACTGGCCCT TCTTGCTGGC CAAGCTGACG | 1440 |
| GACATTTACA AGGTCCCCCT GGACGGGTAC GGCCGCATGA ACGGCCGGGG CGTGTTTCGC | 1500 |
| GTGTGGGACA TAGGCCAGAG CCACTTCCAG AAGCGCAGCA AGATAAAGGT GAACGGCATG | 1560 |
| GTGAGCATCG ACATGTACGG GATTATAACC GACAAGATCA AGCTCTCGAG CTACAAGCTC | 1620 |
| AACGCCGTGG CCGAAGCCGT CCTGAAGGAC AAGAAGAAGG ACCTGAGCTA TCGCGACATC | 1680 |
| CCCGCCTACT ACGCCGCCGG GCCCGCGCAA CGCGGGGTGA TCGGCGAGTA CTGCATACAG | 1740 |
| GATTCCCTGC TGGTGGGCCA GCTGTTTTTT AAGTTTTTGC CCCATCTGGA GCTCTCGGCC | 1800 |
| GTCGCGCGCT TGGCGGGTAT TAACATCACC CGCACCATCT ACGACGGCCA GCAGATCCGC | 1860 |
| GTCTTTACGT GCCTGCTGCG CCTGGCCGAC CAGAAGGGCT TTATTCTGCC GGACACCCAG | 1920 |
| GGGCGATTTA GGGGCGCCGG GGGGGAGGCG CCCAAGCGTC CGGCCGCAGC CCGGGAGGAC | 1980 |
| GAGGAGCGGC CAGAGGAGGA GGGGGAGGAC GAGGACGAAC GCGAGGAGGG CGGGGCGAG | 2040 |
| CGGGAGCCGG ACGGCGCGCG GGAGACCGCC GGCCGGCACG TGGGGTACCA GGGGGCCAGG | 2100 |
| GTCCTTGACC CCACTTCCGG GTTTCACGTG AACCCCGTGG TGGTGTTCGA CTTTGCCAGC | 2160 |
| CTGTACCCCA GCATCATCCA GGCCCACAAC CTGTGCTTCA GCACGCTCTC CCTGAGGGCC | 2220 |
| GACGCAGTGG CGCACCTGGA GGCGGGCAAG GACTACCTGG AGATCGAGGT GGGGGGGCGA | 2280 |
| CGGCTGTTCT TCGTCAAGGC TCACGTGCGA GAGAGCCTCC TCAGCATCCT CCTGCGGGAC | 2340 |
| TGGCTCGCCA TGCGAAAGCA GATCCGCTCG CGGATTCCCC AGAGCAGCCC CGAGGAGGCC | 2400 |
| GTGCTCCTGG ACAAGCAGCA GGCCGCCATC AAGGTCGTGT GTAACTCGGT GTACGGGTTC | 2460 |
| ACGGGAGTGC AGCACGGACT CCTGCCGTGC CTGCACGTTG CCGCGACGGT GACGACCATC | 2520 |
| GGCCGCGAGA TGCTGCTCGC GACCCGCGAG TACGTCCACG CGCGCTGGGC GGCCTTCGAA | 2580 |
| CAGCTCCTGG CCGATTTCCC GGAGGCGGCC GACATGCGCG CCCCCGGGCC CTATTCCATG | 2640 |
| CGCATCATCT ACGGGACACG GGACTCCATA TTTGTGCTGT GCCGCGGCCT CACGGCCGCC | 2700 |
| GGGCTGACGG CCATGGGCGA CAAGATGGCG AGCCACATCT CGCGCGCGCT GTTTCTGCCC | 2760 |
| CCCATCAAAC TCGAGTGCGA AAAGACGTTC ACCAAGCTGC TGCTGATCGC CAAGAAAAAG | 2820 |
| TACATCGGCG TCATCTACGG GGGTAAGATG CTCATCAAGG GCGTGGATCT GGTGCGCAAA | 2880 |
| AACAACTGCG CGTTTATCAA CCGCACCTCC AGGGCCCTGG TCGACCTGCT GTTTTACGAC | 2940 |
| GATACCGTCT CCGGAGCGGC CGCCGCGTTA GCCGAGCGCC CCGCAGAGGA GTGGCTGGCG | 3000 |
| CGACCCCTGC CGAGGGACT GCAGGCGTTC GGGGCCGTCC TCGTAGACGC CCATCGGCGC | 3060 |
| ATCACCGACC GGAGAGGGA CATCCAGGAC TTTGTCCTCA CCGCCGAACT GAGCAGACAC | 3120 |
| CCGCGCGCGT ACACCAACAA GCGCCTGGCC CACCTGACGG TGTATTACAA GCTCATGGCC | 3180 |
| CGCCGCGCGC AGGTCCCGTC CATCAAGGAC CGGATCCCGT ACGTGATCGT GGCCCAGACC | 3240 |
| CGCGAGGTAG AGGAGACGGT CGCGCGGCTG GCCGCCCTCC GCGAGCTAGA CGCCGCCGCC | 3300 |

-continued

```
CCAGGGGACG AGCCCGCCCC CCCCGCGGCC CTGCCCTCCC CGGCCAAGCG CCCCCGGGAG    3360

ACGCCGTCGC CTGCCGACCC CCCGGGAGGC GCGTCCAAGC CCCGCAAGCT GCTGGTGTCC    3420

GAGCTGGCCG AGGATCCCGC ATACGCCATT GCCCACGGCG TCGCCCTGAA CACGGACTAT    3480

TACTTCTCCC ACCTGTTGGG GGCGGCGTGC GTGACATTCA AGGCCCTGTT TGGGAATAAC    3540

GCCAAGATCA CCGAGAGTCT GTTAAAAAGG TTTATTCCCG AAGTGTGGCA CCCCCCGGAC    3600

GACGTGACCG CGCGGCTCCG GGCCGCAGGG TTCGGGCGG TGGGTGCCGG CGCTACGGCG     3660

GAGGAAACTC GTCGAATGTT GCATAGAGCC TTTGATACTC TAGCATGA                 3708
```

(2) INFORMATION FOR SEQ ID NO:30:

(i) SEQUENCE CHARACTERISTICS:
        (A) LENGTH: 1008 amino acids
        (B) TYPE: amino acid
        (C) STRANDEDNESS: single
        (D) TOPOLOGY: linear (xi) SEQUENCE DESCRIPTION: SEQ ID NO:30:

```
Met Ser Phe Tyr Asn Pro Tyr Leu Val Lys Arg Thr Phe Leu Lys Lys
1               5                   10                  15

Ala Ala Pro Ser Arg Pro Thr Lys Glu Tyr Thr Arg Ile Ile Pro Lys
            20                  25                  30

Cys Phe Lys Thr Pro Gly Ala Ala Gly Val Val Pro His Thr Ser Thr
        35                  40                  45

Leu Asp Pro Val Cys Phe Val Gly Asp Lys Glu Thr Pro Ile Leu Tyr
    50                  55                  60

Gly Asp Gly Ser Arg Ser Leu Trp Ser Ala Gly Arg Gly Gly Pro
65                  70                  75                  80

Gly Thr Gly Ala Gly Gln Gly His Thr Pro Val Ala Leu Thr Phe His
                85                  90                  95

Val Tyr Asp Ile Ile Glu Thr Val Tyr Gly Gln Asp Arg Cys Asp His
            100                 105                 110

Val Pro Phe Gln Phe Gln Thr Asp Ile Ile Pro Ser Gly Thr Val Leu
        115                 120                 125

Lys Leu Leu Gly Arg Thr Ser Asp Asp Arg Ser Val Cys Val Asn Val
    130                 135                 140

Phe Arg Gln Glu Leu Tyr Phe Tyr Val Arg Val Pro Glu Gly Leu Lys
145                 150                 155                 160

Leu Asp Phe Leu Ile Gln Gln Cys Ser Arg Glu Asn Phe Asn Phe Ser
                165                 170                 175

Gln Gly Arg Tyr Arg Tyr Glu Lys Thr Ser Lys Arg Val Leu Arg Glu
            180                 185                 190

Tyr Cys Val Glu Ala Arg Glu Val Tyr Arg Val Phe Ala Ser Ser Gln
        195                 200                 205

Gly Phe Val Asp Leu Leu Ala Gly Gly Leu Thr Ala Ala Gly Cys Glu
    210                 215                 220

Val Phe Glu Thr Asn Val Asp Ala Ala Arg Arg Phe Ile Ile Asp Asn
225                 230                 235                 240

Gly Phe Ser Thr Phe Gly Trp Tyr Ser Cys Ala Ala Val Pro Arg
                245                 250                 255

Gln Gly Gly Ala Ala Arg Asp Ser Trp Thr Glu Leu Glu Tyr Asp Cys
            260                 265                 270

Ala Ala Gly Asp Leu Glu Phe His Ala Gly Arg Ala Asp Trp Pro Gly
        275                 280                 285
```

-continued

```
Tyr Asn Val Leu Ser Phe Asp Ile Glu Cys Leu Gly Glu Asn Gly Phe
    290                 295                 300

Pro Asn Ala Ser Arg Asp Glu Asp Met Ile Leu Gln Ile Ser Cys Val
305                 310                 315                 320

Ile Trp Lys Ala Gly Ser Gly Glu Ala Pro Arg Ser Val Leu Leu Asn
                325                 330                 335

Leu Gly Thr Cys Glu Glu Ile Glu Gly Val Glu Val Tyr Gln Cys Pro
            340                 345                 350

Ser Glu Leu Asp Leu Leu Tyr Leu Phe Phe Thr Met Ile Arg Asp Ala
        355                 360                 365

Asp Val Glu Phe Val Thr Gly Tyr Asn Ile Ser Asn Phe Asp Phe Pro
    370                 375                 380

Tyr Val Ile Asp Arg Ala Thr Gln Val Tyr Asn Leu Asn Leu Lys Glu
385                 390                 395                 400

Phe Thr Arg Val Arg Ser Ser Ile Phe Glu Val His Lys Pro Lys
                405                 410                 415

Asn Ser Ser Ala Gly Phe Met Arg Ala Val Ser Lys Val Lys Val Ala
                420                 425                 430

Gly Val Val Pro Ile Asp Met Tyr Gln Val Cys Arg Asp Lys Leu Ser
            435                 440                 445

Leu Ser Asn Tyr Lys Leu Asp Thr Val Ala Gly Glu Cys Val Gly Ala
        450                 455                 460

Lys Lys Glu Asp Val Ser Tyr Lys Glu Ile Pro His Leu Phe Arg Gln
465                 470                 475                 480

Gly Pro Gly Gly Arg Ala Arg Leu Gly Leu Tyr Cys Val Lys Asp Ser
                485                 490                 495

Ala Leu Val Leu Asp Leu Leu Arg Tyr Phe Met Thr His Val Glu Ile
                500                 505                 510

Ser Glu Ile Ala Lys Ile Ala Lys Ile Pro Thr Arg Arg Val Leu Thr
        515                 520                 525

Asp Gly Gln Gln Ile Arg Val Phe Ser Cys Leu Leu Asp Val Ala Gly
    530                 535                 540

Arg Glu Gly Tyr Ile Leu Pro Val Asp Arg His Ala Asp Ala Glu Gly
545                 550                 555                 560

Tyr Gln Gly Ala Thr Val Ile Asp Pro Ser Pro Gly Phe Tyr Asn Thr
                565                 570                 575

Pro Val Leu Val Val Asp Phe Ala Ser Leu Tyr Pro Thr Ile Ile Gln
                580                 585                 590

Ala His Asn Leu Cys Tyr Ser Thr Met Ile Pro Gly Asp Arg Leu Cys
        595                 600                 605

Leu His Pro His Leu Gly Pro Gly Asp Tyr Glu Thr Phe Glu Leu Ala
    610                 615                 620

Ser Gly Pro Val His Phe Val Lys Lys His Lys Ala Val Ser Leu Leu
625                 630                 635                 640

Ala Thr Leu Leu Asn Val Trp Leu Ala Lys Arg Lys Ala Ile Arg Arg
                645                 650                 655

Glu Leu Ala Thr Val Ser Asp Glu Ala Val Arg Thr Ile Leu Asp Lys
            660                 665                 670

Gln Gln Leu Ala Ile Lys Val Thr Cys Asn Ala Val Tyr Gly Phe Thr
        675                 680                 685

Gly Val Ala Ser Gly Ile Leu Pro Cys Leu Lys Ile Ala Glu Thr Val
    690                 695                 700

Thr Phe Gln Gly Arg Arg Met Leu Glu Asn Ser Lys Arg Tyr Ile Glu
705                 710                 715                 720
```

Gly Val Thr Pro Glu Gly Leu Ala Asp Ile Leu Gly Arg Arg Val Glu
                725                 730                 735

Cys Ala Pro Asp Ala Ser Phe Lys Val Ile Tyr Gly Asp Thr Asp Ser
            740                 745                 750

Leu Phe Ile His Cys Arg Gly Tyr Arg Pro Glu Gln Val Thr Gly Phe
                755                 760                 765

Cys Asp Glu Leu Ala Ala His Met Thr Arg Thr Leu Phe Val Asp Pro
770                 775                 780

Ile Lys Leu Glu Ala Glu Lys Thr Phe Lys Cys Leu Ile Leu Leu Thr
785                 790                 795                 800

Lys Lys Arg Tyr Ile Gly Met Met Thr Thr Asp Arg Leu Leu Met Lys
                805                 810                 815

Gly Val Asp Leu Val Arg Lys Thr Ala Cys Arg Phe Val Gln Glu Thr
                820                 825                 830

Thr Lys Ala Ile Leu Asp Leu Val Met Gly Asp Glu Ala Val Arg Ala
                835                 840                 845

Ala Ala Glu Arg Leu Cys Ala Met Arg Val Glu Glu Val Cys Ala Arg
850                 855                 860

Gly Pro Pro Val Gly Phe Leu Lys Val Val Asp Ile Leu Asn Asp Ser
865                 870                 875                 880

Tyr Arg Lys Leu Arg Leu Asn Arg Val Pro Val Gly Gln Leu Ser Phe
                885                 890                 895

Ser Thr Glu Leu Ser Arg Pro Ile Ser Tyr Tyr Lys Thr Leu Thr Leu
                900                 905                 910

Pro His Leu Val Val Tyr His Lys Ile Met Gln Arg Asn Glu Glu Leu
                915                 920                 925

Pro Gln Ile His Asp Arg Ile Ala Tyr Val Phe Val Gln Ser Pro Lys
930                 935                 940

Gly Lys Leu Arg Ser Glu Met Ala Glu Asp Pro Ala Tyr Ala Ala Gln
945                 950                 955                 960

His Asn Ile Pro Pro Ala Val Asp Leu Tyr Phe Asp Lys Val Ile His
                965                 970                 975

Gly Ala Ala Asn Ile Leu Gln Cys Leu Phe Glu Asn Asp Ser Asp Lys
                980                 985                 990

Ala Ala Arg Val Leu Tyr Asn Phe Ala Asp Leu Pro Pro Asp Asp Leu
                995                 1000                1005

(2) INFORMATION FOR SEQ ID NO:31:

(i) SEQUENCE CHARACTERISTICS:
        (A) LENGTH: 1009 amino acids
        (B) TYPE: amino acid
        (C) STRANDEDNESS: single
        (D) TOPOLOGY: linear (xi) SEQUENCE DESCRIPTION: SEQ ID NO:31:

Met Asp Phe Tyr Asn Pro Tyr Leu Ser Lys Lys Pro Thr Asp Thr Lys
1               5                   10                  15

Thr Pro Lys Leu His Thr Thr Arg Gln Ser Ile Cys Arg Leu Val Pro
                20                  25                  30

Lys Cys Phe Arg Asn Pro Thr Glu Lys Gly Val Val Ser Val Ser Ser
            35                  40                  45

Phe Ala Leu Pro Thr Tyr Phe Phe Lys Gly Asn Glu Asn Lys Val Tyr
            50                  55                  60

Leu Glu Asn Gly Lys Ser Met Trp His Leu Arg Arg Pro Cys Lys Asn
65                  70                  75                  80

-continued

```
Ala Leu Leu Glu Glu Gln Ser Ile Thr Phe His Ile Tyr Asp Ile Val
                 85                  90                  95
Glu Thr Thr Tyr Ser Glu Asp Arg Cys Asn Asp Ile Pro Phe Lys Phe
            100                 105                 110
Gln Thr Asp Ile Ile Pro Asn Gly Thr Val Leu Lys Leu Leu Gly Arg
        115                 120                 125
Thr Leu Glu Gly Ala Ser Val Cys Val Asn Val Phe Gly Gln Arg Asn
    130                 135                 140
Tyr Phe Tyr Val Lys Val Pro Glu Gly Gly Asn Ile Thr Tyr Leu Ile
145                 150                 155                 160
Lys Gln Ala Leu Asn Glu Lys Phe Ser Pro Ser Cys Ala Tyr Gln Thr
                165                 170                 175
Glu Ala Val Lys Lys Ile Leu Ser Arg Tyr Asp Pro Glu Glu His
            180                 185                 190
Asp Val Phe Lys Val Thr Val Ser Ser Leu Ser Val Tyr Lys Ile
        195                 200                 205
Ser Asp Ser Leu Val Ser Asn Gly Cys Glu Val Phe Glu Thr Asn Val
    210                 215                 220
Asp Ala Ile Arg Arg Phe Val Ile Asp Asn Asp Phe Ser Thr Phe Gly
225                 230                 235                 240
Trp Tyr Thr Cys Lys Ser Ala Cys Pro Arg Ile Thr Asn Arg Asp Ser
                245                 250                 255
His Thr Asp Ile Glu Phe Asp Cys Gly Tyr Tyr Asp Leu Glu Phe His
            260                 265                 270
Ala Asp Arg Thr Glu Trp Pro Pro Tyr Asn Ile Met Ser Phe Asp Ile
        275                 280                 285
Glu Cys Ile Gly Glu Lys Gly Phe Pro Cys Ala Lys Asn Glu Gly Asp
    290                 295                 300
Leu Ile Ile Gln Ile Ser Cys Val Phe Trp His Ala Gly Ala Leu Asp
305                 310                 315                 320
Thr Thr Arg Asn Met Leu Leu Ser Leu Gly Thr Cys Ser Ala Val Glu
                325                 330                 335
Asn Thr Glu Val Tyr Glu Phe Pro Ser Glu Ile Asp Met Leu His Gly
            340                 345                 350
Phe Phe Ser Leu Ile Arg Asp Phe Asn Val Glu Ile Ile Thr Gly Tyr
        355                 360                 365
Asn Ile Ser Asn Phe Asp Leu Pro Tyr Leu Ile Asp Arg Ala Thr Gln
    370                 375                 380
Ile Tyr Asn Ile Lys Leu Ser Asp Tyr Ser Arg Val Lys Thr Gly Ser
385                 390                 395                 400
Ile Phe Gln Val His Thr Pro Lys Asp Thr Gly Asn Gly Phe Met Arg
                405                 410                 415
Ser Val Ser Lys Ile Lys Ile Ser Gly Ile Ile Ala Ile Asp Met Tyr
            420                 425                 430
Ile Val Cys Lys Asp Lys Leu Ser Leu Ser Asn Tyr Lys Leu Asp Thr
        435                 440                 445
Val Ala Asn His Cys Ile Gly Ala Lys Lys Glu Asp Val Ser Tyr Lys
    450                 455                 460
Asp Ile Met Pro Leu Phe Met Ser Gly Pro Glu Gly Arg Ala Lys Ile
465                 470                 475                 480
Gly Leu Tyr Cys Val Ile Asp Ser Val Leu Val Met Lys Leu Leu Lys
                485                 490                 495
Phe Phe Met Ile His Val Glu Ile Ser Glu Ile Ala Lys Leu Ala Lys
```

-continued

```
                500               505                510
Ile Pro Thr Arg Arg Val Leu Thr Asp Gly Gln Gln Ile Arg Val Phe
        515                 520                525

Ser Cys Leu Leu Ala Ala Ala Arg Ala Glu Asn Tyr Ile Leu Pro Val
530                 535                 540

Ser Asn Asp Val Asn Ala Asp Gly Phe Gln Gly Ala Thr Val Ile Asn
545                 550                 555                 560

Pro Ile Pro Gly Phe Tyr Asn Asn Ala Val Leu Val Val Asp Phe Ala
                565                 570                 575

Ser Leu Tyr Pro Ser Ile Ile Gln Ala His Asn Leu Cys Tyr Ser Thr
                580                 585                 590

Leu Ile Pro His His Ala Leu His Asn Tyr Pro His Leu Lys Ser Ser
                595                 600                 605

Asp Tyr Glu Thr Phe Met Leu Ser Ser Gly Pro Ile His Phe Val Lys
                610                 615                 620

Lys His Ile Gln Ala Ser Leu Leu Ser Arg Leu Leu Thr Val Trp Leu
625                 630                 635                 640

Ser Lys Arg Lys Ala Ile Arg Gln Lys Leu Ala Glu Cys Glu Asp Leu
                645                 650                 655

Asp Thr Lys Thr Ile Leu Asp Lys Gln Leu Ala Ile Lys Val Thr
                660                 665                 670

Cys Asn Ala Val Tyr Gly Phe Thr Gly Val Ala Ser Gly Leu Leu Pro
                675                 680                 685

Cys Ile Ser Ile Ala Glu Thr Val Thr Leu Gln Gly Arg Thr Met Leu
                690                 695                 700

Glu Lys Ser Lys Ile Phe Ile Glu Ala Met Thr Pro Asp Thr Leu Gln
705                 710                 715                 720

Glu Ile Val Pro His Ile Val Lys His Glu Pro Asp Ala Lys Phe Arg
                725                 730                 735

Val Ile Tyr Gly Asp Thr Asp Ser Leu Phe Val Glu Cys Val Gly Tyr
                740                 745                 750

Ser Val Asp Thr Val Val Lys Phe Gly Asp Phe Leu Ala Ala Phe Thr
                755                 760                 765

Ser Glu Lys Leu Phe Asn Ala Pro Ile Lys Leu Glu Ser Glu Lys Thr
770                 775                 780

Phe Gln Cys Leu Leu Leu Ala Lys Lys Arg Tyr Ile Gly Ile Leu
785                 790                 795                 800

Ser Asn Asp Lys Leu Leu Met Lys Gly Val Asp Leu Val Arg Lys Thr
                805                 810                 815

Ala Cys Lys Phe Val Gln Asn Thr Ser Ser Lys Ile Leu Asn Leu Ile
                820                 825                 830

Leu Lys Asp Pro Glu Val Lys Ala Ala Ala Gln Leu Leu Ser Thr Lys
                835                 840                 845

Asp Pro Asp Tyr Ala Phe Arg Glu Gly Leu Pro Asp Gly Phe Leu Lys
                850                 855                 860

Val Ile Asp Ile Leu Asn Glu Ser His Lys Asn Leu Arg Thr Gly Gln
865                 870                 875                 880

Val Pro Val Glu Glu Leu Thr Phe Ser Thr Glu Leu Ser Arg Pro Ile
                885                 890                 895

Ser Ser Tyr Lys Thr Glu Asn Leu Pro His Leu Thr Val Tyr Lys Lys
                900                 905                 910

Ile Ile Thr Arg His Glu Glu Pro Pro Gln Val His Asp Arg Ile Pro
                915                 920                 925
```

```
Tyr Val Phe Val Gly Lys Thr Thr Ser Cys Ile Ser Asn Met Ala Glu
        930                 935                 940

Asp Pro Thr Tyr Thr Val Gln Asn Asn Ile Pro Ile Ala Val Asp Leu
945                 950                 955                 960

Tyr Phe Asp Lys Leu Ile His Gly Val Ala Asn Ile Ile Gln Cys Leu
                965                 970                 975

Phe Lys Asp Ser Ser Lys Thr Val Ser Val Leu Tyr Asn Phe Val Ser
                980                 985                 990

Thr Pro Val Leu Phe Ser Tyr Glu Leu Leu Thr Asp His Ser Val Lys
                995                 1000                1005

Ala
```

(2) INFORMATION FOR SEQ ID NO:32:

(i) SEQUENCE CHARACTERISTICS:
        (A) LENGTH: 1015 amino acids
        (B) TYPE: amino acid
        (C) STRANDEDNESS: single
        (D) TOPOLOGY: linear (xi) SEQUENCE DESCRIPTION: SEQ ID NO:32:

```
Met Ser Gly Gly Leu Phe Tyr Asn Pro Phe Leu Arg Pro Asn Lys Gly
1               5                   10                  15

Leu Leu Lys Lys Pro Asp Lys Glu Tyr Leu Arg Leu Ile Pro Lys Cys
                20                  25                  30

Phe Gln Thr Pro Gly Ala Ala Gly Val Val Asp Val Arg Gly Pro Gln
            35                  40                  45

Pro Pro Leu Cys Phe Tyr Gln Asp Ser Leu Thr Val Val Gly Gly Asp
        50                  55                  60

Glu Asp Gly Lys Gly Met Trp Trp Arg Gln Arg Ala Gln Glu Gly Thr
65                  70                  75                  80

Ala Arg Pro Glu Ala Asp Thr His Gly Ser Pro Leu Asp Phe His Val
                85                  90                  95

Tyr Asp Ile Leu Glu Thr Val Tyr Thr His Glu Lys Cys Ala Val Ile
                100                 105                 110

Pro Ser Asp Lys Gln Gly Tyr Val Pro Cys Gly Ile Val Ile Lys
                115                 120                 125

Leu Leu Gly Arg Arg Lys Ala Asp Gly Ala Ser Val Cys Val Asn Val
            130                 135                 140

Phe Gly Gln Gln Ala Tyr Phe Tyr Ala Ser Ala Pro Gln Gly Leu Asp
145                 150                 155                 160

Val Glu Phe Ala Val Leu Ser Ala Leu Lys Ala Ser Thr Phe Asp Arg
                165                 170                 175

Arg Thr Pro Cys Arg Val Ser Val Glu Lys Val Thr Arg Arg Ser Ile
                180                 185                 190

Met Gly Tyr Gly Asn His Ala Gly Asp Tyr His Lys Ile Thr Leu Ser
            195                 200                 205

His Pro Asn Ser Val Cys His Val Ala Thr Trp Leu Gln Asp Lys His
            210                 215                 220

Gly Cys Arg Ile Phe Glu Ala Asn Val Asp Ala Thr Arg Arg Phe Val
225                 230                 235                 240

Leu Asp Asn Asp Phe Val Thr Phe Gly Trp Tyr Ser Cys Arg Arg Ala
                245                 250                 255

Ile Pro Arg Leu Gln His Arg Asp Ser Tyr Ala Glu Leu Glu Tyr Asp
            260                 265                 270

Cys Glu Val Gly Asp Leu Ser Val Arg Arg Glu Asp Ser Ser Trp Pro
```

```
                  275                 280                 285
Ser Tyr Gln Ala Leu Ala Phe Asp Ile Glu Cys Leu Gly Glu Gly
    290                 295                 300

Phe Pro Thr Ala Thr Asn Glu Ala Asp Leu Ile Leu Gln Ile Ser Cys
305                 310                 315                 320

Val Leu Trp Ser Thr Gly Glu Ala Gly Arg Tyr Arg Ile Leu
                325                 330                 335

Leu Thr Leu Gly Thr Cys Glu Asp Ile Glu Gly Val Glu Val Tyr Glu
                340                 345                 350

Phe Pro Ser Glu Leu Asp Met Leu Tyr Ala Phe Phe Gln Leu Ile Arg
        355                 360                 365

Asp Leu Ser Val Glu Ile Val Thr Gly Tyr Asn Val Ala Asn Phe Asp
    370                 375                 380

Trp Pro Tyr Ile Leu Asp Arg Ala Arg His Ile Tyr Ser Ile Asn Pro
385                 390                 395                 400

Ala Ser Leu Gly Lys Ile Arg Ala Gly Val Cys Glu Val Arg Arg
                405                 410                 415

Pro His Asp Ala Gly Lys Gly Phe Leu Arg Ala Asn Thr Lys Val Arg
                420                 425                 430

Ile Thr Gly Leu Ile Pro Ile Asp Met Tyr Ala Val Cys Arg Asp Lys
                435                 440                 445

Leu Ser Leu Ser Asp Tyr Lys Leu Asp Thr Val Ala Arg His Leu Leu
    450                 455                 460

Gly Ala Lys Lys Glu Asp Val His Tyr Lys Ile Pro Arg Leu Phe
465                 470                 475                 480

Ala Ala Gly Pro Glu Gly Arg Arg Leu Gly Met Tyr Cys Val Gln
                485                 490                 495

Asp Ser Ala Leu Val Met Asp Leu Leu Asn His Phe Val Ile His Val
                500                 505                 510

Glu Val Ala Glu Ile Ala Lys Ile Ala His Ile Pro Cys Arg Arg Val
            515                 520                 525

Leu Asp Asp Gly Gln Gln Ile Arg Val Phe Ser Cys Leu Leu Ala Ala
    530                 535                 540

Ala Gln Lys Glu Asn Phe Ile Leu Pro Met Pro Ser Ala Ser Asp Arg
545                 550                 555                 560

Asp Gly Tyr Gln Gly Ala Thr Val Ile Gln Pro Leu Ser Gly Phe Tyr
                565                 570                 575

Asn Ser Pro Val Leu Val Val Asp Phe Ala Ser Leu Tyr Pro Ser Ile
            580                 585                 590

Ile Gln Ala His Asn Leu Cys Tyr Ser Thr Met Ile Thr Pro Gly Glu
    595                 600                 605

Glu His Arg Leu Ala Gly Leu Arg Pro Gly Glu Asp Tyr Glu Ser Phe
    610                 615                 620

Arg Leu Thr Gly Gly Val Tyr His Phe Val Lys Lys His Val His Glu
625                 630                 635                 640

Ser Phe Leu Ala Ser Leu Leu Thr Ser Trp Leu Ala Lys Arg Lys Ala
                645                 650                 655

Ile Lys Lys Leu Leu Ala Ala Cys Glu Asp Pro Arg Gln Arg Thr Ile
                660                 665                 670

Leu Asp Lys Gln Gln Leu Ala Ile Lys Cys Thr Cys Asn Ala Val Tyr
        675                 680                 685

Gly Phe Thr Gly Val Ala Asn Gly Leu Phe Pro Cys Leu Ser Ile Ala
690                 695                 700
```

-continued

```
Glu Thr Val Thr Leu Gln Gly Arg Thr Met Leu Glu Arg Ala Lys Ala
705                 710                 715                 720

Phe Val Glu Ala Leu Ser Pro Ala Asn Leu Gln Ala Leu Ala Pro Ser
            725                 730                 735

Pro Asp Ala Trp Ala Pro Leu Asn Pro Glu Gly Gln Leu Arg Val Ile
            740                 745                 750

Tyr Gly Asp Thr Asp Ser Leu Phe Ile Glu Cys Arg Gly Phe Ser Glu
            755                 760                 765

Ser Glu Thr Leu Arg Phe Ala Asp Ala Leu Ala Ala His Thr Thr Arg
770                 775                 780

Ser Leu Phe Val Ala Pro Ile Ser Leu Glu Ala Glu Lys Thr Phe Ser
785                 790                 795                 800

Cys Leu Met Leu Ile Thr Lys Lys Arg Tyr Val Gly Val Leu Thr Asp
                805                 810                 815

Gly Lys Thr Leu Met Lys Gly Val Glu Leu Val Arg Lys Thr Ala Cys
                820                 825                 830

Lys Phe Val Gln Thr Arg Cys Arg Arg Val Leu Asp Leu Val Leu Ala
            835                 840                 845

Asp Ala Arg Val Lys Glu Ala Ala Ser Leu Leu Ser His Arg Pro Phe
850                 855                 860

Gln Glu Ser Phe Thr Gln Gly Leu Pro Val Gly Phe Leu Pro Val Ile
865                 870                 875                 880

Asp Ile Leu Asn Gln Ala Tyr Thr Asp Leu Arg Glu Gly Arg Val Pro
                885                 890                 895

Met Gly Glu Leu Cys Phe Ser Thr Glu Leu Ser Arg Lys Leu Ser Ala
                900                 905                 910

Tyr Lys Ser Thr Gln Met Pro His Leu Ala Val Tyr Gln Lys Phe Val
            915                 920                 925

Glu Arg Asn Glu Glu Leu Pro Gln Ile His Asp Arg Ile Gln Tyr Val
930                 935                 940

Phe Val Glu Pro Lys Gly Gly Val Lys Gly Ala Arg Lys Thr Glu Met
945                 950                 955                 960

Ala Glu Asp Pro Ala Tyr Ala Glu Arg His Gly Val Pro Val Ala Val
                965                 970                 975

Asp His Tyr Phe Asp Lys Leu Leu Gln Gly Ala Ala Asn Ile Leu Gln
            980                 985                 990

Cys Leu Phe Asp Asn Asn Ser Gly Ala Ala Leu Ser Val Leu Gln Asn
            995                 1000                1005

Phe Thr Ala Arg Pro Pro Phe
            1010                1015
```

(2) INFORMATION FOR SEQ ID NO:33:

(i) SEQUENCE CHARACTERISTICS:
       (A) LENGTH: 1242 amino acids
       (B) TYPE: amino acid
       (C) STRANDEDNESS: single
       (D) TOPOLOGY: linear (xi) SEQUENCE DESCRIPTION: SEQ ID NO:33:

```
Met Phe Phe Asn Pro Tyr Leu Ser Gly Gly Val Thr Gly Gly Ala Val
1               5                   10                  15

Ala Gly Gly Arg Arg Gln Arg Ser Gln Pro Gly Ser Ala Gln Gly Ser
            20                  25                  30

Gly Lys Arg Pro Pro Gln Lys Gln Phe Leu Gln Ile Val Pro Arg Gly
            35                  40                  45
```

-continued

Val Met Phe Asp Gly Gln Thr Gly Leu Ile Lys His Lys Thr Gly Arg
    50                      55                      60

Leu Pro Leu Met Phe Tyr Arg Glu Ile Lys His Leu Leu Ser His Asp
65                      70                      75                  80

Met Val Trp Pro Cys Pro Trp Arg Glu Thr Leu Val Gly Arg Val Val
                    85                      90                      95

Gly Pro Ile Arg Phe His Thr Tyr Asp Gln Thr Asp Ala Val Leu Phe
                100                     105                     110

Phe Asp Ser Pro Glu Asn Val Ser Pro Arg Tyr Arg Gln His Leu Val
            115                     120                     125

Pro Ser Gly Asn Val Leu Arg Phe Phe Gly Ala Thr Glu His Gly Tyr
        130                     135                     140

Ser Ile Cys Val Asn Val Phe Gly Gln Arg Ser Tyr Phe Tyr Cys Glu
145                     150                     155                     160

Tyr Ser Asp Thr Asp Arg Leu Arg Glu Val Ile Ala Ser Val Gly Glu
                    165                     170                     175

Leu Val Pro Glu Pro Arg Thr Pro Tyr Ala Val Ser Val Thr Pro Ala
                180                     185                     190

Thr Lys Thr Ser Ile Tyr Gly Tyr Gly Thr Arg Pro Val Pro Asp Leu
            195                     200                     205

Gln Cys Val Ser Ile Ser Asn Trp Thr Met Ala Arg Lys Ile Gly Glu
        210                     215                     220

Tyr Leu Leu Glu Gln Gly Phe Pro Val Tyr Glu Val Arg Val Asp Pro
225                     230                     235                     240

Leu Thr Arg Leu Val Ile Asp Arg Arg Ile Thr Thr Phe Gly Trp Cys
                    245                     250                     255

Ser Val Asn Arg Tyr Asp Trp Arg Gln Gln Gly Arg Ala Ser Thr Cys
                260                     265                     270

Asp Ile Glu Val Asp Cys Asp Val Ser Asp Leu Val Ala Val Pro Asp
            275                     280                     285

Asp Ser Ser Trp Pro Arg Tyr Arg Cys Leu Ser Phe Asp Ile Glu Cys
        290                     295                     300

Met Ser Gly Glu Gly Gly Phe Pro Cys Ala Glu Lys Ser Asp Asp Ile
305                     310                     315                     320

Val Ile Gln Ile Ser Cys Val Cys Tyr Glu Thr Gly Gly Asn Thr Ala
                    325                     330                     335

Val Asp Gln Gly Ile Pro Asn Gly Asn Asp Gly Arg Gly Cys Thr Ser
                340                     345                     350

Glu Gly Val Ile Phe Gly His Ser Gly Leu His Leu Phe Thr Ile Gly
            355                     360                     365

Thr Cys Gly Gln Val Gly Pro Asp Val Asp Val Tyr Glu Phe Pro Ser
370                     375                     380

Glu Tyr Glu Leu Leu Leu Gly Phe Met Leu Phe Phe Gln Arg Tyr Ala
385                     390                     395                     400

Pro Ala Phe Val Thr Gly Tyr Asn Ile Asn Ser Phe Asp Leu Lys Tyr
                    405                     410                     415

Ile Leu Thr Arg Leu Glu Tyr Leu Tyr Lys Val Asp Ser Gln Arg Phe
                420                     425                     430

Cys Lys Leu Pro Thr Ala Gln Gly Gly Arg Phe Phe Leu His Ser Pro
            435                     440                     445

Ala Val Gly Phe Lys Arg Gln Tyr Ala Ala Phe Pro Ser Ala Ser
        450                     455                     460

His Asn Asn Pro Ala Ser Thr Ala Ala Thr Lys Val Tyr Ile Ala Gly
465                     470                     475                     480

```
Ser Val Val Ile Asp Met Tyr Pro Val Cys Met Ala Lys Thr Asn Ser
                485                 490                 495

Pro Asn Tyr Lys Leu Asn Thr Met Ala Glu Leu Tyr Leu Arg Gln Arg
            500                 505                 510

Lys Asp Asp Leu Ser Tyr Lys Asp Ile Pro Arg Cys Phe Val Ala Asn
            515                 520                 525

Ala Glu Gly Arg Ala Gln Val Gly Arg Tyr Cys Leu Gln Asp Ala Val
    530                 535                 540

Leu Val Arg Asp Leu Phe Asn Thr Ile Asn Phe His Tyr Glu Ala Gly
545                 550                 555                 560

Ala Ile Ala Arg Leu Ala Lys Ile Pro Leu Arg Arg Val Ile Phe Asp
            565                 570                 575

Gly Gln Gln Ile Arg Ile Tyr Thr Ser Leu Leu Asp Glu Cys Ala Cys
            580                 585                 590

Arg Asp Phe Ile Leu Pro Asn His Tyr Ser Lys Gly Thr Thr Val Pro
            595                 600                 605

Glu Thr Asn Ser Val Ala Val Ser Pro Asn Ala Ala Ile Ile Ser Thr
    610                 615                 620

Ala Ala Val Pro Gly Asp Ala Gly Ser Val Ala Ala Met Phe Gln Met
625                 630                 635                 640

Ser Pro Pro Leu Gln Ser Ala Pro Ser Ser Gln Asp Gly Val Ser Pro
            645                 650                 655

Gly Ser Gly Ser Asn Ser Ser Ser Val Gly Val Phe Ser Val Gly
            660                 665                 670

Ser Gly Ser Ser Gly Gly Val Gly Val Ser Asn Asp Asn His Gly Ala
    675                 680                 685

Gly Gly Thr Ala Ala Val Ser Tyr Gln Gly Ala Thr Val Phe Glu Pro
    690                 695                 700

Glu Val Gly Tyr Tyr Asn Asp Pro Val Ala Val Phe Asp Phe Ala Ser
705                 710                 715                 720

Leu Tyr Pro Ser Ile Ile Met Ala His Asn Leu Cys Tyr Ser Thr Leu
            725                 730                 735

Leu Val Pro Gly Gly Glu Tyr Pro Val Asp Pro Ala Asp Val Tyr Ser
            740                 745                 750

Val Thr Leu Glu Asn Gly Val Thr His Arg Phe Val Arg Ala Ser Val
            755                 760                 765

Arg Val Ser Val Leu Ser Glu Leu Leu Asn Lys Trp Val Ser Gln Arg
    770                 775                 780

Arg Ala Val Arg Glu Cys Met Arg Glu Cys Gln Asp Pro Val Arg Arg
785                 790                 795                 800

Met Leu Leu Asp Lys Glu Gln Met Ala Leu Lys Val Thr Cys Asn Ala
            805                 810                 815

Phe Tyr Gly Phe Thr Gly Val Val Asn Gly Met Met Pro Cys Leu Pro
            820                 825                 830

Ile Ala Ala Ser Ile Thr Arg Ile Gly Arg Asp Met Leu Glu Arg Thr
            835                 840                 845

Ala Arg Phe Ile Lys Asp Asn Phe Ser Glu Pro Cys Phe Leu His Asn
    850                 855                 860

Phe Phe Asn Gln Glu Asp Tyr Val Val Gly Thr Arg Glu Gly Asp Ser
865                 870                 875                 880

Glu Glu Ser Ser Ala Leu Pro Glu Gly Leu Glu Thr Ser Ser Gly Gly
            885                 890                 895

Ser Asn Glu Arg Arg Val Glu Ala Arg Val Ile Tyr Gly Asp Thr Asp
```

```
                      900                 905                 910
Ser Val Phe Val Arg Phe Arg Gly Leu Thr Pro Gln Ala Leu Val Ala
            915                 920                 925

Arg Gly Pro Ser Leu Ala His Tyr Val Thr Ala Cys Leu Phe Val Glu
930                 935                 940

Pro Val Lys Leu Glu Phe Glu Lys Val Phe Val Ser Leu Met Met Ile
945                 950                 955                 960

Cys Lys Lys Arg Tyr Ile Gly Lys Val Glu Gly Ala Ser Gly Leu Ser
                965                 970                 975

Met Lys Gly Val Asp Leu Val Arg Lys Thr Ala Cys Glu Phe Val Lys
            980                 985                 990

Gly Val Thr Arg Asp Val Leu Ser Leu Leu Phe Glu Asp Arg Glu Val
        995                 1000                1005

Ser Glu Ala Ala Val Arg Leu Ser Arg Leu Ser Leu Asp Glu Val Lys
    1010                1015                1020

Lys Tyr Gly Val Pro Arg Gly Phe Trp Arg Ile Leu Arg Arg Leu Val
1025                1030                1035                1040

Gln Ala Arg Asp Asp Leu Tyr Leu His Arg Val Arg Val Glu Asp Leu
                1045                1050                1055

Val Leu Ser Ser Val Leu Ser Lys Asp Ile Ser Leu Tyr Arg Gln Ser
            1060                1065                1070

Asn Leu Pro His Ile Ala Val Ile Lys Arg Leu Ala Ala Arg Ser Glu
        1075                1080                1085

Glu Leu Pro Ser Val Gly Asp Arg Val Phe Tyr Val Leu Thr Ala Pro
    1090                1095                1100

Gly Val Arg Thr Ala Pro Gln Gly Ser Ser Asp Asn Gly Asp Ser Val
1105                1110                1115                1120

Thr Ala Gly Val Val Ser Arg Ser Asp Ala Ile Asp Gly Thr Asp Asp
                1125                1130                1135

Asp Ala Asp Gly Gly Val Glu Glu Ser Asn Arg Arg Gly Gly Glu
            1140                1145                1150

Pro Ala Lys Lys Arg Ala Arg Lys Pro Pro Ser Ala Val Cys Asn Tyr
        1155                1160                1165

Glu Val Ala Glu Asp Pro Ser Tyr Val Arg Glu His Gly Val Pro Ile
    1170                1175                1180

His Ala Asp Lys Tyr Phe Glu Gln Val Leu Lys Ala Val Thr Asn Val
1185                1190                1195                1200

Leu Ser Pro Val Phe Pro Gly Gly Glu Thr Ala Arg Lys Asp Lys Phe
                1205                1210                1215

Leu His Met Val Leu Pro Arg Arg Leu His Leu Glu Pro Ala Phe Leu
            1220                1225                1230

Pro Tyr Ser Val Lys Ala His Glu Cys Cys
        1235                1240

(2) INFORMATION FOR SEQ ID NO:34:

(i) SEQUENCE CHARACTERISTICS:
        (A) LENGTH: 1012 amino acids
        (B) TYPE: amino acid
        (C) STRANDEDNESS: single
        (D) TOPOLOGY: linear (xi) SEQUENCE DESCRIPTION: SEQ ID NO:34:

Met Asp Ser Val Ser Phe Phe Asn Pro Tyr Leu Glu Ala Asn Arg Leu
1               5                   10                  15

Lys Lys Lys Ser Arg Ser Ser Tyr Ile Arg Ile Leu Pro Arg Gly Ile
```

```
                    20                  25                  30
Met His Asp Gly Ala Ala Gly Leu Ile Lys Asp Val Cys Asp Ser Glu
                35                  40                  45

Pro Arg Met Phe Tyr Arg Asp Arg Gln Tyr Leu Leu Ser Lys Glu Met
 50                  55                  60

Thr Trp Pro Ser Leu Asp Ile Ala Arg Ser Lys Asp Tyr Asp His Met
 65                  70                  75                  80

Arg Met Lys Phe His Ile Tyr Asp Ala Val Glu Thr Leu Met Phe Thr
                85                  90                  95

Asp Ser Ile Glu Asn Leu Pro Phe Gln Tyr Arg His Phe Val Ile Pro
               100                 105                 110

Ser Gly Thr Val Ile Arg Met Phe Gly Arg Thr Glu Asp Gly Glu Lys
               115                 120                 125

Ile Cys Val Asn Val Phe Gly Gln Glu Gln Tyr Phe Tyr Cys Glu Cys
               130                 135                 140

Val Asp Gly Arg Ser Leu Lys Ala Thr Ile Asn Asn Leu Met Leu Thr
145                 150                 155                 160

Gly Glu Val Lys Met Ser Cys Ser Phe Val Ile Glu Pro Ala Asp Lys
               165                 170                 175

Leu Ser Leu Tyr Gly Tyr Asn Ala Asn Thr Val Val Asn Leu Phe Lys
               180                 185                 190

Val Ser Phe Gly Asn Phe Tyr Val Ser Gln Arg Ile Gly Lys Ile Leu
               195                 200                 205

Gln Asn Glu Gly Phe Val Val Tyr Glu Ile Asp Val Asp Val Leu Thr
               210                 215                 220

Arg Phe Phe Val Asp Asn Gly Phe Leu Ser Phe Gly Trp Tyr Asn Val
225                 230                 235                 240

Lys Lys Tyr Ile Pro Gln Asp Met Gly Lys Gly Ser Asn Leu Glu Val
               245                 250                 255

Glu Ile Asn Cys His Val Ser Asp Leu Val Ser Leu Glu Asp Val Asn
               260                 265                 270

Trp Pro Leu Tyr Gly Cys Trp Ser Phe Asp Ile Glu Cys Leu Gly Gln
               275                 280                 285

Asn Gly Asn Phe Pro Asp Ala Glu Asn Leu Gly Asp Ile Val Ile Gln
               290                 295                 300

Ile Ser Val Ile Ser Phe Asp Thr Glu Gly Asp Arg Asp Glu Arg His
305                 310                 315                 320

Leu Phe Thr Leu Gly Thr Cys Glu Lys Ile Asp Gly Val His Ile Tyr
               325                 330                 335

Glu Phe Ala Ser Glu Phe Glu Leu Leu Gly Phe Phe Ile Phe Leu
               340                 345                 350

Arg Ile Glu Ser Pro Glu Phe Ile Thr Gly Tyr Asn Ile Asn Asn Phe
               355                 360                 365

Asp Leu Lys Tyr Leu Cys Ile Arg Met Asp Lys Ile Tyr His Tyr Asp
               370                 375                 380

Ile Gly Cys Phe Ser Lys Leu Lys Asn Gly Lys Ile Gly Ile Ser Val
385                 390                 395                 400

Pro His Glu Gln Tyr Arg Lys Gly Phe Leu Gln Ala Gln Thr Lys Val
               405                 410                 415

Phe Thr Ser Gly Val Leu Tyr Leu Asp Met Tyr Pro Val Tyr Ser Ser
               420                 425                 430

Lys Ile Thr Ala Gln Asn Tyr Lys Leu Asp Thr Ile Ala Lys Ile Cys
               435                 440                 445
```

-continued

```
Leu Gln Gln Glu Lys Glu Gln Leu Ser Tyr Lys Glu Ile Pro Lys Lys
    450                 455                 460

Phe Ile Ser Gly Pro Ser Gly Arg Ala Val Val Gly Lys Tyr Cys Leu
465                 470                 475                 480

Gln Asp Ser Val Leu Val Val Arg Leu Phe Lys Gln Ile Asn Tyr His
                485                 490                 495

Phe Glu Val Ala Glu Val Ala Arg Leu Ala His Val Thr Ala Arg Cys
                500                 505                 510

Val Val Phe Glu Gly Gln Gln Lys Lys Ile Phe Pro Cys Ile Leu Thr
            515                 520                 525

Glu Ala Lys Arg Arg Asn Met Ile Leu Pro Ser Met Val Ser Ser His
530                 535                 540

Asn Arg Gln Gly Ile Gly Tyr Lys Gly Ala Thr Val Leu Glu Pro Lys
545                 550                 555                 560

Thr Gly Tyr Tyr Ala Val Pro Thr Val Val Phe Asp Phe Gln Ser Leu
                565                 570                 575

Tyr Pro Ser Ile Met Met Ala His Asn Leu Cys Tyr Ser Thr Leu Val
                580                 585                 590

Leu Asp Glu Arg Gln Ile Ala Gly Leu Ser Glu Ser Asp Ile Leu Thr
            595                 600                 605

Val Lys Leu Gly Asp Glu Thr His Arg Phe Val Lys Pro Cys Ile Arg
610                 615                 620

Glu Ser Val Leu Gly Ser Leu Leu Lys Asp Trp Leu Ala Lys Arg Arg
625                 630                 635                 640

Glu Val Lys Ala Glu Met Gln Asn Cys Ser Asp Pro Met Met Lys Leu
                645                 650                 655

Leu Leu Asp Lys Lys Gln Leu Ala Leu Lys Thr Thr Cys Asn Ser Val
            660                 665                 670

Tyr Gly Val Thr Gly Ala Ala His Gly Leu Leu Pro Cys Val Ala Ile
            675                 680                 685

Ala Ala Ser Val Thr Cys Leu Gly Arg Glu Met Leu Cys Ser Thr Val
690                 695                 700

Asp Tyr Val Asn Ser Lys Met Gln Ser Glu Gln Phe Phe Cys Glu Glu
705                 710                 715                 720

Phe Gly Leu Thr Ser Ser Asp Phe Thr Gly Asp Leu Glu Val Glu Val
                725                 730                 735

Ile Tyr Gly Asp Thr Asp Ser Ile Phe Met Ser Val Arg Asn Met Val
            740                 745                 750

Asn Gln Ser Leu Arg Arg Ile Ala Pro Met Ile Ala Lys His Ile Thr
            755                 760                 765

Asp Arg Leu Phe Lys Ser Pro Ile Lys Leu Glu Phe Glu Lys Ile Leu
770                 775                 780

Cys Pro Leu Ile Leu Ile Cys Lys Lys Arg Tyr Ile Gly Arg Gln Asp
785                 790                 795                 800

Asp Ser Leu Leu Ile Phe Lys Gly Val Asp Leu Val Arg Lys Thr Ser
                805                 810                 815

Cys Asp Phe Val Lys Gly Val Val Lys Asp Ile Val Asp Leu Leu Phe
                820                 825                 830

Phe Asp Glu Glu Val Gln Thr Ala Ala Val Glu Phe Ser His Met Thr
            835                 840                 845

Gln Thr Gln Leu Arg Glu Gln Gly Val Pro Val Gly Ile His Lys Ile
850                 855                 860

Leu Arg Arg Leu Cys Glu Ala Arg Glu Glu Leu Phe Gln Asn Arg Ala
865                 870                 875                 880
```

-continued

```
Asp Val Arg His Leu Met Leu Ser Ser Val Leu Ser Lys Glu Met Ala
            885                 890                 895

Ala Tyr Lys Gln Pro Asn Leu Ala His Leu Ser Val Ile Arg Arg Leu
        900                 905                 910

Ala Gln Arg Lys Glu Glu Ile Pro Asn Val Gly Asp Arg Ile Met Tyr
        915                 920                 925

Val Leu Ile Ala Pro Ser Ile Gly Asn Lys Gln Thr His Asn Tyr Glu
    930                 935                 940

Leu Ala Glu Asp Pro Asn Tyr Val Ile Glu His Lys Ile Pro Ile His
945                 950                 955                 960

Ala Glu Lys Tyr Phe Asp Gln Ile Ile Lys Ala Val Thr Asn Ala Ile
            965                 970                 975

Ser Pro Ile Phe Pro Lys Thr Asp Ile Lys Lys Glu Lys Leu Leu Leu
            980                 985                 990

Tyr Leu Leu Pro Met Lys Val Tyr Leu Asp Glu Thr Phe Ser Ala Ile
        995                 1000                1005

Ala Glu Val Met
    1010
```

(2) INFORMATION FOR SEQ ID NO:35:

(i) SEQUENCE CHARACTERISTICS:
        (A) LENGTH: 1194 amino acids
        (B) TYPE: amino acid
        (C) STRANDEDNESS: single
        (D) TOPOLOGY: linear (xi) SEQUENCE DESCRIPTION: SEQ ID NO:35:

```
Met Ala Ile Arg Thr Gly Phe Cys Asn Pro Phe Leu Thr Gln Ala Ser
1               5                   10                  15

Gly Ile Lys Tyr Asn Pro Arg Thr Gly Arg Gly Ser Asn Arg Glu Phe
            20                  25                  30

Leu His Ser Tyr Lys Thr Thr Met Ser Ser Phe Gln Phe Leu Ala Pro
        35                  40                  45

Lys Cys Leu Asp Glu Asp Val Pro Met Glu Glu Arg Lys Gly Val His
    50                  55                  60

Val Gly Thr Leu Ser Arg Pro Pro Lys Val Tyr Cys Asn Gly Lys Glu
65                  70                  75                  80

Val Pro Ile Leu Asp Phe Arg Cys Ser Ser Pro Trp Pro Arg Arg Val
            85                  90                  95

Asn Ile Trp Gly Glu Ile Asp Phe Arg Gly Asp Lys Phe Asp Pro Arg
            100                 105                 110

Phe Asn Thr Phe His Val Tyr Asp Ile Val Glu Thr Thr Glu Ala Ala
        115                 120                 125

Ser Asn Gly Asp Val Ser Arg Phe Ala Thr Ala Thr Arg Pro Leu Gly
    130                 135                 140

Thr Val Ile Thr Leu Leu Gly Met Ser Arg Cys Gly Lys Arg Val Ala
145                 150                 155                 160

Val His Val Tyr Gly Ile Cys Gln Tyr Phe Tyr Ile Asn Lys Ala Glu
            165                 170                 175

Val Asp Thr Ala Cys Gly Ile Arg Ser Gly Ser Glu Leu Ser Val Leu
            180                 185                 190

Leu Ala Glu Cys Leu Arg Ser Ser Met Ile Thr Gln Asn Asp Ala Thr
        195                 200                 205

Leu Asn Gly Asp Lys Asn Ala Phe His Gly Thr Ser Phe Lys Ser Ala
    210                 215                 220
```

-continued

| | | | | | | | | | | | | | | |
|---|---|---|---|---|---|---|---|---|---|---|---|---|---|---|

Ser Pro Glu Ser Phe Arg Val Glu Val Ile Glu Arg Thr Asp Val Tyr
225                 230                 235                 240

Tyr Tyr Asp Thr Gln Pro Cys Ala Phe Tyr Arg Val Tyr Ser Pro Ser
            245                 250                 255

Ser Lys Phe Thr Asn Tyr Leu Cys Asp Asn Phe His Pro Glu Leu Lys
                260                 265                 270

Lys Tyr Glu Gly Arg Val Asp Ala Thr Thr Arg Phe Leu Met Asp Asn
            275                 280                 285

Pro Gly Phe Val Ser Phe Gly Trp Tyr Gln Leu Lys Pro Gly Val Asp
        290                 295                 300

Gly Glu Arg Val Arg Val Arg Pro Ala Ser Arg Gln Leu Thr Leu Ser
305                 310                 315                 320

Asp Val Glu Ile Asp Cys Met Ser Asp Asn Leu Gln Ala Ile Pro Asn
                325                 330                 335

Asp Asp Ser Trp Pro Asp Tyr Lys Leu Leu Cys Phe Asp Ile Glu Cys
            340                 345                 350

Lys Ser Gly Gly Ser Asn Glu Leu Ala Phe Pro Asp Ala Thr His Leu
        355                 360                 365

Glu Asp Leu Val Ile Gln Ile Ser Cys Leu Leu Tyr Ser Ile Pro Arg
370                 375                 380

Gln Ser Leu Glu His Ile Leu Leu Phe Ser Leu Gly Ser Cys Asp Leu
385                 390                 395                 400

Pro Gln Arg Tyr Val Gln Glu Met Lys Asp Ala Gly Leu Pro Glu Pro
            405                 410                 415

Thr Val Leu Glu Phe Asp Ser Glu Phe Glu Leu Leu Ile Ala Phe Met
                420                 425                 430

Thr Leu Val Lys Gln Tyr Ala Pro Glu Phe Ala Thr Gly Tyr Asn Ile
            435                 440                 445

Val Asn Phe Asp Trp Ala Phe Ile Met Glu Lys Leu Asn Ser Ile Tyr
        450                 455                 460

Ser Leu Lys Leu Asp Gly Tyr Gly Ser Ile Asn Arg Gly Gly Leu Phe
465                 470                 475                 480

Lys Ile Trp Asp Val Gly Lys Ser Gly Phe Gln Arg Arg Ser Lys Val
            485                 490                 495

Lys Ile Asn Gly Leu Ile Ser Leu Asp Met Tyr Ala Ile Ala Thr Glu
                500                 505                 510

Lys Leu Lys Leu Ser Ser Tyr Lys Leu Asp Ser Val Ala Arg Glu Ala
            515                 520                 525

Leu Asn Glu Ser Lys Arg Asp Leu Pro Tyr Lys Asp Ile Pro Gly Tyr
        530                 535                 540

Tyr Ala Ser Gly Pro Asn Thr Arg Gly Ile Ile Gly Glu Tyr Cys Ile
545                 550                 555                 560

Gln Asp Ser Ala Leu Val Gly Lys Leu Phe Phe Lys Tyr Leu Pro His
            565                 570                 575

Leu Glu Leu Ser Ala Val Ala Arg Leu Ala Arg Ile Thr Leu Thr Lys
                580                 585                 590

Ala Ile Tyr Asp Gly Gln Gln Val Arg Ile Tyr Thr Cys Leu Leu Gly
            595                 600                 605

Leu Ala Ser Ser Arg Gly Phe Ile Leu Pro Asp Gly Tyr Pro Ala
        610                 615                 620

Thr Phe Glu Tyr Lys Asp Val Ile Pro Asp Val Gly Asp Val Glu Glu
625                 630                 635                 640

Glu Met Asp Glu Asp Glu Ser Val Ser Pro Thr Gly Thr Ser Ser Gly

-continued

```
                  645                 650                 655
Arg Asn Val Gly Tyr Lys Gly Ala Arg Val Phe Asp Pro Asp Thr Gly
                660                 665                 670

Phe Tyr Ile Asp Pro Val Val Leu Asp Phe Ala Ser Leu Tyr Pro
            675                 680                 685

Ser Ile Ile Gln Ala His Asn Leu Cys Phe Thr Thr Leu Thr Leu Asn
        690                 695                 700

Phe Glu Thr Val Lys Arg Leu Asn Pro Ser Asp Tyr Ala Thr Phe Thr
705                 710                 715                 720

Val Gly Gly Lys Arg Leu Phe Phe Val Arg Ser Asn Val Arg Glu Ser
                725                 730                 735

Leu Leu Gly Val Leu Leu Lys Asp Trp Leu Ala Met Arg Lys Ala Ile
                740                 745                 750

Arg Ala Arg Ile Pro Gly Ser Ser Asp Glu Ala Val Leu Leu Asp
            755                 760                 765

Lys Gln Gln Ala Ala Ile Lys Val Val Cys Asn Ser Val Tyr Gly Phe
770                 775                 780

Thr Gly Val Ala Gln Gly Phe Leu Pro Cys Leu Tyr Val Ala Ala Thr
785                 790                 795                 800

Val Thr Thr Ile Gly Arg Gln Met Leu Leu Ser Thr Arg Asp Tyr Ile
                805                 810                 815

His Asn Asn Trp Ala Ala Phe Glu Arg Phe Ile Thr Ala Phe Pro Asp
                820                 825                 830

Ile Glu Ser Ser Val Leu Ser Gln Lys Ala Tyr Glu Val Lys Val Ile
                835                 840                 845

Tyr Gly Asp Thr Asp Ser Val Phe Ile Arg Phe Lys Gly Val Ser Val
            850                 855                 860

Glu Gly Ile Ala Lys Ile Gly Glu Lys Met Ala His Ile Ile Ser Thr
865                 870                 875                 880

Ala Leu Phe Cys Pro Pro Ile Lys Leu Glu Cys Glu Lys Thr Phe Ile
                885                 890                 895

Lys Leu Leu Leu Ile Thr Lys Lys Tyr Ile Gly Val Ile Tyr Gly
                900                 905                 910

Gly Lys Val Leu Met Lys Gly Val Asp Leu Val Arg Lys Asn Asn Cys
            915                 920                 925

Gln Phe Ile Asn Asp Tyr Ala Arg Lys Leu Val Glu Leu Leu Leu Tyr
    930                 935                 940

Asp Asp Thr Val Ser Arg Ala Ala Glu Ala Ser Cys Val Ser Ile
945                 950                 955                 960

Ala Glu Trp Asn Arg Arg Ala Met Pro Ser Gly Met Ala Gly Phe Gly
                965                 970                 975

Arg Ile Ile Ala Asp Ala His Arg Gln Ile Thr Ser Pro Lys Leu Asp
            980                 985                 990

Ile Asn Lys Phe Val Met Thr Ala Glu Leu Ser Arg Pro Pro Ser Ala
        995                 1000                1005

Tyr Ile Asn Arg Arg Leu Ala His Leu Thr Val Tyr Tyr Lys Leu Val
        1010                1015                1020

Met Arg Gln Gly Gln Ile Pro Asn Val Arg Glu Arg Ile Pro Tyr Val
1025                1030                1035                1040

Ile Val Ala Pro Thr Asp Glu Val Glu Ala Asp Ala Lys Ser Val Ala
                1045                1050                1055

Leu Leu Arg Gly Asp Pro Leu Gln Asn Thr Ala Gly Lys Arg Cys Gly
                1060                1065                1070
```

-continued

```
Glu Ala Lys Arg Lys Leu Ile Ile Ser Asp Leu Ala Glu Asp Pro Ile
            1075                1080                1085

His Val Thr Ser His Gly Leu Ser Leu Asn Ile Asp Tyr Tyr Phe Ser
        1090                1095                1100

His Leu Ile Gly Thr Ala Ser Val Thr Phe Lys Ala Leu Phe Gly Asn
1105                1110                1115                1120

Asp Thr Lys Leu Thr Glu Arg Leu Leu Lys Arg Phe Ile Pro Glu Thr
                1125                1130                1135

Arg Val Val Asn Val Lys Met Leu Asn Arg Leu Gln Ala Ala Gly Phe
            1140                1145                1150

Val Cys Ile His Ala Pro Cys Trp Asp Asn Lys Met Asn Thr Glu Ala
        1155                1160                1165

Glu Ile Thr Glu Glu Gln Ser His Gln Ile Met Arg Arg Val Phe
    1170                1175                1180

Cys Ile Pro Lys Ala Ile Leu His Gln Ser
1185                1190
```

(2) INFORMATION FOR SEQ ID NO:36:

(i) SEQUENCE CHARACTERISTICS:
        (A) LENGTH: 1235 amino acids
        (B) TYPE: amino acid
        (C) STRANDEDNESS: single
        (D) TOPOLOGY: linear (xi) SEQUENCE DESCRIPTION: SEQ ID NO:36:

```
Met Phe Ser Gly Gly Gly Gly Pro Leu Ser Pro Gly Gly Lys Ser Ala
1               5                   10                  15

Ala Arg Ala Ala Ser Gly Phe Phe Ala Pro Ala Gly Pro Arg Gly Ala
            20                  25                  30

Gly Arg Gly Pro Pro Pro Cys Leu Arg Gln Asn Phe Tyr Asn Pro Tyr
        35                  40                  45

Leu Ala Pro Val Gly Thr Gln Gln Lys Pro Thr Gly Pro Thr Gln Arg
    50                  55                  60

His Thr Tyr Tyr Ser Glu Cys Asp Glu Phe Arg Phe Ile Ala Pro Arg
65                  70                  75                  80

Val Leu Asp Glu Asp Ala Pro Pro Glu Lys Arg Ala Gly Val His Asp
                85                  90                  95

Gly His Leu Lys Arg Ala Pro Lys Val Tyr Cys Gly Gly Asp Glu Arg
            100                 105                 110

Asp Val Leu Arg Val Gly Ser Gly Gly Phe Trp Pro Arg Ser Arg
        115                 120                 125

Leu Trp Gly Gly Val Asp His Ala Pro Ala Gly Phe Asn Pro Thr Val
    130                 135                 140

Thr Val Phe His Val Tyr Asp Ile Leu Glu Asn Val Glu His Ala Tyr
145                 150                 155                 160

Gly Met Arg Ala Ala Gln Phe His Ala Arg Phe Met Asp Ala Ile Thr
                165                 170                 175

Pro Thr Gly Thr Val Ile Thr Leu Leu Gly Leu Thr Pro Glu Gly His
            180                 185                 190

Arg Val Ala Val His Val Tyr Gly Thr Arg Gln Tyr Phe Tyr Met Asn
        195                 200                 205

Lys Glu Glu Val Asp Arg His Leu Gln Cys Arg Ala Pro Arg Asp Leu
    210                 215                 220

Cys Glu Arg Met Ala Ala Ala Leu Arg Glu Ser Pro Gly Ala Ser Phe
225                 230                 235                 240
```

-continued

```
Arg Gly Ile Ser Ala Asp His Phe Glu Ala Glu Val Val Glu Arg Thr
                245                 250                 255

Asp Val Tyr Tyr Tyr Glu Thr Arg Pro Ala Leu Phe Tyr Arg Val Tyr
            260                 265                 270

Val Arg Ser Gly Arg Val Leu Ser Tyr Leu Cys Asp Asn Phe Cys Pro
        275                 280                 285

Ala Ile Lys Lys Tyr Glu Gly Val Asp Ala Thr Thr Arg Phe Ile
    290                 295                 300

Leu Asp Asn Pro Gly Phe Val Thr Phe Gly Trp Tyr Arg Leu Lys Pro
305                 310                 315                 320

Gly Arg Asn Asn Thr Leu Ala Gln Pro Arg Ala Pro Met Ala Phe Gly
                325                 330                 335

Thr Ser Ser Asp Val Glu Phe Asn Cys Thr Ala Asp Asn Leu Ala Ile
            340                 345                 350

Glu Gly Gly Met Ser Asp Leu Pro Ala Tyr Lys Leu Met Cys Phe Asp
        355                 360                 365

Ile Glu Cys Lys Ala Gly Gly Glu Asp Glu Leu Ala Phe Pro Val Ala
    370                 375                 380

Gly His Pro Glu Asp Leu Val Ile Gln Ile Ser Cys Leu Leu Tyr Asp
385                 390                 395                 400

Leu Ser Thr Thr Ala Leu Glu His Val Leu Leu Phe Ser Leu Gly Ser
                405                 410                 415

Cys Asp Leu Pro Glu Ser His Leu Asn Glu Leu Ala Ala Arg Gly Leu
            420                 425                 430

Pro Thr Pro Val Val Leu Glu Phe Asp Ser Glu Phe Glu Met Leu Leu
        435                 440                 445

Ala Phe Met Thr Leu Val Lys Gln Tyr Gly Pro Glu Phe Val Thr Gly
    450                 455                 460

Tyr Asn Ile Ile Asn Phe Asp Trp Pro Phe Leu Leu Ala Lys Leu Thr
465                 470                 475                 480

Asp Ile Tyr Lys Val Pro Leu Asp Gly Tyr Gly Arg Met Asn Gly Arg
                485                 490                 495

Gly Val Phe Arg Val Trp Asp Ile Gly Gln Ser His Phe Gln Lys Arg
            500                 505                 510

Ser Lys Ile Lys Val Asn Gly Met Val Ser Ile Asp Met Tyr Gly Ile
        515                 520                 525

Ile Thr Asp Lys Ile Lys Leu Ser Ser Tyr Lys Leu Asn Ala Val Ala
    530                 535                 540

Glu Ala Val Leu Lys Asp Lys Lys Asp Leu Ser Tyr Arg Asp Ile
545                 550                 555                 560

Pro Ala Tyr Tyr Ala Ala Gly Pro Ala Gln Arg Gly Val Ile Gly Glu
                565                 570                 575

Tyr Cys Ile Gln Asp Ser Leu Leu Val Gly Gln Leu Phe Phe Lys Phe
            580                 585                 590

Leu Pro His Leu Glu Leu Ser Ala Val Ala Arg Leu Ala Gly Ile Asn
        595                 600                 605

Ile Thr Arg Thr Ile Tyr Asp Gly Gln Gln Ile Arg Val Phe Thr Cys
    610                 615                 620

Leu Leu Arg Leu Ala Asp Gln Lys Gly Phe Ile Leu Pro Asp Thr Gln
625                 630                 635                 640

Gly Arg Phe Arg Gly Ala Gly Gly Glu Ala Pro Lys Arg Pro Ala Ala
                645                 650                 655

Ala Arg Glu Asp Glu Glu Arg Pro Glu Glu Glu Gly Glu Asp Glu Asp
            660                 665                 670
```

-continued

```
Glu Arg Glu Gly Gly Gly Glu Arg Glu Pro Asp Gly Ala Arg Glu
            675                 680                 685

Thr Ala Gly Arg His Val Gly Tyr Gln Gly Ala Arg Val Leu Asp Pro
        690                 695                 700

Thr Ser Gly Phe His Val Asn Pro Val Val Phe Asp Phe Ala Ser
705                 710                 715                 720

Leu Tyr Pro Ser Ile Ile Gln Ala His Asn Leu Cys Phe Ser Thr Leu
                725                 730                 735

Ser Leu Arg Ala Asp Ala Val Ala His Leu Glu Ala Gly Lys Asp Tyr
            740                 745                 750

Leu Glu Ile Glu Val Gly Gly Arg Arg Leu Phe Phe Val Lys Ala His
            755                 760                 765

Val Arg Glu Ser Leu Leu Ser Ile Leu Leu Arg Asp Trp Leu Ala Met
        770                 775                 780

Arg Lys Gln Ile Arg Ser Arg Ile Pro Gln Ser Ser Pro Glu Glu Ala
785                 790                 795                 800

Val Leu Leu Asp Lys Gln Gln Ala Ala Ile Lys Val Val Cys Asn Ser
                805                 810                 815

Val Tyr Gly Phe Thr Gly Val Gln His Gly Leu Leu Pro Cys Leu His
            820                 825                 830

Val Ala Ala Thr Val Thr Thr Ile Gly Arg Glu Met Leu Leu Ala Thr
            835                 840                 845

Arg Glu Tyr Val His Ala Arg Trp Ala Ala Phe Glu Gln Leu Leu Ala
        850                 855                 860

Asp Phe Pro Glu Ala Ala Asp Met Arg Ala Pro Gly Pro Tyr Ser Met
865                 870                 875                 880

Arg Ile Ile Tyr Gly Asp Thr Asp Ser Ile Phe Val Leu Cys Arg Gly
                885                 890                 895

Leu Thr Ala Ala Gly Leu Thr Ala Met Gly Asp Lys Met Ala Ser His
            900                 905                 910

Ile Ser Arg Ala Leu Phe Leu Pro Pro Ile Lys Leu Glu Cys Glu Lys
            915                 920                 925

Thr Phe Thr Lys Leu Leu Leu Ile Ala Lys Lys Lys Tyr Ile Gly Val
        930                 935                 940

Ile Tyr Gly Gly Lys Met Leu Ile Lys Gly Val Asp Leu Val Arg Lys
945                 950                 955                 960

Asn Asn Cys Ala Phe Ile Asn Arg Thr Ser Arg Ala Leu Val Asp Leu
                965                 970                 975

Leu Phe Tyr Asp Asp Thr Val Ser Gly Ala Ala Ala Leu Ala Glu
            980                 985                 990

Arg Pro Ala Glu Glu Trp Leu Ala Arg Pro Leu Pro Glu Gly Leu Gln
            995                 1000                1005

Ala Phe Gly Ala Val Leu Val Asp Ala His Arg Arg Ile Thr Asp Pro
        1010                1015                1020

Glu Arg Asp Ile Gln Asp Phe Val Leu Thr Ala Glu Leu Ser Arg His
1025                1030                1035                1040

Pro Arg Ala Tyr Thr Asn Lys Arg Leu Ala His Leu Thr Val Tyr Tyr
                1045                1050                1055

Lys Leu Met Ala Arg Arg Ala Gln Val Pro Ser Ile Lys Asp Arg Ile
            1060                1065                1070

Pro Tyr Val Ile Val Ala Gln Thr Arg Glu Val Glu Glu Thr Val Ala
            1075                1080                1085

Arg Leu Ala Ala Leu Arg Glu Leu Asp Ala Ala Ala Pro Gly Asp Glu
```

-continued

```
         1090              1095              1100
Pro Ala Pro Pro Ala Ala Leu Pro Ser Pro Ala Lys Arg Pro Arg Glu
1105              1110              1115              1120

Thr Pro Ser Pro Ala Asp Pro Pro Gly Gly Ala Ser Lys Pro Arg Lys
              1125              1130              1135

Leu Leu Val Ser Glu Leu Ala Glu Asp Pro Ala Tyr Ala Ile Ala His
              1140              1145              1150

Gly Val Ala Leu Asn Thr Asp Tyr Tyr Phe Ser His Leu Leu Gly Ala
              1155              1160              1165

Ala Cys Val Thr Phe Lys Ala Leu Phe Gly Asn Asn Ala Lys Ile Thr
              1170              1175              1180

Glu Ser Leu Leu Lys Arg Phe Ile Pro Glu Val Trp His Pro Pro Asp
1185              1190              1195              1200

Asp Val Thr Ala Arg Leu Arg Ala Ala Gly Phe Gly Ala Val Gly Ala
              1205              1210              1215

Gly Ala Thr Ala Glu Glu Thr Arg Arg Met Leu His Arg Ala Phe Asp
              1220              1225              1230

Thr Leu Ala
       1235
```

(2) INFORMATION FOR SEQ ID NO:37:

(i) SEQUENCE CHARACTERISTICS:
        (A) LENGTH: 1240 amino acids
        (B) TYPE: amino acid
        (C) STRANDEDNESS: single
        (D) TOPOLOGY: linear (xi) SEQUENCE DESCRIPTION: SEQ ID NO:37:

```
Met Phe Cys Ala Ala Gly Gly Pro Ala Ser Pro Gly Gly Lys Ser Ala
1               5                   10                  15

Ala Arg Ala Ala Ser Gly Phe Phe Ala Pro His Asn Pro Arg Gly Ala
                20                  25                  30

Thr Gln Thr Ala Pro Pro Pro Cys Arg Arg Gln Asn Phe Tyr Asn Pro
            35                  40                  45

His Leu Ala Gln Thr Gly Thr Gln Pro Lys Ala Pro Gly Pro Ala Gln
50                  55                  60

Arg His Thr Tyr Tyr Ser Glu Cys Asp Glu Phe Arg Phe Ile Ala Pro
65                  70                  75                  80

Arg Ser Leu Asp Glu Asp Ala Pro Ala Glu Gln Arg Thr Gly Val His
                85                  90                  95

Asp Gly Arg Leu Arg Arg Ala Pro Lys Val Tyr Cys Gly Gly Asp Glu
                100                 105                 110

Arg Asp Val Leu Arg Val Gly Pro Glu Gly Phe Trp Pro Arg Arg Leu
            115                 120                 125

Arg Leu Trp Gly Gly Ala Asp His Ala Pro Glu Gly Phe Asp Pro Thr
        130                 135                 140

Val Thr Val Phe His Val Tyr Asp Ile Leu Glu His Val Glu His Ala
145                 150                 155                 160

Tyr Ser Met Arg Ala Ala Gln Leu His Glu Arg Phe Met Asp Ala Ile
                165                 170                 175

Thr Pro Ala Gly Thr Val Ile Thr Leu Leu Gly Leu Thr Pro Glu Gly
            180                 185                 190

His Arg Val Ala Val His Val Tyr Gly Thr Arg Gln Tyr Phe Tyr Met
        195                 200                 205

Asn Lys Ala Glu Val Asp Arg His Leu Gln Cys Arg Ala Pro Arg Asp
```

-continued

```
            210                 215                 220
Leu Cys Glu Arg Leu Ala Ala Leu Arg Glu Ser Pro Gly Ala Ser
225                 230                 235                 240

Phe Arg Gly Ile Ser Ala Asp His Phe Glu Ala Glu Val Val Glu Arg
                245                 250                 255

Ala Asp Val Tyr Tyr Tyr Glu Thr Arg Pro Thr Leu Tyr Tyr Arg Val
                260                 265                 270

Phe Val Arg Ser Gly Arg Ala Leu Ala Tyr Leu Cys Asp Asn Phe Cys
                275                 280                 285

Pro Ala Ile Arg Lys Tyr Glu Gly Gly Val Asp Ala Thr Thr Arg Phe
290                 295                 300

Ile Leu Asp Asn Pro Gly Phe Val Thr Phe Gly Trp Tyr Arg Leu Lys
305                 310                 315                 320

Pro Gly Arg Gly Asn Ala Pro Ala Gln Pro Arg Pro Thr Ala Phe
                325                 330                 335

Gly Thr Ser Ser Asp Val Glu Phe Asn Cys Thr Ala Asp Asn Leu Ala
                340                 345                 350

Val Glu Gly Ala Met Cys Asp Leu Pro Ala Tyr Lys Leu Met Cys Phe
                355                 360                 365

Asp Ile Glu Cys Lys Ala Gly Gly Glu Asp Glu Leu Ala Phe Pro Val
370                 375                 380

Ala Glu Arg Pro Glu Asp Leu Val Ile Gln Ile Ser Cys Leu Leu Tyr
385                 390                 395                 400

Asp Leu Ser Thr Thr Ala Leu Glu His Ile Leu Leu Phe Ser Leu Gly
                405                 410                 415

Ser Cys Asp Leu Pro Glu Ser His Leu Ser Asp Leu Ala Ser Arg Gly
                420                 425                 430

Leu Pro Ala Pro Val Val Leu Glu Phe Asp Ser Glu Phe Glu Met Leu
                435                 440                 445

Leu Ala Phe Met Thr Phe Val Lys Gln Tyr Gly Pro Glu Phe Val Thr
                450                 455                 460

Gly Tyr Asn Ile Ile Asn Phe Asp Trp Pro Phe Val Leu Thr Lys Leu
465                 470                 475                 480

Thr Glu Ile Tyr Lys Val Pro Leu Asp Gly Tyr Gly Arg Met Asn Gly
                485                 490                 495

Arg Gly Val Phe Arg Val Trp Asp Ile Gly Gln Ser His Phe Gln Lys
                500                 505                 510

Arg Ser Lys Ile Lys Val Asn Gly Met Val Asn Ile Asp Met Tyr Gly
                515                 520                 525

Ile Ile Thr Asp Lys Val Lys Leu Ser Ser Tyr Lys Leu Asn Ala Val
530                 535                 540

Ala Glu Ala Val Leu Lys Asp Lys Lys Asp Leu Ser Tyr Arg Asp
545                 550                 555                 560

Ile Pro Ala Tyr Tyr Ala Ser Gly Pro Ala Gln Arg Gly Val Ile Gly
                565                 570                 575

Glu Tyr Cys Val Gln Asp Ser Leu Leu Val Gly Gln Leu Phe Phe Lys
                580                 585                 590

Phe Leu Pro His Leu Glu Leu Ser Ala Val Ala Arg Leu Ala Gly Ile
                595                 600                 605

Asn Ile Thr Arg Thr Ile Tyr Asp Gly Gln Gln Ile Arg Val Phe Thr
                610                 615                 620

Cys Leu Leu Arg Leu Ala Gly Gln Lys Gly Phe Ile Leu Pro Asp Thr
625                 630                 635                 640
```

```
Gln Gly Arg Phe Arg Gly Leu Asp Lys Glu Ala Pro Lys Arg Pro Ala
                645                 650                 655

Val Pro Arg Gly Glu Gly Arg Pro Gly Asp Gly Asn Gly Asp Glu
        660                 665                 670

Asp Lys Asp Asp Asp Glu Asp Gly Glu Asp Gly Asp Glu Arg Glu
            675                 680                 685

Glu Val Ala Arg Glu Thr Gly Gly Arg His Val Gly Tyr Gln Gly Ala
690                 695                 700

Arg Val Leu Asp Pro Thr Ser Gly Phe His Val Asp Pro Val Val
705                 710                 715                 720

Phe Asp Phe Ala Ser Leu Tyr Pro Ser Ile Ile Gln Ala His Asn Leu
                725                 730                 735

Cys Phe Ser Thr Leu Ser Leu Arg Pro Glu Ala Val Ala His Leu Glu
                740                 745                 750

Ala Asp Arg Asp Tyr Leu Glu Ile Glu Val Gly Gly Arg Arg Leu Phe
                755                 760                 765

Phe Val Lys Ala His Val Arg Glu Ser Leu Leu Ser Ile Leu Leu Arg
            770                 775                 780

Asp Trp Leu Ala Met Arg Lys Gln Ile Arg Ser Arg Ile Pro Gln Ser
785                 790                 795                 800

Pro Pro Glu Glu Ala Val Leu Leu Asp Lys Gln Gln Ala Ala Ile Lys
                805                 810                 815

Val Val Cys Asn Ser Val Tyr Gly Phe Thr Gly Val Gln His Gly Leu
            820                 825                 830

Leu Pro Cys Leu His Val Ala Ala Thr Val Thr Thr Ile Gly Arg Glu
            835                 840                 845

Met Leu Leu Ala Thr Arg Ala Tyr Val His Ala Arg Trp Ala Glu Phe
850                 855                 860

Asp Gln Leu Leu Ala Asp Phe Pro Glu Ala Ala Gly Met Arg Ala Pro
865                 870                 875                 880

Gly Pro Tyr Ser Met Arg Ile Ile Tyr Gly Asp Thr Asp Ser Ile Phe
                885                 890                 895

Val Leu Cys Arg Gly Leu Thr Gly Glu Ala Leu Val Ala Met Gly Asp
            900                 905                 910

Lys Met Ala Ser His Ile Ser Arg Ala Leu Phe Leu Pro Pro Ile Lys
915                 920                 925

Leu Glu Cys Glu Lys Thr Phe Thr Lys Leu Leu Leu Ile Ala Lys Lys
930                 935                 940

Lys Tyr Ile Gly Val Ile Cys Gly Gly Lys Met Leu Ile Lys Gly Val
945                 950                 955                 960

Asp Leu Val Arg Lys Asn Asn Cys Ala Phe Ile Asn Arg Thr Ser Arg
                965                 970                 975

Ala Leu Val Asp Leu Leu Phe Tyr Asp Asp Thr Val Ser Gly Ala Ala
            980                 985                 990

Ala Ala Leu Ala Glu Arg Pro Ala Glu Glu Trp Leu Ala Arg Pro Leu
            995                 1000                1005

Pro Glu Gly Leu Gln Ala Phe Gly Ala Val Leu Val Asp Ala His Arg
        1010                1015                1020

Arg Ile Thr Asp Pro Glu Arg Asp Ile Gln Asp Phe Val Leu Thr Ala
1025                1030                1035                1040

Glu Leu Ser Arg His Pro Arg Ala Tyr Thr Asn Lys Arg Leu Ala His
                1045                1050                1055

Leu Thr Val Tyr Tyr Lys Leu Met Ala Arg Arg Ala Gln Val Pro Ser
                1060                1065                1070
```

Ile Lys Asp Arg Ile Pro Tyr Val Ile Val Ala Gln Thr Arg Glu Val
            1075                1080                1085

Glu Glu Thr Val Ala Arg Leu Ala Ala Leu Arg Glu Leu Asp Ala Ala
    1090                1095                1100

Ala Pro Gly Asp Glu Pro Ala Pro Ala Ala Leu Pro Ser Pro Ala
1105            1110                1115                1120

Lys Arg Pro Arg Glu Thr Pro Ser His Ala Asp Pro Gly Gly Ala
                1125                1130                1135

Ser Lys Pro Arg Lys Leu Leu Val Ser Glu Leu Ala Glu Asp Pro Gly
            1140                1145                1150

Tyr Ala Ile Ala Arg Gly Val Pro Leu Asn Thr Asp Tyr Tyr Phe Ser
            1155                1160                1165

His Leu Leu Gly Ala Ala Cys Val Thr Phe Lys Ala Leu Phe Gly Asn
        1170                1175                1180

Asn Ala Lys Ile Thr Glu Ser Leu Leu Lys Arg Phe Ile Pro Glu Thr
1185                1190                1195                1200

Trp His Pro Pro Asp Asp Val Ala Ala Arg Leu Arg Ala Ala Gly Phe
                1205                1210                1215

Gly Pro Ala Gly Ala Gly Ala Thr Ala Glu Glu Thr Arg Arg Met Leu
            1220                1225                1230

His Arg Ala Phe Asp Thr Leu Ala
        1235                1240

(2) INFORMATION FOR SEQ ID NO:38:

(i) SEQUENCE CHARACTERISTICS:
        (A) LENGTH: 1220 amino acids
        (B) TYPE: amino acid
        (C) STRANDEDNESS: single
        (D) TOPOLOGY: linear (xi) SEQUENCE DESCRIPTION: SEQ ID NO:38:

Met Ala Ala Arg Glu Gln Ala Asn Ser Val Arg Arg Ser Gly Phe Phe
1               5                   10                  15

Asn Pro Phe Ile Gly Lys Arg Pro Phe Arg Pro Gly Ser Gly Gln
            20                  25                  30

Thr Ala Glu Thr Glu Arg Pro Arg Pro Pro Gln His Ser Tyr Cys Thr
        35                  40                  45

Glu Val Gly Ser Phe Lys Phe Ile Ala Pro Arg Cys Leu Asp Glu Glu
    50                  55                  60

Ala Pro Ala Asp Gln Arg Arg Gly Val His Val Gly Thr Leu Glu Arg
65                  70                  75                  80

Pro Pro Lys Val Tyr Cys Asp Gly Ser Glu Tyr Asp Val Leu Asn Phe
                85                  90                  95

Ala Ser Gly Gly Cys Trp Pro Arg Arg Ile Arg Val Trp Asn Gly Gln
            100                 105                 110

Asp Phe Arg Gly Asp Gly Phe Asn Pro Arg Phe Glu Arg Phe His Val
        115                 120                 125

Tyr Asp Ile Val Glu Thr Ser Glu Ser Ala Ser His Asp Asp Pro Ser
    130                 135                 140

Arg Phe Ala Glu Leu Ser Arg Pro Ser Gly Ser Val Val Thr Leu Leu
145                 150                 155                 160

Gly Met Ser Glu Cys Gly Lys Arg Val Ala Val His Val Tyr Gly Val
                165                 170                 175

Arg His Tyr Phe Tyr Met Ala Lys Ala Glu Val Asp Ser Ala Cys Gly
            180                 185                 190

```
Ile Thr Thr Glu Ala Glu Leu Val Arg Ala Met Val Asp Cys Ala His
        195                 200                 205

Ser Ser Ala Leu Ser Ala Leu Gly Asn Gly Asn Gly Gly Lys Gln
    210                 215                 220

Ser Gly Gly Ser Gly Gly Trp Gly Gly Lys His Val Ser Ala
225                 230                 235                 240

Asp Cys Phe Lys Val Glu Thr Val Cys His Thr Thr Leu Tyr Tyr Phe
                245                 250                 255

Gly Ser Lys Pro Ala Leu Tyr Tyr Arg Val Ser Ala Ser Ser Ser Arg
                260                 265                 270

Leu Gly Gly Phe Ile Cys Asp Asn Phe His Pro Glu Ile Thr Lys Phe
            275                 280                 285

Glu Gly Ser Val Asp Val Thr Thr Arg Leu Leu Asp Asn Glu Asn
            290                 295                 300

Phe Thr Ser Phe Gly Trp Tyr Arg Leu Arg Pro Gly Thr His Gly Glu
305                 310                 315                 320

Arg Val Gln Leu Arg Pro Val Glu Arg His Val Thr Ser Ser Asp Val
                325                 330                 335

Glu Ile Asn Cys Thr Pro Asp Asn Leu Glu Pro Ile Pro Asp Glu Ala
            340                 345                 350

Ala Trp Pro Asp Tyr Lys Leu Met Cys Phe Asp Ile Glu Cys Lys Ala
            355                 360                 365

Gly Thr Gly Asn Glu Met Ala Phe Pro Val Ala Thr Asn Gln Glu Asp
370                 375                 380

Leu Val Ile Gln Ile Ser Cys Leu Leu Tyr Ser Leu Ala Thr Gln Asn
385                 390                 395                 400

His Glu His Thr Leu Leu Phe Ser Leu Gly Ser Cys Asp Ile Ser Glu
                405                 410                 415

Glu Tyr Ser Phe Ala Cys Val Gln Arg Gly Glu Pro Arg Pro Thr Val
                420                 425                 430

Leu Glu Phe Asp Ser Glu Tyr Glu Leu Leu Val Ala Phe Leu Thr Phe
            435                 440                 445

Leu Lys Gln Tyr Ser Pro Glu Phe Ala Thr Gly Tyr Asn Ile Val Asn
450                 455                 460

Phe Asp Trp Ala Tyr Ile Val Asn Lys Val Thr Ser Val Tyr Asn Ile
465                 470                 475                 480

Lys Leu Asp Gly Tyr Gly Lys Phe Asn Lys Gly Gly Leu Phe Lys Val
                485                 490                 495

Trp Asp Ile Ala Thr Asn His Phe Gln Lys Lys Ser Lys Val Lys Ile
            500                 505                 510

Asn Gly Leu Ile Ser Leu Asp Met Tyr Ser Val Ala Thr Glu Lys Leu
            515                 520                 525

Lys Leu Pro Ser Tyr Lys Leu Asp Ala Val Val Gly Asp Val Leu Gly
            530                 535                 540

Glu His Lys Ile Asp Leu Pro Tyr Lys Glu Ile Pro Ser Tyr Tyr Ala
545                 550                 555                 560

Gly Gly Pro Asp Arg Arg Gly Val Ile Gly Glu Tyr Cys Ile Gln Asp
                565                 570                 575

Ser Arg Leu Val Gly Lys Leu Phe Phe Lys Tyr Leu Pro His Leu Glu
            580                 585                 590

Leu Ser Ala Val Ala Lys Leu Ala Arg Ile Thr Leu Thr Arg Val Ile
            595                 600                 605

Phe Asp Gly Gln Gln Ile Arg Val Tyr Thr Cys Leu Leu Lys Leu Ala
```

-continued

```
            610                 615                 620
Arg Glu Arg Asn Phe Ile Leu Pro Asp Asn Arg Arg Phe Asp Ser
625                 630                 635                 640

Gln Ala Asp Ala Ala Ser Glu Thr Ser Glu Leu Ala Met Asp Ser Gln
                    645                 650                 655

Ser His Ala Phe Asp Ser Thr Asp Glu Pro Asp Gly Val Asp Gly Thr
                660                 665                 670

Pro Asp Ala Ala Gly Ser Gly Ala Thr Ser Glu Asn Gly Gly Gly Lys
            675                 680                 685

Pro Gly Val Gly Arg Ala Val Gly Tyr Gln Gly Ala Lys Val Leu Asp
            690                 695                 700

Pro Val Ser Gly Phe His Val Asp Pro Val Val Phe Asp Phe Ala
705                 710                 715                 720

Ser Leu Tyr Pro Ser Ile Ile Gln Ala His Asn Leu Cys Phe Thr Thr
                725                 730                 735

Leu Ala Leu Asp Glu Val Asp Leu Ala Gly Leu Gln Pro Ser Val Asp
                740                 745                 750

Tyr Ser Thr Phe Glu Val Gly Asp Gln Lys Leu Phe Phe Val His Ala
                755                 760                 765

His Ile Arg Glu Ser Leu Leu Gly Ile Leu Leu Arg Asp Trp Leu Ala
770                 775                 780

Met Arg Lys Ala Val Arg Ala Arg Ile Pro Thr Ser Thr Pro Glu Glu
785                 790                 795                 800

Ala Val Leu Leu Asp Lys Gln Gln Ser Ala Ile Lys Val Ile Cys Asn
                    805                 810                 815

Ser Val Tyr Gly Phe Thr Gly Val Ala Asn Gly Leu Leu Pro Cys Leu
                820                 825                 830

Arg Ile Ala Ala Thr Val Thr Thr Ile Gly Arg Asp Met Leu Leu Lys
                835                 840                 845

Thr Arg Asp Tyr Val His Ser Arg Trp Ala Thr Arg Glu Leu Leu Glu
850                 855                 860

Asp Asn Phe Pro Gly Ala Ile Gly Phe Arg Asn His Lys Pro Tyr Ser
865                 870                 875                 880

Val Arg Val Ile Tyr Gly Asp Thr Asp Ser Val Phe Ile Lys Phe Val
                    885                 890                 895

Gly Leu Thr Tyr Glu Gly Val Ser Glu Leu Gly Asp Ala Met Ser Arg
                900                 905                 910

Gln Ile Ser Ala Asp Leu Phe Arg Ala Pro Ile Lys Leu Glu Cys Glu
                915                 920                 925

Lys Thr Phe Gln Arg Leu Leu Leu Ile Thr Lys Lys Tyr Ile Gly
                930                 935                 940

Val Ile Asn Gly Gly Lys Met Leu Met Lys Gly Val Asp Leu Val Arg
945                 950                 955                 960

Lys Asn Asn Cys Ser Phe Ile Asn Leu Tyr Ala Arg His Leu Val Asp
                965                 970                 975

Leu Leu Leu Tyr Asp Glu Asp Val Ala Thr Ala Ala Glu Val Thr
                980                 985                 990

Asp Val Pro Pro Ala Glu Trp Val Gly Arg Pro Leu Pro Ser Gly Phe
            995                 1000                1005

Asp Lys Phe Gly Arg Val Leu Val Glu Ala Tyr Asn Arg Ile Thr Ala
        1010                1015                1020

Pro Asn Leu Asp Val Arg Glu Phe Val Met Thr Ala Glu Leu Ser Arg
1025                1030                1035                1040
```

-continued

Ser Pro Glu Ser Tyr Thr Asn Lys Arg Leu Pro His Leu Thr Val Tyr
                1045                1050                1055

Phe Lys Leu Ala Met Arg Asn Glu Glu Leu Pro Ser Val Lys Glu Arg
                1060                1065                1070

Ile Pro Tyr Val Ile Val Ala Gln Thr Glu Ala Ala Glu Arg Glu Ala
                1075                1080                1085

Gly Val Val Asn Ser Met Arg Gly Thr Ala Gln Asn Pro Val Val Thr
                1090                1095                1100

Lys Thr Ala Arg Pro Gln Pro Lys Arg Lys Leu Leu Val Ser Asp Leu
1105                1110                1115                1120

Ala Glu Asp Pro Thr Tyr Val Ser Glu Asn Asp Val Pro Leu Asn Thr
                1125                1130                1135

Asp Tyr Tyr Phe Ser His Leu Leu Gly Thr Ile Ser Val Thr Phe Lys
                1140                1145                1150

Ala Leu Phe Gly Asn Asp Val Arg Thr Thr Glu Asn Leu Leu Lys Arg
                1155                1160                1165

Phe Ile Pro Glu Thr Pro His Lys Thr Pro Thr Lys Thr Gln Ala Leu
                1170                1175                1180

Leu Glu Arg Ala Gly Phe Glu Lys Leu Thr Pro Phe Thr Pro Glu Glu
1185                1190                1195                1200

Glu Ser Arg Arg Ile Leu His Thr Val Phe Cys Thr Leu Glu Ala Ala
                1205                1210                1215

Pro His Gln Ser
                1220

(2) INFORMATION FOR SEQ ID NO:39:

(i) SEQUENCE CHARACTERISTICS:
        (A) LENGTH: 1097 amino acids
        (B) TYPE: amino acid
        (C) STRANDEDNESS: single
        (D) TOPOLOGY: linear (xi) SEQUENCE DESCRIPTION: SEQ ID NO:39:

Met Asp Thr Cys Val Glu Thr Phe Phe Asn Pro Tyr Leu Arg Arg Lys
1               5                   10                  15

Pro Arg Arg Asp Trp Arg Arg Cys Glu Asp Asn Asn Lys Asn Phe Leu
                20                  25                  30

Gln Val Val Pro Arg Gly Val Leu Tyr Asp Gly Ala Thr Gly Leu Ile
                35                  40                  45

Lys Val Gln Ser Gly Met Glu Pro Arg Met Phe Tyr Ala Glu Lys Glu
                50                  55                  60

Tyr Val Leu Asn Pro Asp Lys Pro Trp Pro Thr Leu Arg Thr Arg Gly
65                  70                  75                  80

Trp Cys Arg Gly Pro Tyr Ser Asp Asp Val Arg Phe His Thr Tyr Asp
                85                  90                  95

Gln Val Val Asn Leu Val Leu Ala Asp Ser Asp Glu Gln Ile Ser Pro
                100                 105                 110

Arg Trp Asn Ser His Val Val Pro Ala Gly Asn Val Ile Arg Met Phe
                115                 120                 125

Gly Ala Thr Asp Glu Gly Val Ser Val Cys Val Asn Val Phe Gly Gln
                130                 135                 140

Lys Ala Tyr Phe Tyr Cys Glu Arg Met Gln Ser Glu Asp Leu Lys Asn
145                 150                 155                 160

Thr Val Tyr Asp Ile Ala Asp Lys Val Pro Glu Pro Cys Ser Pro Phe
                165                 170                 175

-continued

```
Ser Val Ser Ile Ser Pro Val Thr Lys Ser Ser Phe Tyr Gly Tyr Gly
            180                 185                 190

Leu Gly His Ile Pro Asn Leu Tyr Arg Leu Ser Phe Asn Asn Trp Asn
            195                 200                 205

Met Cys Arg Lys Ile Gly Lys Arg Met Leu Glu Glu Gly Arg Lys Val
210                 215                 220

Tyr Glu Leu Gly Val Asp Pro Leu Ala Arg Phe Leu Ile Asp Arg Lys
225                 230                 235                 240

Ile Pro Ser Phe Gly Trp Cys Leu Ala Arg Arg Tyr Ser Val Arg Ala
                245                 250                 255

Ala Gly Tyr Val Ser Arg Ala Gln Leu Glu Ile Asp Cys Asp Val Ala
                260                 265                 270

Asp Ile Leu Pro Ile Glu Glu Gln Ser Asn Trp Pro Phe Tyr Arg Cys
            275                 280                 285

Leu Ser Phe Asp Ile Glu Cys Met Ser Gly Thr Gly Ala Phe Pro Ala
            290                 295                 300

Ala Glu Asn Val Asp Asp Ile Ile Gln Ile Ser Cys Val Cys Phe
305                 310                 315                 320

Gly Val Gly Glu Met Val His His Ala Tyr Asp Val His Ala Asp Leu
                325                 330                 335

Ser Thr Pro Ala Val Pro Glu Asn His Leu Phe Thr Ile Gly Pro Cys
                340                 345                 350

Ala Pro Ile Pro Asp Val Lys Ile Tyr Thr Phe Pro Ser Glu Tyr Glu
            355                 360                 365

Met Leu Arg Gly Phe Phe Ile Phe Leu Ser Trp Tyr Ser Pro Glu Phe
            370                 375                 380

Ile Thr Gly Tyr Asn Ile Asn Gly Phe Asp Ile Lys Tyr Ile Leu Thr
385                 390                 395                 400

Arg Ala Glu Lys Leu Tyr Lys Met Asp Val Gly Gln Phe Thr Lys Leu
                405                 410                 415

Arg Arg Gly Gly Arg Met Phe Val Phe Ser Pro Glu Lys Gly Lys Ala
                420                 425                 430

Gly Phe Gly Thr Ser Asn Thr Val Lys Val Phe Trp Ser Gly Thr Val
            435                 440                 445

Val Leu Asp Met Tyr Pro Val Cys Thr Ala Lys Ala Ser Ser Pro Asn
450                 455                 460

Tyr Lys Leu Asp Thr Met Ala Glu Ile Tyr Leu Lys Lys Lys Asp
465                 470                 475                 480

Asp Leu Ser Tyr Lys Glu Ile Pro Val Gln Phe Ser Ala Gly Asp Glu
                485                 490                 495

Gly Arg Ala Pro Gly Lys Tyr Cys Leu Gln Asp Ala Val Leu Val
                500                 505                 510

Arg Glu Leu Phe Glu Met Leu Ala Phe His Phe Glu Ala Ala Ala Ile
            515                 520                 525

Ala Arg Leu Ala Arg Ile Pro Leu Arg Lys Val Ile Phe Asp Gly Gln
530                 535                 540

Gln Ile Arg Ile Tyr Thr Cys Leu Leu Glu Glu Cys Ser Gly Arg Asp
545                 550                 555                 560

Met Ile Leu Pro Asn Met Pro Ser Leu Gly His Gly Ala Ala Ala Ala
                565                 570                 575

Ile Glu Glu Ala Ala Gly Gly Glu Gly Asp Glu Thr Ser Glu Gly
                580                 585                 590

Glu Asn Ser Asn Asn Ser Arg Thr Val Gly Tyr Gln Gly Ala Thr Val
            595                 600                 605
```

-continued

| | | | | | | | | | | | |
|---|---|---|---|---|---|---|---|---|---|---|---|
|Leu|Glu|Pro|Glu|Cys|Gly|Phe|His|Val|Pro|Val|Cys|Val|Phe|Asp|
| |610| | | |615| | | |620| | | | | |
|Phe|Ala|Ser|Leu|Tyr|Pro|Ser|Ile|Ile|Met|Ser|Asn|Asn|Leu|Cys|Tyr|
|625| | | | |630| | | |635| | | | |640|
|Ser|Thr|Leu|Leu|Val|Glu|Gly|Ser|Pro|Glu|Val|Pro|Glu|Lys|Asp|Val|
| | | | |645| | | | |650| | | | |655| |
|Leu|Arg|Val|Glu|Ile|Gly|Asp|Gln|Cys|His|Arg|Phe|Val|Arg|Glu|Asn|
| | | |660| | | | |665| | | | |670| | |
|Val|His|Arg|Ser|Leu|Leu|Ala|Glu|Leu|Leu|Val|Arg|Trp|Leu|Thr|Gln|
| | |675| | | | |680| | | | |685| | | |
|Arg|Lys|Leu|Val|Arg|Glu|Ala|Met|Lys|Gln|Cys|Thr|Asn|Glu|Met|Gln|
| |690| | | | |695| | | | |700| | | | |
|Arg|Met|Ile|Met|Asp|Lys|Gln|Gln|Leu|Ala|Leu|Lys|Val|Thr|Cys|Asn|
|705| | | | |710| | | | |715| | | | |720|
|Ala|Phe|Tyr|Gly|Phe|Thr|Gly|Val|Ala|Ala|Gly|Met|Leu|Pro|Cys|Leu|
| | | | |725| | | | |730| | | | |735| |
|Pro|Ile|Ala|Ala|Ser|Ile|Thr|Lys|Ile|Gly|Arg|Asp|Met|Leu|Leu|Ala|
| | | |740| | | | |745| | | | |750| | |
|Thr|Ala|Gly|His|Ile|Glu|Asp|Arg|Cys|Asn|Arg|Pro|Asp|Phe|Leu|Arg|
| | |755| | | | |760| | | | |765| | | |
|Thr|Val|Leu|Gly|Leu|Pro|Pro|Glu|Ala|Ile|Asp|Pro|Glu|Ala|Leu|Arg|
| |770| | | | |775| | | | |780| | | | |
|Val|Lys|Ile|Ile|Tyr|Gly|Asp|Thr|Asp|Ser|Val|Phe|Ala|Ala|Phe|Tyr|
|785| | | | |790| | | | |795| | | | |800|
|Gly|Ile|Asp|Lys|Glu|Ala|Leu|Leu|Lys|Ala|Val|Gly|Ala|Leu|Ala|Ala|
| | | | |805| | | | |810| | | | |815| |
|Asn|Val|Thr|Asn|Ala|Leu|Phe|Lys|Glu|Pro|Val|Arg|Leu|Glu|Phe|Glu|
| | | |820| | | | |825| | | | |830| | |
|Lys|Met|Phe|Val|Ser|Leu|Met|Met|Ile|Cys|Lys|Lys|Arg|Tyr|Ile|Gly|
| | |835| | | | |840| | | | |845| | | |
|Lys|Val|His|Gly|Ser|Gln|Asn|Leu|Ser|Met|Lys|Gly|Val|Asp|Leu|Val|
| |850| | | | |855| | | | |860| | | | |
|Arg|Arg|Thr|Ala|Cys|Gly|Phe|Val|Lys|Ala|Val|Val|Ser|Asp|Val|Leu|
|865| | | | |870| | | | |875| | | | |880|
|His|Met|Val|Phe|Asn|Asp|Glu|Thr|Val|Ser|Glu|Gly|Thr|Met|Lys|Leu|
| | | | |885| | | | |890| | | | |895| |
|Ser|Arg|Met|Thr|Phe|Asp|Asp|Leu|Lys|Lys|Asn|Gly|Ile|Pro|Cys|Glu|
| | | |900| | | | |905| | | | |910| | |
|Phe|Gly|Pro|Val|Val|Ser|Arg|Leu|Cys|Arg|Ala|Arg|Asp|Asp|Leu|His|
| | |915| | | | |920| | | | |925| | | |
|Leu|Lys|Lys|Val|Pro|Val|Pro|Glu|Leu|Thr|Leu|Ser|Ser|Val|Leu|Ser|
| |930| | | | |935| | | | |940| | | | |
|Gln|Glu|Leu|Ser|Cys|Tyr|Lys|Gln|Lys|Asn|Leu|Pro|His|Leu|Ala|Val|
|945| | | | |950| | | | |955| | | | |960|
|Ile|Arg|Arg|Leu|Ala|Ala|Arg|Lys|Glu|Glu|Leu|Pro|Ala|Val|Gly|Asp|
| | | | |965| | | | |970| | | | |975| |
|Arg|Val|Glu|Tyr|Val|Leu|Thr|Leu|Pro|Asp|Gly|Cys|Lys|Lys|Asn|Val|
| | | |980| | | | |985| | | | |990| | |
|Pro|Asn|Tyr|Glu|Ile|Ala|Glu|Asp|Pro|Arg|His|Val|Val|Glu|Ala|Lys|
| | |995| | | | |1000| | | | |1005| | | |
|Leu|Ser|Ile|Asn|Ala|Glu|Lys|Tyr|Tyr|Glu|Gln|Val|Val|Lys|Ala|Val|
| |1010| | | | |1015| | | | |1020| | | | |
|Thr|Asn|Thr|Leu|Met|Pro|Val|Phe|Pro|Arg|Asp|Met|Pro|Lys|Arg|Glu|

-continued

```
          1025                1030                1035                1040
Lys Phe Phe Ser Leu Val Val Pro Gln Arg Ile Tyr Ile Pro Asp Gln
                    1045                1050                1055

Phe Leu His Leu Cys Gly Asn Val Asn Glu Leu Ala Arg Gly Gly Asp
            1060                1065                1070

Asp Ser Asp Gly Gly Asp Ser Glu Lys Glu Asn Met Asp Thr Glu Arg
            1075                1080                1085

Ser Ser Ser His Glu Ala Met Glu Thr
            1090                1095
```

(2) INFORMATION FOR SEQ ID NO:40:

(i) SEQUENCE CHARACTERISTICS:
        (A) LENGTH: 1094 amino acids
        (B) TYPE: amino acid
        (C) STRANDEDNESS: single
        (D) TOPOLOGY: linear (xi) SEQUENCE DESCRIPTION: SEQ ID NO:40:

```
Met Ser Ala Pro Val Phe Phe Asn Pro Tyr Leu Cys Gly Gly Ala Ala
1               5                   10                  15

Arg Arg Arg Asn Gly Cys Ser Thr Val Asp Ser Arg Arg Val Asn Gly
            20                  25                  30

Pro Thr Lys Gly Lys Lys Ser Phe Leu Gln Val Val Arg Arg Gly
            35                  40                  45

Val Ile Tyr Asp Gly Glu Lys Gly Leu Ile Lys Lys Val Thr Gln His
        50                  55                  60

Pro Pro Arg Met Phe Tyr Asn Asn Val Gln Tyr Leu Leu Glu Pro Gln
65                  70                  75                  80

Met Ser Trp Pro Thr Leu Pro Cys Arg Glu Thr Cys Arg Val Gly Cys
                85                  90                  95

Gly Arg Glu Gln Pro Leu Arg Phe His Thr Phe Asp Gln Ile Asp Ser
            100                 105                 110

Thr Val Tyr Ala Asp Ser Val Glu Gln Ile Phe Leu Gly Tyr Arg Arg
        115                 120                 125

His Val Val Pro Cys Gly Asn Val Ile Arg Met Phe Gly Arg Thr Cys
    130                 135                 140

Asp Gly Ser Ser Val Cys Val Asn Val Phe Gly Gln Pro Ser Tyr Phe
145                 150                 155                 160

Tyr Cys Glu Tyr Asp Gly Ser Gly Gly Tyr Leu Asp Asn Tyr Leu Ser
                165                 170                 175

Thr Val Leu Lys Glu Thr Glu Asp Val Thr Lys Ile Val Phe Thr Leu
            180                 185                 190

Asp Ala Gln Arg Val His Lys Tyr Ser Leu Phe Gly Tyr Asn Thr Lys
        195                 200                 205

Tyr Ile Glu Asn Leu Tyr Arg Val Thr Leu Asn Asn Trp Pro Val Cys
    210                 215                 220

Lys Arg Leu Ala Gln Asn Leu Gln Ser Arg Gly Leu Arg Val Tyr Glu
225                 230                 235                 240

Ala Gly Val Asp Pro Val Ala Arg Phe Cys Val Asp Arg Lys Ile Pro
                245                 250                 255

Ser Phe Gly Trp Cys Val Ile Lys Arg Phe Tyr Ala Arg Ser Ser Gly
            260                 265                 270

Leu Ala Ser Phe Cys Asp Ile Glu Ile Asp Cys Glu Ile Gly Asp Val
        275                 280                 285

Glu Ala Asp Asp Ser Asp Met Ser Trp Pro Glu Tyr Arg Cys Ala Ser
```

```
            290                 295                 300
Phe Asp Ile Glu Cys Met Ser Gly Gly Asp Arg Phe Pro Asp Ser Ser
305                 310                 315                 320

Met Val Asp Asp Ile Val Ile Gln Ile Ser Val Ile Cys Tyr Ala Val
                325                 330                 335

Gly Arg Ser Gly Ala Glu Ser Asp Gly Val Ser Gly Ala Glu Ala Ala
                340                 345                 350

Val Arg Glu His Gln His Leu Phe Thr Leu Gly Pro Cys Ala Pro Ile
                355                 360                 365

Pro Gly Thr His Val Tyr Glu Phe Pro Ser Glu Tyr Glu Leu Leu Leu
370                 375                 380

Gly Phe Phe Ile Phe Phe Lys Ala Tyr Pro Pro Asp Ile Leu Thr Gly
385                 390                 395                 400

Tyr Asn Ile Asn Leu Phe Asp Ile Lys Tyr Leu Leu Gln Arg Met Glu
                405                 410                 415

Lys Ile Tyr His Ala Asn Val Ser Glu Phe Thr Lys Leu Arg Phe Gly
                420                 425                 430

Gly Arg Phe Ser Ile Tyr Val Pro Val Gly Thr Lys Pro Arg Asn Ala
                435                 440                 445

Ser Ser Ala Ser Ile Lys Val His Cys Thr Gly Thr Val Val Leu Asp
450                 455                 460

Met Tyr Pro Val Cys Val Ala Lys Thr Ser Ala Pro Asn Tyr Lys Leu
465                 470                 475                 480

Glu Thr Met Ala Glu Met Tyr Leu Asn Glu His Lys Asp Asp Leu Ser
                485                 490                 495

Tyr Lys Glu Ile Pro Pro Thr Phe Leu Ala Asn Asp Asn Gly Arg Ala
                500                 505                 510

Val Val Gly Arg Tyr Cys Ile Lys Asp Ala Leu Leu Val Lys Arg Leu
                515                 520                 525

Phe Glu Lys Leu Asn Tyr His Tyr Glu Ala Ala Ser Val Ala Arg Leu
530                 535                 540

Ala Arg Ile Pro Leu Arg Ser Val Ile Phe Glu Gly Gln Gln Ile Arg
545                 550                 555                 560

Ile Tyr Ser Cys Ile Leu Glu Glu Ala Gly Glu Arg Asn Met Ile Leu
                565                 570                 575

Pro Ser Phe Leu Thr Ala Lys Arg Pro Gly Glu Leu Ala Thr Glu Ser
                580                 585                 590

Ser Pro Val Ala Ser Phe Glu Glu Asp Ser Glu Gln Thr Ser Asp Ser
                595                 600                 605

Ser Leu Gly Glu Val Ser Ser Gln Gly Ser Ser Asp Gly Gly Val Gly
                610                 615                 620

Tyr Gln Gly Ala Thr Val Leu Glu Pro Asp Val Gly Phe Tyr Asp Thr
625                 630                 635                 640

Pro Val Ala Val Phe Asp Phe Ala Ser Leu Tyr Pro Ser Ile Ile Met
                645                 650                 655

Arg His Asn Leu Cys Tyr Ser Thr Tyr Leu Pro Leu Gly Arg Asp Asp
                660                 665                 670

Gly Leu Ser Asp Asp Asp Val Phe Leu Leu Glu Phe Asp Asp Gly Thr
                675                 680                 685

Arg Tyr Gly Phe Val Arg Glu His Val Arg Lys Ser Ile Leu Gly Glu
                690                 695                 700

Leu Leu Ala Arg Trp Leu Ala Lys Arg Lys Ser Val Arg Lys Val Leu
705                 710                 715                 720
```

```
Ala Glu Cys Gln Asp Glu Val Glu Lys Leu Ile Leu Asp Lys Tyr Gln
            725                 730                 735

Leu Ala Leu Lys Val Thr Cys Asn Ala Phe Tyr Gly Phe Thr Gly Val
            740                 745                 750

Ser Ser Gly Met Met Pro Cys Leu Pro Ile Ala Ala Ile Thr Arg
            755                 760                 765

Ile Gly Arg Asp Met Leu Met Ser Val Val Asp Tyr Val Asn Thr Tyr
            770                 775                 780

Met Gly His Ala Glu Phe Trp Leu Arg Tyr Leu Gly Glu Asp Leu
785                 790                 795                 800

Thr Gly Asp Ala Leu Asn Val Lys Val Ile Tyr Gly Asp Thr Asp Ser
            805                 810                 815

Val Phe Val Ile Cys Gly Gly Val Lys Cys Gly Ser Val Leu Glu His
            820                 825                 830

Gly Glu Ala Ile Ala Gly His Ile Thr Arg Ala Leu Phe Arg Glu Pro
            835                 840                 845

Ile Lys Leu Glu Phe Glu Lys Val Phe Val Asn Leu Met Met Ile Cys
            850                 855                 860

Lys Lys Arg Tyr Val Gly Arg Ile Tyr Gly Gln Thr Lys Leu Ser Met
865                 870                 875                 880

Lys Gly Ile Glu Leu Val Arg Lys Thr Ala Cys Glu Tyr Val Lys Ser
            885                 890                 895

Thr Val Arg Asn Val Leu Asn Met Ile Phe Phe Glu Asp Asp Val Ser
            900                 905                 910

Ala Gly Ala Val Glu Leu Ser Arg Met Thr Met Asp Asp Val Lys Arg
            915                 920                 925

His Gly Val Pro Ser Gly Phe Tyr Arg Ile Val Glu Ala Leu Ser Asn
            930                 935                 940

Ala Arg Asp Glu Leu Tyr Leu Asn Arg Val Asp Val Lys Lys Leu Val
945                 950                 955                 960

Leu Ser Ala Ser Leu Ser Gln Glu Val Ser Ala Tyr Lys Gln Gln Asn
            965                 970                 975

Leu Pro His Leu Arg Val Ile Gln Arg Leu Ala Ala Arg Pro Glu
            980                 985                 990

Leu Pro Ser Val Gly Asp Arg Val Pro Tyr Val Leu Ile Ala Pro Pro
            995                 1000                1005

Pro Gly Ser Ser Lys Asn Val Pro Asn Tyr Glu Ile Ser Glu Asp Pro
            1010                1015                1020

Gly Tyr Val Ile Glu His Lys Leu Pro Val Asn Gly Glu Lys Tyr Phe
1025                1030                1035                1040

Glu His Val Val Lys Thr Val Thr Asn Val Leu Gly Pro Ile Ile Pro
            1045                1050                1055

Lys Asp Cys Ala Arg Lys Glu Lys Phe Leu Ser Tyr Val Leu Pro Gln
            1060                1065                1070

Arg Val Tyr Val Ser Arg Pro Phe Met Pro Tyr Ala Cys Ala Ala Asn
            1075                1080                1085

Glu Leu Val Val Gly Val
            1090
```

(2) INFORMATION FOR SEQ ID NO:41:

(i) SEQUENCE CHARACTERISTICS:
        (A) LENGTH: 985 amino acids
        (B) TYPE: amino acid
        (C) STRANDEDNESS: single
        (D) TOPOLOGY: linear (xi) SEQUENCE DESCRIPTION: SEQ ID NO:41:

```
Met Asp Arg Asn Ala Val Leu Tyr Gly Val Leu Glu His Arg Leu Pro
1               5                   10                  15

Lys Trp Val Glu Leu Ser Asp Thr Asp Leu Glu Pro Phe Phe
            20                  25                  30

Ser Ser Val Arg Tyr Ile Thr Ala Gly Ser Glu Asp Ala Ile Met Ile
            35                  40                  45

Gln Ala Leu Asn Leu Asn Thr Asp Glu Ile Val Val Phe Leu Val Thr
    50                  55                  60

Asn Leu Asn Phe Met Ala Leu Ile Pro Thr Val Tyr Ile Glu Asn Pro
65                  70                  75                  80

Gly Ile Arg Gln Leu Ile Ala Ser Thr Pro Ile Ser Tyr Arg Ser Pro
                85                  90                  95

Ile Thr Val Phe Asn Gly Asp Leu Lys Lys Trp Met Asp Cys Asp Leu
                100                 105                 110

Phe Val Phe Gly Thr Met Ala Ala Gln Lys Ala Phe Ile Lys Ala Gly
            115                 120                 125

Asn Ser Val Leu Gly Ser Leu Gly Gly Asn Val Tyr Thr Tyr Gly Asp
    130                 135                 140

His Val Ser Asn Phe Asp Gly Asn Thr Pro Val Leu Gln Asn Asn Leu
145                 150                 155                 160

Met Cys Ser His Val Tyr Tyr Thr Arg Tyr Lys Thr Asp Val Tyr Ala
                165                 170                 175

Pro Trp Glu Phe Tyr Tyr Asp Gln Lys Arg Asp Gln Gly Tyr Leu Met
                180                 185                 190

Ser Leu Pro Ala Ile Ile Pro Arg Cys Lys Arg Glu Gly Ala Phe Asp
            195                 200                 205

Ile Glu Thr Ile Val His Glu Asn Ala Met Asp Gln Asp Leu Asn Cys
    210                 215                 220

Gln Lys Phe Phe Lys Ser Glu Phe Arg Ser Met Glu Glu Ser Gln Val
225                 230                 235                 240

Leu Ile Gln Arg Phe Arg Glu Ala Gly Val Thr Gly Leu Pro Pro Ser
                245                 250                 255

Pro Phe Val Gly Ile Thr Gln Lys Leu His Glu Ile Val Ser Ile Ser
            260                 265                 270

Leu Val Val Cys Asn Tyr His Lys Thr Gly Pro Lys Lys Lys Glu Tyr
        275                 280                 285

Tyr Val Tyr Tyr Asn Thr Lys Lys Met Glu Asn Pro Met Glu Met Ile
    290                 295                 300

Pro Val Glu His Leu His Leu Asp Ala Ser Arg Ile Lys Phe Glu Ala
305                 310                 315                 320

Cys Lys Asn Glu Phe Tyr Met Leu Leu Ala Phe Ile Asn Arg Leu Arg
                325                 330                 335

Lys Ser Val Asn Val Leu Tyr Val Tyr Asn Ala Gln Phe Asp Ile Gln
            340                 345                 350

Val Ile Gln Gln Arg Leu Arg Tyr Tyr Ala Phe Lys Gln Arg Ala Pro
        355                 360                 365

Arg Cys Cys Lys Gly His Asp Asp Ile Pro His Glu Trp Gly Lys Ala
    370                 375                 380

Leu Met Glu Lys Trp Glu Ala Phe Leu Ser Val Lys Pro Gln Leu Phe
385                 390                 395                 400

Lys Ala Gln Ile Leu Met Gly Gln Asp Ile Leu Lys Ala Asn Tyr Leu
                405                 410                 415
```

```
Lys Leu Leu Glu Gly Ile Gly Ser Val Leu Ala Gln Ala Lys Ser Thr
            420                 425                 430

Met Ala Lys Met Cys Thr Ile Lys Glu Arg Ile Asp Ser Tyr Arg Lys
            435                 440                 445

Met Lys Asp Thr Val Gln Asn Phe Lys Ser His Gly Phe Gly Cys Asp
450                 455                 460

Ile Ile Asp Met Met Tyr Val Cys Lys Arg Lys Glu Phe Glu Ala Lys
465                 470                 475                 480

Asp Gly Ser Leu Asn Thr Val Ala Gln Leu Ile Ile Lys Lys Phe Lys
                485                 490                 495

Pro His Lys Ala Thr Pro Lys Ile His Lys Met Asp Asp Ile Thr Tyr
            500                 505                 510

Asp Lys Leu Asp Gly Tyr Tyr Arg Ala Gly Thr Lys Ile Ala Glu
            515                 520                 525

Cys Leu Ile Tyr Asn Leu Ile Asp Ser Leu Leu Val Ile Arg Ile Ala
530                 535                 540

Lys Asn Leu Lys Pro Met Glu Glu Tyr Ile Tyr Arg Gln Leu Ala Cys
545                 550                 555                 560

Tyr Asn Ile Asp Thr Ala Ala His Thr Arg Gly Val Met Asn Phe Cys
                565                 570                 575

Gly Phe Ile Gln Ser Thr Lys Val Val Glu Val Ser Arg Asn Lys Ala
            580                 585                 590

Arg Leu Asp Ala Gly Ile Val Met Ala Thr Asp Tyr Ile Arg Asn Ser
            595                 600                 605

Leu Phe Thr Pro Glu Thr Ile Pro Arg Arg Gly Gly Phe Val Met Ala
            610                 615                 620

Pro Leu Thr Gly Leu Phe Phe Ala Arg Pro Thr Gln Cys Phe Glu Leu
625                 630                 635                 640

Cys Leu Asp Phe Thr Ser Met Tyr Pro Ser Met Met Cys Asp Leu Asn
                645                 650                 655

Ile Ser Pro Glu Thr Ile Val Asp Ser Asp Lys Thr Asn Arg Val Gly
            660                 665                 670

Asp Tyr Met Gly Tyr Asp Trp Ser Lys Ile Asp Gln Gly Phe Glu Lys
            675                 680                 685

Phe Thr Leu Val Leu Arg Val Asp Arg Thr Asp Pro Glu Asn Pro Lys
            690                 695                 700

Leu Val Arg His Thr Ser Asp Thr Ser Leu Ser Leu Lys Arg Tyr Leu
705                 710                 715                 720

Arg Leu Arg Thr Glu His Lys Arg Ala Leu Lys Gln Ser Ser Gly Ser
                725                 730                 735

Val Ala Glu Tyr His Asn Arg Leu Gln Asn Glu Met Lys Ile Cys Thr
            740                 745                 750

Asn Thr His Tyr Gly Val Ser Glu His Thr Cys Ser Leu Met Ile Thr
            755                 760                 765

Thr Gln Gly Gln His Lys Ile Lys Leu Val Asn Glu Phe Ile Lys Thr
770                 775                 780

Leu Asn Arg Thr Gly His Ser Leu Phe Pro Asn Tyr Gly Asp Thr Asp
785                 790                 795                 800

Ser Thr Met Leu Tyr His Pro Ser Asp Glu Ser Glu Thr Gln Leu Glu
                805                 810                 815

Asp Met Val Thr Leu Glu Asp Glu Met Arg Ala Glu Leu Arg Glu Tyr
            820                 825                 830

Met Leu Lys Lys Leu Ser Ala Glu Leu Val Asn Arg Val Lys Glu Lys
```

```
            835                 840                 845
Thr Lys Arg Thr Asp Thr Phe Val Gln Ser Phe Leu Ser Asp Val Glu
    850                 855                 860

Thr Val Leu Phe Asp Asp Met Val Glu Lys Leu Arg Leu Phe Ser Gln
865                 870                 875                 880

Gly Glu Val Ile Glu Pro Phe Lys Asp Gly Thr Trp Trp Val Val
                885                 890                 895

Asp Pro Leu Thr Gly Ile Trp Met Asp Cys Ser Thr Pro Phe Ser Ser
            900                 905                 910

Glu Leu Ile Cys Lys Leu Glu Tyr Glu Asn Ala Ser Ser Ile Gly Cys
        915                 920                 925

His Val Ala Lys Lys Met Val Ser Ile Gly Ser Thr Tyr Leu Phe Phe
    930                 935                 940

Lys Lys Ile Ser Leu Tyr His Val Arg Val Trp Arg Met Cys Ala Asp
945                 950                 955                 960

Thr Asp Gly Ser Pro Ser His Leu Tyr Phe Pro Val Ser Leu Ser Arg
                965                 970                 975

Thr Arg Ala Lys Gln Arg Gly Asp His
            980                 985

(2) INFORMATION FOR SEQ ID NO:42:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:42:

GTGGTGTTTG ATTTTCAAAG TTTGTATCCG AGCATTATGA TGGCGCATAA TCTGTGTTAT     60

AGTACTTTAG TTTTGGAT                                                  78

(2) INFORMATION FOR SEQ ID NO:43:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:43:

GCCGTGTTCG ACTTTGCCAG CCTCTACCCT TCCATCATCA TGGCCCACAA CCTCTGCTAC     60

TCCACCCTGC TGGTGCCG                                                  78

(2) INFORMATION FOR SEQ ID NO:44:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:44:

GCCGTCTTCG ATTTCGCCAG TCTGTATCCG TCTATCATTA TGCGACACAA CCTGTGTTAC     60

TCGACGTATC TTCCGCTC                                                  78

(2) INFORMATION FOR SEQ ID NO:45:

(i) SEQUENCE CHARACTERISTICS:
        (A) LENGTH: 78 base pairs
        (B) TYPE: nucleic acid
```

```
        (C) STRANDEDNESS: double
        (D) TOPOLOGY: linear (xi) SEQUENCE DESCRIPTION: SEQ ID NO:45:

TGCGTGTTCG ATTTCGCCAG TCTGTATCCG TCCATCATCA TGTCCAACAA TCTGTGCTAC      60

TCCACCCTCT TGGTGGAG                                                   78

(2) INFORMATION FOR SEQ ID NO:46:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:46:

GTGGTGTTCG ACTTTGCCAG CCTGTACCCC AGCATCATCC AGGCCCACAA CCTGTGCTTC      60

AGCACGCTCT CCCTGAGG                                                   78

(2) INFORMATION FOR SEQ ID NO:47:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:47:

GTGGTGTTTG ACTTTGCCAG CCTGTACCCC AGCATCATCC AGGCCCACAA CCTGTGCTTC      60

AGTACGCTCT CCCTGCGG                                                   78

(2) INFORMATION FOR SEQ ID NO:48:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:48:

GTCGTATTGG ATTTTGCAAG TTTATATCCA AGTATAATTC AGGCCCATAA CTTATGTTTT      60

ACCACGCTAA CGTTAAAT                                                   78

(2) INFORMATION FOR SEQ ID NO:49:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:49:

GTGGTGTTTG ACTTCGCTAG CTTATACCCA AGCATTATCC AGGCCCATAA CCTCTGTTTC      60

ACCACCCTGG CGCTCGAT                                                   78

(2) INFORMATION FOR SEQ ID NO:50:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:50:
```

CTGGTGGTGG ACTTTGCCAG CCTCTACCCG AGCATCATTC AGGCTCATAA TCTCTGTTAT    60

TCTACCATGA TAACGCCG    78

(2) INFORMATION FOR SEQ ID NO:51:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:51:

TTAGTAGTAG ACTTTGCTAG CCTGTATCCT AGTATTATAC AAGCTCATAA TCTATGCTAC    60

TCCACTCTTA TACCCCAC    78

(2) INFORMATION FOR SEQ ID NO:52:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (xi) SEQUENCE DESCRIPTION: SEQ ID NO:52:

CTGTGTCTGG ACTTTACCAG CATGTACCCC AGTATGATGT GCGATCTCAA CATCTCTCCT    60

GAAACCATCG TGGACAGC    78

(2) INFORMATION FOR SEQ ID NO:53:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:53:

GCTCTGAAAA CAACATGTAA CTCGGTGTAC GGTGTCACGG GAGCGGCGCA CGGG    54

(2) INFORMATION FOR SEQ ID NO:54:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:54:

GCGCTCAAAG TAACGTGCAA CGCTTTCTAC GGTTTTACCG GCGTGGTCAA CGGT    54

(2) INFORMATION FOR SEQ ID NO:55:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:55:

GCCCTCAAAG TGACGTGCAA CGCGTTTTAC GGTTTCACCG GGTCAGCAG CGGC    54

(2) INFORMATION FOR SEQ ID NO:56:

(i) SEQUENCE CHARACTERISTICS:
        (A) LENGTH: 54 base pairs
        (B) TYPE: nucleic acid
        (C) STRANDEDNESS: double (D) TOPOLOGY: linear (xi) SEQUENCE DESCRIPTION: SEQ ID NO:56:

GCCCTCAAAG TAACGTGCAA CGCTTTCTAC GGTTTCACGG GGGTAGCGGC CGGG          54

(2) INFORMATION FOR SEQ ID NO:57:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:57:

GCCATCAAGG TCGTGTGTAA CTCGGTGTAC GGGTTCACGG GAGTGCAGCA CGGA          54

(2) INFORMATION FOR SEQ ID NO:58:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:58:

GCGATAAAAG TAGTTTGTAA TTCCGTGTAC GGTTTTACTG GAGTTGCGCA GGGA          54

(2) INFORMATION FOR SEQ ID NO:59:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:59:

GCGATTAAGG TGATATGCAA CTCGGTTTAC GGATTCACGG GGGTGGCAAA CGGC          54

(2) INFORMATION FOR SEQ ID NO:60:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:60:

GCCATCAAGT GCACGTGCAA CGCCGTCTAC GGCTTCACCG GGGTGGCCAA CGGC          54

(2) INFORMATION FOR SEQ ID NO:61:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:61:

GCTATTAAAG TAACTTGTAA TGCTGTGTAT GGGTTTACAG GAGTTGCGTC AGGC          54

(2) INFORMATION FOR SEQ ID NO:62:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (xi) SEQUENCE DESCRIPTION: SEQ ID NO:62:

GAAATGAAGA TCTGTACAAA CACCCACTAC GGGGTCTCTG AGCACACGTG TTCG        54

(2) INFORMATION FOR SEQ ID NO:63:

(i) SEQUENCE CHARACTERISTICS:
       (A) LENGTH: 45 base pairs
       (B) TYPE: nucleic acid
       (C) STRANDEDNESS: double
       (D) TOPOLOGY: linear (xi) SEQUENCE DESCRIPTION: SEQ ID NO:63:

GTAATTTATG GTGATACGGA TAGCATCTTT ATGTCTGTCA GAAAT        45

(2) INFORMATION FOR SEQ ID NO:64:

(i) SEQUENCE CHARACTERISTICS:
       (A) LENGTH: 45 base pairs
       (B) TYPE: nucleic acid
       (C) STRANDEDNESS: double
       (D) TOPOLOGY: linear (xi) SEQUENCE DESCRIPTION: SEQ ID NO:64:

ATCATCTACG GGGACACGGA CTCCATATTT GTGCTGTGCC GCGGC        45

(2) INFORMATION FOR SEQ ID NO:65:

(i) SEQUENCE CHARACTERISTICS:
       (A) LENGTH: 45 base pairs
       (B) TYPE: nucleic acid
       (C) STRANDEDNESS: double
       (D) TOPOLOGY: linear (xi) SEQUENCE DESCRIPTION: SEQ ID NO:65:

GTGATATACG GGGACACGGA CAGCGTCTTT GTCATATGCG GCGGT        45

(2) INFORMATION FOR SEQ ID NO:66:

(i) SEQUENCE CHARACTERISTICS:
       (A) LENGTH: 45 base pairs
       (B) TYPE: nucleic acid
       (C) STRANDEDNESS: double
       (D) TOPOLOGY: linear (xi) SEQUENCE DESCRIPTION: SEQ ID NO:66:

ATCATCTACG GCGACACCGA CAGTGTGTTT GCGGCTTTCT ACGGC        45

(2) INFORMATION FOR SEQ ID NO:67:

(i) SEQUENCE CHARACTERISTICS:
       (A) LENGTH: 45 base pairs
       (B) TYPE: nucleic acid
       (C) STRANDEDNESS: double
       (D) TOPOLOGY: linear (xi) SEQUENCE DESCRIPTION: SEQ ID NO:67:

ATCATCTACG GGGACACGGA CTCCATATTT GTGCTGTGCC GCGGC        45

(2) INFORMATION FOR SEQ ID NO:68:

(i) SEQUENCE CHARACTERISTICS:
       (A) LENGTH: 45 base pairs
       (B) TYPE: nucleic acid
       (C) STRANDEDNESS: double
       (D) TOPOLOGY: linear (xi) SEQUENCE DESCRIPTION: SEQ ID NO:68:

```
GTTATATATG GAGATACGGA TTCTGTGTTT ATCCGATTCA AGGGT                45

(2) INFORMATION FOR SEQ ID NO:69:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (xi) SEQUENCE DESCRIPTION: SEQ ID NO:69:

GTTATCTACG GAGACACCGA CTCCGTGTTT ATCAAGTTTG TGGGC                45

(2) INFORMATION FOR SEQ ID NO:70:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (xi) SEQUENCE DESCRIPTION: SEQ ID NO:70:

GTCATATATG GAGACACAGA CTCTCTATTT GTAGAATGTG TTGGG                45

(2) INFORMATION FOR SEQ ID NO:71:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (xi) SEQUENCE DESCRIPTION: SEQ ID NO:71:

GTCATCTACG GGGACACGGA CTCGCTGTTT ATCGAGTGCC GGGGG                45

(2) INFORMATION FOR SEQ ID NO:72:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (xi) SEQUENCE DESCRIPTION: SEQ ID NO:72:

CCCAATTATG GGGATACGGA TAGTACGATG CTGTACCACC CATCG                45

(2) INFORMATION FOR SEQ ID NO:73:

(i) SEQUENCE CHARACTERISTICS:
        (A) LENGTH: 7 amino acids
        (B) TYPE: amino acid
        (C) STRANDEDNESS: double
        (D) TOPOLOGY: linear (xi) SEQUENCE DESCRIPTION: SEQ ID NO:73:

Ile Ala Glu Thr Val Thr Leu
1               5

(2) INFORMATION FOR SEQ ID NO:74:

(i) SEQUENCE CHARACTERISTICS:
        (A) LENGTH: 7 amino acids
        (B) TYPE: amino acid
        (C) STRANDEDNESS: double
        (D) TOPOLOGY: linear (xi) SEQUENCE DESCRIPTION: SEQ ID NO:74:

Val Ala Ser Gly Ile Leu Pro
```

1               5

(2) INFORMATION FOR SEQ ID NO:75:

(i) SEQUENCE CHARACTERISTICS:
        (A) LENGTH: 7 amino acids
        (B) TYPE: amino acid
        (C) STRANDEDNESS: double
        (D) TOPOLOGY: linear (xi) SEQUENCE DESCRIPTION: SEQ ID NO:75:

Gly Ile Leu Pro Cys Leu Asn
1               5

(2) INFORMATION FOR SEQ ID NO:76:

(i) SEQUENCE CHARACTERISTICS:
        (A) LENGTH: 7 amino acids
        (B) TYPE: amino acid
        (C) STRANDEDNESS: double
        (D) TOPOLOGY: linear (xi) SEQUENCE DESCRIPTION: SEQ ID NO:76:

Cys Leu Asn Ile Ala Glu Thr
1               5

(2) INFORMATION FOR SEQ ID NO:77:

(i) SEQUENCE CHARACTERISTICS:
        (A) LENGTH: 7 amino acids
        (B) TYPE: amino acid
        (C) STRANDEDNESS: double
        (D) TOPOLOGY: linear (xi) SEQUENCE DESCRIPTION: SEQ ID NO:77:

Gln Gly Arg Lys Met Leu Glu
1               5

(2) INFORMATION FOR SEQ ID NO:78:

(i) SEQUENCE CHARACTERISTICS:
        (A) LENGTH: 6 amino acids
        (B) TYPE: amino acid
        (C) STRANDEDNESS: double
        (D) TOPOLOGY: linear (xi) SEQUENCE DESCRIPTION: SEQ ID NO:78:

Ser Gln Ala Phe Val Glu
1               5

(2) INFORMATION FOR SEQ ID NO:79:

(i) SEQUENCE CHARACTERISTICS:
        (A) LENGTH: 6 amino acids
        (B) TYPE: amino acid
        (C) STRANDEDNESS: double
        (D) TOPOLOGY: linear (xi) SEQUENCE DESCRIPTION: SEQ ID NO:79:

Ala Arg Phe Lys Val Ile
1               5

(2) INFORMATION FOR SEQ ID NO:80:

(i) SEQUENCE CHARACTERISTICS:
        (A) LENGTH: 7 amino acids
        (B) TYPE: amino acid
        (C) STRANDEDNESS: double
        (D) TOPOLOGY: linear (xi) SEQUENCE DESCRIPTION: SEQ ID NO:80:

Leu Glu Thr Ser Gln Ala Phe
    1               5

(2) INFORMATION FOR SEQ ID NO:81:

(i) SEQUENCE CHARACTERISTICS:
            (A) LENGTH: 7 amino acids
            (B) TYPE: amino acid
            (C) STRANDEDNESS: double
            (D) TOPOLOGY: linear (xi) SEQUENCE DESCRIPTION: SEQ ID NO:81:

Leu Glu Arg Ser Gln Ala Phe
1               5

(2) INFORMATION FOR SEQ ID NO:82:

(i) SEQUENCE CHARACTERISTICS:
            (A) LENGTH: 7 amino acids
            (B) TYPE: amino acid
            (C) STRANDEDNESS: double
            (D) TOPOLOGY: linear (xi) SEQUENCE DESCRIPTION: SEQ ID NO:82:

Glu Gly Ile Ser Pro Thr Ala
1               5

(2) INFORMATION FOR SEQ ID NO:83:

(i) SEQUENCE CHARACTERISTICS:
            (A) LENGTH: 7 amino acids
            (B) TYPE: amino acid
            (C) STRANDEDNESS: double
            (D) TOPOLOGY: linear (xi) SEQUENCE DESCRIPTION: SEQ ID NO:83:

Glu Ala Ile Ser Pro Glu Arg
1               5

(2) INFORMATION FOR SEQ ID NO:84:

(i) SEQUENCE CHARACTERISTICS:
            (A) LENGTH: 7 amino acids
            (B) TYPE: amino acid
            (C) STRANDEDNESS: double
            (D) TOPOLOGY: linear (xi) SEQUENCE DESCRIPTION: SEQ ID NO:84:

Ala Asp Leu Leu Gln Arg Pro
1               5

(2) INFORMATION FOR SEQ ID NO:85:

(i) SEQUENCE CHARACTERISTICS:
            (A) LENGTH: 7 amino acids
            (B) TYPE: amino acid
            (C) STRANDEDNESS: double
            (D) TOPOLOGY: linear (xi) SEQUENCE DESCRIPTION: SEQ ID NO:85:

Ala Gly Leu Leu Arg Arg Pro
1               5

(2) INFORMATION FOR SEQ ID NO:86:

(i) SEQUENCE CHARACTERISTICS:

(A) LENGTH: 7 amino acids
            (B) TYPE: amino acid
            (C) STRANDEDNESS: double
            (D) TOPOLOGY: linear (xi) SEQUENCE DESCRIPTION: SEQ ID NO:86:

Gln Arg Pro Ile Glu Ala Ser
1               5

(2) INFORMATION FOR SEQ ID NO:87:

(i) SEQUENCE CHARACTERISTICS:
            (A) LENGTH: 7 amino acids
            (B) TYPE: amino acid
            (C) STRANDEDNESS: double
            (D) TOPOLOGY: linear (xi) SEQUENCE DESCRIPTION: SEQ ID NO:87:

Arg Arg Pro Ile Asp Val Ser
1               5

(2) INFORMATION FOR SEQ ID NO:88:

(i) SEQUENCE CHARACTERISTICS:
            (A) LENGTH: 7 amino acids
            (B) TYPE: amino acid
            (C) STRANDEDNESS: double
            (D) TOPOLOGY: linear (xi) SEQUENCE DESCRIPTION: SEQ ID NO:88:

Ile Glu Ala Ser Pro Glu Ala
1               5

(2) INFORMATION FOR SEQ ID NO:89:

(i) SEQUENCE CHARACTERISTICS:
            (A) LENGTH: 7 amino acids
            (B) TYPE: amino acid
            (C) STRANDEDNESS: double
            (D) TOPOLOGY: linear (xi) SEQUENCE DESCRIPTION: SEQ ID NO:89:

Ile Asp Val Ser Pro Asp Ala
1               5

(2) INFORMATION FOR SEQ ID NO:90:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:90:

Pro Asp Asp Tyr Glu Thr Phe
1               5

(2) INFORMATION FOR SEQ ID NO:91:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO:91:

Lys Arg Lys Glu Ile Arg Lys
1               5

(2) INFORMATION FOR SEQ ID NO:92:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:92:

```
Leu Ala Lys Arg Lys Glu Ile
1               5
```

(2) INFORMATION FOR SEQ ID NO:93:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:93:

```
Leu Ala Ser Cys Thr Asp Pro
1               5
```

(2) INFORMATION FOR SEQ ID NO:94:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:94:

```
Thr Gly Ser Ala Leu His Gly
1               5
```

(2) INFORMATION FOR SEQ ID NO:95:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:95:

```
Pro Gly Asp Ser Leu His Leu
1               5
```

(2) INFORMATION FOR SEQ ID NO:96:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:96:

```
Ser Ala Leu His Gly His Pro
1               5
```

(2) INFORMATION FOR SEQ ID NO:97:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:97:

```
Asp Ser Leu His Leu His Pro
1               5
```

(2) INFORMATION FOR SEQ ID NO:98:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:98:

```
Gly His Pro Glu Leu Thr Pro
1               5
```

(2) INFORMATION FOR SEQ ID NO:99:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:99:

```
Leu His Pro His Leu Gly Pro
1               5
```

(2) INFORMATION FOR SEQ ID NO:100:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:100:

```
His Leu Ser Gly Gly Thr Val
1               5
```

(2) INFORMATION FOR SEQ ID NO:101:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:101:

```
Val Leu Ser Gly Gly Leu Val
1               5
```

(2) INFORMATION FOR SEQ ID NO:102:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:102:

```
Thr Asp Pro Thr Met Arg Thr
1               5
```

(2) INFORMATION FOR SEQ ID NO:103:

(i) SEQUENCE CHARACTERISTICS:
        (A) LENGTH: 7 amino acids
        (B) TYPE: amino acid -continued (C) STRANDEDNESS: single
            (D) TOPOLOGY: linear (xi) SEQUENCE DESCRIPTION: SEQ ID NO:103:

Thr Asp Pro Ala Leu Lys Thr
1               5

(2) INFORMATION FOR SEQ ID NO:104:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:104:

CAGTATCATC CAAGCGCACA A                                            21

(2) INFORMATION FOR SEQ ID NO:105:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:105:

CCAAGTATCA THCARGCNCA YAA                                          23

(2) INFORMATION FOR SEQ ID NO:106:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:106:

GGAGTAGCAC AARTTRTGNG CYTG                                         24

(2) INFORMATION FOR SEQ ID NO:107:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:107:

TACGAAACCT TTGACCTNAG YGGNGG                                       26

(2) INFORMATION FOR SEQ ID NO:108:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:108:

CGCAAGAACC TGGCCTCNTG YACNGAYCC                                    29

(2) INFORMATION FOR SEQ ID NO:109:

(i) SEQUENCE CHARACTERISTICS:
            (A) LENGTH: 29 base pairs
            (B) TYPE: nucleic acid
            (C) STRANDEDNESS: double (D) TOPOLOGY: linear (xi) SEQUENCE DESCRIPTION: SEQ ID NO:109:

TCTCAGGCGT TCGTAGARGG NATHTCNCC                                              29

(2) INFORMATION FOR SEQ ID NO:110:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:110:

CAGCTGGCCA TCAAGGTCAC                                                        20

(2) INFORMATION FOR SEQ ID NO:111:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:111:

AACGCGGTGT ACGGGTTCAC                                                        20

(2) INFORMATION FOR SEQ ID NO:112:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:112:

Arg Thr Ile Leu Asp Lys Gln Gln Leu Ala Ile Lys Val Thr Cys Asn
1               5                   10                  15

Ala Val Tyr Gly Phe Thr Gly Val Ala Ser Gly Ile Leu Pro Cys Leu
            20                  25                  30

(2) INFORMATION FOR SEQ ID NO:113:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:113:

Ser Ile Ile Gln Ala His Asn Leu Cys Tyr Ser Thr Leu Ile Pro
1               5                   10                  15

(2) INFORMATION FOR SEQ ID NO:114:

(i) SEQUENCE CHARACTERISTICS:
        (A) LENGTH: 172 base pairs
        (B) TYPE: nucleic acid
        (C) STRANDEDNESS: double
        (D) TOPOLOGY: linear (xi) SEQUENCE DESCRIPTION: SEQ ID NO:114:

CGTTGCCTCT GGCATACTGC CTTGCCTAAA CATAGCGGAG ACCGTGACAC TACAAGGGCG           60

AAAGATGCTG GAGAGATCTC AGGCCTTTGT AGAGGCCATC TCGCCGGAAC GCCTAGCGGG          120

TCTCCTGCGG AGGCCAATAG ACGTCTCACC CGACGCCCGA TTCAAGGTCA TA                  172

(2) INFORMATION FOR SEQ ID NO:115:

(i) SEQUENCE CHARACTERISTICS:
        (A) LENGTH: 57 amino acids
        (B) TYPE: amino acid
        (C) STRANDEDNESS: single
        (D) TOPOLOGY: linear (xi) SEQUENCE DESCRIPTION: SEQ ID NO:115:

```
Val Ala Ser Gly Ile Leu Pro Cys Leu Asn Ile Ala Glu Thr Val Thr
 1               5                  10                  15

Leu Gln Gly Arg Lys Met Leu Glu Arg Ser Gln Ala Phe Val Glu Ala
            20                  25                  30

Ile Ser Pro Glu Arg Leu Ala Gly Leu Leu Arg Arg Pro Ile Asp Val
        35                  40                  45

Ser Pro Asp Ala Arg Phe Lys Val Ile
     50                  55
```

(2) INFORMATION FOR SEQ ID NO:116:

(i) SEQUENCE CHARACTERISTICS:
        (A) LENGTH: 2511 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..2511

(xi) SEQUENCE DESCRIPTION: SEQ ID NO:116:

```
GAC GAC CGC AGC GTG TGC GTG AAY GTN TTY GGN CAG CGC TGC TAC TTC      48
Asp Asp Arg Ser Val Cys Val Asn Val Phe Gly Gln Arg Cys Tyr Phe
 1               5                  10                  15

TAC ACA CTA GCA CCC CAG GGG GTA AAC CTG ACC CAC GTC CTC CAG CAG      96
Tyr Thr Leu Ala Pro Gln Gly Val Asn Leu Thr His Val Leu Gln Gln
            20                  25                  30

GCC CTC CAG GCT GGC TTC GGT CGC GCA TCC TGC GGC TTC TCC ACC GAG     144
Ala Leu Gln Ala Gly Phe Gly Arg Ala Ser Cys Gly Phe Ser Thr Glu
        35                  40                  45

CCG GTC AGA AAA AAA ATC TTG CGC GCG TAC GAC ACA CAA CAA TAT GCT     192
Pro Val Arg Lys Lys Ile Leu Arg Ala Tyr Asp Thr Gln Gln Tyr Ala
 50                  55                  60

GTG CAA AAA ATA ACC CTG TCA TCC AGT CCG ATG ATG CGA ACG CTT AGC     240
Val Gln Lys Ile Thr Leu Ser Ser Ser Pro Met Met Arg Thr Leu Ser
 65                  70                  75                  80

GAC CGC CTA ACA ACC TGT GGG TGC GAG GTG TTT GAG TCC AAT GTG GAC     288
Asp Arg Leu Thr Thr Cys Gly Cys Glu Val Phe Glu Ser Asn Val Asp
                 85                  90                  95

GCC ATT AGG CGC TTC GTG CTG GAC CAC GGG TTC TCG ACA TTC GGG TGG     336
Ala Ile Arg Arg Phe Val Leu Asp His Gly Phe Ser Thr Phe Gly Trp
            100                 105                 110

TAC GAG TGC AGC AAC CCG GCC CCC CGC ACC CAG GCC AGA GAC TCT TGG     384
Tyr Glu Cys Ser Asn Pro Ala Pro Arg Thr Gln Ala Arg Asp Ser Trp
        115                 120                 125

ACG GAA CTG GAG TTT GAC TGC AGC TGG GAG GAC CTA AAG TTT ATC CCG     432
Thr Glu Leu Glu Phe Asp Cys Ser Trp Glu Asp Leu Lys Phe Ile Pro
    130                 135                 140

GAG AGG ACG GAG TGG CCC CCA TAC ACA ATC CTA TCC TTT GAT ATA GAA     480
Glu Arg Thr Glu Trp Pro Pro Tyr Thr Ile Leu Ser Phe Asp Ile Glu
145                 150                 155                 160

TGT ATG GGC GAG AAG GGT TTT CCC AAC GCG ACT CAA GAC GAG GAC ATG     528
Cys Met Gly Glu Lys Gly Phe Pro Asn Ala Thr Gln Asp Glu Asp Met
```

-continued

```
                        165                     170                     175
ATT ATA CAA ATC TCG TGT GTT TTA CAC ACA GTC GGC AAC GAT AAA CCG       576
Ile Ile Gln Ile Ser Cys Val Leu His Thr Val Gly Asn Asp Lys Pro
                180                 185                 190

TAC ACC CGC ATG CTA CTG GGC CTG GGG ACA TGC GAC CCC CTT CCT GGG       624
Tyr Thr Arg Met Leu Leu Gly Leu Gly Thr Cys Asp Pro Leu Pro Gly
            195                 200                 205

GTG GAG GTC TTT GAG TTT CCT TCG GAG TAC GAC ATG CTG GCC GCC TTC       672
Val Glu Val Phe Glu Phe Pro Ser Glu Tyr Asp Met Leu Ala Ala Phe
        210                 215                 220

CTC AGC ATG CTC CGC GAT TAC AAT GTG GAG TTT ATA ACG GGG TAC AAC       720
Leu Ser Met Leu Arg Asp Tyr Asn Val Glu Phe Ile Thr Gly Tyr Asn
225                 230                 235                 240

ATA GCA AAC TTT GAC CTT CCA TAC ATC ATA GCC CGG GCA ACT CAG GTG       768
Ile Ala Asn Phe Asp Leu Pro Tyr Ile Ile Ala Arg Ala Thr Gln Val
                245                 250                 255

TAC GAC TTC AAG CTG CAG GAC TTC ACC AAA ATA AAA ACT GGG TCC GTG       816
Tyr Asp Phe Lys Leu Gln Asp Phe Thr Lys Ile Lys Thr Gly Ser Val
            260                 265                 270

TTT GAG GTC CAC CAA CCC AGA GGC GGT TCC GAT GGG GGC AAC TTC ATG       864
Phe Glu Val His Gln Pro Arg Gly Gly Ser Asp Gly Gly Asn Phe Met
        275                 280                 285

AGG TCC CAG TCA AAG GTC AAA ATA TCG GGG ATC GTC CCC ATA GAC ATG       912
Arg Ser Gln Ser Lys Val Lys Ile Ser Gly Ile Val Pro Ile Asp Met
    290                 295                 300

TAC CAG GTT TGC AGG GAA AAG CTG AGT CTG TCA GAC TAC AAG CTG GAC       960
Tyr Gln Val Cys Arg Glu Lys Leu Ser Leu Ser Asp Tyr Lys Leu Asp
305                 310                 315                 320

ACA GTG GCT AAG CAA TGC CTC GGT CGA CAA AAA GAT GAC ATC TCA TAC      1008
Thr Val Ala Lys Gln Cys Leu Gly Arg Gln Lys Asp Asp Ile Ser Tyr
                325                 330                 335

AAG GAC ATA CCC CCG CTT TTT AAA TCT GGG CCT GAT GGT CGC GCA AAG      1056
Lys Asp Ile Pro Pro Leu Phe Lys Ser Gly Pro Asp Gly Arg Ala Lys
            340                 345                 350

GTG GGA AAC TAC TGT GTT ATT GAC TCG GTC CTG GTT ATG GAT CTT CTG      1104
Val Gly Asn Tyr Cys Val Ile Asp Ser Val Leu Val Met Asp Leu Leu
        355                 360                 365

CTA CGG TTT CAG ACC CAT GTT GAG ATC TCG GAA ATA GCC AAG CTG GCC      1152
Leu Arg Phe Gln Thr His Val Glu Ile Ser Glu Ile Ala Lys Leu Ala
    370                 375                 380

AAG ATC CCC ACC CGT AGG GTA CTG ACG GAC GGC CAA CAG ATC AGG GTA      1200
Lys Ile Pro Thr Arg Arg Val Leu Thr Asp Gly Gln Gln Ile Arg Val
385                 390                 395                 400

TTT TCC TGC CTC TTG GAG GCT GCT GCC ACG GAA GGT TAC ATT CTC CCC      1248
Phe Ser Cys Leu Leu Glu Ala Ala Ala Thr Glu Gly Tyr Ile Leu Pro
                405                 410                 415

GTC CCA AAA GGA GAC GCG GTT AGC GGG TAT CAG GGG GCC ACT GTA ATA      1296
Val Pro Lys Gly Asp Ala Val Ser Gly Tyr Gln Gly Ala Thr Val Ile
            420                 425                 430

AGC CCC TCT CCG GGA TTC TAT GAC GAC CCC GTA CTC GTG GTG GAT TTT      1344
Ser Pro Ser Pro Gly Phe Tyr Asp Asp Pro Val Leu Val Val Asp Phe
        435                 440                 445

GCC AGC TTG TAC CCC AGT ATC ATC CAA GCG CAC AAC TTG TGC TAC TCC      1392
Ala Ser Leu Tyr Pro Ser Ile Ile Gln Ala His Asn Leu Cys Tyr Ser
    450                 455                 460

ACA CTG ATA CCC GGC GAT TCG CTC CAC CTG CAC CCA CAC CTC TCC CCG      1440
Thr Leu Ile Pro Gly Asp Ser Leu His Leu His Pro His Leu Ser Pro
465                 470                 475                 480

GAC GAC TAC GAA ACC TTT GTC CTC AGC GGA GGT CCG GTC CAC TTT GTA      1488
Asp Asp Tyr Glu Thr Phe Val Leu Ser Gly Gly Pro Val His Phe Val
```

-continued

```
                            485                      490                      495
AAA AAA CAC AAA AGG GAG TCC CTT CTT GCC AAG CTT CTG ACG GTA TGG       1536
Lys Lys His Lys Arg Glu Ser Leu Leu Ala Lys Leu Leu Thr Val Trp
            500                      505                      510

CTC GCG AAG AGA AAA GAA ATA AGA AAG ACC CTG GCA TCA TGC ACG GAC       1584
Leu Ala Lys Arg Lys Glu Ile Arg Lys Thr Leu Ala Ser Cys Thr Asp
            515                      520                      525

CCC GCA CTG AAA ACT ATT CTA GAC AAA CAA CAA CTG GCC ATC AAG GTT       1632
Pro Ala Leu Lys Thr Ile Leu Asp Lys Gln Gln Leu Ala Ile Lys Val
            530                      535                      540

ACC TGC AAC GCC GTT TAC GGC TTC ACG GGC GTT GCC TCT GGC ATA CTG       1680
Thr Cys Asn Ala Val Tyr Gly Phe Thr Gly Val Ala Ser Gly Ile Leu
545                      550                      555                      560

CCT TGC CTA AAC ATA GCG GAG ACC GTG ACA CTA CAA GGG CGA AAG ATG       1728
Pro Cys Leu Asn Ile Ala Glu Thr Val Thr Leu Gln Gly Arg Lys Met
                    565                      570                      575

CTG GAG AGA TCT CAG GCC TTT GTA GAG GCC ATC TCG CCG GAA CGC CTA       1776
Leu Glu Arg Ser Gln Ala Phe Val Glu Ala Ile Ser Pro Glu Arg Leu
            580                      585                      590

GCG GGT CTC CTG CGG AGG CCA GTA GAC GTC TCA CCC GAC GCC CGA TTC       1824
Ala Gly Leu Leu Arg Arg Pro Val Asp Val Ser Pro Asp Ala Arg Phe
            595                      600                      605

AAG GTC ATA TAC GGC GAC ACT GAC TCT CTT TTC ATA TGC TGC ATG GGT       1872
Lys Val Ile Tyr Gly Asp Thr Asp Ser Leu Phe Ile Cys Cys Met Gly
            610                      615                      620

TTC AAC ATG GAC AGC GTG TCA GAC TTC GCG GAG GAG CTA GCG TCA ATC       1920
Phe Asn Met Asp Ser Val Ser Asp Phe Ala Glu Glu Leu Ala Ser Ile
625                      630                      635                      640

ACC ACC AAC ACG CTG TTT CGT AGC CCC ATC AAG CTG GAG GCT GAA AAG       1968
Thr Thr Asn Thr Leu Phe Arg Ser Pro Ile Lys Leu Glu Ala Glu Lys
                    645                      650                      655

ATC TTC AAG TGC CTT CTG CTC CTG ACT AAA AAG AGA TAC GTG GGG GTA       2016
Ile Phe Lys Cys Leu Leu Leu Leu Thr Lys Lys Arg Tyr Val Gly Val
            660                      665                      670

CTC AGT GAC GAC AAG GTT CTG ATG AAG GGC GTA GAC CTC ATT AGG AAA       2064
Leu Ser Asp Asp Lys Val Leu Met Lys Gly Val Asp Leu Ile Arg Lys
            675                      680                      685

ACA GCC TGT CGT TTT GTC CAG GAA AAG AGC AGT CAG GTC CTG GAC CTC       2112
Thr Ala Cys Arg Phe Val Gln Glu Lys Ser Ser Gln Val Leu Asp Leu
            690                      695                      700

ATA CTG CGG GAG CCG AGC GTC AAG GCC GCG GCC AAG CTT ATT TCG GGG       2160
Ile Leu Arg Glu Pro Ser Val Lys Ala Ala Ala Lys Leu Ile Ser Gly
705                      710                      715                      720

CAG GCG ACA GAC TGG GTG TAC AGG GAA GGG CTC CCA GAG GGG TTC GTC       2208
Gln Ala Thr Asp Trp Val Tyr Arg Glu Gly Leu Pro Glu Gly Phe Val
                    725                      730                      735

AAG ATA ATT CAA GTG CTC AAC GCG AGC CAC CGG GAA CTG TGC GAA CGC       2256
Lys Ile Ile Gln Val Leu Asn Ala Ser His Arg Glu Leu Cys Glu Arg
            740                      745                      750

AGC GTA CCA GTA GAC AAA CTG ACG TTT ACC ACC GAG CTA AGC CGC CCG       2304
Ser Val Pro Val Asp Lys Leu Thr Phe Thr Thr Glu Leu Ser Arg Pro
            755                      760                      765

CTG GCG GAC TAC AAG ACG CAA AAC CTC CCG CAC CTG ACC GTG TAC CAA       2352
Leu Ala Asp Tyr Lys Thr Gln Asn Leu Pro His Leu Thr Val Tyr Gln
            770                      775                      780

AAG CTA CAA GCT AGA CAG GAG GAG CTT CCA CAG ATA CAC GAC AGA ATC       2400
Lys Leu Gln Ala Arg Gln Glu Glu Leu Pro Gln Ile His Asp Arg Ile
785                      790                      795                      800

CCC TAC GTG TTC GTC GAC GCC CCA GGT AGC CTG CGC TCC GAG CTG GCA       2448
Pro Tyr Val Phe Val Asp Ala Pro Gly Ser Leu Arg Ser Glu Leu Ala
```

```
                      805                  810                 815
GAG CAC CCC GAG TAC GTT AAG CAG CAC GGA CTG CGC GTG GCG GTG GAC        2496
Glu His Pro Glu Tyr Val Lys Gln His Gly Leu Arg Val Ala Val Asp
            820                 825                 830

CTG TAT TTC GAC AAG                                                    2511
Leu Tyr Phe Asp Lys
        835
```

(2) INFORMATION FOR SEQ ID NO:117:

(i) SEQUENCE CHARACTERISTICS:
        (A) LENGTH: 837 amino acids
        (B) TYPE: amino acid
        (D) TOPOLOGY: linear (ii) MOLECULE TYPE: protein (xi) SEQUENCE DESCRIPTION: SEQ ID NO:117:

```
Asp Asp Arg Ser Cys Val Asn Val Phe Gly Gln Arg Cys Tyr Phe
 1               5                  10                  15

Tyr Thr Leu Ala Pro Gln Gly Val Asn Leu Thr His Val Leu Gln Gln
            20                  25                  30

Ala Leu Gln Ala Gly Phe Gly Arg Ala Ser Cys Gly Phe Ser Thr Glu
        35                  40                  45

Pro Val Arg Lys Lys Ile Leu Arg Ala Tyr Asp Thr Gln Gln Tyr Ala
    50                  55                  60

Val Gln Lys Ile Thr Leu Ser Ser Pro Met Met Arg Thr Leu Ser
 65              70                  75                  80

Asp Arg Leu Thr Thr Cys Gly Cys Glu Val Phe Glu Ser Asn Val Asp
                85                  90                  95

Ala Ile Arg Arg Phe Val Leu Asp His Gly Phe Ser Thr Phe Gly Trp
                100                 105                 110

Tyr Glu Cys Ser Asn Pro Ala Pro Arg Thr Gln Ala Arg Asp Ser Trp
            115                 120                 125

Thr Glu Leu Glu Phe Asp Cys Ser Trp Glu Asp Leu Lys Phe Ile Pro
        130                 135                 140

Glu Arg Thr Glu Trp Pro Pro Tyr Thr Ile Leu Ser Phe Asp Ile Glu
145                 150                 155                 160

Cys Met Gly Glu Lys Gly Phe Pro Asn Ala Thr Gln Asp Glu Asp Met
                165                 170                 175

Ile Ile Gln Ile Ser Cys Val Leu His Thr Val Gly Asn Asp Lys Pro
            180                 185                 190

Tyr Thr Arg Met Leu Leu Gly Leu Gly Thr Cys Asp Pro Leu Pro Gly
        195                 200                 205

Val Glu Val Phe Glu Phe Pro Ser Glu Tyr Asp Met Leu Ala Ala Phe
    210                 215                 220

Leu Ser Met Leu Arg Asp Tyr Asn Val Glu Phe Ile Thr Gly Tyr Asn
225                 230                 235                 240

Ile Ala Asn Phe Asp Leu Pro Tyr Ile Ile Ala Arg Ala Thr Gln Val
                245                 250                 255

Tyr Asp Phe Lys Leu Gln Asp Phe Thr Lys Ile Lys Thr Gly Ser Val
            260                 265                 270

Phe Glu Val His Gln Pro Arg Gly Gly Ser Asp Gly Asn Phe Met
        275                 280                 285

Arg Ser Gln Ser Lys Val Lys Ile Ser Gly Ile Val Pro Ile Asp Met
    290                 295                 300

Tyr Gln Val Cys Arg Glu Lys Leu Ser Leu Ser Asp Tyr Lys Leu Asp
```

-continued

```
         305                 310                 315                 320
Thr Val Ala Lys Gln Cys Leu Gly Arg Gln Lys Asp Asp Ile Ser Tyr
                 325                 330                 335
Lys Asp Ile Pro Pro Leu Phe Lys Ser Gly Pro Asp Gly Arg Ala Lys
                 340                 345                 350
Val Gly Asn Tyr Cys Val Ile Asp Ser Val Leu Val Met Asp Leu Leu
                 355                 360                 365
Leu Arg Phe Gln Thr His Val Glu Ile Ser Glu Ile Ala Lys Leu Ala
                 370                 375                 380
Lys Ile Pro Thr Arg Arg Val Leu Thr Asp Gly Gln Gln Ile Arg Val
385                 390                 395                 400
Phe Ser Cys Leu Leu Glu Ala Ala Thr Glu Gly Tyr Ile Leu Pro
                 405                 410                 415
Val Pro Lys Gly Asp Ala Val Ser Gly Tyr Gln Gly Ala Thr Val Ile
                 420                 425                 430
Ser Pro Ser Pro Gly Phe Tyr Asp Asp Pro Val Leu Val Asp Phe
                 435                 440                 445
Ala Ser Leu Tyr Pro Ser Ile Ile Gln Ala His Asn Leu Cys Tyr Ser
                 450                 455                 460
Thr Leu Ile Pro Gly Asp Ser Leu His Leu His Pro His Leu Ser Pro
465                 470                 475                 480
Asp Asp Tyr Glu Thr Phe Val Leu Ser Gly Gly Pro Val His Phe Val
                 485                 490                 495
Lys Lys His Lys Arg Glu Ser Leu Ala Lys Leu Leu Thr Val Trp
                 500                 505                 510
Leu Ala Lys Arg Lys Glu Ile Arg Lys Thr Leu Ala Ser Cys Thr Asp
                 515                 520                 525
Pro Ala Leu Lys Thr Ile Leu Asp Lys Gln Gln Leu Ala Ile Lys Val
                 530                 535                 540
Thr Cys Asn Ala Val Tyr Gly Phe Thr Gly Val Ala Ser Gly Ile Leu
545                 550                 555                 560
Pro Cys Leu Asn Ile Ala Glu Thr Val Thr Leu Gln Gly Arg Lys Met
                 565                 570                 575
Leu Glu Arg Ser Gln Ala Phe Val Glu Ala Ile Ser Pro Glu Arg Leu
                 580                 585                 590
Ala Gly Leu Leu Arg Arg Pro Val Asp Val Ser Pro Asp Ala Arg Phe
                 595                 600                 605
Lys Val Ile Tyr Gly Asp Thr Asp Ser Leu Phe Ile Cys Cys Met Gly
                 610                 615                 620
Phe Asn Met Asp Ser Val Ser Asp Phe Ala Glu Glu Leu Ala Ser Ile
625                 630                 635                 640
Thr Thr Asn Thr Leu Phe Arg Ser Pro Ile Lys Leu Glu Ala Glu Lys
                 645                 650                 655
Ile Phe Lys Cys Leu Leu Leu Thr Lys Lys Arg Tyr Val Gly Val
                 660                 665                 670
Leu Ser Asp Asp Lys Val Leu Met Lys Gly Val Asp Leu Ile Arg Lys
                 675                 680                 685
Thr Ala Cys Arg Phe Val Gln Glu Lys Ser Ser Gln Val Leu Asp Leu
                 690                 695                 700
Ile Leu Arg Glu Pro Ser Val Lys Ala Ala Lys Leu Ile Ser Gly
705                 710                 715                 720
Gln Ala Thr Asp Trp Val Tyr Arg Glu Gly Leu Pro Glu Gly Phe Val
                 725                 730                 735
```

-continued

```
Lys Ile Ile Gln Val Leu Asn Ala Ser His Arg Glu Leu Cys Glu Arg
        740                 745                 750

Ser Val Pro Val Asp Lys Leu Thr Phe Thr Thr Glu Leu Ser Arg Pro
        755                 760                 765

Leu Ala Asp Tyr Lys Thr Gln Asn Leu Pro His Leu Thr Val Tyr Gln
        770                 775                 780

Lys Leu Gln Ala Arg Gln Glu Leu Pro Gln Ile His Asp Arg Ile
785                 790                 795                 800

Pro Tyr Val Phe Val Asp Ala Pro Gly Ser Leu Arg Ser Glu Leu Ala
                805                 810                 815

Glu His Pro Glu Tyr Val Lys Gln His Gly Leu Arg Val Ala Val Asp
            820                 825                 830

Leu Tyr Phe Asp Lys
            835
```

(2) INFORMATION FOR SEQ ID NO:118:

(i) SEQUENCE CHARACTERISTICS:
        (A) LENGTH: 454 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 2..454

(xi) SEQUENCE DESCRIPTION: SEQ ID NO:118:

```
C CTA TGT TAC TCT ACC CTG ATT CAG GGG AAC GCC ATT CTC TCG CAC          46
  Leu Cys Tyr Ser Thr Leu Ile Gln Gly Asn Ala Ile Leu Ser His
          840                 845                 850

CCC GAG TTG ACC CCG AAC GAC TAC GAA ACA TTC CAC CTA AGC GGA GGA        94
Pro Glu Leu Thr Pro Asn Asp Tyr Glu Thr Phe His Leu Ser Gly Gly
            855                 860                 865

CCG GTG CAC TTC GTA AAA AAA CAC GTA CGA GAG TCA TTA CTG TCA AAA       142
Pro Val His Phe Val Lys Lys His Val Arg Glu Ser Leu Leu Ser Lys
870                 875                 880

CTT CTG ACG ACT TGG CTA ACA AAA AGA AAA GAG ATC CGC AAA AAT CTC       190
Leu Leu Thr Thr Trp Leu Thr Lys Arg Lys Glu Ile Arg Lys Asn Leu
885                 890                 895                 900

GCC TCG TGC GGA GAC CCA ACC ATG CGA ACC ATC CTT GAT AAG CAG CAG       238
Ala Ser Cys Gly Asp Pro Thr Met Arg Thr Ile Leu Asp Lys Gln Gln
                905                 910                 915

CTG GCC ATC AAG GTC ACA TGT AAT GCG GTG TAC GGG TTT ACC GGC GTC       286
Leu Ala Ile Lys Val Thr Cys Asn Ala Val Tyr Gly Phe Thr Gly Val
            920                 925                 930

GCC TCC GGT ATT CTA CCG TGC CTG AAT ATT GCA GAA ACA GTC ACC CTC       334
Ala Ser Gly Ile Leu Pro Cys Leu Asn Ile Ala Glu Thr Val Thr Leu
        935                 940                 945

CAG GGC AGA AAA ATG CTA GAA ACG TCC CAG GCG TTT GTA GAG GGC ATA       382
Gln Gly Arg Lys Met Leu Glu Thr Ser Gln Ala Phe Val Glu Gly Ile
    950                 955                 960

TCG CCA AAA GAC CTG TCA GAC CTG ATA CAA CGT CCG ATC GAC GCT TCC       430
Ser Pro Lys Asp Leu Ser Asp Leu Ile Gln Arg Pro Ile Asp Ala Ser
965                 970                 975                 980

CCG GAC GCC AGG TTT AAA GTG ATA                                       454
Pro Asp Ala Arg Phe Lys Val Ile
                985
```

(2) INFORMATION FOR SEQ ID NO:119:

(i) SEQUENCE CHARACTERISTICS:

(A) LENGTH: 151 amino acids
(B) TYPE: amino acid
(D) TOPOLOGY: linear (ii) MOLECULE TYPE: protein (xi) SEQUENCE DESCRIPTION: SEQ ID NO:119:

```
Leu Cys Tyr Ser Thr Leu Ile Gln Gly Asn Ala Ile Leu Ser His Pro
 1               5                  10                  15

Glu Leu Thr Pro Asn Asp Tyr Glu Thr Phe His Leu Ser Gly Gly Pro
                20                  25                  30

Val His Phe Val Lys Lys His Val Arg Glu Ser Leu Leu Ser Lys Leu
             35                  40                  45

Leu Thr Thr Trp Leu Thr Lys Arg Lys Glu Ile Arg Lys Asn Leu Ala
 50                  55                  60

Ser Cys Gly Asp Pro Thr Met Arg Thr Ile Leu Asp Lys Gln Gln Leu
 65                  70                  75                  80

Ala Ile Lys Val Thr Cys Asn Ala Val Tyr Gly Phe Thr Gly Val Ala
                 85                  90                  95

Ser Gly Ile Leu Pro Cys Leu Asn Ile Ala Glu Thr Val Thr Leu Gln
                100                 105                 110

Gly Arg Lys Met Leu Glu Thr Ser Gln Ala Phe Val Glu Gly Ile Ser
                115                 120                 125

Pro Lys Asp Leu Ser Asp Leu Ile Gln Arg Pro Ile Asp Ala Ser Pro
                130                 135                 140

Asp Ala Arg Phe Lys Val Ile
145                 150
```

(2) INFORMATION FOR SEQ ID NO:120:

(i) SEQUENCE CHARACTERISTICS:
(A) LENGTH: 57 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:120:

```
Val Ala Ser Gly Ile Leu Pro Cys Leu Asn Ile Ala Glu Thr Val Thr
 1               5                  10                  15

Leu Gln Gly Arg Lys Met Leu Glu Arg Ser Gln Ala Phe Val Glu Ala
                20                  25                  30

Ile Ser Pro Glu Arg Leu Ala Gly Leu Leu Arg Arg Pro Val Asp Val
             35                  40                  45

Ser Pro Asp Ala Arg Phe Arg Val Ile
 50                  55
```

(2) INFORMATION FOR SEQ ID NO:121:

(i) SEQUENCE CHARACTERISTICS:
(A) LENGTH: 57 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:121:

```
Val Ala Ser Gly Ile Leu Pro Cys Leu Asn Ile Ala Glu Thr Val Thr
 1               5                  10                  15

Leu Gln Gly Arg Lys Met Leu Glu Arg Ser Gln Ala Phe Val Glu Ala
```

```
                    20                  25                  30
Ile Ser Pro Glu Arg Leu Ala Gly Leu Leu Arg Arg Pro Ile Asp Val
            35                  40                  45

Ser Pro Asp Ala Arg Phe Lys Val Ile
        50                  55
```

(2) INFORMATION FOR SEQ ID NO:122:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:122:

```
Val Ala Ser Gly Ile Leu Pro Cys Leu Asn Ile Ala Glu Thr Val Thr
1               5                   10                  15

Leu Gln Gly Arg Lys Met Leu Glu Arg Ser Gln Ala Phe Val Glu Ala
            20                  25                  30

Ile Ser Pro Glu Arg Leu Ala Gly Leu Leu Arg Arg Pro Val Asp Val
            35                  40                  45

Ser Pro Asp Ala Arg Phe Lys Val Ile
        50                  55
```

(2) INFORMATION FOR SEQ ID NO:123:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:123:

```
Val Ala Ser Gly Ile Leu Pro Cys Leu Asn Ile Ala Glu Thr Val Thr
1               5                   10                  15

Leu Gln Gly Arg Lys Met Leu Glu Arg Ser Gln Ala Phe Val Glu Ala
            20                  25                  30

Ile Ser Pro Glu Arg Leu Ala Gly Leu Leu Arg Arg Pro Val Asp Val
            35                  40                  45

Ser Pro Asp Ala Arg Phe Arg Val Ile
        50                  55
```

(2) INFORMATION FOR SEQ ID NO:124:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:124:

AACACAGAGT CNGTRTCNCC RTA                                    23

(2) INFORMATION FOR SEQ ID NO:125:

(i) SEQUENCE CHARACTERISTICS:
        (A) LENGTH: 28 base pairs
        (B) TYPE: nucleic acid
        (C) STRANDEDNESS: single
        (D) TOPOLOGY: linear -continued (xi) SEQUENCE DESCRIPTION: SEQ ID NO:125:

AGCATCATCA TGGCCCAYAA YCTNTGYT                                    28

(2) INFORMATION FOR SEQ ID NO:126:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:126:

GAYTTYGCNA GYYTNTAYCC                                             20

(2) INFORMATION FOR SEQ ID NO:127:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:127:

CACCCATRCA YTCDATRTCR AA                                          22

(2) INFORMATION FOR SEQ ID NO:128:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:128:

TACAACGTCC TCTCCTTYGA YATHGARTG                                   29

(2) INFORMATION FOR SEQ ID NO:129:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:129:

GTCTGCGTGA AYGTNTTYGG NCA                                         23

(2) INFORMATION FOR SEQ ID NO:130:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:130:

GACGACCGCA GCGTGTGCGT GAAYGTNTTY GGNCA                            35

(2) INFORMATION FOR SEQ ID NO:131:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:131:

ACGACCGCAG CGTGTGCGTG                                                     20

(2) INFORMATION FOR SEQ ID NO:132:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:132:

TAAAAGTACA GCTCCTGCCC GAANACRTTN ACRCA                                    35

(2) INFORMATION FOR SEQ ID NO:133:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:133:

TAAAAGTACA GCTCCTGCCC GAA                                                 23

(2) INFORMATION FOR SEQ ID NO:134:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:134:

TTTGACTTTG CCAGCCTGTA YCCNAGYATN AT                                       32

(2) INFORMATION FOR SEQ ID NO:135:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:135:

TTTGACTTTG CCAGCCTGTA YCCNTCNATN AT                                       32

(2) INFORMATION FOR SEQ ID NO:136:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:136:

TTTGACTTTG CCAGCCTGTA                                                     20

(2) INFORMATION FOR SEQ ID NO:137:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:137:

CGGCATGCGA CAAACACGGA GTCCGTRTCN CCRTADAT                                 38

(2) INFORMATION FOR SEQ ID NO:138:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:138:

TTAGCTACTC CGTGGAGCAG YTTRTCRAAR TA                    32

(2) INFORMATION FOR SEQ ID NO:139:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:139:

TTGTGCGCTT GGATGATACT G                             21

(2) INFORMATION FOR SEQ ID NO:140:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:140:

GAGGGCCTGC TGGAGGACGT G                             21

(2) INFORMATION FOR SEQ ID NO:141:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:141:

CGGTGGAGAA GCCGCAGGAT G                             21

(2) INFORMATION FOR SEQ ID NO:142:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:142:

ACCTCCCGCA CCTGACCGTG T                             21

(2) INFORMATION FOR SEQ ID NO:143:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:143:

AAGCTAGACA GGAGGAGCTT C                             21

(2) INFORMATION FOR SEQ ID NO:144:

```
         (i) SEQUENCE CHARACTERISTICS:
              (A) LENGTH: 21 base pairs
              (B) TYPE: nucleic acid
              (C) STRANDEDNESS: single
              (D) TOPOLOGY: linear (xi) SEQUENCE DESCRIPTION: SEQ ID NO:144:

ACTTGAATTA TCTTGACGAA C                                              21

(2) INFORMATION FOR SEQ ID NO:145:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (xi) SEQUENCE DESCRIPTION: SEQ ID NO:145:

ACGACAAGGT TCTGATGAAG G                                              21

(2) INFORMATION FOR SEQ ID NO:146:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (xi) SEQUENCE DESCRIPTION: SEQ ID NO:146:

AGAGACTCTT GGACGGAACT G                                              21

(2) INFORMATION FOR SEQ ID NO:147:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (xi) SEQUENCE DESCRIPTION: SEQ ID NO:147:

AGTTTGACTG CAGCTGGGAG G                                              21

(2) INFORMATION FOR SEQ ID NO:148:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (xi) SEQUENCE DESCRIPTION: SEQ ID NO:148:

CGGGTATCAG TGTGGAGTAG C                                              21

(2) INFORMATION FOR SEQ ID NO:149:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (xi) SEQUENCE DESCRIPTION: SEQ ID NO:149:

GAGGACAAAG GTTTCGTAGT C                                              21

(2) INFORMATION FOR SEQ ID NO:150:

(i) SEQUENCE CHARACTERISTICS:
```

(A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:150:

CTATGTTACT CTACCCTGAT T                                                          21

(2) INFORMATION FOR SEQ ID NO:151:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:151:

GTATATCTCT TTAAACCTGG C                                                          21

(2) INFORMATION FOR SEQ ID NO:152:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:152:

AACCTGGCGT CCGGGGAAGC G                                                          21

DNA POLYMERASE OF GAMMA HERPES VIRUSES ASSOCIATED WITH KAPOSI'S SARCOMA AND RETROPERITONEAL FIBROMATOSIS

This application claims benefit of provisional application Serial No. 60/001,148 filed on Jul. 14, 1995.

REFERENCE TO GOVERNMENT GRANT

This invention was made in part during work supported by a grant from the National Institutes of Health (RR00166-34). The Government has certain rights in the invention.

FIELD OF THE INVENTION

The present invention relates generally to the field of virology, particularly viruses of the herpes family. More specifically, it relates to the identification and characterization of DNA polymerase in a virus subfamily, members of which are associated with fibroproliferative and neoplastic conditions in primates, including humans.

BACKGROUND

Kaposi's Sarcoma is a disfiguring and potentially fatal form of hemorrhagic sarcoma. It is characterized by multiple vascular tumors that appear on the skin as darkly colored plaques or nodules. At the histological level, it is characterized by proliferation of relatively uniform spindle-shaped cells, forming fascicles and vascular slits. There is often evidence of plasma cells, T cells and monocytes in the inflammatory infiltrate. Death may ultimately ensue due to bleeding from gastrointestinal lesions or from an associated lymphoma. (See generally Martin et al., Finesmith et al.)

Once a relatively obscure disease, it has leapt to public attention due to its association with AIDS. As many as 20% of certain AIDS-affected populations acquire Kaposi's during the course of the disease. Kaposi's Sarcoma occurs in other conditions associated with immunodeficiency, including kidney dialysis and therapeutic inimunosuppression. However, the epidemiology of the disease has suggested that immunodeficiency is not the only causative factor. In particular, the high degree of association of Kaposi's with certain sexual practices suggests the involvement of an etiologic agent which is not the human immunodeficiency virus (Berel et al.).

A herpes-virus-like DNA sequence has been identified in tissue samples from Kaposi's lesions obtained from AIDS patients (Chang et al., confirmed by Ambroziuk et al.). The sequence was obtained by representational difference analysis (Lisitsyn et al.), in which DNA from affected and unaffected tissue were amplified using unrelated priming oligonucleotides, and then hybridized together to highlight differences between the cells. The sequence was partly identical to known sequences of the Epstein Barr Virus and herpesvirus saimiri. It coded for capsid and tegument proteins, two structural components. In a survey of tissues from various sources, the sequence was found in 95% of Kaposi's sarcoma lesions, regardless of the patients' HIV status (Moore et al.). 21% of uninvolved tissue from the same patients was positive, while 5% of samples from a control population was positive. There was approximately 0.5% sequence variation between samples. The sequence was also detected at a higher copy number in body cavity lymphoma, a lymphomatous effusion with a B-cell genotype occurring uniquely in AIDS patients (Cesarman et al.). Other AIDS-associated lymphomas were negative.

The herpes virus family comprises a number of multi-enveloped viruses about 100 nm in size, and capable of infecting vertebrates. (For general reviews, see, e.g., Emery et al., Fields et al.). The double-stranded DNA genome is unusually large—from about 88 to about 229 kilobases in length. It may produce over 50 different transcripts at various stages in the life cycle of the virus. In one of the stages, a number of nucleotide and polynucleotide processing enzymes are produced that are required for viral replication, including DNA polymerase, DNAse, dUTPase, ribonucleotide reductase, uracil-DNA glycosylase, and thymidine kinase. These functional proteins tend to be relatively well conserved between species, compared with external viral components (Karlin et al.).

The herpes virus family has been divided into several subfamilies. Assignments to each of the categories were originally based on the basis of biologic properties, and are being refined as genomic sequence data emerges. The alpha subfamily comprises viruses that have a broad host range, a short replicative cycle, and an affinity for the sensory ganglia. They include the human simplex virus and the Varicella-zoster virus. The beta subfamily comprises viruses that have a restricted host range, and include Cytomegalovirus and human Herpes Virus 6. The gamma subfamily comprises viruses that are generally lymphotrophic. The DNA is marked by a segment of about 110 kilobases with a low GC content, flanked by multiple tandem repeats of high GC content. The subfamily includes Epstein Barr Virus (EBV), herpes virus saimiri, equine Herpes Virus 2 and 5, and bovine Herpes Virus 4.

Herpes viruses are associated with conditions that have a complex clinical course. A feature of many herpes viruses is the ability to go into a latent state within the host for an extended period of time. Viruses of the alpha subfamily maintain latent forms in the sensory and autonomic ganglia, whereas those of the gamma subfamily maintain latent forms, for example, in cells of the lymphocyte lineage. Latency is associated with the transcription of certain viral genes, and may persist for decades until conditions are optimal for the virus to resume active replication. Such conditions may include an immunodeficiency. In addition, some herpes viruses of the gamma subfamily have the ability to genetically transform the cells they infect. For example, EBV is associated with B cell lymphomas, oral hairy leukoplakia, lymphoid interstitial pneumonitis, and nasopharyngeal carcinoma.

A number of other conditions occur in humans and other vertebrates that involve fibroproliferation and the generation of pre-neoplastic cells. Examples occurring in humans are retroperitoneal fibrosis, nodular fibromatosis, pseudosarcomatous fibromatosis, and sclerosing mesenteritis. Another condition known as Enzootic Retroperitoneal Fibromatosis (RF) has been observed in a colony of macaque monkeys at the University of Washington Regional Primate Research Center (Giddens et al.). Late stages of the disease are characterized by proliferating fibrous tissue around the mesentery and the dorsal part of the peritoneal cavity, with extension into the inguinal canal, through the diaphragm, and into the abdominal wall. Once clinically apparent, the disease is invariably fatal within 1–2 months. The condition has been associated with simian immunodeficiency (SAIDS) due to a type D simian retrovirus, SRV-2 (Tsai et al.). However, other colonies do not show the same frequency of RF amongst monkeys affected with SAIDS, and the frequency of RF at Washington has been declining in recent years.

The study of such conditions in non-human primates is important not only as a model for human conditions, but also because one primate species may act as a reservoir of viruses that affect another species. For example, the herpes virus saimiri appears to cause no disease in its natural host, the squirrel monkey (*Saimiri sciureus*), but it causes polyclonal T-cell lymphomas and acute leukemias in other primates, particularly owl monkeys.

There is a need to develop reagents and methods for use in the detection and treatment of herpes virus infections.

For example, there is a need to develop reagents and methods which can be used in the diagnosis and assessment of Kaposi's sarcoma, and similar conditions. Being able to detect the etiologic agent in a new patient may assist in differential diagnosis; being able to assess the level of the agent in an ongoing condition may assist in clinical management. The tegument encoding polynucleotide of Chang et al. may have limited applicability in this regard. It is desirable to obtain a marker capable of distinguishing active from latent infection. It is also desirable to obtain a marker that is immunogenic, and can be used to assess immunological exposure to the agent as manifest in the antibody response.

Second, there is a need to develop reagents and methods which can be used in the development of new pharmaceuticals for Kaposi's sarcoma, and similar conditions. The current treatment for Kaposi's is radiation in combination with traditional chemotherapy, such as vincristine (Northfelt, Mitsuyasu). While lesions respond to these modalities, the response is temporary, and the downward clinical course generally resumes. Even experimental therapies, such as treatment with cytokines, are directed at the symptoms of the disease rather than the cause. Drug screening and rational drug design based upon the etiologic agent can be directed towards the long-felt need for a clinical regimen with long-term efficacy.

Third, there is a need to develop reagents and methods which can be used to identify viral agents that may be associated with other fibroproliferative conditions. The representational difference analysis technique used by Chang et al. is arduously complex, and probably not appropriate as a general screening test. More desirable are a set of primers or probes to be used as reagents in more routine assays for surveying a variety of tissue samples suspected of containing a related etiologic agent. Preferably, the reagents are sufficiently cross-reactive to identify previously undescribed viral compounds, but sufficiently specific to avoid identifying unwanted viruses or endogenous components of the host.

SUMMARY OF THE INVENTION

It is an objective of this invention to provide isolated polynucleotides, polypeptides, and antibodies derived from or reactive with the products of novel DNA polymerase genes. The genes are present in herpes viruses associated with fibroproliferative conditions and neoplasms, especially those that occur in humans and non-human primates. Another objective of this invention is to provide polynucleotide primers and probes for detecting and characterizing DNA polymerase genes in any member of the herpes virus family, especially the gamma herpes subfamily. Another object of this invention is to provide materials and methods based on these polynucleotides, polypeptides, and antibodies for use in the diagnosis and treatment of gamma herpes virus infection in primates, particularly humans.

Embodiments of the invention include the following:

1. An isolated polynucleotide with a region encoding a DNA polymerase of a herpes virus, the polynucleotide comprising a sequence (preferably 475 nucleotides long) that is at least 69% identical to nucleotides 27 to 501 of a sequence selected from the group consisting of SEQ. ID NO:1 and SEQ. ID NO:3.

2. An isolated polynucleotide comprising a fragment of at least 18, more preferably at least about 35, still more preferably at least about 50 consecutive nucleotides of the DNA polymerase encoding region of the polynucleotide of embodiment 1, wherein the sequence of said fragment is not contained in SEQ. ID NOS:110 or 111. Preferred examples are isolated polynucleotides comprising a fragment of at least 18 consecutive nucleotides contained in SEQ. ID NOS:1, 3, 116, or 118.

3. An isolated polynucleotide with a region encoding a DNA polymerase of a herpes virus, the polynucleotide comprising a sequence of 26 nucleotides at least 80% identical to oligonucleotide LSGGA (SEQ. ID NO:107).

4. An isolated polynucleotide with a region encoding a DNA polymerase of a herpes virus, the polynucleotide comprising a sequence of 29 nucleotides at least 69% identical to oligonucleotide CTDPA (SEQ. ID NO:108).

5. An isolated polynucleotide with a region encoding a DNA polymerase of a herpes virus, the polynucleotide comprising a sequence of 32 nucleotides at least 80% identical to oligonucleotide KMLEA (SEQ. ID NO:22).

6. An isolated polynucleotide with a region encoding a DNA polymerase of a herpes virus, the polynucleotide comprising a sequence of 29 nucleotides at least 69% identical to oligonucleotide GISPA (SEQ. ID NO:109).

7. An isolated polynucleotide comprising a fragment of at least 18, more preferably at least about 35, more preferably at least about 50 consecutive nucleotides of the DNA polymerase encoding region of the polynucleotide of embodiments 3, 4, 5, or 6, wherein the sequence of said fragment is not contained in SEQ. ID NOS:110 or 111.

8. The polynucleotide of embodiment 1 or embodiment 2, wherein said herpes virus is capable of infecting primates.

9. The polynucleotide of embodiment 1 or embodiment 2, wherein said herpes virus is RFHV or KSHV. Also included is the polynucleotide of embodiment 1 or embodiment 2, wherein said herpes virus is RFHV2.

10. An isolated polynucleotide comprising a linear sequence of at least 18 nucleotides identical to a linear sequence within SEQ. ID NOS: 1, 3, 116, or 118, but not to a linear sequence within SEQ. ID NOS:110 or 111.

11. The isolated polynucleotide of embodiment 10, comprising a linear sequence essentially identical to nucleotides 27 to 501 of a sequence selected from the group consisting of SEQ. ID NO:1 and SEQ. ID NO:3. Also included is the isolated polynucleotide of embodiment 10, comprising a linear sequence essentially identical to nucleotides 36 to 2499 of SEQ. ID NO:116, or a linear sequence essentially identical to nucleotides 1 to 454 of SEQ. ID NO:118.

12. An isolated polypeptide encoded by the polynucleotide of embodiment 1, or encoded by any of the polynucleotides of embodiments 2–11.

13. An isolated polypeptide, comprising a linear sequence of at least 11, preferably 12, and more preferably 15 amino acids essentially identical to a sequence between amino acids 10 to 167 inclusive of SEQ. ID NO:2 or between amino acids 10 to 167 inclusive of SEQ. ID NO:4 or between amino acids 13 to 833 inclusive of SEQ. ID NO:117, or in any of SEQ. ID NOS:119–123, but which is not contained in SEQ. ID NOS:112 or in SEQ. ID NO:113.

14. A fusion polypeptide comprising the amino acid sequence of an isolated peptide according to embodiment 13, joined to a second amino acid sequence.

15. The isolated polypeptide of embodiment 13, which has nucleic acid binding activity.

16. The isolated polypeptide of embodiment 13, which has nucleotide binding activity.

17. The isolated polypeptide of embodiment 13, which has DNA polymerase activity.

18. An isolated polypeptide, comprising a linear sequence of amino acids identical to a sequence selected from the group consisting of SEQ. ID NOS:80, 82, 84, 86, 88, and 90 to 103.

19. An isolated polynucleotide encoding the polypeptide of embodiment 13, or any of embodiments 14–18.

20. A non-naturally occurring polynucleotide encoding the polypeptide of embodiment 13, or any of embodiments 14–18.

21. A polynucleotide encoding a fusion polypeptide, comprising the polynucleotide of embodiment 2 joined directly to a second polynucleotide encoding a polypeptide.

22. A recombinant cloning vector comprising a polynucleotide sequence encoding a polypeptide of at least 11, preferably at least 12, more preferably at least 15 consecutive amino acids between amino acids 10–167 inclusive of SEQ. ID NO:2, or between amino acids 10–167 inclusive of SEQ. ID NO:4, or between amino acids 13–833 inclusive of SEQ. ID NO:117, or in any of SEQ. ID NOS:119–123, but not contained in SEQ. ID NO:112 or SEQ. ID NO:113.

23. A recombinant expression vector comprising a polynucleotide sequence encoding a polypeptide of at least 1, preferably at least 12, more preferably at least 15 consecutive amino acids between amino acids 10–167 inclusive of SEQ. ID NO:2, or between amino acids 10–167 inclusive of SEQ. ID NO:4, or between amino acids 13–833 inclusive of SEQ. ID NO:117, or in any of SEQ. ID NOS:119–123, but not contained in SEQ. ID NO:112 or SEQ. ID NO:113, operatively linked to a control polynucleotide sequence.

24. A recombinant cloning vector comprising a linear sequence of at least 18 nucleotides identical to a linear sequence within SEQ. ID NOS:1, 3, 116, or 118, but not in SEQ. ID NOS:110 or 111.

25. A host cell transformed by the polynucleotide of embodiment 19 or embodiment 20, or by the vector of embodiment 22, embodiment 23, or embodiment 24.

26. A monoclonal or isolated polyclonal antibody specific for a DNA polymerase encoded in said encoding region of the polynucleotide of embodiment 1.

27. A monoclonal or isolated polyclonal antibody specific for the polypeptide of embodiment 13.

28. The antibody of embodiment 27, which is a monoclonal antibody.

29. The antibody of embodiment 27, which is an isolated polyclonal antibody.

30. An oligonucleotide essentially identical to an oligonucleotide selected from the group consisting of SEQ. ID NOS:5 to 16, 21, 22, 104–109, and 124–152.

31. A method of obtaining an amplified copy of a polynucleotide encoding a DNA polymerase, comprising the steps of:
    a) contacting the polynucleotide with the oligonucleotide of embodiment 30; and
    b) elongating oligonucleotide that has formed a duplex with the polynucleotide.

32. The method of embodiment 31, wherein said amplification reaction is a polymerase chain reaction (PCR).

33. The method of embodiment 32, wherein said PCR comprises repeated cycles of annealing and elongating, and the annealing is conducted at a temperature of at least 60° C.

34. The method of embodiment 32, wherein said PCR is conducted in a buffer containing 10–30 mM $(NH_4)_2SO_4$ and 1–10 mM $MgCl_2$.

35. The method of embodiment 34, wherein the buffer is WB4 buffer.

36. The method of embodiment 31, wherein the polynucleotide which is amplified is first obtained from a biological sample taken from an individual affected with a disease featuring fibroblast proliferation and collagen deposition.

37. The method of embodiment 31, wherein the polynucleotide which is amplified is first obtained from a biological sample taken from an individual affected with a malignancy of the lymphocyte lineage. Also included is the method of embodiment 31, wherein the polynucleotide which is amplified is first obtained from a biological sample taken from an individual affected with a condition selected from the group consisting of retroperitoneal fibrosis, nodular fibromatosis, pseudosarcomatous fibromatosis, fibrosarcoma, sclerosing mesenteritis, acute respiratory disease syndrome, idiopathic pulmonary fibrosis, diffuse proliferative glomerulonephritis, glioma, glioblastomas, gliosis, leukemia and lymphoma.

38. A method of detecting viral DNA or RNA in a sample of primate origin, comprising the steps of:
    a) contacting the DNA or RNA in the sample with a probe comprising the polynucleotide of embodiment 2 under conditions that would permit the probe to form a stable duplex with a polynucleotide having the sequence shown in SEQ. ID NO:1, and with a polynucleotide having the sequence shown in SEQ. ID NO:3, but not with a polynucleotide having a sequence of any of SEQ. ID NOS:24 to 29; and
    b) detecting the presence of said stable duplex formed in step a), if any. The conditions referred to are a single set of reaction parameters, such as incubation time, temperature, solute concentrations, and washing steps, that fulfills all the criteria listed. Under these conditions, the polynucleotide would be capable of forming a stable duplex if contacted with a polynucleotide having SEQ. ID NO:1. It would also be capable of forming a stable duplex if contacted with a polynucleotide having SEQ. ID NO:3. It would not be capable of forming a stable duplex if contacted with a polynucleotide having a sequence of any of SEQ ID NO:24 to SEQ. ID NO:29. The reaction conditions may optionally be tested by contacting with the polynucleotides consisting only of the sequences indicated, or by contacting with polynucleotides with the sequences indicated linked to additional nucleotides, so long as formation of a stable duplex under the test conditions relies on the sequence indicated. Also included are similar methods using the polynucleotide of embodiment 7.

39. The method of embodiment 38 further comprising conducting an amplification reaction on the DNA or RNA of the sample prior to being contacted with the probe.

40. The method of embodiment 39, wherein the amplification reaction is conducted using an oligonucleotide primer comprising a sequence according to embodiment 30.

41. A method of detecting viral DNA or RNA in a sample of primate origin, comprising the steps of:
    a) contacting the DNA or RNA in the sample with an oligonucleotide probe comprising a sequence shown in SEQ. ID NOS: 21, 22, 107, 108, or 109, under conditions that would permit the probe to form a stable duplex with a polynucleotide having the sequence shown in SEQ. ID NO:1, and with a polynucleotide having the sequence shown in SEQ. ID NO:3, but not with a polynucleotide having a sequence of any of SEQ. ID NOS:24 to 29; and
    b) detecting the presence of said stable duplex formed in step a), if any.

42. A method of detecting viral DNA or RNA in a sample, comprising the steps of:
    a) contacting the DNA or RNA in the sample with an oligonucleotide probe comprising a sequence shown in SEQ. ID NOS:22, 107, 108 or 109 under conditions that would permit the probe to form a stable duplex with a polynucleotide having the sequence shown in SEQ. ID NO:1, and with a polynucleotide having the sequence shown in SEQ. ID NO:3, but not with a polynucleotide having a sequence of any of SEQ. ID NOS:23 to 29; and
    b) detecting the presence of said stable duplex formed in step a), if any.

43. A method of detecting viral DNA or RNA in a sample, comprising the steps of:
    a) conducting an amplification reaction on a polynucleotide in the sample using the oligonucleotide of embodiment 30 as a primer in the reaction; and
    b) detecting the presence of amplified copies of the polynucleotide, if any.

44. An isolated polynucleotide capable of forming a stable duplex with an oligonucleotide comprising a sequence selected from the group consisting of SEQ. ID NO:107, SEQ. ID NO:108, and their respective complementary sequences, under conditions wherein the oligonucleotide is capable of forming a stable duplex with a polynucleotide having the sequence shown in SEQ. ID NO:1, and with a polynucleotide having the sequence shown in SEQ. ID NO:3, but not with a polynucleotide having a sequence of any of SEQ. ID NOS:23 to 29.

45. An isolated polypeptide comprising a linear sequence of at least 11 amino acids, preferably at least 12 amino acids, more preferably at least 15 amino acids encoded within the polynucleotide of embodiment 44.

46. A method for detecting infection of an individual by a herpes virus, comprising detecting viral DNA or RNA in a biological sample obtained from the individual, wherein the detecting of viral DNA or RNA is by the method of embodiment 38 or embodiment 43. Also included is a method for detecting infection of an individual by a herpes virus, comprising detecting viral DNA or RNA in a biological sample obtained from the individual, wherein the detecting of viral DNA or RNA is by the method of: a) contacting the DNA or RNA in the sample with a probe comprising the polynucleotide of embodiment 2 under conditions that would permit the probe to form a stable duplex with a polynucleotide having at least one sequence selected from the group consisting of SEQ. ID NOS:1, 3, 116, or 118, but not with polynucleotides having a sequence of any of SEQ. ID NOS:24 to 29; and b) detecting the presence of said stable duplex formed in step a), if any. Also included is a method for detecting infection of an individual by a herpes virus, comprising detecting viral DNA or RNA in a biological sample obtained from the individual, wherein the detecting of viral DNA or RNA is by the method of: a) contacting the DNA or RNA in the sample with a probe comprising the polynucleotide of embodiment 2 under conditions that would permit the probe to form a stable duplex with a polynucleotide having a sequence shown in SEQ. ID NO:116, but not with polynucleotides having a sequence of any of SEQ. ID NOS:24 to 29; and b) detecting the presence of said stable duplex formed in step a), if any.

47. A diagnostic kit for detecting a herpes virus polynucleotide in a biological sample, comprising a reagent in suitable packaging, wherein the reagent comprises the polynucleotide of embodiment 2.

48. A diagnostic kit for detecting a herpes virus polynucleotide in a biological sample, comprising a reagent in suitable packaging, wherein the reagent comprises the oligonucleotide of embodiment 30.

49. A method of detecting infection of an individual by a herpes virus, comprising the steps of:
    a) contacting antibody from a sample obtained from the individual with the polypeptide of embodiment 12 or embodiment 13 under conditions that permit the formation of a stable antigen-antibody complex; and
    b) detecting said stable complexes formed in step a), if any.

50. A diagnostic kit for detecting an anti-herpesvirus antibody present in a biological sample, comprising a reagent in suitable packaging, wherein the reagent comprises the polypeptide of embodiment 12 or embodiment 13.

51. A method of detecting infection of an individual by a herpes virus, comprising the steps of:
    a) contacting antibody from a sample obtained from the individual with the polypeptide of embodiment 18 under conditions that permit the formation of a stable antigen-antibody complex; and
    b) detecting said stable complexes formed in step a), if any.

52. A diagnostic kit for detecting an anti-herpesvirus antibody present in a biological sample, comprising a reagent in suitable packaging, wherein the reagent comprises the polypeptide of embodiment 18.

53. A method of detecting infection of an individual by a herpes virus, comprising the steps of:
    a) contacting a polypeptide from a sample obtained from the individual with the antibody of embodiment 27 under conditions that permit the formation of a stable antigen-antibody complex; and
    b) detecting said stable complexes formed in step a), if any.

54. A diagnostic kit for detecting a herpes virus polypeptide present in a biological sample, comprising a reagent in suitable packaging, wherein the reagent comprises the antibody of embodiment 27.

55. A composition for use in the treatment of herpes virus infection, comprising the polynucleotide of embodiment 2 and a compatible pharmaceutical excipient. Also included are compositions comprising the polynucleotide of embodiment 7. Also included are compositions comprising the polypeptide of embodiments 12 or 13, or the antibody of embodiment 27.

56. A method of determining whether a pharmaceutical candidate is useful for treating gamma herpes infection, comprising the steps of: a) contacting the polypeptide of embodiment 12 or embodiment 13 with the pharmaceutical candidate; and b) determining whether a biochemical function of the polypeptide is altered by the pharmaceutical candidate. Also included is a method of determining whether a pharmaceutical candidate is useful for treating gamma herpes infection, comprising the steps of: a) genetically altering a cell using the polynucleotide of claim 1; and b) determining the effect of the pharmaceutical candidate on the cell in comparison with a cell not genetically altered with the polynucleotide.

57. The method of embodiment 56, wherein the biochemical function of the polypeptide determined in step b) is the binding of the polypeptide to a nucleic acid.

58. The method of embodiment 56, wherein the biochemical function of the polypeptide determined in step b) is DNA polymerase activity.

59. A method of obtaining a compound for use in treating an individual infected with herpes virus, comprising the steps of:
   a) creating a compound capable of binding a region of the polypeptide of embodiment 12 or embodiment 13 involved in interacting with a nucleic acid; and
   b) determining whether the compound interferes with a biochemical function of the polypeptide.

BRIEF DESCRIPTION OF THE DRAWINGS

FIG. 1 is a listing of polynucleotide sequences amplified from a DNA polymerase encoding region of RFHV and KSHV, along with the encoded polypeptides. The 475-base fragment of each polynucleotide between primers DFASA and GDTD1B is underlined. Also shown in lower-case letters are oligonucleotides useful as amplification primers aligned with corresponding regions of the DNA polymerase gene. DFASA, VYGA and GDTD1B are oligonucleotides with consensus and degenerate segments that can be used to amplify any herpes virus DNA polymerase gene. LSGGA, CTDPA, PCLNA, KMLEA and GISPA are oligonucleotides specific for the RFHV/KSHV subfamily of herpes viruses. VASGA, ILPCA, PIEAB and PEARB are RFHV-specific primers. SGILA, CLNIA, IEASB and EARFB are KSHV-specific primers. Oligonucleotides that initiate amplification in the direction of the coding sequence (with designations ending in "A") are listed 5'→3'. Oligonucleotides that initiate amplification in the direction opposite to that of the coding sequence (with designations ending in "B") are listed 3'→5', to show alignment with the corresponding sequences in the RFHV and KSHV polynucleotide.

FIG. 2 is a listing of the previously known polypeptide sequences of other herpes virus DNA polymerases, showing regions that are relatively conserved between species.

FIG. 3 is a listing of previously known polynucleotide sequences of herpes viruses near conserved REGION 2, showing the alignment of oligonucleotides DFASA and DFQSA with the sequences from which they were designed.

FIG. 4 is a listing of previously known polynucleotide sequences of herpes viruses near conserved REGION 3, showing the alignment of oligonucleotides VYGA, VYGCA and VYGSQA with the sequences from which they were designed.

FIG. 5 is a listing of previously known polynucleotide sequences of herpes viruses near conserved REGION 1, showing the alignment of oligonucleotides GDTD1B and GDTDSQB with the sequences from which they were designed.

FIG. 6 is a listing comparing the polynucleotide sequences of DNA polymerase of the gamma herpes virus subfamily. The fragment shown is the 475 base pairs between the hybridizing site of DFASA and GDTD1B.

FIG. 7 is a listing comparing polypeptide sequences of DNA polymerase for the same viruses over the same fragment as FIG. 6. This figure also shows examples of possible antibody binding regions, including those which are specific for RFHV, KSHV, or the RFHV/KSHV subfamily.

FIG. 8 is a comparison of the polypeptide sequence for the fragment encoded between DFASA and GDTD1B across a broader range of herpes viruses. Sequences are shown for herpes viruses of the alpha, beta, and gamma subfamilies, and for endogenous mammalian DNA polymerase.

FIG. 10 is a listing of the DNA polymerase genes for members of the gamma herpes virus subfamily over the same region as FIG. 6. This Figure shows the alignment of oligonucleotides LSGGA, CTDPA, PCLNA, KMLEA and GISPA aligned with the sequences from which they were designed. These oligonucleotides are specific for DNA polymerase from the RFHV/KSHV virus subfamily.

FIG. 13 is a listing of about 2511 nucleotides of the DNA polymerase encoding sequence of KSHV, estimated to be about 3000 nucleotides long, along with the amino acid translation. Additional sequence data is provided in the 5' and 3' direction from the PCR segment shown in FIG. 1.

FIG. 14 is a listing comparing the KSHV DNA polymerase amino acid sequence with that of other herpes viruses. Asterisks (*) and bullets (•) indicate conserved residues or conservative substitutions. Arrows (↑) indicate residues that are conserved amongst other herpes viruses, but different in the KSHV sequence.

FIG. 15 is a listing showing known variants of the KSHV DNA polymerase amino acid sequence.

FIG. 16 is a listing of polynucleotide sequences amplified from a DNA polymerase encoding region of RFHVMm (designated here as RFMm). RFHVMm is a third member of the RFHV/KSHV herpes virus subfamily identified according to the criteria of this invention. Shown for comparison are DNA polymerase encoding regions of RFHV (designated RFMn) and KSHV.

FIG. 17 is a listing comparing amino acid sequences encoded in a DNA polymerase encoding region of RFHVMm with corresponding sequences of RFHVMn, KSHV, and three other herpes viruses.

DETAILED DESCRIPTION

Figure 9:
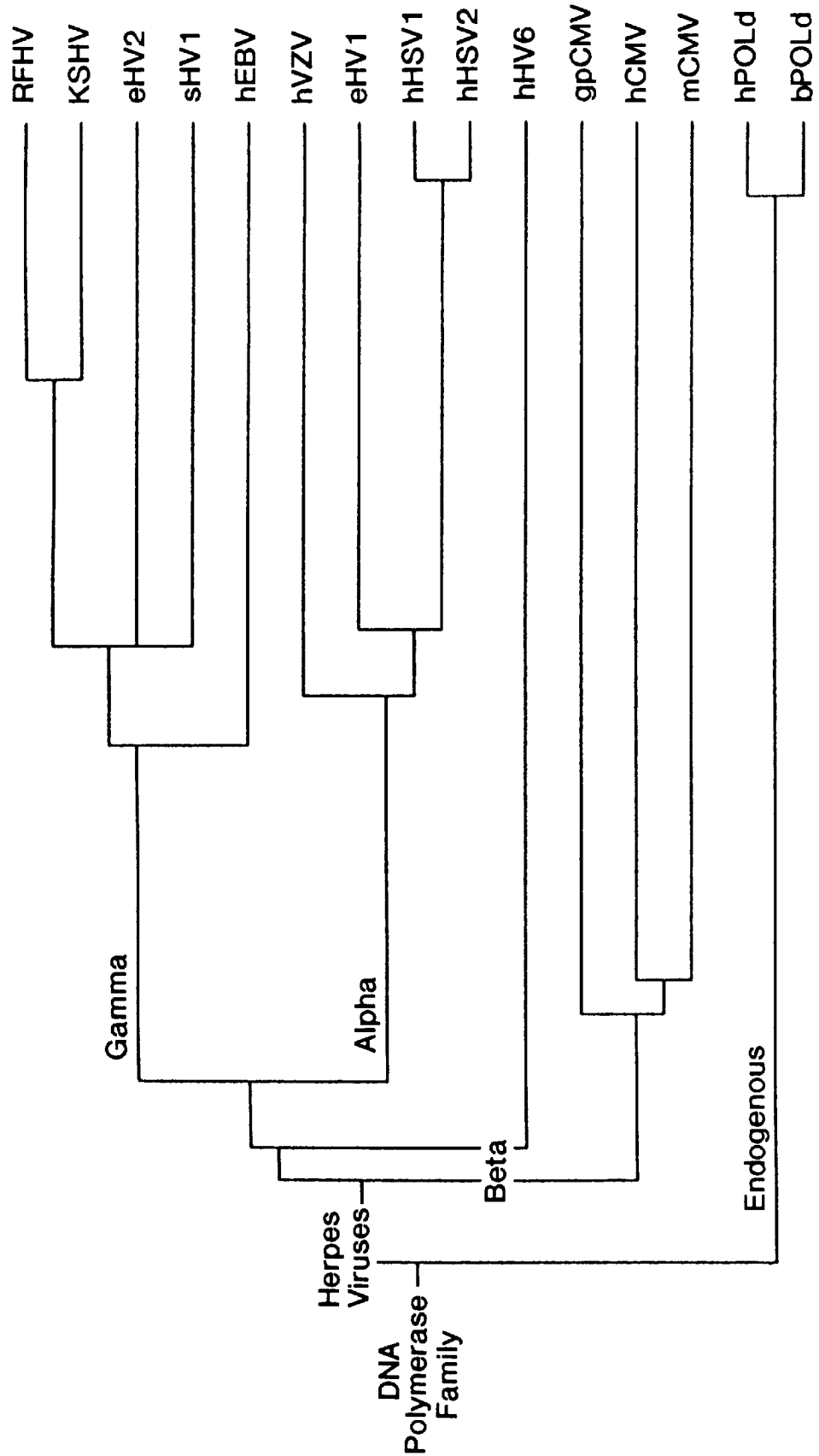
FIG. 9 is a relationship map of DNA polymerases, based on polypeptide sequences shown in FIG. 8.

We have discovered and characterized polynucleotides encoding DNA polymerase from RFHV, RFHV2, and KSHV, which are exemplary members of the RFHV/KSHV subfamily of herpes viruses. The polynucleotides obtained, related polynucleotides, and corresponding polypeptides and antibodies are useful in the diagnosis, clinical monitoring, and treatment of herpes virus infections and related conditions.

Sources for the polynucleotides from RFHV and KSHV were affected tissue samples taken from *Macaque nemestrina* monkeys with retroperitoneal fibromatosis ("RF") and from humans with Kaposi's sarcoma ("KS"), respectively. We predicted that these conditions were associated with viruses distinct from those responsible for any contemporaneous immunodeficiency. We did not know in advance that the RF and KS associated viruses would be related.

We decided to test the premise that viruses associated with both conditions are members of the herpes virus family. Accordingly, we designed oligonucleotides for use in an amplification reaction to obtain polynucleotides encoding a DNA polymerase from a broad spectrum of herpes viruses. Comparing amino acid sequences of herpes viruses that have been previously described, three conserved regions were identified. The corresponding known polynucleotide sequences were used to construct oligonucleotides comprising a degenerate segment and a consensus segment. These oligonucleotides served as primers in amplification reactions that yielded fragments of the DNA polymerase encoding segment from each of the two tissue sources.

The sequences of the polynucleotide fragments obtained from the final step of the amplification reactions are shown in FIG. 1 (SEQ. ID NO:1 and SEQ. ID NO:3, respectively). Both sequences are novel, although they contain regions that are highly homologous to regions of DNA polymerase sequences from other herpes viruses. The virus infecting the *M. nemestrina* monkeys was designated "Retroperitoneal Fibromatosis Herpes Virus" ("RFHV"). The virus infecting the human patients was designated "Kaposi's Sarcoma Herpes Virus" ("KSHV"). The polynucleotide sequences shown include segments at each end corresponding to the hybridizing regions of the DFASA and GDTD1B primers used in the amplification. The 475 base pair fragment between the primers represents an amplified portion of the DNA polymerase gene for RFHV and KSHV.

Since the primers were designed to amplify a broad spectrum of DNA polymerases, we were surprised to find that these two DNA polymerase sequences are apparently more closely related to each other (71% identity at the nucleotide level) than to any other known herpes virus DNA polymerase. The next most closely related polynucleotide sequences are from equine herpes virus 2 (eHV2), saimiri herpes virus 1 (sHV1), and Epstein Barr virus (EBV). We therefore predict that both RFHV and KSHV are members of the herpes gamma subfamily. RFHV and KSHV share with other gamma herpes an association with abnormal cellular or fibrotic growth, and an association with immune abnormalities, including immunosuppression and B cell dysplasias. However, RFHV and KSHV DNA polymerase sequences differ from sHV1 and EBV in the frequency of CpG dinucleotides. RFHV and KSHV DNA polymerase nucleotide sequences and oligonucleotides based upon them define the RFHV/KSHV subfamily as described below. The DNA polymerase sequence of a third member of the subfamily infecting *M. mulatta* monkeys, RFHV2, is also provided.

The degree of conservation between DNA polymerases means that the polynucleotides and polypeptides embodied in this invention are reliable markers amongst different strains of RFHV and KSHV. Because it is a sequestered antigen, DNA polymerase is not under the same degree of immunological pressure to form escape mutants. Furthermore, the sequences are constrained by the critical role that these regions play in the catalytic activity of the DNA polymerase. Thus, the polynucleotides, polypeptides, and antibodies embodied in this invention are useful in such applications as the detection of viral infection in an individual, due to RFHV, KSHV, or other herpes viruses that are of the same subfamily. Embodiments of the invention are also useful in the characterization of herpes virus DNA polymerase, and the design of pharmaceutical therapies.

Because the DNA polymerase plays a critical role in viral replication, it is an appropriate target for pharmacological intervention. Particularly sensitive regions of the molecule are those involved in substrate recognition, template binding, catalysis, and association with regulatory subunits.

Polynucleotides of the RFHV/KSHV subfamily, related oligonucleotide probes and primers, related polypeptides and antigens, related specific antibodies, the preparation and use of these compounds, and related methods and products are described in further detail in the sections that follow.

Abbreviations

The following abbreviations are used herein to refer to species of herpes viruses, and polynucleotides and genes derived therefrom that encode DNA polymerase:

TABLE 1

Abbreviations for Herpes Virus Strains

| Designation | Virus | Provisional Subfamily Assignment |
| --- | --- | --- |
| RFHV | simian Retroperitoneal Fibromatosis-associated HerpesVirus | gamma-HerpesVirus |
| KSHV | human Kaposi's Sarcoma-associated HerpesVirus | |
| eHV2 | equine HerpesVirus 2 | |
| sHV1 | saimiri monkey HerpesVirus 1 | |
| hEBV | human Epstein-Barr Virus | |
| hCMV | human CytoMegaloVirus | beta-HerpesVirus |
| mCMV | murine CytoMegaloVirus | |
| gpCMV | guinea pig CytoMegaloVirus | |
| hHV6 | human HerpesVirus 6 | |
| hVZV | human Varicella-Zoster Virus | alpha-HerpesVirus |
| hHSV1 | human Herpes Simplex Virus 1 | |
| hHSV2 | human Herpes Simplex Virus 2 | |
| eHV1 | equine HerpesVirus 1 | |
| iHV1 | ictalurid catfish HerpesVirus | |
| hPOLd | human endogenous DNA polymerase | eukaryotic delta DNA polymerase |
| bPOLd | bovine endogenous DNA polymerase | |

Definitions

"RFHV" and "KSHV" are viruses of the herpes family detected in tissue samples of infected *macaque nemestrina* monkeys and humans, respectively. Cells infected with these viruses contain polynucleotides encoding the respective DNA polymerases as described herein. "RFHV" is synonymous with the terms "RFHV1", "RFHVMn", and "RFMn". A third member of the RFHV/KSHV subfamily is a virus identified in a M. mulatta monkey. The virus is referred to herein as "RFHV2". "RFHV2" is synonymous with the terms "RFHVMm" and "RFMm".

The "RFHV/KSHV subfamily" is a term used herein to refer to a collection of herpes viruses capable of infecting vertebrate species. The subfamily consists of members that have sequences that are more closely related to the corresponding sequences of RFHV or KSHV than either of these viruses are to any other virus listed in Table 1. The sequence comparison may be made at either the polynucleotide or the polypeptide level, and may be across intact genes or proteins, or across fragments thereof. As used herein, the subfamily refers to herpes viruses that contain a portion of a DNA-polymerase-encoding polynucleotide that is more closely identical to the corresponding region of RFHV or KSHV than either of these viruses are to the viruses in Table 1. Preferably, the polynucleotide encoding the polymerase comprises a segment that is at least 69% identical to that of RFHV (SEQ. ID NO:1) or KSHV (SEQ. ID NO:3) between residues 27 and 501; or at least 80% identical to the oligonucleotide LSGGA; or at least 69% identical to the oligonucleotide CTDPA; or at least 80% identical to the oligonucleotide KMLEA; or at least 69% identical to the oligonucleotide GISPA.

As used herein, a "DNA polymerase" is a protein or a protein analog, that under appropriate conditions is capable of catalyzing the assembly of a DNA polynucleotide with a sequence that is complementary to a polynucleotide used as a template. A DNA polymerase may also have other catalytic activities, such as 3'-5' exonuclease activity; any of the activities may predominate. A DNA polymerase may require association with additional proteins or co-factors in order to exercise its catalytic function. "DNA polymerase activity" refers to the catalytic activity directed at DNA polynucleotide assembly. A "DNA polymerase reaction" is any step in a reaction mechanism on the pathway to polymerization of nucleotides, including association with substrates, cofactors, and regulatory subunits, the formation of intermediates, and the formation of reaction products.

The term "DNA polymerase gene" includes any gene that encodes a polypeptide capable of a DNA polymerase reaction. It also includes any gene that is believed to be derived from an ancestral gene that encoded a DNA polymerase, because of homology with other DNA polymerase genes or its location relative to neighboring genes; such a gene may encode a non-functional DNA polymerase analog, a DNA polymerase fragment or mutant, or it may be untranscribed or untranslated.

A "regulatory subunit" for a first polypeptide that has DNA polymerase activity is a second polypeptide that regulates DNA polymerase activity of the first polypeptide when associated with it. UL42 is an example of a regulatory subunit.

"UL42" or "UL42 subunit" is an accessory protein that is encoded in the genome of some herpes viruses. It is capable of associating with the DNA polymerase of the virus. Under certain conditions, it enhances the DNA polymerase activity of a polypeptide encoded by a DNA polymerase gene, and may be required for the virus to replicate. As used herein, the definition is a functional one, and does not depend on the structure or genomic location of the corresponding gene. Thus, a UL42 subunit of RFHV or KSHV may have a sequence that is not essentially identical to the UL42 subunit of other viruses.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide. A "partial sequence" is a linear sequence of part of a polynucleotide which is known to comprise additional residues in one or both directions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogsteen binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

Hybridization reactions can be performed under conditions of different "stringency". Conditions that increase the stringency of a hybridization reaction are widely known and published in the art: see, for example, Sambrook Fritsch & Maniatis. Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 min to 24 h; and washes of increasing duration, increasing frequency, or decreasing buffer concentrations.

"$T_m$" is the temperature in degrees Centigrade at which 50% of a polynucleotide duplex made of complementary strands hydrogen bonded in an antiparallel direction by Watson-Crick base paring dissociates into single strands under the conditions of the experiment. $T_m$ may be predicted according to standard formula; for example:

$T_m$=81.5+16.6 log [Na$^+$]+0.41 (% G/C)−0.61 (% F)−600/L where Na$^+$ is the cation concentration (usually sodium ion) in mol/L; (% G/C) is the number of G and C residues as a percentage of total residues in the duplex; (% F) is the percent formamide in solution (wt/vol); and L is the number of nucleotides in each strand of the duplex.

A "stable duplex" of polynucleotides, or a "stable complex" formed between any two or more components in a biochemical reaction, refers to a duplex or complex that is sufficiently long-lasting to persist between the formation of the duplex or complex, and its subsequent detection. The duplex or complex must be able to withstand whatever conditions exist or are introduced between the moment of formation and the moment of detection, these conditions being a function of the assay or reaction which is being performed. Intervening conditions which may optionally be present and which may dislodge a duplex or complex include washing, heating, adding additional solutes or solvents to the reaction mixture (such as denaturants), and competing with additional reacting species. Stable duplexes or complexes may be irreversible or reversible, but must meet the other requirements of this definition. Thus, a transient complex may form in a reaction mixture, but it does not constitute a stable complex if it dissociates spontaneously or as a result of a newly imposed condition or manipulation introduced before detection.

When stable duplexes form in an antiparallel configuration between two single-stranded polynucleotides, particularly under conditions of high stringency, the strands are essentially "complementary". A double-stranded polynucleotide can be "complementary" to another polynucleotide, if a stable duplex can form between one of the strands of the first polynucleotide and the second. A complementary sequence predicted from the sequence of a single stranded polynucleotide is the optimum sequence of standard nucleotides expected to form hydrogen bonding with the single-stranded polynucleotide according to generally accepted base-pairing rules.

A "sense" strand and an "antisense" strand when used in the same context refer to single-stranded polynucleotides which are complementary to each other. They may be opposing strands of a double-stranded polynucleotide, or one strand may be predicted from the other according to generally accepted base-pairing rules. Unless otherwise specified or implied, the assignment of one or the other strand as "sense" or "antisense" is arbitrary.

A linear sequence of nucleotides is "identical" to another linear sequence, if the order of nucleotides in each sequence is the same, and occurs without substitution, deletion, or material substitution. It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution. An RNA and a DNA polynucleotide have identical sequences when the sequence for the RNA reflects the order of nitrogenous bases in the polyribonucleotide, the sequence for the DNA reflects the order of nitrogenous bases in the polydeoxyribonucleotide, and the two sequences satisfy the other requirements of this definition. Where at least one of the sequences is a degenerate oligonucleotide comprising an ambiguous residue, the two sequences are identical if at least one of the alternative forms of the degenerate oligonucleotide is identical to the sequence with which it is being compared. For example, AYAAA is identical to ATAAA, if AYAAA is a mixture of ATAAA and ACAAA.

When comparison is made between polynucleotides, it is implicitly understood that complementary strands are easily generated, and the sense or antisense strand is selected or predicted that maximizes the degree of identity between the polynucleotides being compared. For example, where one or both of the polynucleotides being compared is double-stranded, the sequences are identical if one strand of the first polynucleotide is identical with one strand of the second polynucleotide. Similarly, when a polynucleotide probe is described as identical to its target, it is understood that it is the complementary strand of the target that participates in the hybridization reaction between the probe and the target.

A linear sequence of nucleotides is "essentially identical" to another linear sequence, if both sequences are capable of hybridizing to form duplexes with the same complementary polynucleotide. Sequences that hybridize under conditions of greater stringency are more preferred. It is understood that hybridization reactions can accommodate insertions, deletions, and substitutions in the nucleotide sequence. Thus, linear sequences of nucleotides can be essentially identical even if some of the nucleotide residues do not precisely correspond or align. Sequences that correspond or align more closely to the invention disclosed herein are comparably more preferred. Generally, a polynucleotide region of about 25 residues is essentially identical to another region, if the sequences are at least about 80% identical; more preferably, they are at least about 90% identical; more preferably, they are at least about 95% identical; still more preferably, the sequences are 100% identical. A polynucleotide region of 40 residues or more will be essentially identical to another region, after alignment of homologous portions if the sequences are at least about 75% identical; more preferably, they are at least about 80% identical; more preferably, they are at least about 85% identical; even more preferably, they are at least about 90% identical; still more preferably, the sequences are 100% identical.

In determining whether polynucleotide sequences are essentially identical, a sequence that preserves the functionality of the polynucleotide with which it is being compared is particularly preferred. Functionality can be determined by different parameters. For example, if the polynucleotide is to be used in reactions that involve hybridizing with another polynucleotide, then preferred sequences are those which hybridize to the same target under similar conditions. In general, the $T_m$ of a DNA duplex decreases by about 1° C. for every 1% decrease in sequence identity for duplexes of 200 or more residues; or by about 5° C. for duplexes of less than 40 residues, depending on the position of the mismatched residues (see, e.g., Meinkoth et al.). Essentially identical sequences of about 100 residues will generally form a stable duplex with each other's respective complementary sequence at about 20° C. less than $T_m$; preferably, they will form a stable duplex at about 15° C. less; more preferably, they will form a stable duplex at about 10° C. less; even more preferably, they will form a stable duplex at about 5° C. less; still more preferably, they will form a stable duplex at about $T_m$. In another example, if the polypeptide encoded by the polynucleotide is an important part of its functionality, then preferred sequences are those which encode identical or essentially identical polypeptides. Thus, nucleotide differences which cause a conservative amino acid substitution are preferred over those which cause a non-conservative substitution, nucleotide differences which do not alter the amino acid sequence are more preferred, while identical nucleotides are even more preferred. Insertions or deletions in the polynucleotide that result in insertions or deletions in the polypeptide are preferred over those that result in the down-stream coding region being rendered out of phase; polynucleotide sequences comprising no insertions or deletions are even more preferred. The relative importance of hybridization properties and the encoded polypeptide sequence of a polynucleotide depends on the application of the invention.

A polynucleotide has the same "characteristics" of another polynucleotide if both are capable of forming a stable duplex with a particular third polynucleotide under similar conditions of maximal stringency. Preferably, in addition to similar hybridization properties, the polynucleotides also encode essentially identical polypeptides.

"Conserved" residues of a polynucleotide sequence are those residues which occur unaltered in the same position of two or more related sequences being compared. Residues that are relatively conserved are those that are conserved amongst more related sequences than residues appearing elsewhere in the sequences.

"Related" polynucleotides are polynucleotides that share a significant proportion of identical residues.

As used herein, a "degenerate" oligonucleotide sequence is a designed sequence derived from at least two related originating polynucleotide sequences as follows: the residues that are conserved in the originating sequences are preserved in the degenerate sequence, while residues that are not conserved in the originating sequences may be provided as several alternatives in the degenerate sequence. For example, the degenerate sequence AYASA may be designed from originating sequences ATACA and ACAGA, where Y is C or T and S is C or G. Y and S are examples of "ambiguous" residues. A degenerate segment is a segment of a polynucleotide containing a degenerate sequence.

It is understood that a synthetic oligonucleotide comprising a degenerate sequence is actually a mixture of closely related oligonucleotides sharing an identical sequence, except at the ambiguous positions. Such an oligonucleotide is usually synthesized as a mixture of all possible combinations of nucleotides at the ambiguous positions. Each of the oligonucleotides in the mixture is referred to as an "alternative form". The number of forms in the mixture is equal to $$\prod_{i=1}^{n} k_i$$

where $k_i$ is the number of alternative nucleotides allowed at each position.

As used herein, a "consensus" oligonucleotide sequence is a designed sequence derived from at least two related originating polynucleotide sequences as follows: the residues that are conserved in all originating sequences are preserved in the consensus sequence; while at positions where residues are not conserved, one alternative is chosen from amongst the originating sequences. In general, the nucleotide chosen is the one which occurs in the greatest frequency in the originating sequences. For example, the consensus sequence AAAAA may be designed from originating sequences CAAAA, AAGAA, and AAAAT. A consensus segment is a segment of a polynucleotide containing a consensus sequence.

A polynucleotide "fragment" or "insert" as used herein generally represents a sub-region of the full-length form, but the entire full-length polynucleotide may also be included.

Different polynucleotides "correspond" to each other if one is ultimately derived from another. For example, messenger RNA corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. Polynucleotides also "correspond" to each other if they serve a similar function, such as encoding a related polypeptide, in different species, strains or variants that are being compared.

A "probe" when used in the context of polynucleotide manipulation refers to an oligonucleotide which is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" is an oligonucleotide, generally with a free 3'-OH group, that binds to a target potentially present in a sample of interest by hybridizing with the target, and thereafter promotes polymerization of a polynucleotide complementary to the target.

Processes of producing replicate copies of the same polynucleotide, such as PCR or gene cloning, are collectively referred to herein as "amplification" or "replication". For example, single or double-stranded DNA may be replicated to form another DNA with the same sequence. RNA may be replicated, for example, by an RNA-directed RNA polymerase, or by reverse-transcribing the DNA and then performing a PCR. In the latter case, the amplified copy of the RNA is a DNA with the identical sequence.

A "polymerase chain reaction" ("PCR") is a reaction in which replicate copies are made of a target polynucleotide using one or more primers, and a catalyst of polymerization, such as a reverse transcriptase or a DNA polymerase, and particularly a thermally stable polymerase enzyme. Generally, a PCR involves reiteratively forming three steps: "annealing", in which the temperature is adjusted such that oligonucleotide primers are permitted to form a duplex with the polynucleotide to be amplified; "elongating", in which the temperature is adjusted such that oligonucleotides that have formed a duplex are elongated with a DNA polymerase, using the polynucleotide to which they've formed the duplex as a template; and "melting", in which the temperature is adjusted such that the polynucleotide and elongated oligonucleotides dissociate. The cycle is then repeated until the desired amount of amplified polynucleotide is obtained. Methods for PCR are taught in U.S. Pat. Nos. 4,683,195 (Mullis) and 4,683,202 (Mullis et al.).

Elements within a gene include but are not limited to promoter regions, enhancer regions, repressor binding regions, transcription initiation sites, ribosome binding sites, translation initiation sites, protein encoding regions, introns and exons, and termination sites for transcription and translation.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements are known in the art. For example, a "promoter" is an example of a control element. A promoter is a DNA region capable under certain conditions of binding RNA polymerase and initiating transcription of a coding region located downstream (in the 3' direction) from the promoter.

"Operatively linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

In the context of polypeptides, a "linear sequence" or a "sequence" is an order of amino acids in a polypeptide in an N-terminal to C-terminal direction in which residues that neighbor each other in the sequence are contiguous in the primary structure of the polypeptide. A "partial sequence" is a linear sequence of part of a polypeptide which is known to comprise additional residues in one or both directions.

A linear sequence of amino acids is "essentially identical" to another sequence if the two sequences have a substantial degree of sequence identity. It is understood that the folding and the biochemical function of proteins can accommodate insertions, deletions, and substitutions in the amino acid sequence. Thus, linear sequences of amino acids can be essentially identical even if some of the residues do not precisely correspond or align. Sequences that correspond or align more closely to the invention disclosed herein are more preferred. It is also understood that some amino acid substitutions are more easily tolerated. For example, substitution of an amino acid with hydrophobic side chains, aromatic side chains, polar side chains, side chains with a positive or negative charge, or side chains comprising two or fewer carbon atoms, by another amino acid with a side chain of like properties can occur without disturbing the essential identity of the two sequences. Methods for determining homologous regions and scoring the degree of homology are well known in the art; see for example Altschul et al. and Henikoff et al. Well-tolerated sequence differences are referred to as "conservative substitutions". Thus, sequences with conservative substitutions are preferred over those with other substitutions in the same positions; sequences with identical residues at the same positions are still more preferred.

Generally, a polypeptide region of about 25 residues is essentially identical to another region if the sequences are at least about 80% identical; more preferably, they are at least about 85% identical; more preferably, they are at least about 90% identical; more preferably, they are at least about 95% identical; still more preferably, the sequences are 100% identical. A polypeptide region of 40 residues or more will be essentially identical to another region, after alignment of homologous portions, if the sequences are at least about 70% identical; more preferably, they are at least about 70% identical, and comprise at least another 10% which are either identical or are conservative substitutions; more preferably, they are at least about 80% identical; more preferably, they are at least about 80% identical, and comprise at least another 10% which are either identical or are conservative substitutions; more preferably, they are at least about 90% identical; still more preferably, the sequences are 100% identical.

In determining whether polypeptide sequences are essentially identical, a sequence that preserves the functionality of the polypeptide with which it is being compared is particularly preferred. Functionality may be established by different parameters, such as enzymatic activity, the binding rate or affinity in a substrate-enzyme or receptor-ligand interaction, the binding affinity with an antibody, and X-ray crystallographic structure.

A polypeptide has the same "characteristics" of another polypeptide if it displays the same biochemical function, such as enzyme activity, ligand binding, or antibody reactivity. Preferred characteristics of a polypeptide related to a DNA polymerase or a DNA polymerase fragment are DNA polymerase activity, DNA template binding, and the binding of deoxyribonucleotide triphosphates. Also preferred is a polypeptide that displays the same biochemical function as the polypeptide with which it is being compared, and in addition, is believed to have a similar three-dimensional conformation, as predicted by computer modeling or determined by such techniques as X-ray crystallography.

The "biochemical function" or "biological activity" of a polypeptide includes any feature of the polypeptide detectable by suitable experimental investigation. "Altered" biochemical function can refer to a change in the primary, secondary, tertiary, or quaternary structure of the polypeptide; detectable, for example, by molecular weight determination, circular dichroism, antibody binding, difference spectroscopy, or nuclear magnetic resonance. It can also refer to a change in reactivity, such as the ability to catalyze a certain reaction, or the ability to bind a cofactor, substrate, inhibitor, drug, hapten, or other polypeptide. A substance may be said to "interfere" with the biochemical function of a polypeptide if it alters the biochemical function of the polypeptide in any of these ways.

A "fusion polypeptide" is a polypeptide comprising regions in a different position in the sequence than occurs in nature. The regions may normally exist in separate proteins and are brought together in the fusion polypeptide; or they may normally exist in the same protein but are placed in a new arrangement in the fusion polypeptide. A fusion polypeptide may be created, for example, by chemical synthesis, or by creating and translating a polynucleotide in which the peptide regions are encoded in the desired relationship.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also fragments thereof, mutants thereof, fusion proteins, humanized antibodies, and any other modified configuration of the immunoglobulin molecule that comprises an antigen recognition site of the required specificity.

"Immunological recognition" or "immunological reactivity" refers to the specific binding of a target through at least one antigen recognition site in an immunoglobulin or a related molecule, such as a B cell receptor or a T cell receptor.

The term "antigen" refers to the target molecule that is specifically bound by an antibody through its antigen recognition site. The antigen may, but need not be chemically related to the immunogen that stimulated production of the antibody. The antigen may be polyvalent, or it may be a monovalent hapten. Examples of kinds of antigens that can be recognized by antibodies include polypeptides, polynucleotides, other antibody molecules, oligosaccharides, complex lipids, drugs, and chemicals.

An "immunogen" is an antigen capable of stimulating production of an antibody when injected into a suitable host, usually a mammal. Compounds may be rendered immunogenic by many techniques known in the art, including crosslinking or conjugating with a carrier to increase valency, mixing with a mitogen to increase the immune response, and combining with an adjuvant to enhance presentation.

A "vaccine" is a pharmaceutical preparation for human or animal use, which is administered with the intention of conferring the recipient with a degree of specific immunological reactivity against a particular target, or group of targets. The immunological reactivity may be antibodies or cells (particularly B cells, plasma cells, T helper cells, and cytotoxic T lymphocytes, and their precursors) that are immunologically reactive against the target, or any combination thereof. Possible targets include foreign or pathological compounds, such as an exogenous protein, a pathogenic virus, or an antigen expressed by a cancer cell. The immunological reactivity may be desired for experimental purposes, for the treatment of a particular condition, for the elimination of a particular substance, or for prophylaxis against a particular condition or substance.

A "passive vaccine" is a vaccine that does not require participation of the recipient's immune response to exert its effect. Usually, it is comprised of antibody molecules reactive against the target. The antibodies may be obtained from a donor subject and sufficiently purified for administration to the recipient, or they may be produced in vitro, for example, from a culture of hybridoma cells, or by genetically engineering a polynucleotide encoding an antibody molecule.

An "active vaccine" is a vaccine administered with the intention of eliciting a specific immune response within the recipient, that in turn has the desired immunological reactivity against the target. An active vaccine comprises a suitable immunogen. The immune response that is desired may be either humoral or cellular, systemic or secretory, or any combination of these.

A "reagent" polynucleotide, polypeptide, or antibody, is a substance provided for a reaction, the substance having some known and desirable parameters for the reaction. A reaction mixture may also contain a "target", such as a polynucleotide, antibody, or polypeptide that the reagent is capable of reacting with. For example, in some types of diagnostic tests, the amount of the target in a sample is determined by adding a reagent, allowing the reagent and target to react, and measuring the amount of reaction product. In the context of clinical management, a "target" may also be a cell, collection of cells, tissue, or organ that is the object of an administered substance, such as a pharmaceutical compound.

An "isolated" polynucleotide, polypeptide, protein, antibody, or other substance refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

A polynucleotide used in a reaction, such as a probe used in a hybridization reaction, a primer used in a PCR, or a polynucleotide present in a pharmaceutical preparation, is referred to as "specific" or "selective" if it hybridizes or reacts with the intended target more frequently, more rapidly, or with greater duration than it does with alternative substances. Similarly, a polypeptide is referred to as "specific" or "selective" if it binds an intended target, such as a ligand, hapten, substrate, antibody, or other polypeptide more frequently, more rapidly, or with greater duration than it does to alternative substances. An antibody is referred to as "specific" or "selective" if it binds via at least one antigen recognition site to the intended target more frequently, more rapidly, or with greater duration than it does to alternative substances. A polynucleotide, polypeptide, or antibody is said to "selectively inhibit" or "selectively interfere with" a reaction if it inhibits or interferes with the reaction between particular substrates to a greater degree or for a greater duration than it does with the reaction between alternative substrates.

A "pharmaceutical candidate" or "drug candidate" is a compound believed to have therapeutic potential, that is to be tested for efficacy. The "screening" of a pharmaceutical candidate refers to conducting an assay that is capable of evaluating the efficacy and/or specificity of the candidate. In this context, "efficacy" refers to the ability of the candidate to affect the cell or organism it is administered to in a beneficial way: for example, the limitation of the pathology due to an invasive virus.

The "effector component" of a pharmaceutical preparation is a component which modifies target cells by altering their function in a desirable way when administered to a subject bearing the cells. Some advanced pharmaceutical preparations also have a "targeting component", such as an antibody, which helps deliver the effector component more efficaciously to the target site. Depending on the desired action, the effector component may have any one of a number of modes of action. For example, it may restore or enhance a normal function of a cell, it may eliminate or suppress an abnormal function of a cell, or it may alter a cell's phenotype. Alternatively, it may kill or render dormant a cell with pathological features, such as a virally infected cell. Examples of effector components are provided in a later section.

A "cell line" or "cell culture" denotes higher eukaryotic cells grown or maintained in vitro. It is understood that the descendants of a cell may not be completely identical (either morphologically, genotypically, or phenotypically) to the parent cell.

A "host cell" is a cell which has been transformed, or is capable of being transformed, by administration of an exogenous polynucleotide. A "host cell" includes progeny of the original transformant.

"Genetic alteration" refers to a process wherein a genetic element is introduced into a cell other than by natural cell division. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, contacting with a polynucleotide-liposome complex, or by transduction or infection with a DNA or RNA virus or viral vector. The alteration is preferably but not necessarily inheritable by progeny of the altered cell.

An "individual" refers to vertebrates, particularly members of a mammalian species, and includes but is not limited to domestic animals, sports animals, and primates, including humans.

The term "primate" as used herein refers to any member of the highest order of mammalian species. This includes (but is not limited to) prosimians, such as lemurs and lorises; tarsioids, such as tarsiers; new-world monkeys, such as squirrel monkeys (*Saimiri sciureus*) and tamarins; old-world monkeys such as macaques (including *Macaca nemestrina*, *Macaca fascicularis*, and *Macaca fuscata*); hylobatids, such as gibbons and siamangs; pongids, such as orangutans, gorillas, and chimpanzees; and hominids, including humans.

The "pathology" caused by a herpes virus infection is anything that compromises the well-being or normal physiology of the host. This may involve (but is not limited to) destructive invasion of the virus into previously uninfected cells, replication of the virus at the expense of the normal metabolism of the cell, generation of toxins or other unnatural molecules by the virus, irregular growth of cells or intercellular structures (including fibrosis), irregular or suppressed biological activity of infected cells, malignant transformation, interference with the normal function of neighboring cells, aggravation or suppression of an inflammatory or immunological response, and increased susceptibility to other pathogenic organisms and conditions.

"Treatment" of an individual or a cell is any type of intervention in an attempt to alter the natural course of the individual or cell. For example, treatment of an individual may be undertaken to decrease or limit the pathology caused by a herpes virus infecting the individual. Treatment includes (but is not limited to) administration of a composition, such as a pharmaceutical composition, and may be performed either prophylactically, or therapeutically, subsequent to the initiation of a pathologic event or contact with an etiologic agent.

It is understood that a clinical or biological "sample" encompasses a variety of sample types obtained from a subject and useful in an in vitro procedure, such as a diagnostic test. The definition encompasses solid tissue samples obtained as a surgical removal, a pathology specimen, or a biopsy specimen, tissue cultures or cells derived therefrom and the progeny thereof, and sections or smears prepared from any of these sources. Non-limiting examples are samples obtained from infected sites, fibrotic sites, unaffected sites, and tumors. The definition also encompasses blood, spinal fluid, and other liquid samples of biologic origin, and may refer to either the cells or cell fragments suspended therein, or to the liquid medium and its solutes. The definition also includes samples that have been solubilized or enriched for certain components, such as DNA, RNA, protein, or antibody.

Oligonucleotide primers and probes described herein have been named as follows: The first part of the designation is the single amino acid code for a portion of the conserved region of the DNA polymerase they are based upon, usually 4 residues long. This is followed with the letter A or B, indicating respectively that the oligonucleotide is complementary to the sense or anti-sense strand of the DNA polymerase encoding region. Secondary consensus oligonucleotides used for sequencing have the letters SQ at the end of the designation.

General techniques

The practice of the present invention will employ, unless otherwise indicated, conventional techniques of molecular biology, microbiology, recombinant DNA, and immunology, which are within the skill of the art. Such techniques are explained fully in the literature. See, for example, "Molecular Cloning: A Laboratory Manual", Second Edition (Sambrook, Fritsch & Maniatis, 1989), "Oligonucleotide Synthesis" (M. J. Gait, ed., 1984), "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.), "Gene Transfer Vectors for Mammalian Cells" (J. M. Miller & M. P. Calos, eds., 1987), "Current Protocols in Molecular Biology" (F. M. Ausubel et al., eds., 1987); and "Current Protocols in Immunology" (J. E. Coligan et al., eds., 1991).

All patents, patent applications, articles and publications mentioned herein, both supra and infra, are hereby incorporated herein by reference.

Polynucleotides encoding DNA polymerase of the herpes virus RFHV/KSHV subfamily

This invention embodies isolated polynucleotide segments derived from DNA polymerase genes present in herpes viruses, preferably that encode a fragment of a polypeptide that is capable of a DNA polymerase reaction. Polynucleotides provided are from the RFHV/KSHV subfamily of herpes viruses. Preferred polynucleotides are those encoding a fragment of a DNA polymerase from either RFHV or KSHV. Preferred fragments are those that have been amplified and isolated from the DNA polymerase gene, as described in the Examples below. Exemplary fragments are shown in FIG. 1, and designated SEQ. ID NO:1 and SEQ. ID NO:3, respectively. Especially preferred are polynucleotides comprising the sequence between residues 27 and 501 of the RFHV sequence (SEQ. ID NO:1), and the sequence between residues 27 and 329 of the KSHV sequence (SEQ. ID NO:3).

The polynucleotide segments of RFHV and KSHV between residues 27 and 501 (the 475 base pair fragment underlined in FIG. 1) are 71% identical. Shared residues are indicated in FIG. 1 by "*". The largest number of consecutive bases shared between RFHV and KSHV within this segment is 17.

The 475 base pair fragments of RFHV and KSHV are more identical to each other than either of them are to the corresponding segment of any of the previously sequenced herpes viruses of Table 1. The next most closely related sequence is the DNA polymerase from the eHV2 virus, which is about 68% identical in this region to either RFHV or KSHV. Contained within this region is a first 20 base pair subfragment (SEQ. ID NO:110) and a second 20 base pair subfragment (SEQ. ID NO:111) which is shared identically between eHV2 and RFHV. The 475 base pair region is less than about 65% identical between either RFHV or KSHV and the other known DNA polymerase sequences from herpes viruses capable of infecting primates, including sHV1 and EBV. The longest subfragment shared identically between RFHV or KSHV, and sHV1, is about 14 bases in length. The longest subfragment shared identically between RFHV or KSHV, and EBV, is about 15 bases in length. It is predicted that polynucleotide sequences are more likely to be conserved between herpes virus DNA polymerase encoding regions than with other polynucleotides. Therefore, other than the two subfragments shared with eHV2, it is believed that any subfragment of the RFHV or KSHV sequence of 18 base pairs or longer will be unique to the RFHV/KSHV subfamily, or to particular herpes virus species and variants within the subfamily.

This invention embodies subfragments contained in the DNA polymerase gene of the RFHV/KSHV subfamily, preferably contained in the region corresponding to the 475 base pair fragment between residues 27–501, as shown in FIG. 1. Preferably, the subfragments are at least about 16 residues in length; more preferably they are at least 18 residues in length; more preferably they are at least 20 nucleotides in length; more preferably they are at least about 25 nucleotides in length; more preferably they are at least about 35 nucleotides in length; still more preferably they are at least about 50 nucleotides in length; yet more preferably they are at least about 75 nucleotides in length, and even more preferably they are 100 nucleotides in length or more. Also embodied in this invention are polynucleotides comprising the entire open reading frame of each respective herpes virus DNA polymerase.

The RFHV/KSHV subfamily consists of members that have sequences that are more closely identical to the corresponding sequences of RFHV or KSHV, than RFHV or KSHV are to any other virus listed in Table 1. Preferred members of the family may be identified on the basis of the sequence of the DNA polymerase gene in the region corresponding to that of FIG. 1. Table 2 provides the degree of sequence identities in this region:

TABLE 2

Sequence Identities Between DNA Polymerase of Select Herpes Viruses and RFHV and KSHV

| Viral DNA Polymerase Sequence | SEQ. ID NO: | Identity to RFHV fragment (SEQ. ID NO:1) | | | Identity to KSHV fragment (SEQ. ID NO:3) | | |
|---|---|---|---|---|---|---|---|
| | | Bases 27–501 | Bases 27–329 | Bases 330–501 | Bases 27–501 | Bases 29–329 | Bases 320–501 |
| RFHV | 1 | (100%) | (100%) | (100%) | 71% | 72% | 70% |
| KSHV | 3 | 71% | 72% | 70% | (100%) | (100%) | (100%) |
| eHV2 | 23 | 68% | 68% | 67% | 68% | 71% | 63% |
| sHV1 | 24 | 59% | 60% | 59% | 62% | 65% | 58% |
| EBV | 25 | 64% | 66% | 58% | 62% | 62% | 57% |
| hCMV | 26 | 53% | 54% | <50% | 49% | 49% | <50% |
| hHV6 | 27 | 46% | 52% | <50% | 48% | 50% | <50% |
| hVZV | 28 | 45% | 46% | <50% | 48% | 47% | <50% |
| hHSV1 | 29 | 53% | 58% | <50% | 53% | 53% | <50% |

To predict the role encoded peptide fragments play in the biological function of the DNA polymerase, comparisons may be made with other DNA polymerases. Conserved regions in the amino acid sequence of DNA polymerase from various herpes viruses are shown in FIG. 2. The areas labeled ExoI, ExoII, and ExoIII have been shown to be important binding sites for metal ligands at the 3'-5' exonuclease active site (Derbyshire et al., Bernard et al. (1989), Simon et al., Soengas et al.). The area designated as REGION 1 has been shown to be important in polymerization activity, and functions both as a drug binding site and polymerization substrate (deoxyribonucleotide triphosphate) binding site (Dorsky et al. (1988, 1990), Bernard et al. (1990)). A mutation of the amino acid G to A in this region of herpes simplex (HSV) 1 DNA polymerase inhibits polymerase activity in virus-infected cells. A mutation of F to C, Y or M yield different sensitivities to drugs such as nucleoside and pyrophosphate analogs, and aphidicolin. REGION 2 and REGION 3 of the HSV1 DNA polymerase appear to be involved in drug and substrate recognition (Gibbs et al. (1988a, 1988b), Basco et al. (1993)). REGION 3 is involved in binding to the DNA template (Basco et al. (1992)). REGION 7 may be important in polymerization activity (Basco et al. (1993)). In some herpes viruses such as HSV1, amino acids near the C-terminal are involved in binding to a regulatory subunit known as UL42, encoded elsewhere in the herpes genome, and essential for DNA polymerase activity associated with replication of the virus (Dignard et al., Stow).

The RFHV and KSHV polynucleotides shown in FIG. 1 are near regions of the polynucleotide that encode functionally important parts of the DNA polymerase. Specifically, the oligonucleotides DFASA, VYGA, and GDTD1B map respectively to REGION 2, REGION 3, and REGION 1. The fragment between DFASA and GDTD1B obtained for KSHV encompasses the entire REGION 4 and REGION 3 sequences, and overlaps with the REGION 2 and REGION 1 sequences.

The percentage of sequence identity is calculated by first aligning the encoded amino acid sequence, determining the corresponding alignment of the encoding polynucleotide, and then counting the number of residues shared between the sequences being compared at each aligned position. No penalty is imposed for the presence of insertions or deletions, but insertions or deletions are permitted only where required to accommodate an obviously increased number of amino acid residues in one of the sequences being aligned. Offsetting insertions just to improve sequence alignment are not permitted at either the polypeptide or polynucleotide level. Thus, any insertions in the polynucleotide sequence will have a length which is a multiple of 3. The percentage is given in terms of residues in the test sequence that are identical to residues in the comparison or reference sequence.

The degree of identity between viruses in Table 2 has been calculated for segments of the RFHV and KSHV sequence numbered as shown in FIG. 1.

Preferred DNA polymerase-encoding polynucleotide sequences of this invention are those derived from the RFHV/KSHV herpes virus subfamily. They include those sequences that are at least 69% identical with the RFHV or KSHV sequence between bases 27 and 501 as shown in FIG. 1; more preferably, the sequences are at least 70% identical; more preferably, the sequences are at least about 72% identical; more preferably, the sequences are at least about 75% identical; more preferably, the sequences are at least about 80% identical; more preferably, the sequences are at least about 85% identical; more preferably, the sequences are at least about 90% identical; even more preferably, the sequences are over 95% identical. Also preferred are sequences that are at least 69% identical to the RFHV sequence between bases 27 and 329; more preferably, they are 70% identical; more preferably, they are at least 72% identical; more preferably, they are at least 75% identical; more preferably, they are at least 80% identical; more preferably, the sequences are at least 90% identical; even more preferably, the sequences are at least 95% identical.

Also preferred are sequences that are at least 72% identical to the KSHV sequence between bases 27 and 329; more preferably, they are at least 75% identical; more preferably, they are at least 80% identical; more preferably, they are at least 90% identical; even more preferably, they are 95% identical or more.

Other preferred DNA polymerase-encoding polynucleotide sequences may be identified by the percent identity with RFHV/KSHV subfamily-specific oligonucleotides, described in more detail in a further section. The percent identity of RFHV and KSHV DNA polymerase with example oligonucleotides is shown in Table 3:

TABLE 3

Sequence Identities Between DNA Polymerase of Select Herpes Viruses and RFHV/KSHV Subfamily Specific Oligonucleotides

| Viral DNA Polymerase Sequence | SEQ. ID NO: | Identity to LSGGA (SEQ. ID NO:107) | Identity to CTDPA (SEQ. ID NO:108) | Identity to PCLNA (SEQ. ID NO:21) | Identity to KMLEA (SEQ. ID NO:22) | Identity to GISPA (SEQ. ID NO:109) |
|---|---|---|---|---|---|---|
| RFHV | 1 | 92% | 86% | 93% | 94% | 100% |
| KSHV | 3 | 96% | 86% | 93% | 88% | 90% |
| eHV2 | 23 | 77% | 55% | 93% | 72% | 66% |
| sHV1 | 24 | 65% | 62% | 76% | 78% | 66% |
| EBV | 25 | 65% | 66% | 73% | 78% | 66% |
| hCMV | 26 | <50% | <50% | 54% | 53% | 48% |
| hHV6 | 27 | <50% | <50% | <50% | 47% | 38% |
| hVZV | 28 | 54% | <50% | <50% | <50% | 38% |
| hHSV1 | 29 | 50% | <50% | 50% | 58% | 52% |

The percent identity shown in Table 3 was calculated for the corresponding residues of the viral sequences, aligned as shown in FIG. 6.

Preferred DNA polymerase sequences are those which over the corresponding region are at least about 80% identical to LSGGA; more preferably they are at least about 83% identical; more preferably they are at least about 86% identical; more preferably they are at least about 90% identical; even more preferably, they are at least 95% identical. Other preferred DNA polymerase sequences are those which over the corresponding region are at least about 69% identical to CTDPA; more preferably they are at least about 72% identical; more preferably they are at least about 75% identical; more preferably they are at least about 80% identical; more preferably they are at least about 85% identical; even more preferably, they are at least about 95% identical. Other preferred DNA polymerase sequences are those which over the corresponding region are at least about 95% identical to PCLNA. Other preferred DNA polymerase sequences are those which over the corresponding region are at least about 80% identical to KMLEA; more preferably they are at least about 83% identical; more preferably they are at least about 86% identical; more preferably they are at least about 90% identical; even more preferably, they are at least 95% identical or more. Other preferred DNA polymerase sequences are those which over the corresponding region are at least about 69% identical to GISPA; more preferably they are at least about 72% identical; more preferably they are at least about 75% identical; more preferably they are at least about 80% identical; more preferably they are at least about 85% identical; even more preferably, they are at least about 95% identical.

DNA polymerase encoding sequences from members of the RFHV/KSHV subfamily identified by any of the aforementioned sequence comparisons, using either RFHV or KSHV sequences, or the subfamily-specific oligonucleotides, are equally preferred. Especially preferred are DNA polymerase encoding sequences of RFHV and KSHV. Also embodied in this invention are fragments of DNA polymerase encoding sequences of the subfamily, and longer polynucleotides comprising such polynucleotide fragments.

The polynucleotide sequences described in this section provide a basis for obtaining the synthetic oligonucleotides, proteins and antibodies outlined in the sections that follow. These compounds may be prepared by standard techniques known to a practitioner of ordinary skill in the art, and may be used for a number of investigative, diagnostic, and therapeutic purposes, as described below.

Preparation of polynucleotides

Polynucleotides and oligonucleotides of this invention may be prepared by any suitable method known in the art. For example, oligonucleotide primers can be used in a PCR amplification of DNA obtained from herpes virus infected tissue, as in Example 3 and Example 5, described below. Alternatively, oligonucleotides can be used to identify suitable bacterial clones of a DNA library, as described below in Example 10.

Polynucleotides may also be prepared directly from the sequence provided herein by chemical synthesis. Several methods of synthesis are known in the art, including the triester method and the phosphite method. In a preferred method, polynucleotides are prepared by solid-phase synthesis using mononucleoside phosphoramidite coupling units. See, for example Horise et al., Beaucage et al., Kumar et al., and U.S. Pat. No. 4,415,732.

A typical solid-phase synthesis involves reiterating four steps: deprotection, coupling, capping, and oxidation. This results in the stepwise synthesis of an oligonucleotide in the 3' to 5' direction.

In the first step, the growing oligonucleotide, which is attached at the 3'-end via a (—O—) group to a solid support, is deprotected at the 5' end. For example, the 5' end may be protected by a -ODMT group, formed by reacting with 4,4'-dimethoxytrityl chloride (DMT-Cl) in pyridine. This group is stable under basic conditions, but is easily removed under acid conditions, for example, in the presence of dichloroacetic acid (DCA) or trichloroacetic acid (TCA). Deprotection provides a 5'-OH reactive group.

In the second step, the oligonucleotide is reacted with the desired nucleotide monomer, which itself has first been converted to a 5'-protected, 3'-phosphoramidite. The 5'-OH of the monomer may be protected, for example, in the form of a -ODMT group, and the 3'-OH group may be converted to a phosphoramidite, such as —OP(OR')NR$_2$; where R is the isopropyl group —CH(CH$_3$)$_2$; and R' is, for example, —H (yielding a phosphoramidite diester), or —CH$_3$, —CH$_2$CH$_3$, or the beta-cyanoethyl group —CH$_2$CH$_2$CN (yielding a phosphoramidite triester). The 3'-phosphoramidite group of the monomer reacts with the 5'-OH group of the growing oligonucleotide to yield the phosphite linkage 5'-OP(OR')O-3'.

In the third step, oligonucleotides that have not coupled with the monomer are withdrawn from further synthesis to prevent the formation of incomplete polymers. This is achieved by capping the remaining 5'-OH groups, for example, in the form of acetates (—OC(O)CH$_3$,) by reaction with acetic anhydride (CH$_3$C(O)—O—C(O)CH$_3$).

In the fourth step, the newly formed phosphite group (i.e., 5'-OP(OR')O-3') is oxidized to a phosphate group (i.e., 5'-OP(=O)(OR')O-3'); for example, by reaction with aqueous iodine and pyridine.

The four-step process may then be reiterated, since the oligonucleotide obtained at the end of the process is 5'-protected and is ready for use in step one. When the desired full-length oligonucleotide has been obtained, it may be cleaved from the solid support, for example, by treatment with alkali and heat. This step may also serve to convert phosphate triesters (i.e., when R' is not —H) to the phosphate diesters (—OP(=O)$_2$O—), and to deprotect base-labile protected amino groups of the nucleotide bases.

Polynucleotides prepared by any of these methods can be replicated to provide a larger supply by any standard technique, such as PCR amplification or gene cloning.

Cloning and expression vectors comprising a DNA polymerase encoding polynucleotide Cloning vectors and expression vectors are provided in this invention that comprise a sequence encoding a herpes virus DNA polymerase or variant or fragment thereof. Suitable cloning vectors may be constructed according to standard techniques, or may be selected from the large number of cloning vectors available in the art. While the cloning vector selected may vary according to the host cell intended to be used, useful cloning vectors will generally have the ability to self-replicate, may possess a single target for a particular restriction endonuclease, and may carry genes for a marker that can be used in selecting transfected clones. Suitable examples include plasmids and bacterial viruses; e.g., pUC18, mp18, mp19, pBR322, pMB9, ColE1, pCR1, RP4, phage DNAs, and shuttle vectors like pSA3 and pAT28.

Expression vectors generally are replicable polynucleotide constructs that encode a polypeptide operatively linked to suitable transcriptional and translational controlling elements. Examples of transcriptional controlling elements are promoters, enhancers, transcription initiation sites, and transcription termination sites. Examples of translational controlling elements are ribosome binding sites, translation initiation sites, and stop codons. Protein processing elements may also be included: for example, regions that encode leader or signal peptides and protease cleavage sites required for translocation of the polypeptide across the membrane or secretion from the cell. The elements employed would be functional in the host cell used for expression. The controlling elements may be derived from the same DNA polymerase gene used in the vector, or they may be heterologous (i.e., derived from other genes and/or other organisms).

Polynucleotides may be inserted into host cells by any means known in the art. Suitable host cells include bacterial cells such as E. coli, mycobacteria, other procaryotic microorganisms and eukaryotic cells (including fungal cells, insect cells, plant cells, and animal cells). The cells are transformed by inserting the exogenous polynucleotide by direct uptake, endocytosis, transfection, f-mating, or electroporation. Subsequently, the exogenous polynucleotide may be maintained within the cell as a non-integrated vector, such as a plasmid, or may alternatively be integrated into the host cell genome.

Cloning vectors may be used to obtain replicate copies of the polynucleotides they contain, or as a means of storing the polynucleotides in a depository for future recovery. Expression vectors and host cells may be used to obtain polypeptides transcribed by the polynucleotides they contain. They may also be used in assays where it is desirable to have intact cells capable of synthesizing the polypeptide, such as in a drug screening assay.

Synthetic oligonucleotides for herpes virus DNA polymerase useful as hybridization probes and amplification primers Oligonucleotides designed from sequences of herpes virus DNA polymerase, as embodied in this invention, can be used as probes to identify related sequences, or as primers in an amplification reaction such as a PCR.

Different oligonucleotides with different properties are described in the sections that follow. Oligonucleotides designated as Type 1 are designed to hybridize with polynucleotides encoding any herpes virus DNA polymerase, and may be used to detect previously known species of herpes virus. They may also be used to detect and characterize new species of herpes virus. Oligonucleotides designated as Type 2 are designed to hybridize with DNA polymerase encoding polynucleotides of the RFHV/KSHV subfamily, including members not yet identified, but not with polynucleotides of other herpes viruses. Oligonucleotides designated as Type 3 are designed to hybridize specifically with polynucleotides encoding DNA polymerase only from RFHV, or alternatively from KSHV.

Preferred examples of Type 1 oligonucleotides are listed in Table 4. These oligonucleotides have a specificity for DNA polymerase encoding polynucleotides of a broad range of herpes viruses.

TABLE 4

Type 1 Oligonucleotides used for Detecting, Amplifying, or Characterizing Herpes Virus Polynucleotides encoding DNA Polymerase

| Designation | Sequence (5' to 3') | Length | No. of forms | Target: | Orientation | SEQ ID: |
|---|---|---|---|---|---|---|
| DFASA | GTGTTCGACTTYGCNAGYYTNTAYCC | 26 | 256 | Herpes DNA polymerase | 5'→3' | 5 |
| DFQSA | GTGTTCGACTTYCARAGYYTNTAYCC | 26 | 128 | Herpes DNA polymerase, especially the beta subfamily | 5'→3' | 6 |
| VYGA | ACGTGCAACGCGGTGTAYGGNKTNACNGG | 29 | 256 | Herpes DNA polymerase | 5'→3' | 7 |
| VYGCA | ACGTGCAACGCGGTGTACGGSGTSACSGG | 29 | 8 | Herpes DNA polymerase (GC-rich) | 5'→3' | 8 |
| VYGSQA | ACGTGCAACGCGGTGTA | 17 | 1 | Herpes DNA polymerase | 5'→3' | 9 |
| GDTD1B | CGGCATGCGACAAACACGGAGTCNGTRTCNCCRTA | 35 | 64 | Herpes DNA polymerase | 3'→5' | 11 |
| GDTDSQB | CGGCATGCGACAAACACGGA | 20 | 1 | Herpes DNA polymerase | 3'→5' | 12 |

The orientation indicated is relative to the encoding region of the polynucleotide. Oligomers with a 5'→3' orientation will hybridize to the strand antisense to the coding strand and initiate amplification in the direction of the coding sequence. Oligomers with a 3'→5' orientation will hybridize to the coding strand and initiate amplification in the direction opposite to the coding sequence.

These oligonucleotides have been designed with several properties in mind: 1) sensitivity for target DNA even when present in the source material at very low copy numbers; 2) sufficient specificity to avoid hybridizing with unwanted sequences; for example, endogenous DNA polymerase sequences present in the host; 3) sufficient cross-reactivity so that differences between an unknown target and the sequence used to design it do not prevent the oligonucleotide from forming a stable duplex with the target.

For some applications, a particularly effective design is oligonucleotides that have a degenerate segment at the 3' end, designed from a region of at least 2 known polynucleotides believed to be somewhat conserved with the polynucleotide target. The various permutations of the ambiguous residues help ensure that at least one of the alternative forms of the oligonucleotide will be able to hybridize with the target. Adjacent to the degenerate segment at the 5' end of the oligonucleotide is a consensus segment which strengthens any duplex which may form and permits hybridization or amplification reactions to be done at higher temperatures. The degenerate segment is located at the 3' end of the molecule to increase the likelihood of a close match between the oligonucleotide and the target at the site where elongation begins during a polymerase chain reaction.

The ambiguous residues in the degenerate part of the sequences are indicated according to the following code:

TABLE 5

Single Letter Codes for Ambiguous Positions

| Code | Represents |
|---|---|
| R | A or G (purine) |
| Y | C or T (pyrimidine) |
| W | A or T |
| S | C or G |
| M | A or C |
| K | G or T |
| B | C or G or T (not A) |
| D | A or G or T (not C) |
| H | A or C or T (not G) |
| V | A or C or G (not T) |
| N | A or C or G or T |

The Type 1 oligonucleotides shown in Table 4 are generally useful for hybridizing with DNA polymerase encoding polynucleotide segments. This may be conducted to detect the presence of the polynucleotide, or to prime an amplification reaction so that the polynucleotide can be characterized further. Suitable targets include polynucleotides encoding a region of a DNA polymerase from a wide spectrum of herpes viruses, including those in the alpha, beta, and gamma herpes viruses, those infecting any vertebrate animal, including humans and non-human primates, whether or not the polymerase or the virus has been previously known or described. Non-limiting examples include polynucleotides encoding DNA polymerase from any of the herpes viruses listed in Table 1. We have used these oligonucleotides to obtain segments of the DNA polymerase from RFHV, KSHV, EBV, HSV1, HHV6 and HHV7—a group that includes representatives from the alpha, beta, and gamma subfamilies.

The oligonucleotides may be used, inter alia, to prime a reaction to amplify a region of the target polynucleotide in the 3' direction from the site where the oligonucleotide hybridizes. DFASA, DFQSA, VYGA, VYGCA and GDTD1B are oligonucleotides with a consensus segment adjoining a degenerate segment, and are useful for that purpose, and also may be used when the sequence of the target DNA is unknown. Selection between oligonucleotides DFASA and DFQSA depends on the sequence of the target polynucleotide. DFQSA promotes amplification of HHV6-like sequences somewhat better than other sequences; DFASA promotes amplification of both HHV6- and non-HHV6-like sequences. VYGA has a broad cross-reactivity and is especially useful as a primer for a second amplification reaction preformed using polynucleotides first amplified by another primer, such as DFASA. VYGCA is a GC-rich analog of VYGA, producing less complex amplification mixtures and allowing hybridization reactions to occur at higher temperatures. VYGSQA and GDTDSQB are specific non-degenerate oligonucleotides which can be used, inter alia, to sequence amplification products made with VYGA or GDTD1B, respectively; or for more specific amplification of a target polynucleotide after a preliminary amplification with a degenerate primer.

A preferred source of DNA for use as a target for the oligonucleotides of Table 4 is any biological sample (including solid tissue and tissue cultures), particularly of vertebrate animal origin, known or suspected to harbor a herpes virus. DNA is extracted from the source by any method known in the art, including extraction with organic solvents or precipitation at high salt concentration.

A preferred method of amplification is a polymerase chain reaction: see generally U.S. Pat. No. 4,683,195 (Mullis) and U.S. Pat. No. 4,683,202 (Mullis et al.); see U.S. Pat. No. 5,176,995 (Sninsky et al.) for application to viral polynucleotides. An amplification reaction may be conducted by combining the target polynucleotide to be amplified with short oligonucleotides capable of hybridizing with the target and acting as a primer for the polymerization reaction. Also added are substrate mononucleotides and a heat-stable DNA-dependent DNA polymerase, such as Taq. The conditions used for amplification reactions are generally known in the art, and can be optimized empirically using sources of known viruses, such RFHV, KSHV, EBV or HSV1. Conditions can be altered, for example, by changing the time and temperature of the amplification cycle, particularly the hybridization phase; changing the molarity of the oligonucleotide primers; changing the buffer concentration; and changing the number of amplification cycles. Fine-tuning the amplification conditions is a routine matter for a practitioner of ordinary skill in the art.

In one method, a single primer of this invention is used in the amplification, optionally using a second primer, such as a random primer, to initiate replication downstream from the first primer and in the opposite direction. In a preferred method, at least two of the primers of this invention are used in the same reaction to initiate replication in opposite directions. The use of at least two specific primers enhances the specificity of the amplification reaction, and defines the size of the fragment for comparison between samples. For example, amplification may be performed using primers DFASA and GDTD1B. More preferred is the use of all three primers in a nested fashion to enhance the amplification. Nesting is accomplished by performing a first amplification using primers that encompass an intermediate fragment comprising a binding site for a third primer. This is followed by a second amplification using the third primer, thereby providing a final fragment that is a subfragment of the intermediate fragment. Particularly preferred is a first amplification using primer DFASA and primer GDTD1B, followed by a second amplification using primer VYGA and primer GDTD1B. When performed on a polynucleotide from a DNA polymerase gene of RFHV or KSHV, the size of the fragment is about 236 bases.

The amplified polynucleotides can be characterized at any stage during the amplification reaction, for example, by size determination. Preferably, this is performed by running the polynucleotide on a gel of about 1–2% agarose. If present in sufficient quantity, the polynucleotide in the gel can be stained with ethidium bromide and detected under ultraviolet light. Alternatively, the polynucleotide can be labeled with a radioisotope such as $^{32}$P or $^{35}$S before loading on a gel of about 6% polyacrylamide, and the gel can subsequently be used to produce an autoradiogram. A preferred method of labeling the amplified polynucleotide is to end-label an oligonucleotide primer such as VYGA or VYGSQA with $^{32}$P using a polynucleotide kinase and gamma-[$^{32}$P]-ATP, and continuing amplification for about 5–15 cycles.

If desired, size separation may also be used as a step in the preparation of the amplified polynucleotide. This is particularly useful when the amplification mixture is found to contain artifact polynucleotides of different size, such as may have arisen through cross-reactivity with undesired targets. A separating gel, such as described in the preceding paragraph, is dried onto a paper backing and used to produce an autoradiogram. Positions of the gel corresponding to the desired bands on the autoradiogram are cut out and extracted by standard techniques. The extracted polynucleotide can then be characterized directly, cloned, or used for a further round of amplification.

Unwanted polynucleotides in the mixture from an amplification reaction can also be proportionally reduced by shifting to more specific oligonucleotide primers. For example, an initial 3–5 cycles of amplification can be conducted using primers VYGA and GDTD1B at ⅕ to ¹⁄₂₅ the normal amount. Then a molar excess (for example, 50 pmol) of GDTDSQB and/or VYGSQA are added, and the amplification is continued for an additional 30–35 cycles. This reduces the complexity of the oligonucleotides present in the amplification mixture, and enables the reaction temperatures to be increased to reduce amplification of unwanted polynucleotides.

Preferred examples of Type 2 oligonucleotides are listed in Table 6:

TABLE 6

Type 2 Oligonucleotides Specific for Polynucleotides Encoding DNA Polymerase from Viruses of the RFHV/KSHV Subfamily

| Designation | Sequence (5' to 3') | Length | No. of forms | Target: | Orientation | SEQ ID: |
|---|---|---|---|---|---|---|
| LSGGA | TACGAAACCTTTGACCTNAGYGGNGG | 26 | 32 | DNA polymerase of the RFHV/KSHV subfamily | 5'→3' | 107 |
| CTDPA | CGCAAGAACCTGGCCTCNTGYACNGAYCC | 29 | 64 | | 5'→3' | 108 |
| PCLNA | GTCGCCTCTGGCATCCTNCCNTGYCTNAA | 29 | 128 | | 5'→3' | 21 |
| KMLEA | CAGGGCCGGMGATGCTGGARACRTCNCARGC | 32 | 32 | | 5'→3' | 22 |
| GISPA | TCTCAGGCGTTCGTAGARGGNATHTCNCC | 29 | 96 | | 5'→3' | 109 |

LSGGA, CTDPA, PCLNA, KMLEA and GISPA are all oligonucleotides with a consensus segment at the 5' end joined directly to a degenerate segment at the 3' end. They are capable of forming stable duplexes with a polynucleotide encoding DNA polymerase from either RFHV, KSHV, or from other viruses of the RFHV/KSHV subfamily. They can be used for any purpose in which such specificity is desired, such as the detection or amplification of polynucleotides from the RFHV/KSHV subfamily.

In one application, these Type 2 oligonucleotides are used individually or in combination as amplification primers. In one example of this application, the oligonucleotides are used directly on DNA obtained from a tissue sample to obtain a DNA polymerase segment derived from RFHV, KSHV, or closely related viruses, but not more distantly related viruses such as EBV, CMV or HSV. In another example, the DNA from a tissue sample is first amplified with a less specific set of probes, such as DFASA or VYGA, in combination with GDTD1B. One of the oligonucleotides of Table 6 is then used in a second round of amplification, thereby providing a sensitive nested amplification assay which is specific for RFHV, KSHV, and other members of the RFHV/KSHV subfamily.

In another application, Type 2 oligonucleotides, or oligonucleotides comprising these sequences or fragments thereof, are used as probes in a detection assay. For example, they can be provided with a suitable label such as $^{32}P$, and then used in a hybridization assay with a suitable target, such as DNA amplified using DFASA and/or VYGA, along with GDTD1B.

Preferred examples of Type 3 oligonucleotides are shown in Table 7:

TABLE 7

Type 3 Oligonucleotides Specific for Polynucleotides Encoding DNA Polymerase from RFHV or KSHV

| Desig-nation | Sequence (5' to 3') | Length | No. of forms | Target: | Orien-tation | SEQ ID: |
|---|---|---|---|---|---|---|
| VASGA | CGTCGCTTCCGGCATCCTACC | 21 | 1 | RFHV DNA polymerase | 5'→3' | 13 |
| ILPCA | GGCATCCTACCGTGCCTGAAC | 21 | 1 | | 5'→3' | 14 |
| PIEAB | CCGGAGACGCCTCGATCGGTC | 21 | 1 | | 3'→5' | 15 |
| PEARB | AACCTGGCTTCCGGAGACGC | 21 | 1 | | 3'→5' | 16 |
| SGILA | GCGTTGCCTCTGGCATACTG | 20 | 1 | KSHV DNA polymerase | 5'→3' | 17 |
| CLNIA | CTGCCTTGCCTAAACATAGCG | 21 | 1 | | 5'→3' | 18 |
| IEASB | GGTGAGACGTCTATTGGCCT | 20 | 1 | | 3'→5' | 19 |
| EARFB | AATCGGGCGTCGGGTGAGACG | 21 | 1 | | 3'→5' | 20 |

These are non-degenerate oligonucleotides designed to be specific for DNA polymerase encoding polynucleotides of particular herpes viruses; namely RFHV or KSHV. The particular sequence chosen is from a segment of the encoding region that is more different from that of the other virus than neighboring segments.

VASGA, ILPCA, PIEAB, and PEARB are specific non-degenerate oligonucleotides for the RFHV DNA polymerase, and can be used in hybridization reactions conducted at high stringency. For example, they can be used alone or in combination as primers for amplifying a target polynucleotide encoding RFHV DNA polymerase. Preferably, the amplification is done using the oligonucleotides in a nested fashion: e.g., a first amplification is conducted using VASGA and PEARB as primers; then a second amplification is conducted using ILPCA and PIEAB as primers.

Similarly, SGILA, CLNIA, IEASB, and EARFB are specific non-degenerate oligonucleotides for the KSHV DNA polymerase, and can be used in a similar fashion, including as primers for an amplification reaction. Preferably, the amplification is done using the oligonucleotides in a nested fashion: e.g., a first amplification is conducted using SGILA and EARFB as primers; then a second amplification is conducted using CLNIA and IEASB as primers. This provides an extremely sensitive amplification assay that is specific for KSHV DNA polymerase.

Practitioners skilled in the art will immediately recognize that oligonucleotides of Types 1, 2, and 3 (in particular, those shown in Tables 4, 6, and 7) can be used in combination with each other in a PCR to amplify different sections of a DNA polymerase encoding polynucleotide. The specificity of the amplification reaction generally is determined by the primer with the least amount of cross reactivity. The size and location of the amplified fragment is determined by the primers used in the final round of amplification. For example, LSSGA used in combination with GDTD1B will amplify about 361 bases of DNA polymerase encoding polynucleotide from a virus of the RFHV/KSHV subfamily. Similarly, VYGA used in combination with PEARB will amplify about 444 bases of DNA polymerase encoding polynucleotide from RFHV. Suitable combinations of oligonucleotides may be used as amplification primers in a nested fashion.

Use of synthetic oligonucleotides to characterize polynucleotide targets

As described in the previous section, the oligonucleotides embodied in this invention, can be used as primers for amplification of polynucleotides encoding a herpes virus DNA polymerase, particularly in a polymerase chain reaction.

The conditions for conducting the PCR depend on the nature of the oligonucleotide being used. In particular, when using oligonucleotides comprising a degenerate segment, or a consensus segment that is only partly identical to the corresponding segment of the target, and when the target polynucleotide comprises an unknown sequence, the selection of conditions may be important to the success of the amplification. Optimizing conditions for a new primer or new polynucleotide target are routine for a practitioner of ordinary skill. What follows is a guide to assist in that objective.

First, the temperature of the annealing step of the PCR is optimized to increase the amount of target polynucleotide being amplified above the amount of unrelated polynucleotide amplified. Ideally, the temperature permits the primers to hybridize with the target sequence but not with other sequences. For primers comprising a consensus segment, the temperature of the annealing step is generally at least about 55° C.; preferably it is at least about 60° C. Primers which are virus-specific are more selective, and may be effective over a broader temperature range; between 50° C. and 65° C.

Second, the buffer conditions are optimized. We have found that buffers supplied with commercial preparations of Taq polymerase are sometimes difficult to use, in part because of a critical dependence on the concentration of magnesium ion. PCRs performed using the oligonucleotides of this invention generally are more easily performed using a buffer such as that suggested by M. Wigler (Lisitsyn et al.). Preferably, the final PCR reaction mixture contains $(NH_4)_2SO_4$ instead of KCl as the principal ion source. Preferably, the concentration of $(NH_4)_2SO_4$ in the final reaction mixture is about 5–50 mM, more preferably about 10–30 mM, even more preferably 16 mM. The buffering component is preferably Tris, preferably at a final concentration of about 67 mM and a pH of about 8.8. Under these conditions, the $MgCl_2$ concentration is less critical. Preferably the final concentration is about 1–10 mM, more preferably it is about 3–6 mM, optimally it is about 4 mM. The reaction mixture may also contain about 10 mM β-mercaptoethanol and 0.05–1 mg/mL bovine serum albumin. An especially preferred buffer is WB4 buffer (67 mM Tris buffer pH 8.8, 4 mM MgCl$_2$, 16 mM (NH$_4$)$_2$SO$_4$, 10 mM β-mercaptoethanol and 0.1 mg/mL albumin. Preferred conditions for performing the reaction are provided below in Example 3.

Amplification reactions using any the oligonucleotides of this invention as primers yield polynucleotide fragments encoding a portion of a DNA polymerase. These fragments can be characterized by a number of techniques known to a practitioner of ordinary skill in the art. Some non-limiting methods for characterizing a fragment are as follows:

In one method, a fragment may be sequenced according to any method of sequence determination known in the art, including the Maxam & Gilbert method, or the Sanger & Nicholson method. Alternatively, the fragment may be submitted to any of the commercial organizations that provide a polynucleotide sequencing service. The fragment may optionally be cloned and/or amplified before sequencing. The nucleotide sequence can be used to predict the amino acid sequence encoded by the fragment. Sequence data can be used for comparison with other sequenced DNA polymerases, either at the polynucleotide level or the amino acid level, to identify the species of herpes virus present in the original source material. Sequence data can also be used in modeling algorithms to predict antigenic regions or three-dimensional structure.

In a second method of characterizing, the size of the fragment can be determined by any suitable method, such as running on a polyacrylamide or agarose gel, or centrifuging through an appropriate density gradient. For example, for RFHV and KSHV, the fragment between VYGA and GDTD1B is about 172 bases. Hence, the length of the entire amplified fragment including primer binding regions is about 236 bases. The corresponding EBV fragment contains an additional 9 base pairs. The EBV fragment can therefore be distinguished from that of RFHV or KSHV, for example, by running amplified polynucleotide fragments from each in neighboring lanes of a separating gel, or by running the EBV fragment beside suitable molecular weight standards. Polynucleotide fragments identical in size to that of RFHV and KSHV may be derived from a variant strain of one of these viruses, or a closely related species. Fragments substantially different in size are more likely to be derived from a different herpes virus.

In a third method of characterizing, a fragment can be tested by attempting to hybridize it with an oligonucleotide probe. In a preferred example, a fragment is tested for relatedness to the DNA polymerase encoding region of RFHV or KSHV. The test is conducted using a probe comprising a sequence of a DNA polymerase encoding region, or its genetic complement. Suitable probes are polynucleotides comprising sequences from RFHV or KSHV, a mixture of such polynucleotides, or a polynucleotide comprising a degenerate sequence derived from RFHV and KSHV, such as the oligonucleotides listed in Table 6.

The length and nature of the probe and the hybridization conditions are selected depending on the objectives of the test. If the objective is to detect only polynucleotides from RFHV or KSHV, including minor variants, then hybridization is performed under conditions of high stringency. A sequence from the respective RFHV or KSHV DNA polymerase is used. Longer length sequences improve the specificity of the test and can be used under conditions of higher stringency. Preferably, the probe will comprise a DNA polymerase sequence of at least about 30 nucleotides; more preferably, the sequence will be at least about 50 nucleotides; even more preferably, the sequence will be at least about 75 nucleotides in length.

If the objective is to detect polynucleotides that are related to RFHV or KSHV, such as in a screening test or a test to recruit previously undescribed viruses of the RFHV/KSHV subfamily, then different conditions are chosen. Sequences from RFHV or KSHV may be used, but a mixture of the two or a degenerate probe is generally preferred. The length of the sequence and the conditions of the hybridization reaction are selected to provide sufficient specificity to exclude unwanted sequences, but otherwise provide a maximum degree of cross-reactivity amongst potential targets. Suitable conditions can be predicted using the formulas given earlier, by calculating the T$_m$ and then calculating the corresponding temperature for the maximum degree of mismatch to be tolerated. The suitability of the conditions can be tested empirically by testing the cross-reactivity of the probes with samples containing known target polynucleotides encoding herpes DNA polymerases.

The minimum degree of complementarity required for a stable duplex to form under the conditions of the assay will determine what DNA polymerase sequences will hybridize with the probe. Consider, for example, a target obtained from a human or non-human primate, amplified to produce a fragment corresponding to bases 330–501 of FIG. 1, and then probed with the corresponding fragment of the RFHV polynucleotide. According to the data in Table 2, if the hybridization reaction is performed under conditions that require only about 50% identity for a stable duplex to form, the probe may hybridize with targets from any of the sequenced gamma herpes DNA polymerase genes, including EBV and sHV1. If the reaction is performed under conditions that require at least about 62% identity between probe and target, preferably at least about 65% identity, more preferably at least about 68% identity, and even more preferably at least about 70% identity for a stable duplex to form, the assay will detect a target polynucleotide from RFHV, KSHV, or from a related herpes virus DNA polymerase that has not yet been sequenced. Polynucleotides encoding DNA polymerase from EBV or sHV1 are not expected to form a stable duplex under these conditions. A polynucleotide encoding DNA polymerase from eHV2 is not expected to be present in the DNA tested, because eHV2 is not believed to be capable of infecting primates.

It is possible to combine characterization by size and characterization by hybridization. For example, the amplified polynucleotide may be separated on a gel of acrylamide or agarose, blotted to a membrane of suitable material, such as nitrocellulose, and then hybridized with a probe with a suitable label, such as $^{32}$P. The presence of the label after washing reflects the presence of hybridizable material in the sample, while the migration distance compared with appropriate molecular weight standards reflects the size of the material. A fragment sequence hybridizing with one of the aforementioned probes under conditions of high stringency but having an unexpected size would indicate a DNA polymerase sequence with a high degree of identity to the probe, but distinct from RFHV or KSHV.

Use of polynucleotides and oligonucleotides to detect herpes virus infection

Polynucleotides encoding herpes virus DNA polymerase, and synthetic oligonucleotides based thereupon, as embodied in this invention, are useful in the diagnosis of clinical conditions associated with herpes virus infection. For example, the presence of detectable herpes DNA polymerase in a clinical sample may suggest that the respective herpes virus participated as an etiologic agent in the development of the condition. The presence of polymerase in a particular tissue, but not in surrounding tissue, may be useful in the localization of an infected lesion. Differentiating between gamma herpes virus and other herpes viruses in clinical samples, or differentiating between RFHV, KSHV, and EBV, may be useful in predicting the clinical course of an infection or selecting a drug suitable for treatment.

In addition, since DNA polymerase is actively involved in the replication of the herpes virus, it may be preferred over other markers for certain applications. DNA polymerase is not expressed in the latent state of Varicella-Zoster herpes, but is expressed in the replicative state (Meier et al.). Thus, an assay for DNA polymerase may help determine whether an individual infected with gamma herpes is currently in an active phase of the disease. The capacity of a strain of HSV1 to move from the eye to the brain is related to DNA polymerase activity (Yeung et al.). Thus, an assay for DNA polymerase may help predict the aggressiveness or invasiveness of a gamma herpes infection.

The procedures for conducting diagnostic tests are extensively known in the art, and are routine for a practitioner of ordinary skill. Generally, to perform a diagnostic method of this invention, one of the compositions of this invention is provided as a reagent to detect a target in a clinical sample with which it reacts. For example, a polynucleotide of this invention may be used as a reagent to detect a DNA or RNA target, such as might be present in a cell infected with a herpes virus. A polypeptide of this invention may be used as a reagent to detect a target with which it is capable of forming a specific complex, such as an antibody molecule or (if the polypeptide is a receptor) the corresponding ligand. An antibody of this invention may be used as a reagent to detect a target it specifically recognizes, such as a polypeptide expressed by virally infected cells.

The target is supplied by obtaining a suitable tissue sample from an individual for whom the diagnostic parameter is to be measured. Relevant test samples are those obtained from individuals suspected of harboring a herpes virus. Many types of samples are suitable for this purpose, including those that are obtained near the suspected site of infection or pathology by biopsy or surgical dissection, in vitro cultures of cells derived therefrom, solubilized extracts, blood, and blood components. If desired, the target may be partially purified from the sample or amplified before the assay is conducted. The reaction is performed by contacting the reagent with the sample under conditions that will allow a complex to form between the reagent and the target. The reaction may be performed in solution, or on a solid tissue sample, for example, using histology sections. The formation of the complex is detected by a number of techniques known in the art. For example, the reagent may be supplied with a label and unreacted reagent may be removed from the complex; the amount of remaining label thereby indicating the amount of complex formed. Further details and alternatives for complex detection are provided in the descriptions that follow.

To determine whether the amount of complex formed is representative of herpes infected or uninfected cells, the assay result is preferably compared with a similar assay conducted on a control sample. It is generally preferable to use a control sample which is from an uninfected source, and otherwise similar in composition to the clinical sample being tested. However, any control sample may be suitable provided the relative amount of target in the control is known or can be used for comparative purposes. It is often preferable to conduct the assay on the test sample and the control sample simultaneously. However, if the amount of complex formed is quantifiable and sufficiently consistent, it is acceptable to assay the test sample and control sample on different days or in different laboratories.

Accordingly, polynucleotides encoding DNA polymerase of the RFHV/KSHV subfamily, and the synthetic oligonucleotides embodied in this invention, can be used to detect gamma herpes virus polynucleotide that may be present in a biological sample. General methods for using polynucleotides in specific diagnostic assays are well known in the art: see, e.g., Patent Application JP 5309000 (Iatron).

An assay employing a polynucleotide reagent may be rendered specific, for example: 1) by performing a hybridization reaction with a specific probe; 2) by performing an amplification with a specific primer, or 3) by a combination of the two.

To perform an assay that is specific due to hybridization with a specific probe, a polynucleotide is chosen with the required degree of complementarity for the intended target. Preferred probes include polynucleotides of at least about 16 nucleotides in length encoding a portion of the DNA polymerase of RFHV, KSHV, or a member of the RFHV/KSHV subfamily. Increasingly preferred are probes comprising at least about 18, 20, 25, 30, 50, or 100 nucleotides of the DNA polymerase encoding region. Also preferred are degenerate probes capable of forming stable duplexes with polynucleotides of the RFHV/KSHV subfamily, but not with that of other herpes viruses.

The probe is generally provided with a label. Some of the labels often used in this type of assay include radioisotopes such as $^{32}$P and $^{33}$P, chemiluminescent or fluorescent reagents such as fluorescein, and enzymes such as alkaline phosphatase that are capable of producing a colored solute or precipitant. The label may be intrinsic to the reagent, it may be attached by direct chemical linkage, or it may be connected through a series of intermediate reactive molecules, such as a biotin-avidin complex, or a series of inter-reactive polynucleotides. The label may be added to the reagent before hybridization with the target polynucleotide, or afterwards. To improve the sensitivity of the assay, it is often desirable to increase the signal ensuing from hybridization. This can be accomplished by using a combination of serially hybridizing polynucleotides or branched polynucleotides in such a way that multiple label components become incorporated into each complex. See U.S. Pat. No. 5,124,246 (Urdea et al.).

If desired, the target polynucleotide may be extracted from the sample, and may also be partially purified. To measure viral particles, the preparation is preferably enriched for DNA; to measure active transcription of DNA polymerase, the preparation is preferably enriched for RNA. Generally, it is anticipated that the level of polynucleotide of a herpes virus will be low in clinical samples: there may be just a few copies of DNA encoding the polymerase per cell where the virus is latent, or up to several hundred copies of DNA per cell where the virus is replicating. The level of mRNA will be higher in cells where the polymerase is actively expressed than those where the polymerase gene is inactive. It may therefore be desirable to enhance the level of target in the sample by amplifying the DNA or RNA. A suitable method of amplification is a PCR, which is preferably conducted using one or more of the oligonucleotide primers embodied in this invention. RNA may be amplified by making a cDNA copy using a reverse transcriptase, and then conducting a PCR using the aforementioned primers.

The target polynucleotide can be optionally subjected to any combination of additional treatments, including digestion with restriction endonucleases, size separation, for example by electrophoresis in agarose or polyacrylamide, and affixation to a reaction matrix, such as a blotting material.

Hybridization is allowed to occur by mixing the reagent polynucleotide with a sample suspected of containing a target polynucleotide under appropriate reaction conditions. This may be followed by washing or separation to remove unreacted reagent. Generally, both the target polynucleotide and the reagent must be at least partly equilibrated into the single-stranded form in order for complementary sequences to hybridize efficiently. Thus, it may be useful (particularly in tests for DNA) to prepare the sample by standard denaturation techniques known in the art.

The level of stringency chosen for the hybridization conditions depends on the objective of the test. If it is desired that the test be specific for RFHV or KSHV, then a probe comprising a segment of the respective DNA polymerase is used, and the reaction is conducted under conditions of high stringency. For example, a preferred set of conditions for use with a preferred probe of 50 nucleotides or more is 6×SSC at 37° C. in 50% formamide, followed by a wash at low ionic strength. This will generally require the target to be at least about 90% identical with the polynucleotide probe for a stable duplex to form. The specificity of the reaction for RFHV or KSHV can also be increased by increasing the length of the probe used. Thus, longer probes are particularly preferred for this application of the invention.

Alternatively, if it is desired that the test be able to detect gamma herpes viruses related to RFHV or KSHV, then a lower stringency is used. Suitable probes include fragments from the RFHV or KSHV DNA polymerase, a mixture thereof, or degenerate oligonucleotides such as those listed in Table 6.

Appropriate hybridization conditions are determined to permit hybridization of the probe only to DNA polymerase sequences that have the desired degree of identity with the probe. The stringency required depends on the length of the polynucleotide probe, and the degree of identity between the probe and the desired target sequence. Consider, for example, a probe consisting of the KSHV polynucleotide fragment between the hybridization sites of DFASA and GDTD1B. Conditions requiring a minimum identity of 55% would result in a stable duplex formed with a corresponding polynucleotide of KSHV, RFHV, and EBV; conditions requiring a minimum identity of 68% would result in a stable duplex forming with a polynucleotide from KSHV, RFHV, or a related polynucleotide, but not EBV; conditions requiring a minimum identity of 80% would result in a stable duplex forming with a polynucleotide from KSHV, but not RFHV or EBV (see Table 2).

Conditions can be estimated beforehand using the formula given earlier. Preferably, the exact conditions are confirmed by testing the probe with separate samples known to contain polynucleotides, both those desired to be detected and those desired to go undetected in the assay. Such samples may be provided either by synthesizing the polynucleotides from published sequences, or by extracting and amplifying DNA from tissues believed to be infected with the respective herpes virus. Determining hybridization conditions is a matter of routine adjustment for a practitioner of ordinary skill, and does not require undue experimentation. Since eHV2, sHV1 and EBV are more closely identical to RFHV or KSHV than members of the alpha and beta subfamilies, conditions that exclude polynucleotides of those viruses will generally also exclude the other herpes viruses listed in Table 1. In addition, if it is believed that certain viruses will not be present in the sample to be tested in the ultimate determination (such as eHV2 in a human tissue sample), then the corresponding target sequences may optionally be omitted when working out the conditions of the assay. Thus, conditions can be determined that would permit an oligonucleotide probe such as LSGGA, CTDPA, KMLEA or GISPA to form a stable duplex both with polypeptides comprising SEQ. ID NO:1 and SEQ. ID NO:3, but not a sequence selected from the group consisting of SEQ. ID NO:23 to SEQ. ID NO:29. Conditions can also be determined that would permit an oligonucleotide probe such as PCLNA (SEQ. ID NO:21) or any suitable fragment comprising at least 18 or more consecutive bases of SEQ. ID NO:1 or SEQ. ID NO:3 to form a stable duplex both with a polynucleotide comprising SEQ. ID NO:1 and with a polynucleotide comprising SEQ. ID NO:3, but not a polynucleotide comprising one of SEQ. ID NO:23 to SEQ. ID NO:29.

Alternatively, to conduct an assay that is specific due to amplification with a specific primer. DNA or RNA is prepared from the biological sample as before. Optionally, the target polynucleotide is pre-amplified in a PCR using primers which are not species specific, such as those listed in Table 4. The target is then amplified using specific primers, such as those listed in Table 6 or Table 7. For example, if it is desired that the test be specific for RFHV, then VASGA, ILPCA, PIEAB, PEARB, or a combination thereof may be used. If it is desired that the test be specific for KSHV, then SGILA, CLNIA, IEASB, EARFB, or a combination thereof may be used. If it is desired that the test be able to detect gamma herpes viruses related to RFHV or KSHV, then degenerate or cross-reactive probes, such as those listed in Table 6, or a combination thereof may be used. In a preferred embodiment, two rounds of amplification are performed, using oligonucleotide primers in a nested fashion: virus-specific or non-specific in the first round; virus-specific in the second round. This provides an assay which is both sensitive and specific.

Use of a specific primer during amplification is sufficient to provide the required specificity. A positive test may be indicated by the presence of sufficient reaction product at the end of the amplification series. Amplified polynucleotide can be detected, for example, by blotting the reaction mixture onto a medium such as nitrocellulose and staining with ethidium bromide. Alternatively, a radiolabeled substrate may be added to the mixture during a final amplification cycle; the incorporated label may be separated from unincorporated label (e.g., by blotting or by size separation), and the label may be detected (e.g. by counting or by autoradiography). If run on a gel of agarose or polyacrylamide, the size of the product may help confirm the identity of the amplified fragment. Specific amplification can also be followed by specific hybridization, by using the amplification mixture obtained from the foregoing procedure as a target source for the hybridization reaction outlined earlier.

Use of polynucleotides for gene therapy

Embodied in this invention are pharmaceuticals comprising virus-specific polynucleotides, polypeptides, or antibodies as an active ingredient. Such compositions may decrease the pathology of the virus or infected cells on their own, or render the virus or infected cells more susceptible to treatment by non-specific pharmaceutical compounds.

Polynucleotides of this invention encoding part of a herpes virus DNA polymerase may be used, for example, for administration to an infected individual for purposes of gene therapy (see generally U.S. Pat. No. 5,399,346: Anderson et al.). The general principle is to administer the polynucleotide in such a way that it interferes with the expression of the corresponding gene, such as by complexing with the gene itself or with the RNA transcribed from the gene. Entry of the polynucleotide into the cell is facilitated by suitable techniques known in the art, such as providing the polynucleotide in the form of a suitable vector, or encapsulation of the polynucleotide in a liposome. The polynucleotide may be injected systemically, or provided to the site of infection by an antigen-specific homing mechanism, or by direct injection.

A preferred mode of gene therapy is to provide the polynucleotide in such a way that it will replicate inside the cell, enhancing and prolonging the interference effect. Thus, the polynucleotide is operatively linked to a suitable promoter, such as the natural promoter of the corresponding gene, a heterologous promoter that is intrinsically active in infected cells, or a heterologous promoter that can be induced by a suitable agent. Preferably, the construct is designed so that the polynucleotide sequence operatively linked to the promoter is complementary to the sequence of the corresponding gene. Thus, once integrated into the cellular genome, the transcript of the administered polynucleotide will be complementary to the transcript of the gene, and capable of hybridizing with it. This approach is known as anti-sense therapy.

RFHV/KSHV subfamily polypeptides with DNA polymerase activity and fragments thereof The RFHV and KSHV polynucleotides shown in FIG. 1 each have an open reading frame. The polypeptides encoded are respectively designated SEQ. ID NO:2 and SEQ. ID NO:4. The polypeptides have a significant number of homologous residues to DNA polymerases of other sequenced herpes viruses. They are more closely identical to each other within this fragment than to the corresponding fragment of the other sequenced viruses. The fragment is believed to encompass residues that are near the nucleotide substrate binding site of the intact protein. This region may play a role in the catalytic activity of the polymerase. Polypeptides with DNA polymerase activity from other members of the RFHV/KSHV subfamily are expected to share a large proportion of identical residues over this region. In general, residues conserved between RFHV and KSHV are expected to be relatively conserved within the subfamily.

Beginning at about amino acid 89 of SEQ. ID NO:2, there is a linear sequence of about 46 residues that is shared identically between the DNA polymerase of RFHV and KSHV. Beginning at about amino acid 88 of SEQ. ID NO:2, there is a linear sequence of about 31 residues shared between the DNA polymerase of RFHV and eHV2. The sequence shared with eHV2 is listed separately in SEQ. ID NO:112. Also contained in SEQ. ID NO:112 is a sequence of about 26 amino acids shared between RFHV and sHV1, and two sequences of 12 amino acids shared between RFHV and EBV. Beginning at about amino acid 10 of SEQ. ID NO:4, there is a linear sequence of about 15 residues shared between KSHV and various other gamma herpes viruses. This shared sequence is listed separately in SEQ. ID NO:113. The longest sequence contained in SEQ. ID NOS:2 or 4 but not in SEQ. ID NOS:112 or 113 that is shared with other known herpes virus DNA polymerases is 10 amino acids in length. Hence, any fragment of the RFHV or KSHV DNA polymerase protein sequence that is 11 amino acids or longer, and not in SEQ. ID NOS:112 or 113, is believed to be specific for the RFHV/KSHV subfamily, or species and variants therein.

This invention embodies both intact DNA polymerase from herpes viruses of the RFHV/KSHV subfamily, and any fragment thereof that is specific for the subfamily. Preferred DNA polymerase fragments of this invention are at least 11 amino acids in length; more preferably they are about 12 amino acids in length, more preferably they are at least about 15 amino acids in length; even more preferably they are at least about 20 amino acids in length, still more preferably they are at least about 30 amino acids in length.

The amino acid sequence of the RFHV and KSHV DNA polymerase fragments can be used to identify virus-specific and cross-reactive antigenic regions.

In principle, a specific antibody could recognize any amino acid difference between sequences that is not also shared by the species from which the antibody is derived. Antibody binding sites are generally big enough to encompass 5–9 amino acid residues of an antigen, and are quite capable of recognizing a single amino acid difference. Specific antibodies may be part of a polyclonal response arising spontaneously in animals infected with a virus expressing the DNA polymerase. Specific antibodies may also be induced by injecting an experimental animal with either the intact polymerase or a polymerase fragment.

Thus, any peptide of 5 amino acids or more that is unique to RFHV or KSHV is a potential virus-specific antigen, and could be recognized by a RFHV- or KSHV-specific antibody. Peptides of at least 5 amino acids shared between RFHV and KSHV, but not EBV, eHV2 and sHV1 are potential RFHV/KSHV subfamily specific antigens.

Some examples of preferred peptides are shown in Table 8. Practitioners in the art will immediately recognize that other peptides with similar specificities may be designed by minor alterations to the length of the peptides listed and/or moving the frame of the peptide a few residues in either direction.

The Class I peptides shown in Table 8 are conserved between all known DNA polymerase polypeptide sequences of the gamma herpes virus subfamily. An antibody directed against one such DNA polymerase in this region is expected to cross-react with the others. Class II peptides are conserved between RFHV and KSHV, but not with sHV1 and EBV. An antibody directed against this region is expected to cross-react between RFHV, KSHV, and other viruses of the RFHV/KSHV subfamily. Class III peptides are different between RFHV and KSHV. An antibody binding to this region, particularly to non-identical residues, is expected to distinguish the RFHV DNA polymerase from the KSHV DNA polymerase.

TABLE 8

Antigen Peptides

| Specificity | Sequence | SEQ. ID NO: |
|---|---|---|
| Class I: Shared amongst some members of the RFHV/KSHV subfamily and other gamma herpes viruses | Peptides contained within RTILDKQQLAIKVTCNAVYGFTGVASGILPCL (SEQ. ID NO:112) | |
| | Peptides contained within SIIQAHNLCYSTLIP (SEQ. ID NO:113) | |
| | IAETVTL | 73 |
| Class II: Shared amongst members of the RFHV/KSHV subfamily[1] | PDDYETF | 90 |
| | KRKEIRK | 91 |
| | LAKRKEI | 92 |
| | LASCTDP | 93 |
| | VASGILP[2] | 74 |
| | GILPCLN | 75 |
| | CLNIAET | 76 |
| | QGRKMLE | 77 |
| | SQAFVE | 78 |

TABLE 8-continued

Antigen Peptides

| Specificity | Sequence | SEQ. ID NO: |
|---|---|---|
| | ARFKVI | 79 |
| Class III: | TGSALHG (RFHV) | 94 |
| RFHV or KSHV | PGDSLHL (KSHV) | 95 |
| specific[3] | SALHGHP (RFHV) | 96 |
| | DSLHLHP (KSHV) | 97 |
| | GHPELTP (RFHV) | 98 |
| Class III | LHPHLGP (KSHV) | 99 |
| | HLSGGTV (RFHV) | 100 |
| | VLSGGLV (KSHV) | 101 |
| | TDPTMRT (RFHV) | 102 |
| | TDPALKT (KSHV) | 103 |
| | LETSQAF (RFHV) | 80 |
| | LERSQAF (KSHV) | 81 |
| | EGISPTA (RFHV) | 82 |
| | EAISPER (KSHV) | 83 |
| | ADLLQRP (RFHV) | 84 |
| | AGLLRRP (KSHV) | 85 |
| | QRPIEAS (RFHV) | 86 |
| | RRPIDVS (KSHV) | 87 |
| | IEASPEA (RFHV) | 88 |
| | IDVSPDA (KSHV) | 89 |

[1]Not shared with eHV2, sHV1 or EBV, except where indicated
[2]Also shared with eHV2 but not with sHV1 or EBV
[3]Not shared with any other sequenced herpes virus; may be present in some unsequenced RFHV/KSHV subfamily viruses Particularly preferred peptides from Classes II and III are QGRKMLE, ARFKVI, RRPIDVS, QRPIEAS, IEASPEA, and IDVSPDA. Given the complete sequence of a DNA polymerase from RFHV and/or KSHV, virus- or subfamily-specific peptides can be predicted for other regions of the molecule by a similar analysis.

Preparation of polypeptides

Polypeptides of this invention, including intact protein, protein fragments, and antigenic regions, can be prepared by several different methods, all of which will be known to a practitioner of ordinary skill. For example, the appropriate strand of the full-length cDNA can be operatively linked to a suitable promoter, and transfected into a suitable host cell. The host cell is then cultured under conditions that allow transcription and translation to occur, and the polypeptide is subsequently recovered. For a description of the expression and recovery of a herpes virus DNA polymerase by transfecting S. cerevisiae, see Haffey et al. and Patent Application EP 0337441. For a description of the expression of another herpes virus protein in mammalian cells, see U.S. Pat. No. 5,244,792 (Burke et al.).

Polypeptides may also be prepared directly from sequence data by chemical synthesis. Several methods of synthesis are known in the art. A preferred method is the solid-phase Merrifield technique. Alternatively, a polynucleotide encoding the desired polypeptide may be prepared by any of the methods described earlier, and translated using an in vitro translation system, such as the rabbit reticulocyte system. See, e.g., Dorsky et al.

Use of polypeptides to assess herpes virus infection

The polypeptides embodied in this invention may be used to detect or assess the status of a herpes virus infection in an individual in several different applications.

In one application, a polypeptide encoding a portion of a herpes virus DNA polymerase is supplied as a reagent for an assay to detect the presence of antibodies that can specifically recognize it. Such antibodies may be present, for example, in the circulation of an individual with current or past herpes virus infection.

The presence of antibodies to DNA polymerase in the circulation may provide an early indication of a pathological condition. The antibody to hepatitis B virus DNA polymerase is an early indication of acute hepatitis B virus infection (WO 8904964: Fietelson et al.). Antibodies to DNA polymerase are useful in diagnosis of nasopharyngeal carcinoma (Lin et al., Liu et al.). Similarly, it may be useful to monitor for the presence of antibodies to DNA polymerase of KSHV in HIV-infected humans before Kaposi's sarcoma lesions are clinically apparent.

Suitable clinical samples in which to measure antibody levels include serum or plasma from an individual suspected of having a gamma herpes virus infection. The presence of the antibody is determined, for example, by an immunoassay.

A number of immunoassay methods are established in the art for performing the quantitation of antibody using viral peptides (see, e.g., U.S. Pat. No. 5,350,671: Houghton et al.). For example, the test sample potentially containing the specific antibody may be mixed with a pre-determined non-limiting amount of the reagent polypeptide. The reagent may contain a directly attached label, such as an enzyme or a radioisotope. For a liquid-phase assay, unreacted reagents are removed by a separation technique, such as filtration or chromatography. Alternatively, the antibody in the sample may be first captured by a reagent on a solid phase. This may be, for example, the specific polypeptide, an anti-immunoglobulin, or protein A. The captured antibody is then detected with a second reagent, such as the specific polypeptide, anti-immunoglobulin, or protein A with an attached label. At least one of the capture reagent or the detecting reagent must be the specific polypeptide. In a third variation, cells or tissue sections containing the polypeptide may be overlaid first with the test sample containing the antibody, and then with a detecting reagent such as labeled anti-immunoglobulin. In all these examples, the amount of label captured in the complex is positively related to the amount of specific antibody present in the test sample. Similar assays can be designed in which antibody in the test sample competes with labeled antibody for binding to a limiting amount of the specific peptide. The amount of label in the complex is then negatively correlated with the amount of specific antibody in the test sample. Results obtained using any of these assays are compared between test samples, and control samples from an uninfected source.

By selecting the reagent polypeptide appropriately, antibodies of a desired specificity may be detected. For example, if the intact DNA polymerase is used, or a fragment comprising regions that are conserved between herpes virus, then antibodies detected in the test samples may be virus specific, cross-reactive, or both. A reagent of this nature is preferred for a general screening assay for herpes virus infection. To render the assay specific for antibodies directed either against RFHV or against KSHV, antigen peptides comprising non-conserved regions of the appropriate viral DNA polymerase are selected, such as those listed in Class III of Table 8. Preferably, a mixture of such peptides is used. To simultaneously detect antibodies against RFHV, KSHV, and closely related viruses of the gamma herpes family, but not sHV1 and EBV, antigen peptides are selected with the properties of those listed in Class II of Table 8. Preferably, a mixture of such peptides is used.

Antibodies stimulated during a herpes virus infection may subside once the infection resolves, or they may persist as part of the immunological memory of the host. In the latter instance, antibodies due to current infection may be distinguished from antibodies due to immunological memory by determining the class of the antibody. For example, an assay may be conducted in which antibody in the test sample is captured with the specific polypeptide, and then developed with labeled anti-IgM or anti-IgG. The presence of specific antibody in the test sample of the IgM class indicates ongoing infection, while the presence of IgG antibodies alone indicates that the activity is due to immunological memory of a previous infection or vaccination.

In another application of the invention, herpes virus encoded DNA polymerase is isolated from a sample, and the amount present is determined by an enzymatic assay. Assays for DNA polymerase activity in a biological sample can be conducted, for example, by extracting the polymerase and performing a suitable polymerization assay. The polymerase may be solubilized by standard techniques from a solid tissue sample or tissue homogenate, for example, by using non-ionic detergents such as TRITON™ X-100 or deoxycholate. Alternatively, if the polymerase is secreted by infected cells, it may be possible to perform the assay on a liquid sample, such as plasma or lymph.

Methods for conducting DNA polymerase assays are known in the art. For example, a polymerization mixture is prepared that contains the putative DNA polymerase, a mixture of nucleotides containing at least one labeled nucleotide, a DNA template such as M13 phage DNA, and, if necessary, a regulatory subunit. The mixture is incubated at 37° C. for a time sufficient to allow polymerization to occur. Polymerase activity, or lack thereof, is determined by measuring the amount of incorporation of label into the polynucleotide. Optimal conditions for conducting a DNA polymerase assay are readily ascertained without undue experimentation by a practitioner of ordinary skill in the art. For example, conditions for the DNA polymerase of HSV have been published by O'Donnell et al. Optimal conditions for DNA polymerase from RFHV and KSHV are expected to be analogous.

Use of polypeptides as components in active vaccines

An example of how polypeptides embodied in this invention can be effectively used in treatment is through vaccination.

In one embodiment of this application, the polypeptide is administered as part of an active vaccine in order to stimulate antibodies that will react against the pathogenic organism; in this case, a herpesvirus of the RFHV/KSHV subfamily. The development of active vaccines from isolated herpes virus components is known in the art: see, e.g., U.S. Pat. No. 5,171,568 (Berke et al.). This type of vaccine is especially useful in prophylaxis, since the antibodies it stimulates may be able to neutralize subsequently encountered organisms before they have a chance to invade the host's cells and begin a replicative cycle.

Methods for preparing and administering polypeptide vaccines are known in the art. Peptides may be capable of eliciting an immune response on their own, or they may be rendered more immunogenic by chemical manipulation, such as cross-linking or attaching to a protein carrier like KLH. Preferably, the vaccine also comprises an adjuvant, such as alum, muramyl dipeptides, liposomes, or DETOX™. The vaccine may optionally comprise auxiliary substances such as wetting agents, emulsifying agents, and organic or inorganic salts or acids. It also comprises a pharmaceutically acceptable excipient which is compatible with the active ingredient and appropriate for the route of administration. The desired dose for peptide vaccines is generally from 10 µg to 1 mg, with a broad effective latitude. The vaccine is preferably administered first as a priming dose, and then again as a boosting dose, usually at least four weeks later. Further boosting doses may be given to enhance the effect. The dose and its timing are usually determined by the person responsible for the treatment.

In another embodiment of this application, the polypeptide is an active ingredient of a vaccine designed to stimulate specific cytotoxic T lymphocytes. This type of vaccine may be especially useful in the treatment of a herpes virus infection already present in a subject. The DNA polymerase of a herpes virus is a suitable target for a cytotoxic T cell vaccine; not only because of its relatively conserved structure, but also because it is an important internal component of the virus. External virus components are expressed by circulating intact virus and defective viral particles, and have the potential of diverting the immune system away from infected cells. However, internal viral components are expressed extracellularly only by virally infected cells, which display them in the context of histocompatibility class I molecules. Such cells are ideal targets for specific cytotoxic T cells, as they represent the site of viral replication and are therefore the virus's most vulnerable location within the host.

Cytotoxic T cell vaccines may comprise different antigenic regions than those required to stimulate antibodies. T cell epitopes are different from antibody epitopes; they generally depend less on conformational context, and/or develop from regions of the peptide capable of folding into an amphipathic alpha-helix. Cytotoxic T cell vaccines may also comprise additional active ingredients or cytokines which may enhance the presentation of the peptide to the T cell population and/or assist in the recruitment of cells of the cytotoxic T cell lineage.

In a variation of either of the preceding embodiments, the immunizing peptide is provided not as an isolated protein or protein fragment, but in the form of an expression vector. A polynucleotide encoding the peptide is operatively linked to suitable controlling elements of transcription and translation, and then transfected into a suitable vector. Suitable vectors include a vaccinia virus, or an attenuated form of a herpes virus.

Use of polypeptides to design or screen anti-viral drugs

Interfering with the DNA polymerase gene or gene product would modify the infection process, or the progress of this disease. It is an objective of this invention to provide a method by which useful pharmaceutical compositions and methods of employing such compounds in the treatment of gamma herpes virus infection can be developed and tested. Particularly preferred are pharmaceutical compounds useful in treating infections by RFHV and KSHV. Suitable drugs are those that interfere with transcription or translation of the DNA polymerase gene, and those that interfere with the catalytic function of the polypeptide encoded by the gene. It is not necessary that the mechanism of interference be known; only that the interference be preferential for reactions associated with the infectious process.

Preferred drugs include those that competitively interfere with the binding of the DNA polymerase to the substrate nucleotide triphosphate, the DNA template. Also preferred are nucleotide analogs that can be incorporated into the polymerizing strand synthesized by the enzyme, but form a dead-end complex that prevents further polymerization (Reardon et al.) Some non-limiting examples of preferred drugs which may be tested by the procedures described herein are aphidicolon, acyclovir, gancyclovir, foscarnet, oosporein, BHCG, PMEA, other nucleotide analogs, isotrenes of these compounds, and other compounds that are structurally or functionally related to those listed.

Also preferred are drugs that interfere with the association of DNA polymerase with regulatory subunits that are necessary for catalytic activity. As described earlier, the UL42 subunit is essential for the DNA polymerase activity of HSV during the replicative process. Small peptides designed from the UL42 sequence inhibit binding between UL42 and the DNA polymerase, and are effective inhibitors of polymerase activity (U.S. Pat. No. 5,223,391: Coen et al.). The C-terminal region of the HSV DNA polymerase is responsible for binding the UL42 subunit. It is therefore expected that under certain conditions (such as those required for viral replication), the RFHV and KSHV DNA polymerase will require a regulatory subunit which may or may not be an analog of UL42, in order to express full polymerase activity. Thus, peptides functionally equivalent to those described in U.S. Pat. No. 5,223,391, adapted appropriately for gamma herpes viruses, are expected to have inhibitory activity and be therapeutically useful.

This invention provides methods for screening pharmaceutical candidates to determine which are suitable for clinical use. The methods may be brought to bear on antiviral compounds that are currently known, and those which may be designed in the future.

The method involves combining an active DNA polymerase with the pharmaceutical candidate, and determining whether the biochemical function is altered by the pharmaceutical candidate. The DNA polymerase may be any fragment encoded by the DNA polymerase gene of RFHV or KSHV that has DNA polymerase activity. Suitable fragments may be obtained by expressing a genetically engineered polypeptide encoding the active sites of the molecule, or by cleaving the DNA polymerase with proteases and purifying the active fragments. In a preferred embodiment, the entire DNA polymerase is provided. The reaction mixture will also comprise a suitable DNA template, substrate deoxyribonucleotide triphosphates, and whatever regulatory subunits are necessary for the reaction to proceed.

One embodiment of the screening method is to perform a DNA polymerase assay in vitro. The DNA polymerase is provided in isolated form, and mixed with the other reacting compounds in a suitable buffer. A DNA polymerase assay is conducted and monitored as outlined in an earlier section. The amount of polymerase activity per mole or per gram of enzyme in the reaction mixture is measured, for example, by the rate of incorporation of radiolabeled nucleotide into the synthesized strand. The effect of the candidate drug may be determined by running two reactions in parallel, both with the same mixture of reacting substances except that one contains the candidate. Alternatively, the effect of the candidate drug may be determined by adding it to a polymerase reaction in progress, and determining whether the reaction rate is altered. A desirable effect is one that eliminates or decreases the rate of synthesis of the labeled DNA.

Another embodiment of the screening method is to express a polynucleotide encoding an active region of the DNA polymerase in a host cell. Transfection with the polynucleotide may enhance the rate of replication of the host cell, in which case the activity of the polymerase can be monitored by measuring the rate of replication of the cells. Alternatively, activity of the polymerase may be measured as the rate of production of a product, such as a labeled polynucleotide, inside the cell. The effect of the drug can therefore be determined by following its effect on DNA polymerase activity. Suitable control experiments include measuring DNA polymerase activity in the absence of the drug, and measuring the effect of the drug on untransformed host cells.

A further embodiment of the screening method is to measure binding of the pharmaceutical candidate to the isolated DNA polymerase, or a fragment thereof. Compounds that bind to the catalytic site or the binding site of a regulatory subunit are expected to interfere with DNA polymerase activity. Thus, the entire DNA polymerase, or a fragment comprising the catalytic site or the binding site of a regulatory subunit, is mixed with the pharmaceutical candidate. Binding of the candidate can be measured directly, for example, by providing the candidate in a radio-labeled or stable-isotope labeled form. The presence of label bound to the polymerase can be determined, for example, by precipitating the polymerase with a suitable antibody, or by providing the polymerase attached to a solid phase, and washing the solid phase after the reaction. Binding of the candidate to the polymerase may also be observed as a conformational change in the polymerase, detected for example by difference spectroscopy, nuclear magnetic resonance, or circular dichroism. Alternatively, binding may be determined in a competitive assay: for example, DNA polymerase is mixed with the candidate, and then labeled nucleotide or a fragment of a regulatory subunit is added later. Binding of the candidate to the biochemically relevant site should inhibit subsequent binding of the labeled compound.

This invention also provides for the development of pharmaceuticals for the treatment of herpes infection by rational drug design. See, generally, Hodgson, and Erickson et al. In this embodiment, the three-dimensional structure of the DNA polymerase is determined, either by predictive modeling based on the amino acid sequence, or preferably, by experimental determination. Experimental methods include antibody mapping, mutational analysis, and the formation of anti-idiotypes. Especially preferred is X-ray crystallography. Knowing the three-dimensional structure of the protease, especially the orientation of important amino acid groups near the nucleotide and regulatory subunit binding sites, a compound is designed de novo, or an existing compound is suitably modified. The designed compound will have an appropriate charge balance, hydrophobicity, and/or shape to enable it to attach near an active site of the polymerase, and sterically interfere with the normal biochemical function of that site. Preferably, compounds designed by this method are subsequently tested in a drug screening assay, such as those outlined above.

Antibodies against DNA polymerase and their preparation

The amino acid sequence of the herpes virus DNA polymerases embodied herein are foreign to the hosts they infect. The polymerases are large, and potentially comprise a large number of antigenic regions. They are sequestered within the capsid of the respective virus, and are unlikely to be mimicking host antigens. It is therefore expected that these polymerases will be substantially immunogenic. Antibodies may be generated against them spontaneously by a vertebrate host during the course of an infection with an intact herpes virus. It is also expected that antibodies can be raised in experimental animals by injection of isolated DNA polymerase and suitably prepared fragments. These expectations are supported by the observations described in Example 5 and Example 10.

Antibodies against a polypeptide are generally prepared by any method known in the art. To stimulate antibody production in an animal experimentally, it is often preferable to enhance the immunogenicity of a polypeptide by such techniques as polymerization with glutaraldehyde, or combining with an adjuvant, such as Freund's adjuvant. The immunogen is injected into a suitable experimental animal: preferably a rodent for the preparation of monoclonal antibodies; preferably a larger animal such as a rabbit or sheep for preparation of polyclonal antibodies. It is preferable to provide a second or booster injection after about 4 weeks, and begin harvesting the antibody source no less than about 1 week later.

Sera harvested from the immunized animals provide a source of polyclonal antibodies. Detailed procedures for purifying specific antibody activity from a source material are known within the art. If desired, the specific antibody activity can be further purified by such techniques as protein A chromatography, ammonium sulfate precipitation, ion exchange chromatography, high-performance liquid chromatography and immunoaffinity chromatography on a column of the immunizing polypeptide coupled to a solid support.

Polyclonal antibodies raised by immunizing with an intact DNA polymerase or a fragment comprising conserved sequences may be cross-reactive between herpes viruses. Antibodies that are virus or subfamily specific may be raised by immunizing with a suitably specific antigen, such as those listed above in Table 8. Alternatively, polyclonal antibodies raised against a larger fragment may be rendered specific by removing unwanted activity against other virus DNA polymerases, for example, by passing the antibodies over an adsorbant made from those polymerases and collecting the unbound fraction.

Alternatively, immune cells such as splenocytes can be recovered from the immunized animals and used to prepare a monoclonal antibody-producing cell line. See, for example, Harrow & Lane (1988), U.S. Pat. No. 4,472,500 (Milstein et al.), and U.S. Pat. No. 4,444,887 (Hoffman et al.)

Briefly, an antibody-producing line can be produced inter alia by cell fusion, or by transforming antibody-producing cells with Epstein Barr Virus, or transforming with oncogenic DNA. The treated cells are cloned and cultured, and clones are selected that produce antibody of the desired specificity. Specificity testing can be performed on culture supernatants by a number of techniques, such as using the immunizing polypeptide as the detecting reagent in a standard immunoassay, or using cells expressing the polypeptide in immunohistochemistry. A supply of monoclonal antibody from the selected clones can be purified from a large volume of tissue culture supernatant, or from the ascites fluid of suitably prepared host animals injected with the clone.

Effective variations of this method include those in which the immunization with the polypeptide is performed on isolated cells. Antibody fragments and other derivatives can be prepared by methods of standard protein chemistry, such as subjecting the antibody to cleavage with a proteolytic enzyme. Genetically engineered variants of the antibody can be produced by obtaining a polynucleotide encoding the antibody, and applying the general methods of molecular biology to introduce mutations and translate the variant.

Monoclonal antibodies raised by injecting an intact DNA polymerase or a fragment comprising conserved sequences may be cross-reactive between herpes viruses. Antibodies that are virus or subfamily specific may be raised by immunizing with a suitably specific antigen, as may be selected from Table 8. Alternatively, virus-specific clones may be selected from the cloned hybridomas by using a suitable antigen, such as one selected from Table 8, in the screening process.

Use of antibodies for detecting DNA polymerase in biological samples

Antibodies can be used to detect DNA polymerase polypeptides and fragments of viral origin that may be present, for example, in solid tissue samples and cultured cells. Immunohistological techniques to carry out such determinations will be obvious to a practitioner of ordinary skill. Generally, the tissue is preserved by a combination of techniques which may include freezing, exchanging into different solvents, fixing with agents such as paraformaldehyde, drying with agents such as alcohol, or embedding in a commercially available medium such as paraffin or OCT. A section of the sample is suitably prepared and overlaid with a primary antibody specific for the protein.

The primary antibody may be provided directly with a suitable label. More frequently, the primary antibody is detected using one of a number of developing reagents which are easily produced or available commercially. Typically, these developing reagents are anti-immunoglobulin or protein A, and they typically bear labels which include, but are not limited to: fluorescent markers such as fluorescein, enzymes such as peroxidase that are capable of precipitating a suitable chemical compound, electron dense markers such as colloidal gold, or radioisotopes such as $^{125}$I. The section is then visualized using an appropriate microscopic technique, and the level of labeling is compared between the suspected virally infected and a control cell, such as cells surrounding the area of infection or taken from a remote site.

Proteins encoded by a DNA polymerase gene can also be detected in a standard quantitative immunoassay. If the protein is secreted or shed from infected cell in any appreciable amount, it may be detectable in plasma or serum samples. Alternatively, the target protein may be solubilized or extracted from a solid tissue sample. Before quantitating, the protein may optionally be affixed to a solid phase, such as by a blot technique or using a capture antibody.

A number of immunoassay methods are established in the art for performing the quantitation. For example, the protein may be mixed with a pre-determined non-limiting amount of the reagent antibody specific for the protein. The reagent antibody may contain a directly attached label, such as an enzyme or a radioisotope, or a second labeled reagent may be added, such as anti-immunoglobulin or protein A. For a solid-phase assay, unreacted reagents are removed by washing. For a liquid-phase assay, unreacted reagents are removed by some other separation technique, such as filtration or chromatography. The amount of label captured in the complex is positively related to the amount of target protein present in the test sample. A variation of this technique is a competitive assay, in which the target protein competes with a labeled analog for binding sites on the specific antibody. In this case, the amount of label captured is negatively related to the amount of target protein present in a test sample. Results obtained using any such assay are compared between test samples, and control samples from an uninfected source.

Specific antibodies against herpes virus DNA polymerase have a number of uses in developmental, diagnostic and therapeutic work. For example, antibodies can be used in drug screening (see U.S. Pat. No. 5,120,639), or to prepare a passive vaccine. They may also be used for detecting herpes virus in a biological sample and for drug targeting, as described in the following sections.

Use of antibodies for drug targeting

An example of how antibodies can be used in therapy of herpes virus infection is in the specific targeting of effector components. Virally infected cells generally display peptides of the virus (including internal viral components) on their cell surface in the context of histocompatibility class I antigens. The peptide therefore provides a marker for infected cells that a specific antibody can bind to. An effector component attached to the antibody therefore becomes concentrated near the infected cells, improving the effect on those cells and decreasing the effect on uninfected cells. Furthermore, if the antibody is able to induce endocytosis, this will enhance entry of the effector into the cell interior.

For the purpose of targeting, an antibody specific for the viral polypeptide (in this case, a region of a DNA polymerase) is conjugated with a suitable effector component, preferably by a covalent or high-affinity bond. Suitable effector components in such compositions include radionuclides such as $^{131}$I, toxic chemicals, and toxic peptides such as diphtheria toxin. Another suitable effector component is an antisense polynucleotide, optionally encapsulated in a liposome.

In most applications of antibody molecules in human therapy, it is preferable to use human monoclonals, or antibodies that have been humanized by techniques known in the art. This helps prevent the antibody molecules themselves from becoming a target of the host's immune system.

Diagnostic kits

Diagnostic procedures using the polynucleotides, oligonucleotides, peptides, or antibodies of this invention may be performed by diagnostic laboratories, experimental laboratories, practitioners, or private individuals. This invention provides diagnostic kits which can be used in these settings. The presence of a herpes virus in the individual may be manifest in a clinical sample obtained from that individual as an alteration in the DNA, RNA, protein, or antibodies contained in the sample. An alteration in one of these components resulting from the presence of a herpes virus may take the form of an increase or decrease of the level of the component, or an alteration in the form of the component, compared with that in a sample from a healthy individual. The clinical sample is optionally pre-treated for enrichment of the target being tested for. The user then applies a reagent contained in the kit in order to detect the changed level or alteration in the diagnostic component.

Each kit necessarily comprises the reagent which renders the procedure specific: a reagent polynucleotide, used for detecting target DNA or RNA; a reagent antibody, used for detecting target protein; or a reagent polypeptide, used for detecting target antibody that may be present in a sample to be analyzed. The reagent is supplied in a solid form or liquid buffer that is suitable for inventory storage, and later for exchange or addition into the reaction medium when the test is performed. Suitable packaging is provided. The kit may optionally provide additional components that are useful in the procedure. These optional components include buffers, capture reagents, developing reagents, labels, reacting surfaces, means for detection, control samples, instructions, and interpretive information.

Other members of the RFHV/KSHV subfamily

RFHV and KSHV are exemplary members of the RFHV/KSHV subfamily. This invention embodies polynucleotide sequences encoding DNA polymerase of other members of the subfamily, as defined herein. We anticipate that other members of the subfamily will be identified and characterized, including some that are capable of infecting primates, including humans. One such member is another virus infecting monkeys, designated RFHV2. A segment of the DNA polymerase encoding sequence for this virus was cloned from RF tissue obtained from a Macaca mulatta monkey, as described in Example 11.

In order to identify and characterize other members of the family, reagents and methods of this invention are applied to DNA extracted from tissue samples suspected of being infected with such a virus. Suitable sources include biological samples obtained from a wide range of conditions occurring in humans and other vertebrates. Preferred are conditions in which the agent is suspected of being lymphotrophic, similar to other members of the gamma herpes virus subfamily; for example, infectious mononucleosis of non-EBV origin. More preferred are conditions which resemble in at least one of their clinical or histological features the conditions with which RFHV or KSHV are associated. These include: a) conditions in which fibroproliferation is part of the pathology of the disease, especially in association with collagen deposition, and especially where the fibrous tissue is disorganized; b) conditions involving vascular dysplasia; c) conditions involving malignant transformation, especially but not limited to cells of lymphocyte lineage; d) conditions for which an underlying immunodeficiency contributes to the frequency or severity of the disease; e) conditions which arise idiopathically at multiple sites in an organ or in the body as a whole; f) conditions which epidemiological data suggests are associated with an infectious or environmental agent. Conditions which fulfill more than one of these criteria are comparably more preferred. Some examples of especially preferred conditions include retroperitoneal fibrosis, nodular fibromatosis, pseudosarcomatous fibromatosis, fibrosarcomas, sclerosing mesenteritis, acute respiratory disease syndrome, idiopathic pulmonary fibrosis, diffuse proliferative glomerulonephritis of various types, gliomas, glioblastomas, gliosis, and all types of leukemias and lymphomas.

The process of identification of members of the RFHV/KSHV subfamily preferably involves the use of the methods and reagents provided in this invention, either singularly or in combination.

One method involves amplifying and/or characterizing a polynucleotide encoding a DNA polymerase in the sample. This can be performed, for example, by amplifying the polynucleotide in a reaction such as a PCR, using an RFHV/KSHV subfamily specific oligonucleotide, such as those listed in Table 6, as a primer in the reaction. The presence of amplified reaction product suggests polynucleotide in the sample derived from a member of the RFHV/KSHV subfamily.

Members of the subfamily can also be identified by performing a hybridization assay on the polynucleotide of the sample, using a suitable probe. The polynucleotide to be tested may optionally be amplified before conducting the hybridization assay, such as by using an oligonucleotide listed in Table 4 or Table 6 in a PCR. Preferred probes for the hybridization assay include the oligonucleotides of Table 6. Other preferred probes are fragments of 16 nucleotides or more of the polynucleotide encoding DNA polymerase from either RFHV or KSHV, preferably contained in SEQ. ID NO:1 or SEQ. ID NO:3. The hybridization reaction is performed under the least stringent conditions wherein the probe will not form a stable duplex with a polynucleotide comprising any of SEQ. ID NOS:23 to 29, but will form a stable duplex with a polynucleotide comprising SEQ. ID NO:1 or a polynucleotide comprising SEQ. ID NO:3, and preferably either one. Formation of a stable duplex with the test polynucleotide under these conditions suggests the presence of a polynucleotide in the sample derived from a member of the RFHV/KSHV subfamily.

Members of the subfamily can also be identified by using a reagent antibody of a specificity that cross-reacts between antigens produced by members of the subfamily, but not with other antigens, including those produced by herpes viruses not members of the subfamily. Methods for producing such antibodies were outlined in an earlier section. The test is performed, for example, by using the antibodies in an immunohistochemistry study of tissue sections prepared from individuals with the conditions listed above. Positive staining of a tissue section with the antibody suggests the presence of DNA polymerase in the sample from a member of the RFHV/KSHV subfamily, probably because the tissue is infected with the virus. Similarly, if antibodies cross-reactive with RFHV or KSHV antigens but not with other herpes virus antigens are found in the circulation of an individual, this suggests that the individual has been subject to a present or past infection with a member of the RFHV/KSHV subfamily.

Once a member of the RFHV/KSHV subfamily is suspected in a biological sample, it is desirable to obtain a fragment of the DNA polymerase gene corresponding to nucleotides 330–501 of FIG. 1. The fragment is sequenced according to standard techniques to determine whether the virus is a bone fide member of the RFHV/KSHV subfamily, as defined herein. A preferred method of identifying members of the RFHV/KSHV subfamily is provided below in Examples 11 and 12.

Once a new member of the RFHV/KSHV subfamily has been identified, other embodiments of this invention may be brought into play for purposes of detection, diagnosis, and pharmaceutical development. Changes to render them suitable for the new subfamily member, if required, are expected to be minor and will be obvious based on the new sequence data, or will be a matter of routine adjustment.

Altered forms of DNA polymerase from the RFHV/KSHV subfamily

This invention also embodies altered forms of DNA polymerase of the RFHV/KSHV subfamily. As described earlier, work with DNA polymerase from other herpes viruses has helped pinpoint active regions and residues of the molecule involved in substrate binding, polymerase activity, or drug resistance. Some of the residues described appear in conserved regions of the polymerase molecule, and are identical between RFHV, KSHV, and the virus in which they were originally described. By analogy, mutation of the same residue in the DNA polymerase of the RFHV/KSHV subfamily is expected to have a similar effect:

TABLE 9

Possible Effect of Amino Acid Substitutions in DNA Polymerase of the RFHV/KSHV Subfamily

| Change | Position | Effect |
|---|---|---|
| Y → F | 8 | Reduction of DNA polymerase activity |
| N → Y | 103 | |
| Y → F or S | 106 | |
| G → D | 107 | |
| Y → F | 168 | |
| G → R | 169 | |
| D → G or N | 170 | |
| T → K or P | 171 | |
| D → A or G | 172 | |
| A → V | 5 | Increased resistance to antiviral compounds |
| S → N | 10 | |
| P → T | 85 | |
| T → M | 101 | |
| R → S | 130 | |

The numbering of the residues in Table 9 begins with the first amino acid encoded by the entire DNA polymerase polynucleotide fragment of KSHV shown in FIG. 1 (i.e., the first amino acid of SEQ. ID NO:4).

DNA polymerase activity is believed to be essential for replication of a herpes virus. Mutations shown in Table 9 that are expected to impair DNA polymerase activity may therefore be useful in creating attenuated forms of the respective virus. Other mutations may increase or decrease the resistance of the RFHV or KSHV polymerase to antiviral drugs.

Herpes viruses, particularly attenuated forms, are useful in developing viral vectors for therapeutic purposes (Johnson et al., Ward et al.). One such use is in the development of polyvalent vaccines. It is desirable, especially in developing countries, to provide prophylactic vaccines capable of stimulating the immune system against several potential pathogens simultaneously. Viruses that are engineered to express immunogenic peptides of several different pathogens may accomplish this purpose. Herpes viruses may be especially suitable vectors, because the large genome may easily accommodate several kilobases of extra DNA encoding the peptides. Ideally, the viral vector is sufficiently intact to exhibit some biological activity and attract the attention of the host's immune system, while at the same time being sufficiently attenuated not to cause significant pathology. Thus, an attenuated virus of the RFHV/KSHV subfamily may be useful as a vaccine against like virulent forms, and may be modified to express additional peptides and extend the range of immune protection.

Another use for attenuated forms of herpes viruses is as delivery vehicles for gene therapy (Latchman et al., Glorioso et al.). In order to be effective, polynucleotides in gene therapy must be delivered to the target tissue site. In the treatment of fibrotic diseases, malignancies and related conditions, attenuated viral vectors of the RFHV/KSHV subfamily may be preferable over other targeting mechanisms, including other herpes viruses, since they have the means by which to target towards the affected tissues. In this embodiment, the virus is first attenuated, and then modified to contain the polynucleotide that is desired for gene therapy, such as those that are outlined in a previous section.

The foregoing description provides, inter alia, a detailed explanation of how DNA polymerase encoding regions of herpes viruses can be identified and their sequences obtained. Polynucleotide sequences for regions of the DNA polymerase gene of RFHV and KSHV are provided.

The polynucleotide sequences provided are believed to be an accurate rendition of the sequences contained in the polynucleotides from the herpes viruses in the tissue samples used for this study. However, it is recognized that sequences obtained by amplification methods such as PCR may comprise occasional errors in the sequence as a result of amplification. The error rate is estimated to be between about 0.44% and 0.75% for single determinations; about the same rate divided by $\sqrt{(n-1)}$ for the consensus of n different determinations. Nevertheless, the error rate may be as high as 2% or more. Sequences free of amplification errors can be obtained by creating a library of herpes virus polynucleotide sequences, using oligonucleotides such as those provided in Table 7 to select relevant clones, and sequencing the DNA in the selected clones. The relevant methodology is well known to a practitioner of ordinary skill in the art: see, e.g., Example 9.

It is recognized that allelic variants and escape mutants of herpes viruses occur.

Polynucleotides and polypeptides may be isolated or derived that incorporate mutations, either naturally occurring, or accidentally or deliberately induced, without departing from the spirit of this invention.

The examples presented below are provided as a further guide to a practitioner of ordinary skill in the art, and are not meant to be limiting in any way.

EXAMPLES

Example 1
Oligonucleotide primers for Herpes Virus DNA polymerase

Amino acid sequences of known herpes virus DNA polymerases were obtained from the PIR protein database, or derived from DNA sequences obtained from the GenBank database. The sequences were aligned by computer-aided alignment programs and by hand. Several conserved regions were apparent. Three of the most highly conserved regions were chosen for design of amplification primers. The regions selected are indicated in FIG. 2 as REGION 1, REGION 2, and REGION 3.

Having identified suitable conserved regions from the amino acid sequences, the DNA sequences for these regions were used to design the oligonucleotide primers. The primers were designed to have a degenerate segment of 12–14 base pairs at the 3' end, and a consensus segment of 18–30 bases at the 5' end. This provides primers with optimal sensitivity and specificity.

The degenerate segment extended across the most highly conserved region of herpes virus DNA polymerase sequences, encompassing the least number of alternative codons. The primers could therefore be synthesized with alternative nucleotide residues at the degenerate positions and yield a minimum number of combinations. There were no more than 256 alternative forms for each of the primers derived.

The consensus segment was derived from the corresponding flanking region of the DNA polymerase sequences. Generally, the consensus segment was derived by choosing the most frequently occurring nucleotide at each position of all the DNA polymerase sequences analyzed. However, selection was biased in favor of C or G nucleotides, to maximize the ability of the primers to form stable duplexes.

Results are shown in FIGS. 3–5, and summarized in Table 4. FIG. 3 shows DNA sequences of known herpes virus DNA polymerase genes near REGION 2. These sequences were used to design the oligonucleotides DFASA and DFQSA, as shown. In a PCR, these oligonucleotides would act as primers by hybridizing with the strand antisense to the coding strand, and initiating polymerization in the same direction as the DNA polymerase encoding sequence. FIG. 4 shows DNA sequences near REGION 3, from which the oligonucleotides VYGA, VYGCA and VYGSQA were designed for initiating polymerization in the 5' direction. FIG. 5 shows DNA sequences near REGION 3, from which the oligonucleotides GDTD1B and GDTDSQB were designed. These oligonucleotides would hybridize with the coding strand and initiate polymerization in the direction opposite to that of the DNA polymerase encoding sequence.

Synthetic oligonucleotides according to the designed sequences were ordered and obtained from Oligos Etc, Inc.

Example 2

DNA extraction

Biopsy specimens were obtained from Kaposi's sarcoma lesions from human subjects diagnosed with AIDS. Specimens were also obtained from retroperitoneal fibromatosis lesions in a colony of *Macaca nemestrina, Macaca fascicularis*, and *Macaca fuscata* at the University of Washington Regional Primate Research Center.

The specimens were fixed in paraformaldehyde and embedded in paraffin, which were processed for normal histological examination.

Fragments of the paraffin samples were extracted with 500 μL of xylene in a 1.5 mL EPPENDORF™ conical centrifuge tube. The samples were rocked gently for 5 min at room temperature, and the tubes were centrifuged in an EPPENDORF™ bench-top centrifuge at 14,000 rpm for 5 min. After removing the xylene with a Pasteur pipette, 500 μL of 95% ethanol was added, the sample was resuspended, and then re-centrifuged. The ethanol was removed, and the wash step was repeated. Samples were then air-dried for about 1 hour. 500 μL of proteinase-K buffer (0.5% TWEEN™ 20, a detergent; 50 mM Tris buffer pH 7.5, 50 mM NaCl) and 5 μL of proteinase K (20 mg/mL) were added, and the sample was incubated for 3 h at 55° C. The proteinase K was inactivated by incubating at 95° C. for 10 min.

Example 3

Obtaining amplified segments of RFHV and KSHV DNA polymerase

The oligonucleotides obtained in Example 1 were used to amplify DNA extracted in Example 2, according to the following protocol.

A first PCR reaction was conducted using 1 μL of DNA template, 1 μL of oligonucleotide DFASA (50 pmol/μL), 1 μL of oligonucleotide GDTD1B (50 pmol/μL), 10 μL of 10×WB4 buffer (0.67 M Tris buffer pH 8.8, 40 mM $MgCl_2$, 0.16 M $(NH_4)_2SO_4$, 0.1 M β-mercaptoethanol, 1 mg/mL bovine serum albumin), 1 μL containing 2.5 mM of each of the deoxyribonucleotide triphosphates (dNTPs), 66 μL distilled water, and 50 μL mineral oil. The mixture was heated to 75° C. in a Perkin-Elmer (model 480) PCR machine. 0.5 μL Taq polymerase (BRL, 5 U/μL) and 19.5 μL water was then added. 35 cycles of amplification were conducted in the following sequence: 1 min at 94° C., 1 min at 60° C., and 1 min at 72° C.

A second PCR reaction was conducted as follows: to 1 μL of the reaction mixture from the previous step was added 10 μL 9–10×WB4 buffer, 1 μL dNTPs, 0.5 μL Taq polymerase, 86.5 μL water, and 50 μL mineral oil. The mixture was heated to 75° C., and 1 μL each of oligonucleotide VYGA (50 pmol/μL) and oligonucleotide GDTD1B (50 pmol/μL) was added. 35 cycles of amplification were conducted as before.

Example 4

Sequence of the 236 base fragment

An aliquot of the final amplification mixture of each of the samples was purified by electrophoresis on a 2% agarose gel. Of 9 *M. nemestrina* and 1 *M. fasicularis* samples used, 4 *M. nemestrina* samples yielded amplification product. Amplification product was also obtained from human samples. The agarose gel was stained with ethidium bromide and the DNA was visualized using U.V. light. Bands of the correct size were eluted onto DEAE paper. Each extracted polynucleotide was ligated to a PGEM-T™ vector and transformed into competent bacteria (*E. coli* JM-109). Bacterial clones containing the amplified DNA were picked and cultured. The bacteria were lysed and the DNA was extracted using phenol-chloroform followed by precipitation with ethanol. Sequencing was performed by the Sanger & Nicholson dideoxynucleotide method, using M13 forward and reverse primers.

The length of the fragment in between the primer hybridizing regions was 172 base pairs in length. For the four *M. nemestrina* samples used, all yielded identical sequence data. About 70% of the residues are identical in the fragment between RFHV and KSHV. Compared with the most closely related known sequences of the herpes virus family, differences in between sequences are distributed along the entire length of this fragment. The longest stretch of consecutive nucleotides that is identical between any two sequences in this fragment is 11.

The polypeptide encoded in this fragment is 81% identical between RFHV and KSHV, of which the first 24 residues are 100% identical, and the first 31 are 97% identical. The longest stretch of consecutive amino acids that is identical between RFHV or KSHV and any of the other known herpes virus DNA polymerases in this fragment is 10.

Example 5
RFHV and KSHV specific amplification assays

Four oligonucleotides were prepared based on the sequence of the polynucleotide fragment of the RFHV and KSHV DNA polymerase for use in nested virus-specific amplification reactions. Primers VASGA, ILPCA, PIEAB and PEARB were based on the RFHV sequence; primers SGILA, CLNIA, IEASB, and EARFB were based on the KSHV sequence (Table 7). The RFHV primers were used to amplify DNA samples obtained from the PBL of macaque monkeys as follows:

Uncoagulated whole blood samples were collected from 20 *M. nemestrina* born in the colony at the University of Washington. 30 blood samples were obtained from wild-caught *M. nemestrina*. None of the animals had overt symptoms of fibromatosis. Plasma and blood cells were separated by centrifugation. Peripheral blood mononuclear cells (PBMC) were prepared by centrifuging the cells through a density gradient, according to standard blood separation techniques. DNA was extracted from the cells according to the method of Example 2. The DNA was then amplified, first using primers VASGA and PEARB, then using primers ILPCA and PIEAB. The conditions of the amplification were similar to that of Example 3. The reaction product was run on an agarose gel, stained with ethidium bromide, and examined under U.V. light.

When the assay was performed in duplicate and under conditions to avoid cross-contamination of PCR reaction products, none of the RF symptom-free monkeys were found to have detectable levels of RFHV polynucleotide encoding DNA polymerase in their peripheral blood by this assay.

PBMC may also be examined by immunohistology techniques to confirm correlation between positive PCR products and RFHV antigenemia. PBMC are coated onto microscope slides, and fixed with a mixture of 50% methanol, 20% acetone and 30% water. They are overlaid with a primary serum, washed, overlaid with FITC-(rabbit anti-monkey IgG) (Nordic Labs), washed again, and then examined by fluorescence microscopy.

Antibody-containing serum may be obtained from a monkey giving a positive RFHV amplification assay result, or an animal immunized with RFHV, or an RFHV extract. Serum from a monkey with a negative result may be used as control. PBMC from animals giving a positive result in the amplification test will also give a positive immunohistology result due to antigenemia of an RFHV antigen component.

To conduct an amplification assay for KSHV, DNA is extracted from tissue suspected of harboring the virus; particularly biopsy samples from human subjects with Kaposi's Sarcoma lesions and body cavity B-cell lymphoma. The DNA is amplified in two stages, using primers SGILA and EARFB in the first stage, and CLNIA and IEASB in the second stage. As before, a positive result is indicated by the presence of abundant polynucleotide in the reaction product, as detected by ethidium bromide staining.

Example 6
Upstream sequence of the RFHV and KSHV DNA polymerase

DNA from Kaposi's Sarcoma tissue similar to that used in Example 3 was used in additional amplification reactions to obtain a longer fragment of the gene encoding KSHV DNA polymerase. The oligonucleotides DFASA and GDTD1B were used to prime a first-stage amplification reaction, as in Example 3, and the reaction product was separated on an agarose gel. The size of the fragment from DFASA to GDTD1B (now known to be 536 bases long) was estimated from the known sHV1 and EBV sequences, and a corresponding band was recovered from the gel. The extracted polynucleotide was subjected to a second round of amplification using the same primers. The product was cloned into *E. coli* as in Example 4.

Clones containing suitable inserts were identified from three different amplifications of the DNA extracted from the tissue. The clone inserts were sequenced from both ends using vector-specific oligonucleotides (M13 forward and reverse primers). About 160 nucleotides from the 5' end (including the DFASA hybridizing region) and about 233 nucleotides from the 3' end (including the GDTD1B hybridizing region) were sequenced for all three amplifications. The centermost portion of the fragment was sequenced in one of the three amplifications.

A consensus sequence for the fragment was obtained by combining results of the three determinations with the results of Example 4, as appropriate. The data are shown in FIG. 1, in comparison with the sequence determined for the RFHV DNA polymerase fragment in Example 4. Numbering of both sequences begins at the first position of primer DFASA.

Regions of each sequence corresponding to hybridization sites for DFASA and GDTD1B may not be accurate reflections of the target sequence. The fragment between the primers is believed to represent the DNA from which the polynucleotide used for sequencing was amplified. However, occasional errors may have been introduced during the amplification. Assuming the consensus sequence of KSHV to be an accurate reflection of the sequence of the DNA extracted from the tissue, there was about a 0.75% error rate in the sequence of each amplified product in the nucleotides towards the 5' end, and about a 0.44% error rate in the sequence towards the 3' end, not including the region hybridizing with the primers.

To obtain the corresponding RFHV polynucleotide sequence, DNA from frozen RF tissue of a macaque monkey was first amplified using the broad specificity DNA polymerase primer DFASA in conjunction with the RFHV specific primer PEARB, and then by DFASA in conjunction with the RFHV specific primer PIEAB.

The procedure was as follows: 5 μL of DNA template was mixed with 1 μL of each of the primers (50 pmol/μL), 10 μL of 10×WB4 buffer, 1 μL 2.5 mM dNTP, 59–65 μL water, and 60 μL mineral oil. The temperature was raised to 60° C., and Taq polymerase (0.5 μL diluted to 20 μL in water) was added. The DNA was amplified for 35 cycles of 94° C. for 1 min, 55° C. for 1 min, and 72° C. for 1 min. 2 μL of the amplified product was added to 10 μL 10×WB4 buffer, 1 μL 2.5 mM dNTP, 66.5 μL water, 0.5 μL Taq polymerase, and 60 μL mineral oil. The temperature was raised to 60° C., and then a mixture of 1 μL PIEAB (50 pmol/μL), 2 μL DFASA (50 pmol/μL), and 18 μL of water was added. Amplification cycles were conducted as before. Finally, a third round of amplification was performed to introduce a radiolabel. Oligonucleotide PIEAB was end-labeled with gamma $^{32}$P-ATP, and 1 μL was added to 20 μL of the reaction mixture from the previous amplification step, along with 1 μL 2.5 mM dNTP and 1 μL Taq polymerase. Amplification was conducted through five cycles of 94° C., 55° C. and 72° C., as before.

An aliquot of the radiolabeled reaction product was electrophoresed on a 6% polyacrylamide sequencing gel. A band of the correct size (predicted by analogy with the KSHV sequence) was identified by autoradiography, and cut out of the dried gel. DNA was eluted by incubation in 50 μL water. A further amplification reaction was performed using 2 μL of eluted DNA, 10 μL 10×WB4 butter, 1 μL 2.5 mM dNTP, 1 μL PIEAB (50 pmol/μL), 1 μL DFASA (50 pmol/μL), 0.5 μL Taq polymerase, and 84.5 μL water. Amplification was conducted through 35 cycles of 95° C. for 30 sec, 60° C. for 30 sec, and 72° C. for 65 sec. The amplified product was isolated using a QUIAEX™ gel extraction kit, and the DNA was cloned into pGEM™-t vector. JM-109 cells were transformed with the DNA, and colonies containing inserts were isolated. Colonies containing inserts of the correct size were used to obtain DNA for sequencing.

Data from these experiments were combined with that from Example 4 to provide the sequence of 536 base pairs corresponding to the RFHV and KSHV DNA polymerase gene. Omitting the outermost primer-hybridizing regions, 475 base pairs of each sequence have been determined for both RFHV and KSHV. These sequences are listed in FIG. 6, in comparison with the corresponding region of the DNA polymerase gene from other sequenced gamma herpes viruses. The longest region that is identical between the RFHV sequence and any of the other viruses is a first 20 base pair subfragment (SEQ. ID NO:110) and a second 20 base pair fragment (SEQ. ID NO:111) shared with eHV2.

FIG. 7 shows the corresponding encoded polypeptide sequences. There is a linear sequence of about 31 residues near the middle of SEQ. ID NO:2 shared between the DNA polymerase of RFHV and eHV2. This shared sequence is listed separately in SEQ. ID NO:112. A sequence of 26 amino acids is shared in the same area between RFHV and sHV1, and two sequences of 12 amino acids shared between RFHV and EBV. These areas of homology map near conserved REGION 3 of the other herpes virus DNA polymerase sequences (FIG. 2). A second shared sequence occurs near the beginning of SEQ. ID NO:4 between KSHV and other gamma herpes viruses. This sequence maps near conserved REGION 2 of other herpes virus DNA polymerase sequences. This sequence fragment shared between KSHV and other gamma herpes viruses is listed separately in SEQ. ID NO:113.

FIG. 8 provides a comparison of the protein sequence across the spectrum of different herpes viruses corresponding to the sequence encoded by the 475 base pair sequence obtained herein for RFHV and KSHV.

The degree of identity between sequences can be used to construct a relationship map between DNA polymerases, as shown in FIG. 9. The relationship between the species may reflect the relative ancestral relationship between the polypeptides, and between the organisms that encode them. Based on this analysis, RFHV and KSHV are provisionally assigned to the gamma subfamily of herpes viruses, which also includes eHV2, sHV1 and EBV. Other viruses of the RFHV/KSHV subfamily would be assignable to the herpes virus gamma subfamily on this basis.

Example 7
Oligonucleotide primers and probes for the RFHV/KSHV subfamily

Based on the sequence of the 475 base pair polynucleotide fragment obtained for RFHV and KSHV, five oligonucleotides were designed that could be used either as PCR primers or as hybridization probes with members of the RFHV/KSHV subfamily. These oligonucleotides were designated LSGGA, CTDPA, PCLNA, KMLEA, and GISPA.

These oligonucleotides are shown in FIG. 10, alongside the sequences they were derived from. Like the oligonucleotides of Example 1, they have a consensus segment towards the 5' end, and a degenerate segment towards the 3' end. However, these oligonucleotides are based only on the RFHV and KSHV sequences, and will therefore preferentially form stable duplexes with DNA polymerase of the RFHV/KSHV subfamily.

Under hybridization conditions that permit them to form stable duplexes with the RFHV or KSHV encoding polynucleotide fragment, they are expected to form stable duplexes with more members of the RFHV/KSHV subfamily than would equal-length polynucleotides of the RFHV or KSHV sequence, either alone or in combination.

Both oligonucleotides are oriented in the same direction. In a PCR amplification reaction, one or the other of these oligonucleotides may be used as primers in combination with a primer with the opposite orientation, such as GDTD1B.

Example 8
Antigenic and immunogenic regions of RFHV and KSHV DNA polymerase

Based on the 475 base pair polynucleotide sequence of the RFHV and KSHV DNA polymerase encoding region, it is possible to predict what sites on the protein unique for each virus, and therefore constitute potential sites for the binding of virus-specific antibodies.

FIG. 7 shows example peptides of 6 or 7 amino acids in length. Some of the peptides comprise one or more residues that are distinct either for RFHV or KSHV (Class III), or for the RFHV/KSHV subfamily (Class II) compared with the corresponding gamma herpes virus peptides. These peptides were listed earlier in Table 8. The numbering of the amino acid residues in both FIG. 7 and Table 8 begins with the first amino acid coded after the hybridization site of the VYGA primer (nucleotide position 331 of FIG. 1).

To confirm that regions contained within this 57-amino acid region of the DNA polymerase may be recognized by antibody, computer analysis was performed to generate Hopp and Woods antigenicity plots. The Hopp and Woods determination is based in part on the relative hydrophilicity and hydrophobicity of consecutive amino acid residues (Hopp et al).

Figure 11:
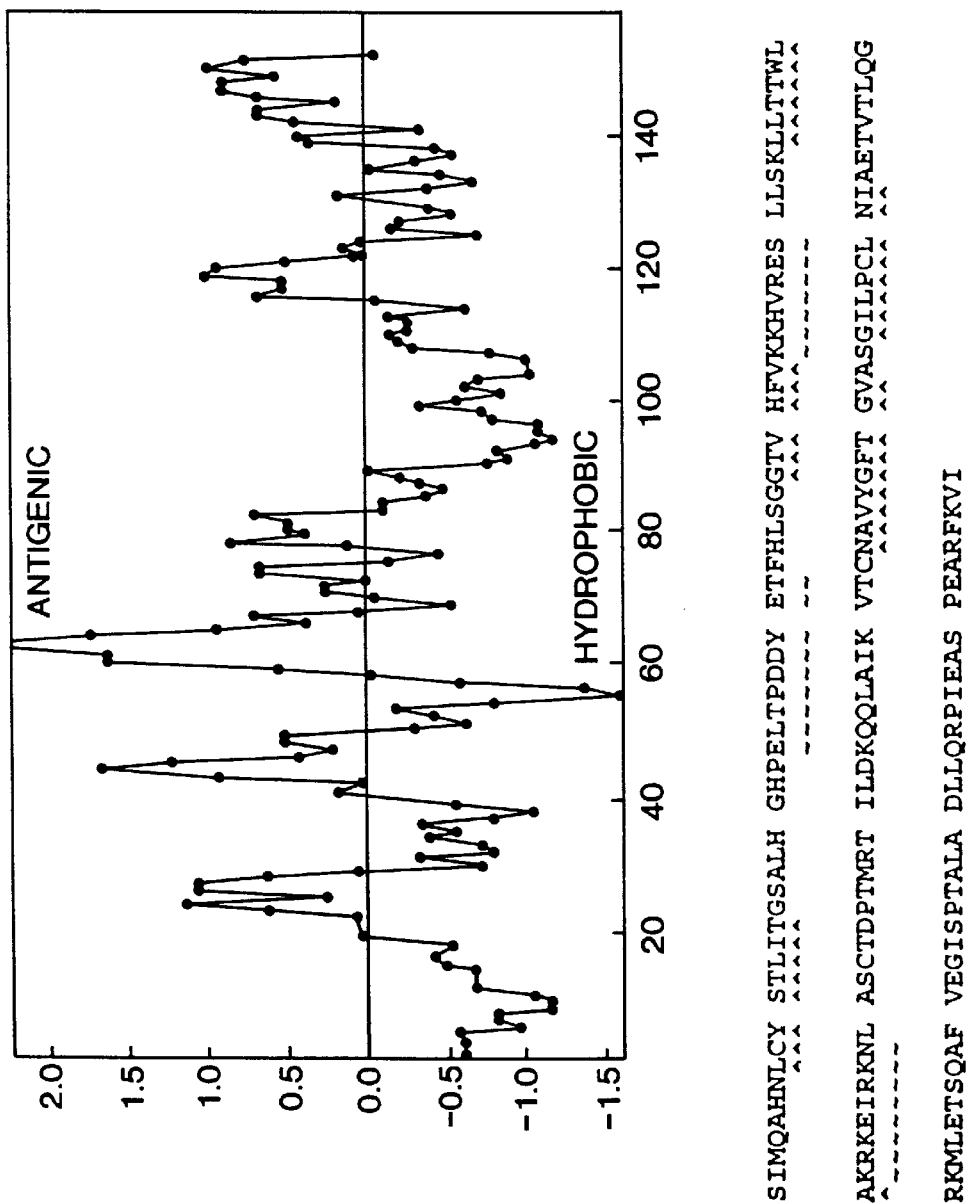
FIG. 11 is a Hopp-Woods antigenicity plot for the polypeptide fragment of RFHV encoded between VYGA and GDTD1B. Indicated below are spans of hydrophobic and antigenic residues in the sequence.
Figure 12:
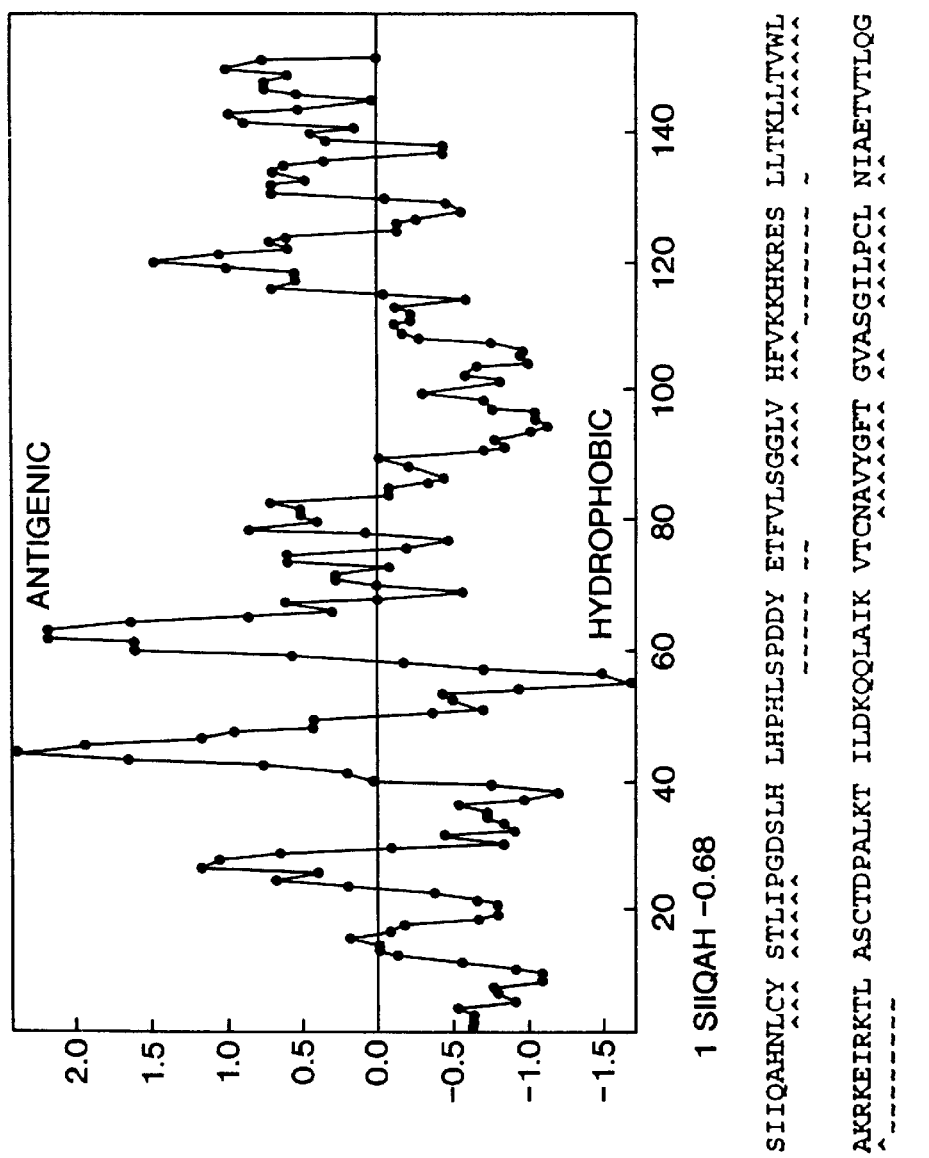
FIG. 12 is a Hopp-Woods antigenicity plot for the polypeptide fragment of KSHV encoded between DFASA and GDTD1B. Indicated below are spans of hydrophobic and antigenic residues in the sequence.

Results are shown in FIG. 11 and FIG. 12. The numbering of RFHV begins with the first amino acid coded after the VYGA primer (as in FIG. 7). The numbering of the KSHV polypeptide residues in FIG. 12 begins with the first amino acid coded after the hybridization site of the DFASA primer (nucleotide position 28 of FIG. 1).

Both RFHV and KSHV contain several regions predicted to be likely antibody target sites. For example, the RFHV shows several hydrophobic and antigenic patches along the amino acid sequence. KSHV shows hydrophobic patches beginning at residues 26, 44, 52, 121 and 151; and antigenic patches beginning at residues 8, 37, 45, and 94. The peptides of FIG. 7 that correspond to some of these regions may be especially antigenic.

Example 9
Sequencing the complete RFHV and KSHV DNA polymerase coding region

Additional sequence data for the KSHV DNA polymerase encoding region has been obtained to the 5' and 3' direction of the segment described in Example 6.

Two Kaposi's sarcoma samples, designated K-12 and K-15, were used to prepare DNA according to the method of Example 2.

Additional Type 1 oligonucleotide primers were designed to hybridize with herpes virus DNA polymerase nucleic acid sequences flanking the KSHV sequence already obtained. Examples are shown in Table 10:

pelleted separately. Proteinase-K buffer was added to each pellet and incubated at 65° C. for 1 h. DNA was extracted twice with 1:1 (vol:vol) phenol:chloroform, precipitated and washed in ethanol, and resuspended in 10 mM Tris buffer pH 8.0.

Approximately 0.5 µg total genomic DNA from BC-1 and BC-2 cell lines was used with 25 pmol of oligonucleotide

TABLE 10

Additional Type 1 Oligonucleotides used for Detecting, Amplifying, or Characterizing Herpes Virus Polynucleotides encoding DNA Polymerase

| Designation | Sequence (5' to 3') | Length | No. of forms | Target: | Orientation | SEQ ID: |
|---|---|---|---|---|---|---|
| QAHNA | CCAAGTATCATHCARGCNCAYAA | 23 | 48 | Herpes DNA polymerase | 5'→3' | 105 |
| QAHNB | GGAGTAGCACAARTTRTGNGCYTG | 24 | 32 | Herpes DNA polymerase | 3'→5' | 106 |
| YGDT1B | AACACAGAGTCNGTRTCNCCRTA | 23 | 64 | Herpes DNA polymerase | 3'→5' | 124 |
| HNLCA | AGCATCATCATGGCCCAYAAYCTNTGYT | 28 | 32 | Herpes DNA polymerase | 5'→3' | 125 |
| DFASLYA | GAYTTYGCNAGYYTNTAYCC | 20 | 512 | Herpes DNA polymerase | 5'→3' | 126 |
| FDIEC1B | CACCCATRCAYTCDATRTCRAA | 22 | 48 | Herpes DNA polymerase | 3'→5' | 127 |
| DIECA | TACAACGTCCTCTCCTTYGAYATHGARTG | 29 | 24 | Herpes DNA polymerase | 5'→3' | 128 |
| CVN1A | GTCTGCGTGAAYGTNTTYGGNCA | 23 | 64 | Herpes DNA polymerase | 5'→3 | 129 |
| CVNVA | GACGACCGCAGCGTGTGCGTGAAYGTNTTYGGNCA | 35 | 64 | Herpes DNA polymerase | 5'→3' | 130 |
| CVNVSQA | ACGACCGCAGCGTGTGCGTG | 20 | 1 | Herpes DNA polymerase | 5'→3' | 131 |
| CVNVB | TAAAAGTACAGCTCCTGCCCGAANACRTTNACRCA | 35 | 64 | Herpes DNA polymerase | 3'→5' | 132 |
| CVNVSQB | TAAAAGTACAGCTCCTGCCCGAA | 23 | 1 | Herpes DNA polymerase | 3'→5' | 133 |
| SLYP1A | TTTGACTTTGCCAGCCTGTAYCCNAGYATNAT | 32 | 256 | Herpes DNA polymerase | 5'→3' | 134 |
| SLYP2A | TTTGACTTTGCCAGCCTGTAYCCNTCNATNAT | 32 | 128 | Herpes DNA polymerase | 5'→3' | 135 |
| SLYPSQA | TTTGACTTTGCCAGCCTGTA | 20 | 1 | Herpes DNA polymerase | 5'→3' | 136 |
| GDTD2B | CGGCATGCGACAAACACGGAGTCCGTRTCNCCRTADAT | 38 | 48 | Herpes DNA polymerase | 3'→5' | 137 |
| YFDKB | TTAGCTACTCCGTGGAGCAGYTTRTCRAARTA | 32 | 16 | Herpes DNA polymerase (especially gamma) | 3'→5' | 138 |

PCR amplification was conducted as follows: 100 ng of DNA from each sample was first amplified in 50 µL total reaction buffer under the following conditions: 1×PCR buffer (67 mM Tris buffer pH 8.8, 16 mM (NH4)2SO4, 10 mM β-mercaptoethanol, 0.1 mg/niL bovine serum albumin), 2 mM MgCl2, 50 pmol of each oligonucleotide CVN1A and FDIEC1B, 100 µM (each) dATP, dCTP, dGTP, dTTP, 1.25 units Taq DNA polymerase (AMPLITAQ™, Perkin-Elmer Cetus). Amplification was conducted through 45 cycles of 95° C. for 30 sec; 50° C. for 30 sec, and 72° C. for 30 sec. PCR products were electrophoresed on a 2% agarose gel and visualized by ethidium bromide staining.

PCR products were purified using QIAQUICK SPIN™ PCR purification kit (Qiagen, Chatsworth Calif.). Products were cloned into PT7BLUE® Vectors (Novagen, Madison Wis.). Plasmids were purified using QUIAGEN SPIN™ plasmid miniprep kit. Purified plasmids were sequenced using ABI automated sequencing methodology, using M13 forward and reverse primers. Five clones were sequenced from each of K-12 and K-15.

DNA was isolated from BC-1 and BC-2 cell lines as follows: 5×10⁵ cells from each line were washed in PBS and primers CVNVA and EARFB, 2.5 units Taq DNA polymerase (Boehringer-Mannheim), 250 µM dNTP, and 4 mM MgCl$_2$ in a total volume of 100 µL of 1×PCR buffer. PCR amplification was conducted using a "hot start" at 70° C. for 1 min prior to adding the Taq polymerase, and conducted through 35 cycles of 94° C. for 45 sec; 60° C. for 45 sec, and 72° C. for 90 sec. PCR products were electrophoresed on a 2% agarose gel and visualized by ethidium bromide staining.

PCR products were purified and cloned into PT7BLUE® vectors as before. Purified plasmids were sequenced using ABI automated sequencing methodology using KSHV sequence specific primers RDSWA, FDCSA, YSTLB, and DYETB. DNA sequences were analyzed using the GenePro algorithm for single alignments open reading frames. The ClustalW algorithm was used for determining consensus sequences for multiple alignments.

The nucleotide sequence obtained is shown in FIG. 13 (SEQ. ID NO:116) along with the encoded amino acid sequence (SEQ. ID NO:117). In total, 2511 nucleotides are shown, of which the first 35 correspond to the CVNVA primer, and the last 12 correspond to the YFDKB primer. Bases 36 to 2499 of SEQ. ID NO:116, corresponding to amino acids 13 to 833 of SEQ. ID NO:117, represent the KSHV DNA polymerase sequence.

Alignment of the KSHV DNA polymerase amino acid sequence with other herpes viruses is shown in FIG. 14. Residues marked with an asterisk (*) are identical amongst all the sequences shown. Residues marked with a bullet (•) represent conservative amino acid substitutions. Residues marked with an arrow (↑) are of interest, because they are conserved between other herpes viruses but are different in KSHV. One of these is a histidine in KSHV in the position of an aspartic acid in other viruses, which is a non-conservative difference. Residues marked with an arrow may be suitable targets for antibodies or drugs that are specific for KSHV or for the RFHV/KSHV subfamily.

Amongst four KSHV DNA polymerase nucleotide sequences obtained, variations were noted in four positions. These are believed to represent naturally occurring allelic variants. At about nucleotide 319, the sequence TTCTCG was alternatively found as TTTTCG, which is a silent variation (not affecting the encoded protein sequence). At about nucleotide 348, the sequence AACCCG was alternatively found as AATCCG, which is also a silent mutation. At about nucleotide 1795, the sequence CCAGTA was alternatively found to be CCAATA, which represents a change of the encoded peptide from -Pro-Val- to -Pro-Ile. At about nucleotide 1822, the sequence TTCAAG was alternatively found to be TTCAGG, which represents a change of the encoded peptide from -Phe-Lys- to -Phe-Arg-. Alignment of the KSHV amino acid sequence variants with DNA polymerase sequences of other herpes viruses is shown in FIG. 15.

Comparison of the KSHV DNA polymerase nucleotide sequence with that of other herpes viruses led to design of additional Type 3 (virus-specific) oligonucleotides, listed in Table 11:

the 5' and 3' direction of the sequence shown. The remaining sequence may be determined by conducting the approach described on samples of affected tissue, using Type 1 oligonucleotides to sequence in from genes flanking the DNA polymerase in both the upstream and downstream direction.

Alternatively, complete DNA polymerase sequences may be obtained by generating DNA libraries from affected tissue. For the RFHV sequence, libraries are prepared from macaque monkey PBMC known from the amplification assay of Example 5 to contain RFHV DNA. For the KSHV sequence, libraries are prepared from Kaposi's sarcoma lesions or B cell body cavity lymphoma.

The DNA lysate is digested with proteinase K, and DNA is extracted using phenolchloroform. After extensive dialysis, the preparation is partially digested with the Sau3A I restriction endonuclease. The digest is centrifuged on a sucrose gradient, and fragments of about 10–23 kilobases are recovered. The lambda DASH-2™ vector phage (Stratagene) is prepared by cutting with BamHI. The size-selected fragments are then mixed with the vector and ligated using DNA ligase.

The ligated vector is prepared with the packaging extract from Stratagene according to manufacturer's directions. It is used to infect XL1-BLUE™ MRA bacteria. About 200,000 of the phage-infected bacteria are plated onto agar at a density of about 20,000 per plate. After culturing, the plates are overlaid with nitrocellulose, and the nitrocellulose is cut into fragments. Phage are eluted from the fragments and their DNA are subjected to an amplification reaction using appropriate virus-specific primers. The reaction products are run on an agarose gel, and stained with ethidium bromide. Phage are recovered from regions of the plate giving amplified DNA of the expected size. The recovered phage are used to infect new XL1 bacteria and re-plated in fresh cultures. The process is repeated until single clones are obtained at limiting dilution.

Each clone selected by this procedure is then mapped using restriction nucleases to ascertain the size of the

TABLE 11

Additional Type 3 Oligonucleotides Specific for Polynucleotides Encoding DNA Polymerase from KSHV

| Designation | Sequence (5' to 3') | Length | No. of forms | Target: | Orientation | SEQ ID: |
|---|---|---|---|---|---|---|
| SIIQB | TTGTGCGCTTGGATGATACTG | 21 | 1 | KSHV DNA polymerase | 5'→3' | 139 |
| HVLQB | GAGGGCCTGCTGGAGGACGTG | 21 | 1 | | 3'→5' | 140 |
| SCGFB | CGGTGGAGAAGCCGCAGGATG | 21 | 1 | | 3'→5' | 141 |
| LPHLA | ACCTCCCGCACCTGACCGTGT | 21 | 1 | | 5'→3' | 142 |
| QARQA | AAGCTAGACAGGAGGAGCTTC | 21 | 1 | | 5'→3' | 143 |
| KIIQG | ACTTGAATTATCTTGACGAAC | 21 | 1 | | 5'→3' | 144 |
| KVLMA | ACGACAAGGTTCTGATGAAGG | 21 | 1 | | 5'→3' | 145 |
| RDSWA | AGAGACTCTTGGACGGAACTG | 21 | 1 | KSHV DNA polymerase | 5'→3' | 146 |
| FDCSA | AGTTTGACTGCAGCTGGGAGG | 21 | 1 | | 5'→3' | 147 |
| YSTLB | CGGGTATCAGTGTGGAGTAGC | 21 | 1 | | 3'→5' | 148 |
| DYEFTB | GAGGACAAAGGTTTCGTAGTC | 21 | 1 | | 3'→5' | 149 |

Based upon other gamma herpes viruses, the KSHV DNA polymerase sequence is predicted to comprise a total of about 3000 base pairs, with additional nucleotides in both fragment incorporated. Inserts sufficiently large to incorporate the entire DNA polymerase sequence are sequenced at both ends using vector-specific primers. Sequences are compared with the known polynucleotide sequence of the entire EBV genome to determine whether the fragment spans the intact DNA polymerase sequence. DNA is obtained from suitable clones, sheared, and sequenced by shot-gun cloning according to standard techniques.

Example 10
Identifying immunogenic sites

To identify what antibodies may be generated during the natural course of infection with RFHV, serial serum samples are obtained from 10–20 macaque monkeys giving a positive result in an RFHV DNA polymerase amplification test with PBMC, as in Example 5. To test for antibodies against KSHV, serum samples are obtained from 10–20 AIDS subjects with Kaposi's Sarcoma lesions, from 10–20 HIV-positive symptom-negative subjects, and 10–20 HIV-negative controls. In initial studies, sera in each population are pooled for antibody analysis.

Peptides 12 residues long are synthesized according to the RFHV or KSHV sequence, as appropriate. Sequential peptides are prepared covering the entire sequence, and overlapping by 8 residues. The peptides are prepared on a nylon membrane support by standard F-Moc chemistry, using a SPOTS™ kit from Genosys according to manufacturer's directions. Prepared membranes are overlaid with the serum, washed, and overlaid with beta-galactose conjugated anti-monkey IgG or anti-human IgG, as appropriate. The test is developed by adding the substrate X-gal. Positive staining indicates IgG antibody reactivity in the serum against the corresponding peptide.

Example 11

Obtaining other DNA polymerase sequences of the RFHV/KSHV subfamily

A DNA polymerase encoding sequence from a third member of the RFHV/KSHV herpes virus subfamily was obtained as follows.

DNA was extracted from two frozen tissue samples from a *Macaca mulatta* monkey with retroperitoneal fibromatosis. Extraction was conducted according to Example 1. The extracted DNA was precipitated with ethanol in the presence of 40 μg glycogen as carrier, washed in 70% ethanol, and resuspended in 10 mM Tris buffer, pH 8.0.

A 151 base pair fragment of a DNA polymerase encoding sequence was amplified using a triple-nested PCR: 100 ng of DNA from each sample was first amplified in 100 μL total reaction buffer under the following conditions: 1×PCR buffer (67 mM Tris buffer pH 8.8, 16 mM $(NH4)_2SO_4$, 10 mM β-mercaptoethanol, 0.1 mg/ML bovine serum albumin), 4mM $MgCl_2$, 25 pmol of each oligonucleotide VYGA and VYGCA, and 50 pmol of oligonucleotide GDTD1B, 25 μM (each) dATP, dCTP, dGTP, dTTP, 2.5 units Taq DNA polymerase (Boehringer-Mannheim). Amplification was conducted using a "hot start" at 70° C. for 1 min prior to adding the Taq polymerase, and conducted through 42 cycles of 94° C. for 30 sec; 60° C. for 30 sec, and 72° C. for 30 sec. A second amplification used 2 μL of the primary PCR product as template in 50 μL reaction volume as before, except that 25 pmol of each oligonucleotide PCLNA and GDTDSQB and 1.25 units Taq polymerase were used. Amplification was conducted using a "hot start" and 35 cycles of the same conditions as before. A third amplification used 2 μL of the secondary PCR product as template in 50 μL reaction volume as before, except that 25 pmol of each oligonucleotide KMLEA and GDTDSQB and 1.25 units Taq polymerase were used. Amplification was conducted using a "hot start" and 35 cycles of 94° C. for 30 sec; 65° C. for 30 sec, and 72° C. for 30 sec.

The final PCR product was electrophoresed on a 3% agarose gel, and visualized by ethidium bromide staining. PCR products were purified using QIAQUICK SPIN™ PCR purification kit (Qiagen, Chatsworth Calif.). Products were cloned into PC7BLUE® vectors (Novagen, Madison Wis.). Plasmids were purified using QUIAGEN SPIN™ plasmid miniprep kit. Purified plasmids were sequenced using M13 forward and reverse primers with the USB Sequenase 7-deaza-dGTP kit.

Based on the sequence of the 151 base pair fragment, two sequence-specific (Type 3) oligonucleotides were designed, designated KVIYB and ASPDB. These were used in a nested PCR amplification with the Type 1 oligonucleotide QAHNA to obtain a 468 base pair fragment. The first amplification was conducted by using ~1 μg of each DNA sample in 100 μL PCR mixture as before, except that 50 pmol of each of QAHNA and KVIYB were used as primers. Amplification was conducted using a "hot start" and 35 cycles of 94° C. for 30 sec; 55° C. for 60 sec, and 72° C. for 60 sec. The second amplification was conducted using 3 μL primary PCR product as template in 100 μL reaction volume and 50 pmol of QAHNA and ASPDB as primers. Amplification was conducted using a "hot start" and 40 cycles of 94° C. for 30 sec; 60° C. for 60 sec, and 72° C. for 60 sec. PCR products were then electrophoresed on a 2.5% agarose gel, and visualized by ethidium bromide staining. PCR products were cloned into PC7BLUE® vectors and sequenced as before.

The nucleotide sequence obtained is shown in FIG. 16, shown with the designation "RFMm" (SEQ. ID NO:118). This corresponds to a DNA polymerase encoding sequence referred to elsewhere in this application as "RFHVMm" or "RFHV2". The encoded protein sequence is shown in FIG. 17 (SEQ. ID NO:119).

Identity analysis with DNA polymerase sequences of RFHVMm with other herpes viruses is shown in Table 12:

TABLE 12

Sequence Identities Between RFHV2 and other herpes viruses

| Viral DNA Polymerase Sequence | SEQ. ID NO: | Identity to RFHV 2 fragment (SEQ. ID NO:118) Bases 1–454 | Identity to RFHV fragment (SEQ. ID NO:1) Bases 48–501 | Identity to KSHV fragment (SEQ. ID NO:3) Bases 48–501 |
|---|---|---|---|---|
| RFHV/KSHV subfamily: | | | | |
| RFHV2 (RFHVMm) | 118 | — | 83% (90%) | 71% (84%) |
| RFHV1 (RFHVMn) | 1 | 83% (90%) | — | 69% (81%) |
| KSHV | 3 | 69% (81%) | 71% (84%) | — |

TABLE 12-continued

Sequence Identities Between RFHV2 and other herpes viruses

| Viral DNA Polymerase Sequence | SEQ. ID NO: | Identity to RFHV 2 fragment (SEQ. ID NO:118) Bases 1–454 | Identity to RFHV fragment (SEQ. ID NO:1) Bases 48–501 | Identity to KSHV fragment (SEQ. ID NO:3) Bases 48–501 |
|---|---|---|---|---|
| gamma herpes | | | | |
| eHV2 | 23 | 63% (66%) | 68% (68%) | 68% (73%) |
| sHV1 | 24 | 60% (64%) | 59% (64%) | 62% (68%) |
| EBV | 25 | 57% (62%) | 54% (63%) | 62% (68%) |
| alpha herpes | | | | |
| HSV1 | 36 | 52% (43%) | 53% (46%) | 53% (46%) |
| HSV2 | 37 | 53% (44%) | 53% (46%) | 53% (46%) |
| VZV | 35 | 42% (41%) | 45% (43%) | 48% (45%) |
| beta herpes | | | | |
| hCMV | 33 | 45% (38%) | 53% (41%) | 49% (40%) |
| hHV6 | 42 | 44% (38%) | 46% (41%) | 48% (41%) |

Figure 18:
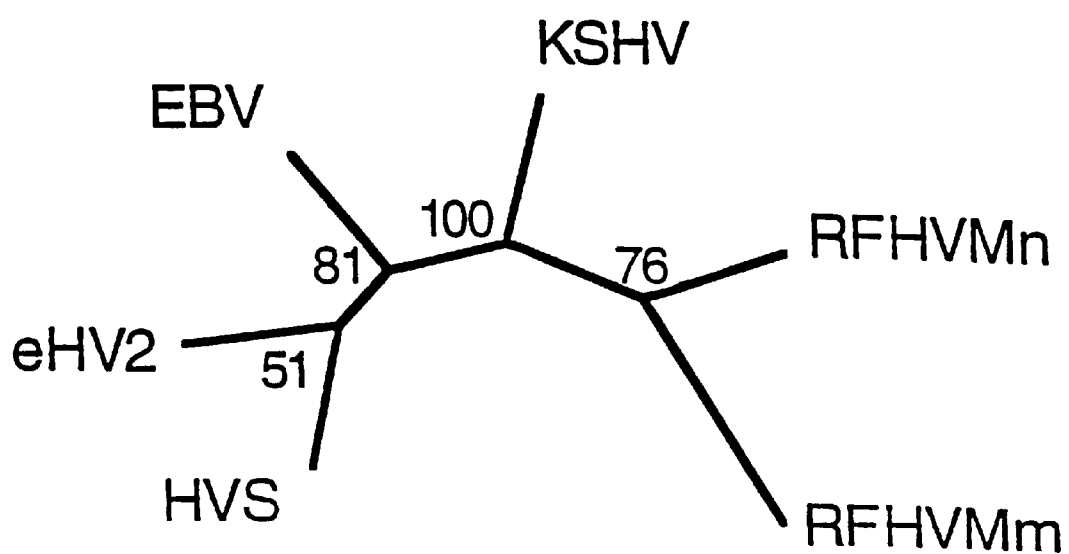
FIG. 18 is a statistical phylogeneic analysis of the amino acid alignments in FIG. 17. The numbers shown are bootstrap values out of 100 repetitions.

Phylogenetic studies were performed using distance matrices, neighbor joining and bootstrap analysis, as implemented in the PHYLIP analysis package. FIG. 18 shows the results of the bootstrap analysis, with the numbers indicated being the score out of 100 supporting the branch points shown. This analysis strongly supports a branch point that separates the RFHV/KSHV subfamily from other gamma herpes viruses. RFHVMm and RFHVMn are more closely related to each other than either are to KSHV.

Sequences were also analyzed for G+C content. Results are shown in Table 13. The percentage of G+C across the region corresponding to the 454 bp of RFHVMm is shown, as calculated using GenePro software (Riverside Scientific). Values in parenthesis are G+C content calculated for the entire DNA polymerase sequence, where known. Also shown are CpG ratios, which is the ratio of observed:expected frequencies of CpG, taking into consideration the monomucleotide composition.

TABLE 13

G + C mononucleotide and CpG dinucleotide frequencies in the DNA polymerase genes of different herpesviruses

| Herpes Virus | Subfamily | G + C | CpG ratio |
|---|---|---|---|
| RFHVMn | RFHV/KSHV | 55.9% | 0.96 |
| RFHVMm | (gamma) | 51.1% | 1.13 |
| KSHV | | 54.4% | 0.91 |
| eHV2 | other gamma | 64.8% (63.6%) | 0.71 (0.75) |
| sHV1 | | 39.9% (34.9%) | 0.28 (0.33) |
| EBV | | 64.4% (61.8%) | 0.73 (0.70) |

TABLE 13-continued

G + C mononucleotide and CpG dinucleotide frequencies in the DNA polymerase genes of different herpesviruses

| Herpes Virus | Subfamily | G + C | CpG ratio |
|---|---|---|---|
| HSV1 | alpha | 67.6% (65.8%) | 0.99 (1.06) |
| VSV | | 41.5% (42.2%) | 1.37 (1.15) |
| hCMV | beta | 60.2% (59.9%) | 1.27 (1.23) |
| hHV6 | | 46.0% (40.9%) | 1.00 (1.12) |

The G+C frequences of the KS and RF sequences are quite similar to each other, falling midway between the high G–C content of EBV and eHV2 and the low G+C content of sHV1. The CpG dinucleotide frequencies of KS and RF are quite similar, close to the expected value (1.00) based on their mononucleotide compositions. These values are closer to those for alpha and beta herpes viruses, than for gamma herpes viruses outside the RFHV/KSHV subfamily. The CpG data suggest that RFHVMn, RFHVMm and KSHV genomes remain latent in non-dividing cells, in contrast to sHV1 and EBV which are latent in proliferating lymphoblastoid cells.

The phylogenetic analysis, the CpG analysis, and the similarity between symptoms caused by the three viruses support the use of the monkey viruses as models for KSHV, and other members of the RFHV/KSHV subfamily that may infect humans.

Examples of RFHVMm-specific Type 3 oligonucleotides is shown in Table 14:

TABLE 14

Type 3 Oligonucleotides Specific for Polynucleotides Encoding DNA Polymerase from RFHV2

| Designation | Sequence (5' to 3') | Length | No. of forms | Target: | Orientation | SEQ ID: |
|---|---|---|---|---|---|---|
| LCYSA | CTATGTTACTCTACCCTGATT | 21 | 1 | RFHVMm DNA Polymerase | 5'→3' | 150 |
| KV1YB | GTATATCTCTTTAAACCTGGC | 21 | 1 | | 3'→5' | 151 |
| ASPDB | AACCTGGCGTCCGGGGAAGCG | 21 | 1 | | 3'→5' | 152 |

Figure 19A:
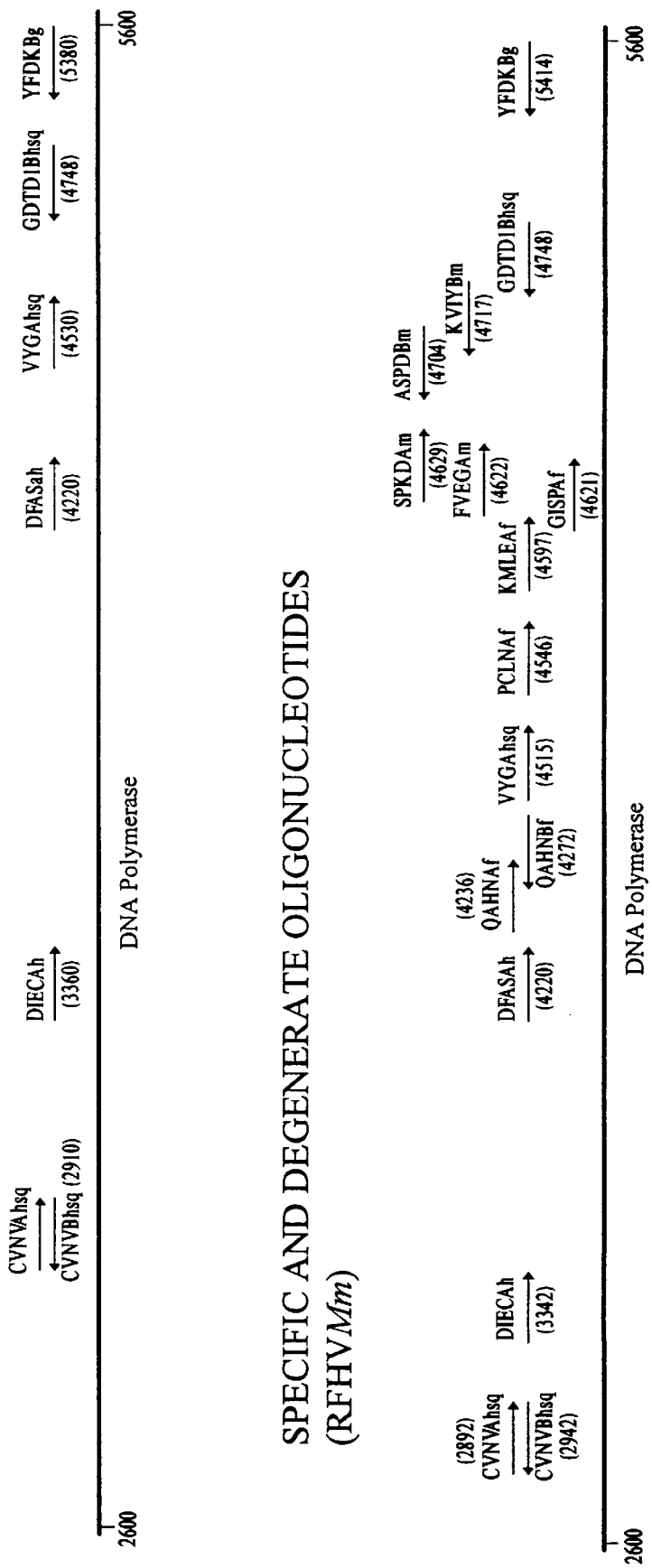
FIG. 19 is a map showing approximate hybridization positions of Type 1, Type 2, and Type 3 oligonucleotide probes in the DNA polymerase nucleotide sequences of members of the RFHV/KSHV subfamily.
Figure 19C:
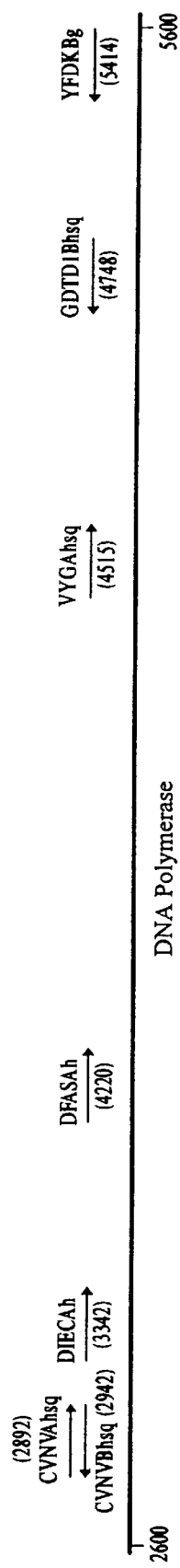

FIG. 19 is a map showing the approximate relative positions for hybridization of certain oligonucleotides of this invention along the DNA polymerase encoding sequence. Numbering of nucleotide residues is approximate, and based on a starting position in the Glycoprotein B encoding region, which flanks the DNA polymerase encoding region in the upstream direction. Following each oligonucleotide designation is an abbreviation in lower case which indicates the type of oligonucleotide: h=all herpes viruses (Type 1); sq=additional sequencing tail available; g=gamma herpes viruses (Type 1); f=RFHV/KSHV subfamily herpes viruses (Type 2); m=RFHVMm specific (Type 3); n=RFHVMn specific (Type 3); ks=KSHV specific (Type 3).

The phylogenetic analysis, the CpG analysis, and the similarity between symptoms caused by the three viruses support the use of the monkey viruses as models for KSHV, and other members of the RFHV/KSHV subfamily that may infect humans.

Figure 20:
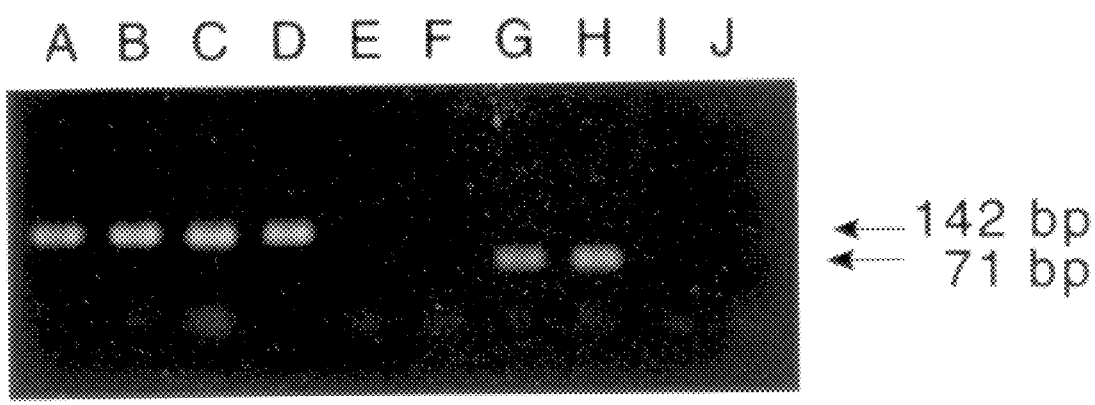
FIG. 20 is a representative screen for the prevalence of RFHVMn and RFHVMm herpesvirus sequences in *M. nemestrina* monkeys (lanes A–D, I, and J), and *M. mulatta* monkeys (lanes G and H) in a nested amplification assay using virus-specific oligonucleotide primers.

Oligonucleotide primers were used in a screening assay to detect the presence of DNA polymerase encoding sequences in various biological samples. The results are shown in FIG. 20. Results of RF samples of M. nemestrina monkeys #2, #3, #4, #7, #1 and #5 are shown in lanes A–D, I, and J respectively. Results from RF samples from a M. mulatta monkey is shown in lanes G & H. Results from peripheral blood lymphocytes of unaffected SRV2-negative M. nemestrina monkeys are shown in lanes E & F. Samples were assayed using nested PCR as follows: for the M. nemestrina samples, outer primers were VASGA and PEARB; inner primers were PEARB and PIEAB. For the M. mulatta samples, outer primers were FVEGA and KVIYB; inner primers were SPKDA and ASPDB. In this and other experiment, we found that the presence of amplification product correlates with the source of the samples in two ways: First, amplification was virus-specific (the RFHVMn specific oligonucleotides failed to amplify sequence from the M. mulatta RF lesion, but the RFHVMm specific oligonucleotides did. Second, M. nemestrina samples absent of RF-related symptoms did not yield reaction product, even when other viruses were present. A variety of tissues, including thymus, bone marrow, spleen, salivary gland, liver, mesenteric lymph node, ileocecal junction, duodenum, kidney and gonads naturally infected with SRV-2 were negative for the presence of RFHVMn sequences.

Example 12
Other human-infecting gamma herpes DNA polymerase sequences of the RFHV/KSHV subfamily Human tissue samples suspected of containing a previously undescribed gamma herpes virus, particularly fibroproliferative conditions, lymphocyte malignancies, and conditions associated with immunodeficiency and immunosuppression, such as acute respiratory disease syndrome (ARDS), are preserved by freezing, and the DNA is extracted as in Example 2. Two rounds of PCR amplification are conducted using the three herpes virus oligonucleotide primers, DFASA, VYGA and GDTD1B, according to Example 3. Alternatively, subfamily-specific (Type 2) primers may be used as described earlier in this example in the discovery of RFHV2.

The amplified polynucleotide is electrophoresed in agarose and blotted onto a nylon membrane. The blot is hybridized with a probe comprising the polynucleotide fragment obtained from the RFHV polynucleotide encoding DNA polymerase (residues 330–501 of FIG. 1), labeled with $^{32}$P. The hybridization reaction is done under conditions that will permit a stable complex forming between the probe and DNA polymerase from a herpes virus, but not between the probe and endogenous eukaryotic DNA polymerase. The conditions will require approximately 60% identity between hybridizing segments of the probe and the target for a stable complex to form. These conditions are calculated using the formula given earlier, depending on the length and sequence of the probe and the corresponding sequence of the target. The conditions are estimated to be: a) allowing the probe to hybridize with the target in 6×SSC (0.15 M NaCl, 15 mM sodium citrate buffer) at room temperature in the absence of formamide; and b) washing newly formed duplexes for a brief period (5–10 min) in 2×SSC at room temperature.

Amplified polynucleotides that hybridize to the labeled probe under these conditions are selected for further characterization. The expected size is 236 base pairs for the amplified inner fragment including the primer-binding regions, for a virus that has no insertions or deletions relative to RFHV or KSHV, and has been amplified using VYGA and GDTD1B as inner primers. The sequence of the fragment is determined as in Example 4. Samples containing fragments different from RFHV or KSHV are selected for determination of the entire DNA polymerase gene sequence by a method similar to that in Example 9.

REFERENCES

Altschul et al. (1986). Bull. Math. Bio. 48:603–616.
Ambroziuk et al. (1995). Science 268:582–583.
Basco et al. (1992). J. Biol. Chem. 267:19427–19434.
Basco et al. (1993). Chromosoma 102:32–38.
Berel V. et al. (1990). Lancet 335:123–128.
Bernard et al. (1989). Cell 59:219–228.
Bernard et al. (1990). Proc. Natl. Acad. Sci. USA 87:4610–4614.
Beaucage et al. (1981). Tetra. Lett. 22:1859–1862.
Cesarman E. et al. (1995). New Engl. J. Med. 332:1186–1191.
Chang Y. et al. (1994). Science 266:1865–1869.
Derbyshire et al. (1991). EMBO J., 10:17–24.
Digard P. et al. (1995). Proc. Natl. Acad. Sci. USA 92:1456–1460.
Dorsky D. I. et al. (1990). J. Virol. 64:1394–1397.
Dorsky D. I. et al. (1988). J. Virol. 62:3224–3232.
Emery V. C. et al. (1992). pp. 257–277 in Molecular and Cell Biology of Opportunistic Infections in AIDS; S. Myint & A. Cann, eds, Chapman & Hall.
Erickson et al. (1990). Science 249:527–533.
Fields B. N. & Knipe D. M., eds. (1991). Fundamental Virology, 2nd Edition, Raven Press.
Firesmith T. H. et al. (1994). Int. J. Dermatol. 33:755–762.
Gibbs J. S. et al. (1988a). Proc. Natl. Acad. Sci. USA 85:6672–6676.
Gibbs J. S. et al. (1988b). Proc. Natl. Acad. Sci. USA 85:7969–7973.
Giddens W. E. Jr. et al. (1983). pp. 249–253 in Viral and Immunological Diseases in Nonhuman Primates; Alan R. Liss Inc.
Glorioso J. C. et al. (1994). Dev. Biol. Stand 82:79–87.
Haffey M. L. et al. (1988). J. Virol. 62:4493–4498.
Hall J. D. et al. (1989). Nucl. Acids Res. 17:9231–9244.
Henikoff et al. (1992) Proc. Natl. Acad. Sci. USA 89:10915–10919.
Hirose et al. (1978). Tetra. Lett (1978) 19:2449–2452.
Hodgson (1991). Bio/Technology 9:19–21.
Hopp T. P. et al. (1981). Proc. Natl. Acad. Sci. USA 78:3824–3828.
Johnson P. A. et al. (1994). Methods Cell Biol. 43A: 191–210.
Karlin S. et al. (1994). J. Virol. 68:1886–1902.

Knopf C. W. et al. (1988). Biochim. Biophys. Acta 951:298–314.
Kumar et al. (1984). J. Org. Chem. 49:4905–4912.
Larder B. A. et al. (1987). EMBO J. 6:169–175.
Latchman D. S. et al. (1994). Molec. Biotechnol. 2:179–195.
Lin L. S. et al. (1995). J. Med. Virol. 45:99–105.
Lisitsyn N. et al. (1993). Science 259:946-.
Liu M. Y. et al. (1989). J. Med Virol. 28:101–105.
Marcy A. I. et al. (1990). J. Virol. 64:5883–5890.
Martin R. W. et al. (1993). Medicine 72:245–26.
Meier J. L. et al. (1993). J. Virol. 67:7573–7581.
Meinkoth J. et al. (1984). Anal. Biochem. 138:267-.
Miles S. A. (1994). Curr. Opin. Oncol. 6:497–502.
Mitsuyasu R. T. (1993). Curr. Opin. Oncol. 5:835–844.
Moore P. S. et al. (1995). New Engl. J. Med. 332:1181–1185.
Northfelt. D. W. (1994). Drugs (New Zealand) 48:569–582.
O'Donnell M. E. et al. (1987). J Biol. Chem. 262:4252–4259.
Reardon J. E. et al. (1989). J. Biol. Chem. 264:7405–7411.
Simon et al. (1991). EMBO J. 10:2165–2171.
Soengas et al. (1992). EMBO J. 11:4227–4237.
Stow N. D. (1993). Nucl. Acids Res. 21:87–92.
Tsai C. -C. et al. (1986). Lab. Animal Sci. 36:119–124.
VanDevanter et al. (1996). J. Clin. Microbiol. 34:1666–1671.
Wang T. S. -F. et al. (1989). FASEB J. 3:14–21.
Ward P. L. et al. (1994). Trends Genet. 10:267–274.
Yeung K. C. et al. (1991). Curr. Eye Res. 10 (Suppl.) 31–37.

| Patents and Patent Applications: | | |
|---|---|---|
| US 4415732 | Caruthers M. H. et al. | (polynucleotide synthesis) |
| US 4444887 | Hoffman M. K. | (mAb method) |
| US 4472500 | Milstein C. et al. | (mAb cell) |
| US 4683195 | Mullis K. B. | (PCR) |
| US 4683202 | Mullis K. B. et al. | (PCR) |
| US 4642333 | Person S. | (HSV Gb expression) |
| US 5120639 | Haffey M. L. et al. | (Ab vs POL in drug screening) |
| US 5124246 | Urdea M. S. et al. | (branched DNA) |
| US 5171568 | Burke R. L. et al. | (HSV Gb/Gd vaccine) |
| US 5176995 | Sninsky J. J. et al. | (PCR method for viruses) |
| US 5223391 | Coen D. M. et al. | (UL42 peptides as POL inhibitors) |
| US 5244792 | Burke R. L. et al. | (HSV Gb expression) |
| US 5350671 | Houghton M. et al. | (HCV diagnostics) |
| US 5354653 | Matsumoto T. et al. | (HSV strain probe assay) |
| US 5399346 | Anderson W. F. et al. | (gene therapy) |
| EP 0337441 | Haffey M. L. | (expression of HSV1 POL in yeast) |
| WO 8904964 | Feitelson M. et al. | (anti-HBV DNA POL in diagnosis) |
| JP 5309000 | Iatron Lab Inc. | (PCR assay for EBV POL) |

SEQUENCE LISTINGS:

| SEQ. ID | Designation | Description | Type | Source |
|---|---|---|---|---|
| 1 | RFHV | DNA polymerase PCR segment | DNA | This invention |
| 2 | RFHV | DNA polymerase PCR segment | Protein | This invention |
| 3 | KSHV | DNA polymerase PCR segment | DNA | This invention |
| 4 | KSHV | DNA polymerase PCR segment | Protein | This invention |
| 5 | DFASA | Herpes virus degenerate oligonucleotide | DNA | This invention |
| 6 | DFQSA | Herpes virus degenerate oligonucleotide | DNA | This invention |
| 7 | VYGA | Herpes virus degenerate oligonucleotide | DNA | This invention |
| 8 | VYGCA | Herpes virus degenerate oligonucleotide | DNA | This invention |
| 9 | VYGSQA | Herpes virus oligonucleotide | DNA | This invention |
| 10 | GDTD1A | Herpes virus degenerate oligonucleotide | DNA | This invention |
| 11 | GDTD1B | Herpes virus degenerate oligonucleotide | DNA | This invention |
| 12 | GDTDSQB | Herpes virus oligonucleotide | DNA | This invention |
| 13 | VASGA | RFHV specific oligonucleotide | DNA | This invention |
| 14 | ILPCA | RFHV specific oligonucleotide | DNA | This invention |
| 15 | PIEAB | RFHV specific oligonucleotide | DNA | This invention |
| 16 | PEARB | RFHV specific oligonucleotide | DNA | This invention |
| 17 | SGILA | KSHV specific oligonucleotide | DNA | This invention |
| 18 | CLNIA | KSHV specific oligonucleotide | DNA | This invention |
| 19 | IEASB | KSHV specific oligonucleotide | DNA | This invention |
| 20 | EARFB | KSHV specific oligonucleotide | DNA | This invention |
| 21 | PCLNA | RFHV/KSHV subfamily degenerate oligonucleotide | DNA | This invention |
| 22 | KMLEA | RFHV/KSHV subfamily degenerate oligonucleotide | DNA | This invention |
| 23 | eHV2 | DNA polymerase | DNA | Genbank locus EHVU20824 |
| 24 | sHV1 | DNA polymerase | DNA | Genbank locus HSVSPOLGBP |
| 25 | EBV | DNA polymerase | DNA | Genbank locus EBV |

-continued

SEQUENCE LISTINGS:

| SEQ. ID | Designation | Description | Type | Source |
|---|---|---|---|---|
| 26 | hCMV | DNA polymerase | DNA | Genbank locus HS5POL |
| 27 | hHV6 | DNA polymerase | DNA | Genbank locus HH6DNAPOL |
| 28 | hVZV | DNA polymerase | DNA | Genbank locus HEVZVXX |
| 29 | hHSV1 | DNA polymerase | DNA | Genbank locus HEHSV1DP |
| 30 | eHV2 | DNA polymerase | Protein | Genbank locus EHVU20824 |
| 31 | sHV1 | DNA polymerase | Protein | Genbank locus HSVSPOLGBP |
| 32 | EBV | DNA polymerase | Protein | Genbank locus EBV |
| 33 | hCMV | DNA polymerase | Protein | Genbank locus HS5POL |
| 34 | hHV6 | DNA polymerase | Protein | Genbank locus HH6DNAPOL |
| 35 | hVZV | DNA polymerase | Protein | Genbank locus HEVZVXX |
| 36 | hHSV1 | DNA polymerase | Protein | Genbank locus HEHSV1DP |
| 37 | hHSV2 | DNA polymerase | Protein | PIR locus DJBE21 |
| 38 | eHV1 | DNA polymerase | Protein | PIR locus DJBEC3 |
| 39 | mCMV | DNA polymerase | Protein | PIR locus DJBEMC |
| 40 | gpCMV | DNA polymerase | Protein | PIR locus L25706-B |
| 41 | iHV1 | DNA polymerase | Protein | PIR locus DJBEI1 |
| 42 | hHV6 | DNA polymerase segment | DNA | Figure 3 |
| 43 | hCMV | DNA polymerase segment | DNA | Figure 3 |
| 44 | gpCMV | DNA polymerase segment | DNA | Figure 3 |
| 45 | mCMV | DNA polymerase segment | DNA | Figure 3 |
| 46 | hHSV1 | DNA polymerase segment | DNA | Figure 3 |
| 47 | hHSV2 | DNA polymerase segment | DNA | Figure 3 |
| 48 | hVZV | DNA polymerase segment | DNA | Figure 3 |
| 49 | eHV2 | DNA polymerase segment | DNA | Figure 3 |
| 50 | hEBV | DNA polymerase segment | DNA | Figure 3 |
| 51 | sHV1 | DNA polymerase segment | DNA | Figure 3 |
| 52 | iHV1 | DNA polymerase segment | DNA | Figure 3 |
| 53 | hHV6 | DNA polymerase segment | DNA | Figure 4 |
| 54 | hCMV | DNA polymerase segment | DNA | Figure 4 |
| 55 | gpCMV | DNA polymerase segment | DNA | Figure 4 |
| 56 | mCMV | DNA polymerase segment | DNA | Figure 4 |
| 57 | hHSV1 | DNA polymerase segment | DNA | Figure 4 |
| 58 | hVZV | DNA polymerase segment | DNA | Figure 4 |
| 59 | eHV2 | DNA polymerase segment | DNA | Figure 4 |
| 60 | hEBV | DNA polymerase segment | DNA | Figure 4 |
| 61 | sHV1 | DNA polymerase segment | DNA | Figure 4 |
| 62 | iHV1 | DNA polymerase segment | DNA | Figure 4 |
| 63 | hHV6 | DNA polymerase segment | DNA | Figure 5 |
| 64 | hCMV | DNA polymerase segment | DNA | Figure 5 |
| 65 | gpCMV | DNA polymerase segment | DNA | Figure 5 |
| 66 | mCMV | DNA polymerase segment | DNA | Figure 5 |
| 67 | hHSV1 | DNA polymerase segment | DNA | Figure 5 |
| 68 | hVZV | DNA polymerase segment | DNA | Figure 5 |
| 69 | eHV2 | DNA polymerase segment | DNA | Figure 5 |
| 70 | sHV1 | DNA polymerase segment | DNA | Figure 5 |
| 71 | hEBV | DNA polymerase segment | DNA | Figure 5 |
| 72 | iHV1 | DNA polymerase segment | DNA | Figure 5 |
| 73 | IAETVTL | gamma-herpes antigen | Protein | This invention |
| 74 | VASGILP | RFHV/KSHV subfamily antigen | Protein | This invention |
| 75 | GILPCLN | RFHV/KSHV subfamily antigen | Protein | This invention |
| 76 | CLNIAET | RFHV/KSHV subfamily antigen | Protein | This invention |
| 77 | QGRKMLE | RFHV/KSHV subfamily antigen | Protein | This invention |
| 78 | SQAFVE | RFHV/KSHV subfamily antigen | Protein | This invention |
| 79 | ARFKVI | RFHV/KSHV subfamily antigen | Protein | This invention |
| 80 | LETSQAF | RFHV specific antigen | Protein | This invention |
| 81 | LERSQAF | KSHV specific antigen | Protein | This invention |
| 82 | EGISPTA | RFHV specific antigen | Protein | This invention |
| 83 | EAISPER | KSHV specific antigen | Protein | This invention |
| 84 | ADLLQRP | RFHV specific antigen | Protein | This invention |
| 85 | AGLLRRP | KSHV specific antigen | Protein | This invention |
| 86 | QRPIEAS | RFHV specific antigen | Protein | This invention |
| 87 | RRPIDVS | KSHV specific antigen | Protein | This invention |
| 88 | IEASPEA | RFHV specific antigen | Protein | This invention |
| 89 | IDVSPDA | KSHV specific antigen | Protein | This invention |
| 90 | PDDYETF | RFHV/KSHV subfamily antigen | Protein | This invention |
| 91 | KRKEIRK | RFHV/KSHV subfamily antigen | Protein | This invention |
| 92 | LAKRKEI | RFHV/KSHV subfamily antigen | Protein | This invention |
| 93 | LASCTDP | RFHV/KSHV subfamily antigen | Protein | This invention |
| 94 | TGSALHG | RFHV specific antigen | Protein | This invention |
| 95 | PGDSLHL | KSHV specific antigen | Protein | This invention |
| 96 | SALHGHP | RFHV specific antigen | Protein | This invention |
| 97 | DSLHLHP | KSHV specific antigen | Protein | This invention |
| 98 | GHPELTP | RFHV specific antigen | Protein | This invention |
| 99 | LHPHLGP | KSHV specific antigen | Protein | This invention |
| 100 | HLSGGTV | RFHV specific antigen | Protein | This invention |

-continued

SEQUENCE LISTINGS:

| SEQ. ID | Designation | Description | Type | Source |
|---|---|---|---|---|
| 101 | VLSGGLV | KSHV specific antigen | Protein | This invention |
| 102 | TDPTMRT | RFHV specific antigen | Protein | This invention |
| 103 | TDPALKT | KSHV specific antigen | Protein | This invention |
| 104 | SIIQB | KSHV specific oligonucleotide | DNA | This invention |
| 105 | QAHNA | Gamma herpes degenerate oligonucleotide | DNA | This invention |
| 106 | QAHNB | Gamma herpes degenerate oligonudeotide | DNA | This invention |
| 107 | LSGGA | RFHV/KSHV subfamily specific degenerate oligonucleotide | DNA | This invention |
| 108 | CTDPA | RFHV/KSHV subfamily specific degenerate oligonucleotide | DNA | This invention |
| 109 | GISPA | RFHV/KSHV subfamily specific degenerate oligonucleotide | DNA | This invention |
| 110 | RFHV fragment | Shared polynucleotide sequence | DNA | This invention |
| 111 | RFHV fragment | Shared polynucleotide sequence | DNA | This invention |
| 112 | RFHV fragment | Shared polypeptide sequence | Protein | This invention |
| 113 | KSHV fragment | Shared polypeptide sequence | Protein | This invention |
| 114 | KSHV fragment | KSHV fragment | DNA | This invention |
| 115 | KSHV fragment | KSHV fragment | Protein | This invention |
| 116 | KSHV | DNA polymerase segment | DNA | This invention |
| 117 | KSHV | DNA polymerase segment | Protein | This invention |
| 118 | RFHV2 | DNA polymerase PCR segment | DNA | This invention |
| 119 | RFHV2 | DNA polymerase PCR segment | Protein | This invention |
| 120 | KSHV | DNA polymerase variant | Protein | This invention |
| 121 | KSHV | DNA polymerase variant | Protein | This invention |
| 122 | KSHV | DNA polymerase variant | Protein | This invention |
| 123 | KSHV | DNA polymerase variant | Protein | This invention |
| 124 to 138 | | Herpes virus (Type 1) oligonucleotides | DNA | This invention Table 10 |
| 139to- 149 | | KSHV specific oligonucleotides | DNA | This invention Table 11 |
| 150 to 152 | | RFHV2 specific oligonucleotides | DNA | This invention Table 14 |

We claim:

1. An isolated DNA polymerase of a herpes virus comprising a sequence selected from the group consisting of SEQ ID NO:1 and SEQ ID NO:3.

2. An isolated polypeptide comprising a linear sequence of at least 12 to 837 consecutive amino acids encoded by an isolated polynucleotide selected from the group consisting of SEQ ID NO:107, SEQ ID NO:108, and their respective complementary sequences, under conditions wherein the oligonucleotide forms a stable duplex with a polynucleotide having the sequence shown in SEQ ID NO:1 or with a polynucteotide having the sequence shown in SEQ ID NO:3, but not by a polynucleotide having a sequence of any of SEQ ID NOS:23 to 29.

3. An isolated DNA polymerase of a herpes virus comprising a linear sequence of at least 12 to 837 consecutive amino acids having a biological activity of a sequence selected from the group consisting of SEQ ID NO:4 between amino acids 10 to 167 inclusive, of SEQ ID NO:117 between amino acids 13 to 833 inclusive, and each of SEQ ID NOS:119–123, but not by a polypeptide encoded by a polynucleotide having the sequence of SEQ ID NO:24.

4. The isolated polypeptide of claim 1, wherein the polynucicotide scquence is a KSHV sequence.

5. An isolated DNA polymerase of a herpes virus comprising a linear sequence of at least 12 to 837 consecutive amino acids identical to a sequence of SEQ ID NO:2 between amino acids 10 to 167, inclusive, or of SEQ ID NO:4 between amino acids 10 to 167, inclusive, or of SEQ ID NO:117 between amino acids 13 to 833, inclusive, or in any of SEQ ID NOS:119–123, but which is not contained in any of the sequences of SEQ ID NOS:30–36.

6. The isolated polypeptide of claim 5, wherein the linear amino acid sequence is a KSHV sequence.

7. The isolated polypeptide of claim 5, which has an activity selected from the group consisting of nucleic acid binding activity, nucleotide binding activity, or DNA polymerase activity.

* * * * *